US012692553B2

(12) United States Patent
Namsaraev et al.

(10) Patent No.: US 12,692,553 B2
(45) Date of Patent: Jul. 28, 2026

(54) METHODS AND SYSTEMS FOR TUMOR DETECTION

(71) Applicants: The Chinese University of Hong Kong, Shatin (HK); GRAIL, Inc., Menlo Park, CA (US)

(72) Inventors: Eugeni Namsaraev, Palo Alto, CA (US); Yuk-Ming Dennis Lo, Homantin (CN); Rossa Wai Kwun Chiu, Shatin (CN); Kwan Chee Chan, Jordan (CN); Peiyong Jiang, Pak Shek Kok (CN); Kun Sun, Shatin (CN); Wai Kei Lam, Kowloon (CN)

(73) Assignees: The Chinese University of Hong Kong, Shatin (HK); GRAIL, Inc., Menlo Park, CA (US)

( * ) Notice: Subject to any disclaimer, the term of this patent is extended or adjusted under 35 U.S.C. 154(b) by 0 days.

(21) Appl. No.: 19/275,781

(22) Filed: Jul. 21, 2025

(65) Prior Publication Data
US 2025/0346961 A1      Nov. 13, 2025

Related U.S. Application Data

(63) Continuation of application No. 17/884,498, filed on Aug. 9, 2022, which is a continuation of application No. 15/793,830, filed on Oct. 25, 2017, now Pat. No. 11,459,616, which is a continuation of application No. PCT/US2017/058099, filed on Oct. 24, 2017.

(60) Provisional application No. 62/507,154, filed on May 16, 2017, provisional application No. 62/450,541, filed on Jan. 25, 2017, provisional application No. 62/411,929, filed on Oct. 24, 2016.

(51) Int. Cl.
| | |
|---|---|
| *G01N 33/48* | (2006.01) |
| *C12Q 1/6806* | (2018.01) |
| *C12Q 1/686* | (2018.01) |
| *C12Q 1/6886* | (2018.01) |
| *C12Q 1/70* | (2006.01) |
| *G01N 33/50* | (2006.01) |
| *G16B 20/00* | (2019.01) |
| *G16B 20/10* | (2019.01) |
| *G16B 20/20* | (2019.01) |
| *G16B 30/10* | (2019.01) |
| *G16B 40/20* | (2019.01) |
| *G16H 10/40* | (2018.01) |
| *G16B 30/00* | (2019.01) |
| *G16B 40/00* | (2019.01) |

(52) U.S. Cl.
CPC ......... *C12Q 1/6886* (2013.01); *C12Q 1/6806* (2013.01); *C12Q 1/686* (2013.01); *C12Q 1/701* (2013.01); *C12Q 1/705* (2013.01); *G16B 20/00* (2019.02); *G16B 20/10* (2019.02); *G16B 20/20* (2019.02); *G16B* *30/10* (2019.02); *G16B 40/20* (2019.02); *G16H 10/40* (2018.01); *C12Q 2535/122* (2013.01); *C12Q 2600/154* (2013.01); *C12Q 2600/156* (2013.01); *C12Q 2600/158* (2013.01); *G01N 2333/05* (2013.01); *G16B 30/00* (2019.02); *G16B 40/00* (2019.02)

(58) Field of Classification Search
CPC .... C12Q 1/6886; C12Q 1/6806; C12Q 1/686; C12Q 1/701; C12Q 1/705; C12Q 2535/122; C12Q 2600/154; C12Q 2600/156; C12Q 2600/158; C12Q 1/708; G16B 20/00; G16B 20/10; G16B 20/20; G16B 30/10; G16B 40/20; G16B 30/00; G16B 40/00; G16H 10/40; G01N 2333/05
See application file for complete search history.

(56) References Cited

U.S. PATENT DOCUMENTS

| | | |
|---|---|---|
| 10,633,703 B2 | 4/2020 | Wang et al. |
| 2015/0317490 A1 | 11/2015 | Carey et al. |
| 2023/0132951 A1 | 5/2023 | Namsaraev et al. |

FOREIGN PATENT DOCUMENTS

| | | | |
|---|---|---|---|
| AU | 2018212272 B2 | 4/2022 | |
| WO | WO-2014043763 A1 * | 3/2014 | ........... C12Q 1/6886 |

OTHER PUBLICATIONS

Bock C. Analysing and interpreting DNA methylation data. Nature Reviews: Genetics, vol. 13, pp. 705-719. (Year: 2012).*
Yong et al. Profiling genome-wide DNA methylation. Epigentics & Chromatin, vol. 9, Jun. 29, 2016, article 26, 16 pages. (Year: 2016).*

(Continued)

*Primary Examiner* — Russell S Negin
(74) *Attorney, Agent, or Firm* — Kilpatrick Townsend & Stockton LLP

(57) ABSTRACT

Methods are provided to improve the positive predictive value for cancer detection using cell-free nucleic acid samples. Various embodiments are directed to applications (e.g., diagnostic applications) of the analysis of the fragmentation patterns and size of cell-free DNA, e.g., plasma DNA and serum DNA, including nucleic acids from pathogens, including viruses. Embodiments of one application can determine if a subject has a particular condition. For example, a method of present disclosure can determine if a subject has cancer or a tumor, or other pathology. Embodiments of another application can be used to assess the stage of a condition, or the progression of a condition over time. For example, a method of the present disclosure may be used to determine a stage of cancer in a subject, or the progression of cancer in a subject over time (e.g., using samples obtained from a subject at different times).

30 Claims, 101 Drawing Sheets

(56)                    References Cited

OTHER PUBLICATIONS

Javier et al. The history of tumor virology. Cancer Research, vol. 68, pp. 7693-7706. (Year: 2008).*

U.S. Appl. No. 16/912,410, Non-Final Office Action mailed on Jul. 11, 2024, 12 pages.

Australian Application No. 2022205234, First Examination Report mailed on Jul. 8, 2024, 3 pages.

Bianchi et al., Large Amounts of Cell-Free Fetal DNA are Present in Amniotic Fluid, Clinical Chemistry, vol. 47, No. 10, Oct. 2001, pp. 1867-1869.

Canick et al., The Impact of Maternal Plasma DNA Fetal Fraction on Next Generation Sequencing Tests for Common Fetal Aneuploidies, Prenatal Diagnosis, vol. 33, No. 7, Jul. 2013, pp. 667-674.

Chan et al., Hypermethylated RASSF1A in Maternal Plasma: A Universal Fetal DNA Marker that Improves the Reliability of Noninvasive Prenatal Diagnosis, Clinical Chemistry, vol. 52, No. 12, Dec. 2006, pp. 2211-2218.

Chan et al., Second Generation Noninvasive Fetal Genome Analysis Reveals De Novo Mutations, Single-Base Parental Inheritance, and Preferred DNA Ends, Proceedings of the National Academy of Sciences of the United States of America, vol. 113, No. 50, Dec. 13, 2016, pp. 1-10.

Chan et al., Size Distributions of Maternal and Fetal DNA in Maternal Plasma, Clinical Chemistry, vol. 50, No. 1, Jan. 2004, pp. 88-92.

Chiu et al., Noninvasive Prenatal Diagnosis of Fetal Chromosomal Aneuploidy by Massively Parallel Genomic Sequencing of DNA in Maternal Plasma, Proceedings of the National Academy of Sciences of the United States of America, vol. 105, No. 51, Dec. 23, 2008, pp. 20458-20463.

Chinese Application No. 201780080329.5, Office Action mailed on Sep. 1, 2023, 11 pages (3 pages of English Translation and 8 pages of original document).

Chinese Application No. 201780080329.5, Office Action mailed on Dec. 1, 2023, 18 pages (10 pages of English Translation and 8 pages of Original document).

Eurasian Application No. 201500027, Office Action mailed on Mar. 10, 2017, 19 pages (8 pages of English Translation and 11 pages of original document).

Fan et al., Analysis of the Size Distributions of Fetal and Maternal Cell-Free DNA by Paired-End Sequencing, Clinical Chemistry, vol. 56, No. 8, Aug. 2010, pp. 1279-1286.

Fan et al., Non-Invasive Prenatal Measurement of the Fetal Genome, Nature, vol. 487, No. 7407, Jul. 19, 2012, pp. 1-7.

Fan et al., Sensitivity of Noninvasive Prenatal Detection of Fetal Aneuploidy from Maternal Plasma Using Shotgun Sequencing is Limited Only by Counting Statistics, Public Library of Science One, vol. 5, No. 5, Mar. 2010, pp. 1-7.

Finning et al., Effect of High Throughput RHD Typing of Fetal DNA in Maternal Plasma on Use of Anti-RhD Immunoglobulin in Rhd Negative Pregnant Women: Prospective Feasibility Study, British Medical Journal, vol. 336, No. 7648, Apr. 12, 2008, 6 pages.

Hudecova et al., Maternal Plasma Fetal DNA Fractions in Pregnancies with Low and High Risks for Fetal Chromosomal Aneuploidies, Public Library of Science One, vol. 9, No. 2, Feb. 28, 2014, pp. 1-7.

Indonesian Application No. PID201904301, Office Action mailed on May 19, 2022, 4 pages.

Jiang et al., FetalQuant: Deducing Fractional Fetal DNA Concentration from Massively Parallel Sequencing of DNA in Maternal Plasma, Bioinformatics, vol. 28, No. 22, Nov. 15, 2012, pp. 2883-2890.

Japanese Application No. 2023-126899, Office Action mailed on Aug. 6, 2024, 11 pages (7 pages of English Translation and 4 pages of Original document).

Lapaire et al., Array-CGH Analysis of Cell-Free Fetal DNA in 10 mL of Amniotic Fluid Supernatant, Prenatal Diagnosis, vol. 27, No. 7, May 17, 2007, pp. 616-621.

Lapaire et al., Cell-Free Fetal DNA in Amniotic Fluid: Unique Fragmentation Signatures in Euploid and Aneuploid Fetuses, Clinical Chemistry, vol. 53, No. 3, Mar. 2007, pp. 405-411.

Larrabee et al., Microarray Analysis of Cell-Free Fetal DNA in Amniotic Fluid: A Prenatal Molecular Karyotype, American Journal of Human Genetics, vol. 75, No. 3, Sep. 1, 2004, pp. 485-491.

Li et al., Detection of Paternally Inherited Fetal Point Mutations for β-Thalassemia Using Size-Fractionated Cell-Free DNA in Maternal Plasma, Journal of the American Medical Association, vol. 293, No. 7, Feb. 16, 2005, pp. 843-849.

Li et al., Size Separation of Circulatory DNA in Maternal Plasma Permits Ready Detection of Fetal DNA Polymorphisms, Clinical Chemistry, vol. 50, No. 6, Jun. 2004, pp. 1002-1011.

Lo et al., Detection of Single-Copy Fetal DNA Sequence from Maternal Blood, The Lancet; Letters to the Editor, vol. 335, No. 8703, Jun. 16, 1990, pp. 1463-1464.

Lo et al., Maternal Plasma DNA Sequencing Reveals the Genome-Wide Genetic and Mutational Profile of the Fetus, Science Translational Medicine, vol. 2, No. 61, Dec. 8, 2010, pp. 1-13.

Lo et al., Prenatal Diagnosis of Fetal RhD Status by Molecular Analysis of Maternal Plasma, The New England Journal of Medicine, vol. 339, No. 24, Dec. 10, 1998, pp. 1734-1738.

Lo et al., Presence of Fetal DNA in Maternal Plasma and Serum, The Lancet, vol. 350, Aug. 16, 1997, pp. 485-487.

Lo et al., Quantitative Analysis of Fetal DNA in Maternal Plasma and Serum: Implications for Noninvasive Prenatal Diagnosis, American Journal of Human Genetics, vol. 62, No. 4, Apr. 1998, pp. 768-775.

Lun et al., Microfluidics Digital PCR Reveals a Higher than Expected Fraction of Fetal DNA in Maternal Plasma, Clinical Chemistry, vol. 54, No. 10, Oct. 2008, pp. 1664-1672.

New et al., Noninvasive Prenatal Diagnosis of Congenital Adrenal Hyperplasia Using Cell-Free Fetal DNA in Maternal Plasma, The Journal of Clinical Endocrinology and Metabolism, vol. 99, No. 6, Jun. 2014, pp. E1022-E1030.

Nygren et al., Quantification of Fetal DNA by Use of Methylation-Based DNA Discrimination, Clinical Chemistry, vol. 56, No. 10, Aug. 20, 2010, pp. 1627-1635.

Papageorgiou et al., Fetal-Specific DNA Methylation Ratio Permits Noninvasive Prenatal Diagnosis of Trisomy 21, Nature Medicine, vol. 17, No. 4, Apr. 2011, 13 pages.

Porreco et al., Noninvasive Prenatal Screening for Fetal Trisomies 21, 18, 13 and the Common Sex Chromosome Aneuploidies from Maternal Blood Using Massively Parallel Genomic Sequencing of DNA, American Journal of Obstetrics and Gynecology, vol. 211, No. 4, Oct. 2014, p. 365.e1-p. 365.e12.

Reed et al., Non-Invasive Determination of the Paternal HLA Haplotype of a Fetus Using Kinetic PCR to Detect Fetal Microchimerism in Maternal Plasma, Bone Marrow Transplantation, vol. 29, No. 6, Mar. 2002, pp. 527-529.

Sehnert et al., Optimal Detection of Fetal Chromosomal Abnormalities by Massively Parallel DNA Sequencing of Cell-Free Fetal DNA From Maternal Blood, Clinical Chemistry, vol. 57, No. 7, Apr. 25, 2011, pp. 1042-1049.

Snyder et al., Noninvasive Fetal Genome Sequencing: A Primer, NIH Public Access Author Manuscript in PMC, vol. 33, No. 6, Jun. 2013, pp. 547-554.

Straver et al., Calculating the Fetal Fraction for Noninvasive Prenatal Testing Based on Genome-Wide Nucleosome Profiles, Supplementary Data, vol. 36, 2016, 15 pages.

Viet Nam Application No. 1-2019-02728, Office Action mailed on Aug. 7, 2023, 5 pages (2 pages of English Translation and 3 pages of Original document).

Wang et al., Gestational Age and Maternal Weight Effects on Fetal Cell-free DNA in Maternal Plasma, Prenatal Diagnosis, vol. 33, Jul. 2013, pp. 662-666.

Yu et al., Combined Count- and Size-Based Analysis of Maternal Plasma DNA for Noninvasive Prenatal Detection of Fetal Subchromosomal Aberrations Facilitates Elucidation of the Fetal and/or Maternal Origin of the Aberrations, Clinical Chemistry, vol. 63, No. 2, Feb. 1, 2017, pp. 495-502.

Office Action dated Oct. 30, 2025 in CA Patent Application No. 3,041,647. 6 pages.

(56)               References Cited

OTHER PUBLICATIONS

Substantive Examination Adverse Report mailed Feb. 24, 2026 in MY Patent Application PI2023000893. 5 pages.
Non-Final Office Action mailed Mar. 2, 2026 in U.S. Appl. No. 17/968,155, filed Oct. 18, 2022. 7 pages.

* cited by examiner

FIG. 1

Lo, Y. M. Dennis, et al. "Quantitative Analysis of Cell-free Epstein-Barr Virus DNA in Plasma of Patients with Nasopharyngeal Carcinoma." *Cancer Research*, March 1999.

Lo, Y. M. Dennis, et al. "Quantitative Analysis of Cell-free Epstein-Barr Virus DNA in Plasma of Patients with Nasopharyngeal Carcinoma." *Cancer Research*, March 1999.

| Groups | N |
|---|---|
| Total number of subjects tested | 20,174 |
| EBV positive in First assay | 1,078 |
| EBV positive in Second assay | 300 |
| Confirmed NPC by endoscopy | 34 |
| Confirmed NPC case missed in First Assay | 1 |

FIG. 6A

| Cutoff of EBV copies | Sensitivity (%) | Specificity (%) |
|---|---|---|
| No cut off | 97.1 | 94.5 |
| 10 | 85.7 | 96.1 |
| 20 | 74.3 | 98.5 |
| 30 | 65.7 | 99.3 |
| 40 | 54.3 | 99.6 |
| 50 | 40.0 | 99.7 |
| 60 | 31.4 | 99.8 |
| 70 | 25.7 | 99.8 |
| 80 | 25.7 | 99.8 |
| 90 | 25.7 | 99.9 |
| 100 | 22.9 | 99.9 |

FIG. 8A

| Cutoff of EBV copies | Sensitivity (%) | Specificity (%) |
|---|---|---|
| No cut off | 97.1 | 12 |
| 10 | 85.7 | 38.4 |
| 20 | 74.3 | 75.7 |
| 30 | 65.7 | 89.5 |
| 40 | 54.3 | 93.5 |
| 50 | 40.0 | 95.7 |
| 60 | 31.4 | 96.5 |
| 70 | 25.7 | 97.3 |
| 80 | 25.7 | 97.4 |
| 90 | 25.7 | 97.9 |
| 100 | 22.9 | 98.1 |

AUC: 79.7% (70.4%-88.9%)

FIG. 11

Li, Jing, et al. "A Comparison between the Sixth and Seventh Editions of the UICC/AJCC Staging System for Nasopharyngeal Carcinoma in a Chinese Cohort." *PLoS One*, December 2014

Ending positions for DNA fragments across mutations present in plasma

Preferred ending positions for fragments carrying wildtype alleles

Preferred ending positions for fragments carrying mutant-specific alleles 22,432
Set F 2,890
Set G 11,498
Set E

FIG. 17

Nucleotide of interest

Sample: TBR125
Staging: T4N3M0

*Percentage of bins showing*
*aberrations*
Methy analysis: 49.7%
CNA analysis: 42.3%

Jiang, Peiyong, et al. "Lengthening and shortening of plasma DNA in hepatocellular carcinoma patients." *PNAS*, March 2015

Fragments covering z nt upstream
to z nt downstream of the target nucleotide : a, b, c and d Fragments covering the target nucleotide: a, b, c, d, e, f and g $$P_i = \frac{4}{7}$$

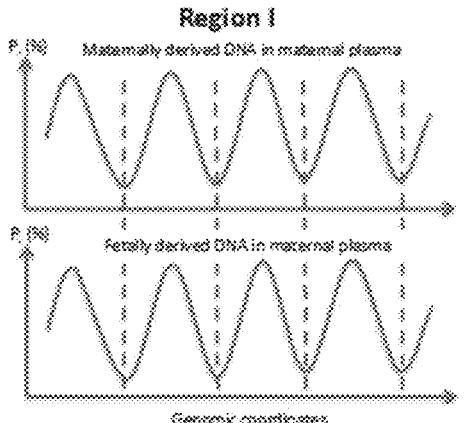
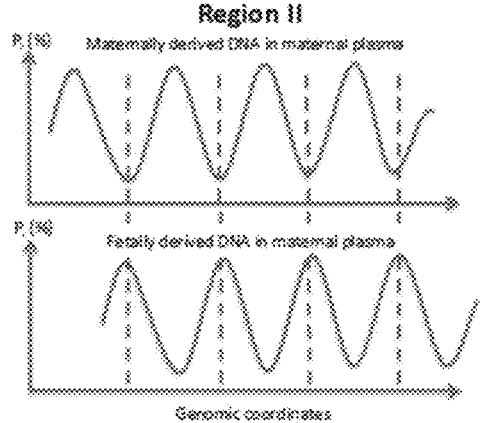
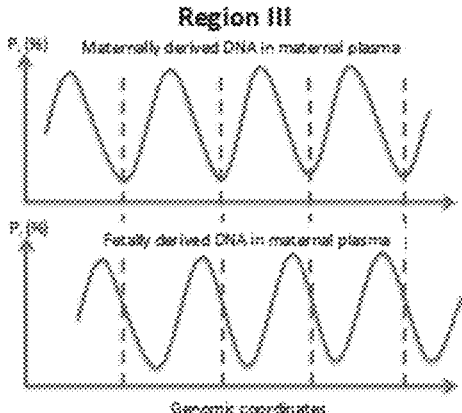
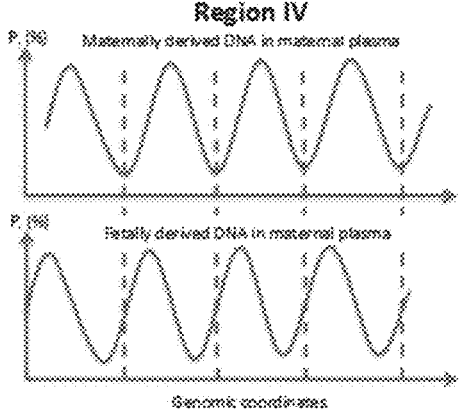
*FIG. 26*

500

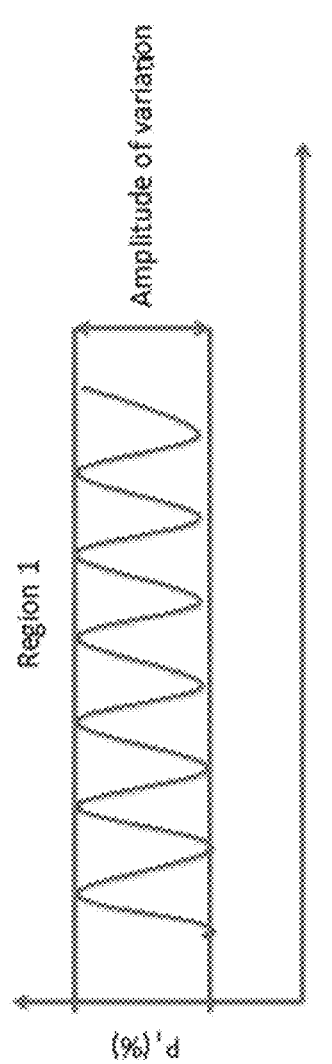
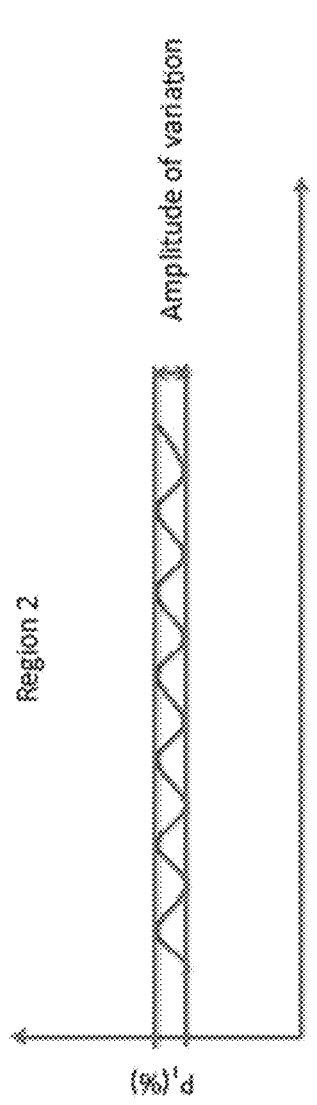
*FIG. 29*

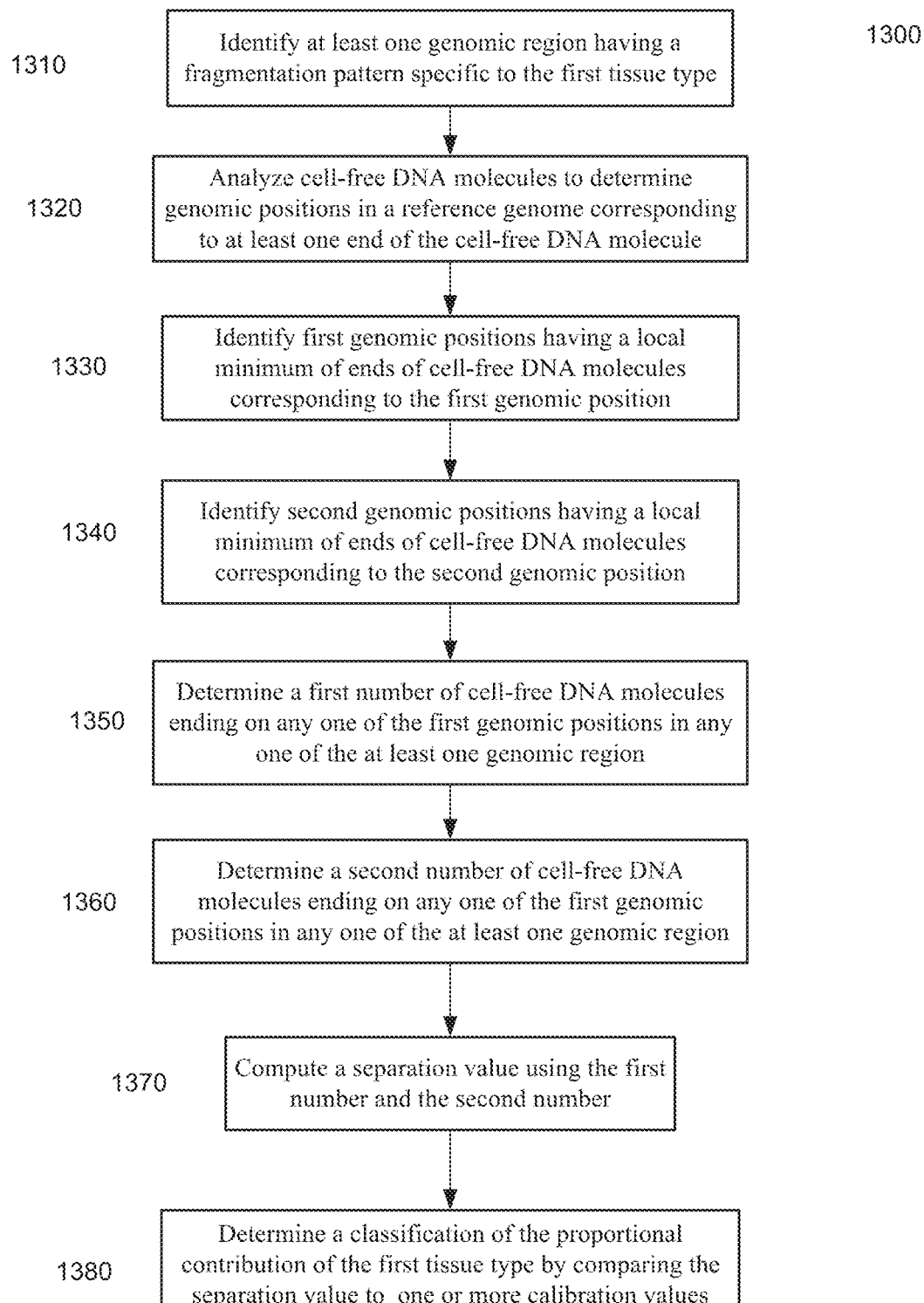

1300

1310    Identify at least one genomic region having a
        fragmentation pattern specific to the first tissue type 1320    Analyze cell-free DNA molecules to determine
        genomic positions in a reference genome corresponding
        to at least one end of the cell-free DNA molecule 1330    Identify first genomic positions having a local
        minimum of ends of cell-free DNA molecules
        corresponding to the first genomic position 1340    Identify second genomic positions having a local
        minimum of ends of cell-free DNA molecules
        corresponding to the second genomic position 1350    Determine a first number of cell-free DNA molecules
        ending on any one of the first genomic positions in any
        one of the at least one genomic region 1360    Determine a second number of cell-free DNA
        molecules ending on any one of the first genomic
        positions in any one of the at least one genomic region 1370    Compute a separation value using the first
        number and the second number 1380    Determine a classification of the proportional
        contribution of the first tissue type by comparing the
        separation value to one or more calibration values

FIG. 35

Specific for the pregnant woman 536,772

Shared by both cases 463,228

Specific for the HCC case 536,772

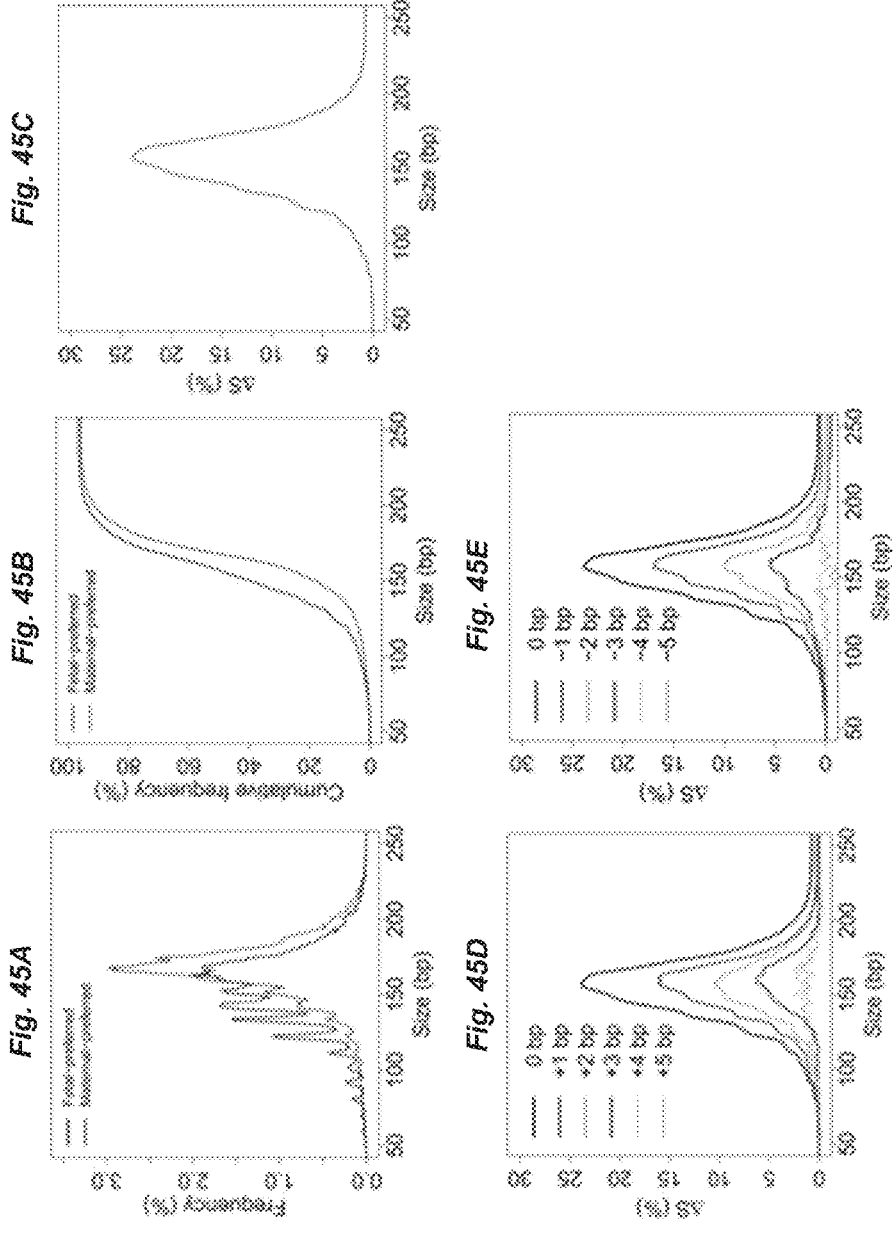

Ending positions for DNA fragments across mutations present in plasma

Preferred ending positions for fragments carrying mutant-specific alleles

Preferred ending positions for fragments carrying wildtype alleles 11,498 Set E    2,890 Set G    22,432 Set F Pearson's r = 0.53
P-value < 0.001

Preferred ending sites
for plasma DNA fragments

3600

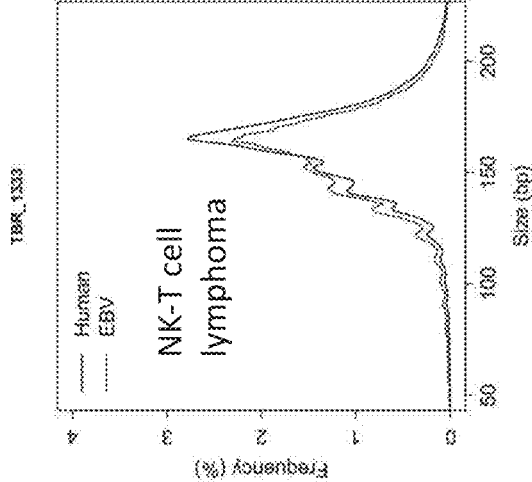
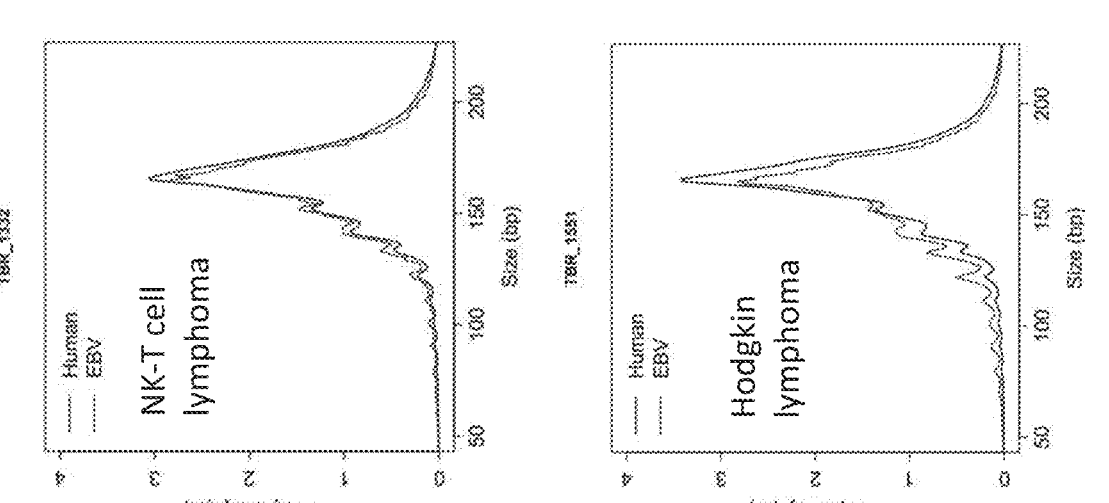
*FIG. 63*

400 most common ending positions for plasma EBV DNA

Subject without any pathology

NPC patient

A 383    C 17    B 383

Persistently positive
for plasma EBV DNA
but no pathology

NPC patients
identified by
screening

B/A ratio

The percentage of EBV
DNA fragments below 150
bp in plasma (%)

20,000-subject cohort

Baseline 1,112 positive for plasma EBV DNA
- 34 NPC
- 1,078 false positives

Fragment size and dosage analysis
- 34 NPC
- 146 false positives

False positive rate:
5.5% -> 0.72%

|  | Transiently positive | Persistently positive | NPC |
|---|---|---|---|
| EBV count ≥0.0009% | N=26 | N=14 | N=32 |
| Positive with Size (≤7%) | N=8 | N=13 | N=32 |
|  | N=3 | N=2 | N=32 |

Percentage classified as screen-positive
- NPC patients 100%
- Subjects without NPC but EBV DNA+ 5/37 = 13.5%

*FIG. 86*

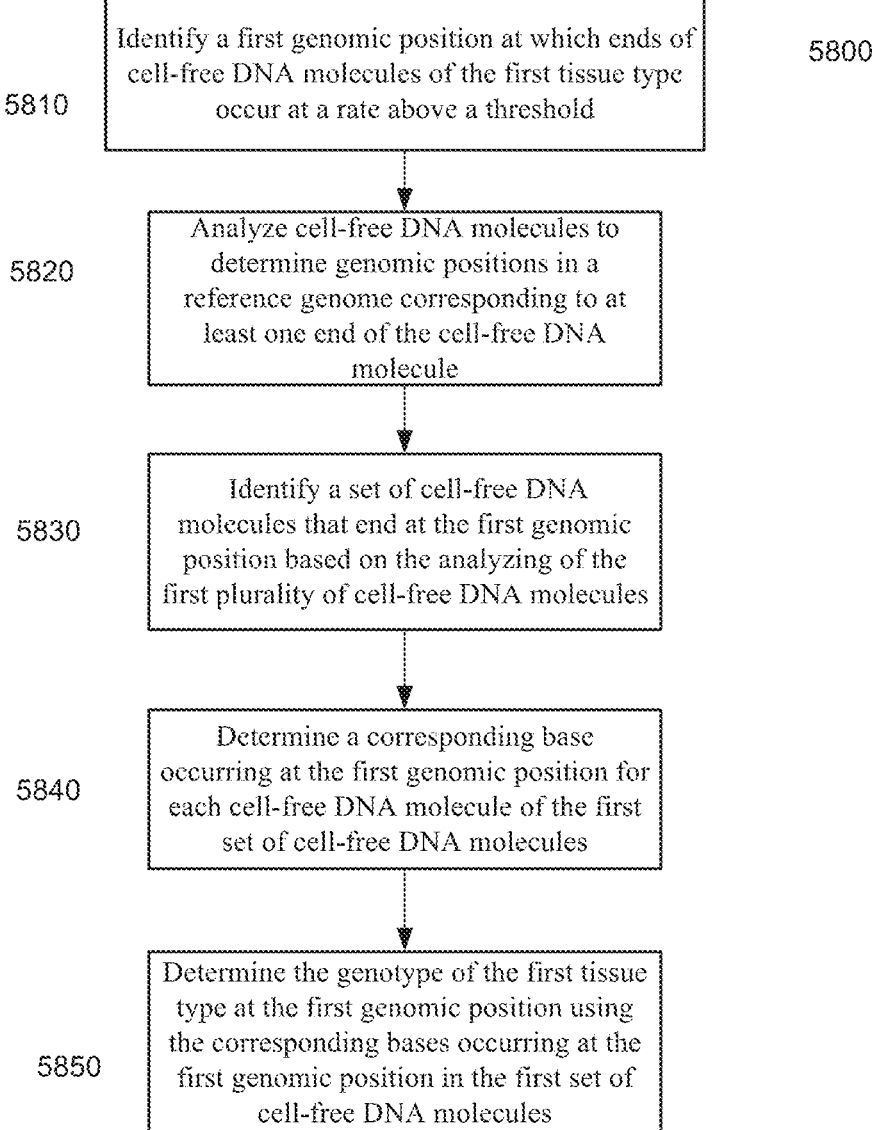

5800

5810 — Identify a first genomic position at which ends of cell-free DNA molecules of the first tissue type occur at a rate above a threshold 5820 — Analyze cell-free DNA molecules to determine genomic positions in a reference genome corresponding to at least one end of the cell-free DNA molecule 5830 — Identify a set of cell-free DNA molecules that end at the first genomic position based on the analyzing of the first plurality of cell-free DNA molecules 5840 — Determine a corresponding base occurring at the first genomic position for each cell-free DNA molecule of the first set of cell-free DNA molecules 5850 — Determine the genotype of the first tissue type at the first genomic position using the corresponding bases occurring at the first genomic position in the first set of cell-free DNA molecules

FIG. 88

Training set

Training set

FIG. 92A
Validation set

Validation set
Size cutoff: 0.143

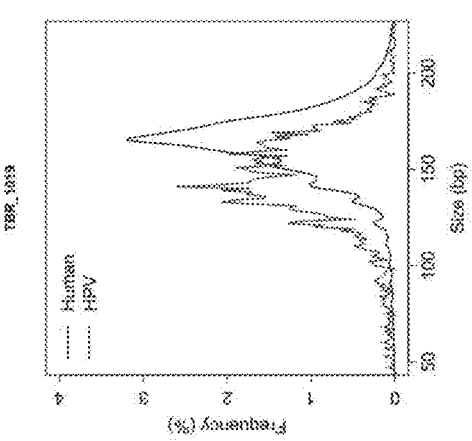
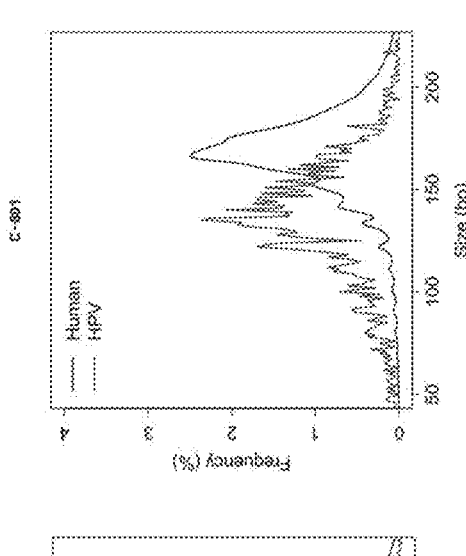
FIG. 94
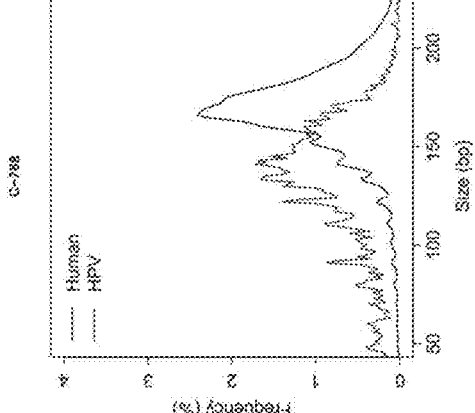

METHODS AND SYSTEMS FOR TUMOR DETECTION

CROSS-REFERENCES TO RELATED APPLICATIONS

This application is a continuation application of U.S. patent application Ser. No. 17/884,498, filed on Aug. 9, 2022, which is a continuation application of U.S. patent application Ser. No. 15/793,830, filed on Oct. 25, 2017, now U.S. Pat. No. 11,459,616, which is a continuation application of International Patent Application No. PCT/US2017/058099, filed on Oct. 24, 2017, which claims the benefit of U.S. Provisional Patent Application No. 62/507,154, filed on May 16, 2017, U.S. Provisional Patent Application No. 62/450,541, filed on Jan. 25, 2017, and U.S. Provisional Patent Application No. 62/411,929, filed on Oct. 24, 2016, each of which is entirely incorporated herein by reference. This application is related to U.S. patent application Ser. No. 15/218,497, filed on Jul. 25, 2016, which claims priority from U.S. Provisional Patent Application No. 62/294,948, filed on Feb. 12, 2016, and U.S. Provisional Patent Application No. 62/196,250, filed on Jul. 23, 2015, and from International Patent Application No. PCT/CN2016/073753, filed on Feb. 14, 2016, each of which is entirely incorporated herein by reference.

BACKGROUND OF THE INVENTION

The discovery that tumor cells deposit tumor-derived DNA into the blood stream has sparked the development of non-invasive methods capable of determining the presence, location and/or type of tumor in a subject using cell-free samples (e.g., plasma). Many tumors can be treatable if detected early in their development. However, current methods can lack the sensitivity and/or specificity to detect a tumor at an early stage and can return a large number of false positive or false negative results. The sensitivity of a test can refer to the likelihood that a subject that is positive for a condition tests positive for the condition. The specificity of a test can refer to the likelihood that a subject that is negative for a condition tests negative for that condition. The problems of sensitivity and specificity can be exaggerated in assays for the early detection of tumors, e.g., because samples on which such tumor detection methods are performed can have relatively small amounts of tumor-derived DNA and because the condition itself can have a relatively low prevalence among individuals tested in the early stage. Accordingly, there is a clinical need for methods having higher sensitivity and/or specificity for the detection of tumors.

Previous studies—have shown that plasma deoxyribonucleic acid (DNA) mostly includes short fragments of less than 200 base pairs (bp) (Lo et al. Sci Transl Med 2010; 2(61):61ra91). In the size distribution of plasma DNA, a peak could be observed at 166 bp. In addition, it was observed that the sequenced tag density would vary with a periodicity of around 180 bp close to transcriptional start sites (TSSs) when maternal plasma DNA was sequenced (Fan et al. PNAS 2008; 105:16266-71). These results are one set of evidence that the fragmentation of plasma DNA may not be a random process. However, the precise patterns of DNA fragmentation in plasma, as well as the factors governing the patterns, have not been clear. Further, practical applications of using the DNA fragmentation have not been fully realized.

BRIEF SUMMARY OF THE INVENTION

In some aspects, the present disclosure provides a method of screening for a tumor in a subject. In some embodiments, the method comprises obtaining a first biological sample from the subject, wherein the first biological sample comprises cell-free nucleic acid from the subject and potentially cell-free nucleic acid from a pathogen. In some embodiments, the method comprises performing a first assay comprising measuring a copy number of the cell-free nucleic acid from the pathogen in the first biological sample. In some embodiments, the method comprises obtaining a second biological sample from the subject, wherein the second biological sample comprises cell-free nucleic acid from the subject and potentially cell-free nucleic acid from a pathogen. In some embodiments, the method comprises performing a second assay comprising massively parallel sequencing of the cell-free nucleic acid in the second biological sample to generate sequence reads. In some embodiments, the method comprises determining an amount of the sequence reads that align to a reference genome of the pathogen. In some embodiments, the method comprises determining an amount of the cell-free nucleic acid molecules that have a size within a given range and align to a reference genome of the pathogen based on the massively parallel sequencing. In some embodiments, the method comprises screening for the tumor based on performing a first assay comprising measuring a copy number of the cell-free nucleic acid from the pathogen in the first biological sample, and performing a second assay comprising massively parallel sequencing of the cell-free nucleic acid in the second biological sample to generate sequence reads. In some embodiments, the first biological sample and the second biological sample are the same. In some embodiments, the method further comprises determining a percentage of the sequence reads that align to a reference genome of the pathogen. In some embodiments, the method further comprises comparing the percentage of the sequence reads that align to a reference genome of the pathogen to a cutoff value. In some embodiments, the method further comprises determining a size ratio of a first proportion of the cell-free nucleic acid molecules from the second biological sample that align to the reference genome of the pathogen with a size within the given range and a second proportion of the cell-free nucleic acid molecules from the second biological sample that align to a reference genome of the subject with a size within the given range. In some embodiments, the method further comprises determining a size index, wherein the size index is an inverse of the size ratio, and comparing the size index to a second cutoff value. In some embodiments, the tumor is nasopharyngeal cancer. In some embodiments, the pathogen is Epstein-Barr Virus (EBV). In some embodiments, measuring a copy number of the cell-free nucleic acid from the pathogen in the first biological sample comprises amplification. In some embodiments, the amplification comprises polymerase chain reaction (PCR). In some embodiments, the PCR comprises quantitative PCR (qPCR). In some embodiments, the first biological sample and the second biological sample are plasma.

In some aspects, the present disclosure provides a method of screening for a tumor in a subject. In some embodiments, the method comprises obtaining a first biological sample from the subject, wherein the first biological sample comprises cell-free nucleic acid from the subject and potentially cell-free nucleic acid from a pathogen. In some embodiments, the method comprises performing a first assay comprising measuring a copy number of the cell-free nucleic acid from the pathogen in the first biological sample, wherein the first assay comprises a positive predictive value for a presence of the tumor in the subject. In some embodiments, the method comprises performing a second assay on a second biological sample from the subject, wherein the second biological sample comprises cell-free nucleic acid from the subject and potentially cell-free nucleic acid from the pathogen, and wherein a positive predictive value for a presence of the tumor in the subject of the first assay and the second assay is at least 5-fold greater than the positive predictive value of the first assay. In some embodiments, the positive predictive value for a presence of the tumor in the subject of the first assay and the second assay is at least 7.5-fold greater than the positive predictive value of the first assay. In some embodiments, the positive predictive value for a presence of the tumor in the subject of the first assay and the second assay is at least 15%. In some embodiments, the positive predictive value for a presence of the tumor in the subject of the first assay and the second assay is at least 25%. In some embodiments, the first biological sample and the second biological sample are the same. In some embodiments, the first biological sample and the second biological sample are plasma. In some embodiments, the tumor is nasopharyngeal cancer. In some embodiments, the pathogen is Epstein-Barr Virus (EBV). In some embodiments, measuring a copy number of the cell-free nucleic acid from the pathogen in the first biological sample comprises amplification. In some embodiments, the amplification comprises polymerase chain reaction (PCR). In some embodiments, the PCR comprises quantitative PCR (qPCR). In some embodiments, the second assay comprises massively parallel sequencing of the cell-free nucleic acid in the second biological sample to generate sequence reads. In some embodiments, the second assay comprises of determining an amount of the sequence reads that align to a reference genome of the pathogen. In some embodiments, the second assay comprises determining an amount of the cell-free nucleic acid molecules in the second biological sample that have a size within a given range and align to a reference genome of the pathogen.

In some aspects the present disclosure provides a method of screening for a tumor in a subject. In some embodiments, the method comprises obtaining a first biological sample from the subject, wherein the first biological sample comprises cell-free nucleic acid from the subject and potentially cell-free nucleic acid from a pathogen. In some embodiments, the method comprises performing a first assay comprising measuring a copy number of the cell-free nucleic acid from the pathogen in the first biological sample, wherein the first assay has a false positive rate for a presence of the tumor in the subject. In some embodiments, the method comprises performing a second assay on a second biological sample from the subject, wherein the second biological sample comprises cell-free nucleic acid from the subject and potentially cell-free nucleic acid from the pathogen, wherein a false positive rate for a presence of the tumor in the subject of the first assay and the second assay is at least 5-fold lower than the false positive rate of the first assay. In some embodiments, the false positive rate for a presence of the tumor in the subject of the first assay and the second assay is at least 10-fold lower than the false positive rate of the first assay. In some embodiments, the false positive rate for a presence of the tumor in the subject of the first assay and the second assay is less than 1%. In some embodiments, the first biological sample and the second biological sample are the same. In some embodiments, the first biological sample and the second biological sample are plasma. In some embodiments, the tumor is nasopharyngeal cancer. In some embodiments, the pathogen is Epstein-Barr Virus (EBV). In some embodiments, measuring a copy number of the cell-free nucleic acid from the pathogen in the first biological sample comprises amplification. In some embodiments, the amplification comprises polymerase chain reaction (PCR). In some embodiments, the PCR comprises quantitative PCR (qPCR). In some embodiments, the second assay comprises massively parallel sequencing of the cell-free nucleic acid in the second biological sample to generate sequence reads. In some embodiments, the second assay comprises of determining an amount of the sequence reads that align to a reference genome of the pathogen. In some embodiments, the second assay comprises determining an amount of the cell-free nucleic acid molecules in the second biological sample that have a size within a given range and align to a reference genome of the pathogen.

In some aspects, the present disclosure provides a method of analyzing a biological sample, including a mixture of cell-free nucleic acid molecules, to determine a level of pathology in a subject from which the biological sample is obtained, the mixture including nucleic acid molecules from the subject and potentially nucleic acid molecules from a pathogen. In some embodiments, the method comprises analyzing a first plurality of cell-free nucleic acid molecules from a biological sample of the subject, wherein the analyzing comprises determining a genomic position in a reference genome corresponding to at least one end of the first plurality of cell-free nucleic acid molecules, the reference genome corresponding to the pathogen. In some embodiments, the method comprises determining a first amount of the first plurality of cell-free nucleic acid molecules that end within one of first windows, each first window comprising at least one of a first set of genomic positions at which ends of cell-free nucleic acid molecules are present at a rate above a first threshold in subjects with a pathology associated with the pathogen. In some embodiments, the method comprises computing a relative abundance of the first plurality of cell-free nucleic acid molecules ending within one of the first windows by normalizing the first amount using a second amount of the first plurality of cell-free nucleic acid molecules from the biological sample, wherein the second amount of the first plurality of cell-free nucleic acid molecules includes cell-free nucleic acid molecules ending at a second set of genomic positions outside of the first windows including the first set of genomic positions. In some embodiments, the method comprises determining the level of pathology in the subject by processing the relative abundance against one or more cutoff values. In some embodiments, the relative abundance against one or more cutoff values includes determining whether the relative abundance is greater than the one or more cutoff values. In some embodiments, the method further comprises determining the second amount of the first plurality of cell-free nucleic acid molecules that end within one of second windows, each second window comprising at least one of the second set of genomic positions at which ends of cell-free nucleic acid molecules are present at a rate above a second threshold in subjects without a pathology resulting from pathogen, wherein normalizing the first amount includes computing the relative abundance using the first amount and the second amount. In some embodiments, the method further comprises identifying the second set of genomic positions. In some embodiments, the identifying comprises analyzing, by a computer system, the cell-free nucleic acid molecules of a reference sample from a reference subject that does not have the pathology. In some embodiments, analyzing each of the plurality of cell-free nucleic acid molecules comprises determining a genomic position in the reference genome corresponding to at least one end of the cell-free nucleic acid molecule. In some embodiments, the reference subject is healthy. In some embodiments, the relative abundance comprises a ratio of the first amount and the second amount. In some embodiments, the method further comprises identifying the first set of genomic positions at which ends of cell-free nucleic acid molecules occur at the rate above a first threshold. In some embodiments, identifying the first set of genomic positions comprises analyzing, by a computer system, a second plurality of cell-free nucleic acid molecules from at least one first additional sample to identify ending positions of the second plurality of cell-free nucleic acid molecules, wherein the at least one first additional sample is known to have the pathology associated with the pathogen and is of a same sample type as the biological sample. In some embodiments, the method further comprises, for each genomic window of a plurality of genomic windows, computing a corresponding number of the second plurality of cell-free nucleic acid molecules ending on the genomic window, and comparing the corresponding number to a reference value to determine whether the rate of cell-free nucleic acid molecules ending on one or more genomic positions within the genomic window is above the first threshold. In some embodiments, a first genomic window of the plurality of genomic windows has a width of at least one genomic position, and wherein each of the genomic positions within the first genomic window are identified as having the rate of cell-free nucleic acid molecules ending on the genomic position be above the first threshold when the corresponding number exceeds the reference value. In some embodiments, the first set of genomic positions have the highest N values for the corresponding numbers, wherein N is at least 100. In some embodiments, each genomic position of the first set of genomic positions has at least a specified number of cell-free nucleic acid molecules of the second plurality of cell-free nucleic acid molecules ending on the genomic position. In some embodiments, the reference value is an expected number of cell-free nucleic acid molecules ending within the genomic window according to a probability distribution and an average length of cell-free nucleic acid molecules in the at least one first additional sample. In some embodiments, the probability distribution is a Poisson distribution, and wherein determining whether the rate of cell-free nucleic acid molecules ending on one or more genomic positions within the genomic window is above the first threshold comprises determining a corresponding p-value using the corresponding number and the expected number, wherein the first threshold corresponds to a cutoff p-value, the corresponding p value being less than the cutoff p-value indicating that the rate of cell-free nucleic acid molecules ending within the genomic window is above the first threshold. In some embodiments, the genomic positions whose rate of the second plurality of cell-free nucleic acid molecules ending on the genomic position is above the first threshold comprises a first superset, and wherein identifying the first set of genomic positions further comprises analyzing, by the computer system, a third plurality of cell-free nucleic acid molecules from at least one second additional sample identified as not having the pathology to identify a second superset of the third plurality of cell-free nucleic acid molecules ending on the genomic position is above the first threshold, and identifying the first set of genomic positions as comprising the genomic positions that are in the first superset and that are not in the second superset. In some embodiments, the reference value comprises a measured number of cell-free nucleic acid molecules ending within the genomic window, the measured number determined from a third plurality of cell-free nucleic acid molecules of at least one second additional sample identified as not having the pathology. In some embodiments, comparing the corresponding number to the reference value comprises computing a first ratio of the corresponding number and a third number of the third plurality of cell-free nucleic acid molecules covering the genomic window, and comparing the first ratio to the reference value, the reference value comprising a reference ratio of the measured number of reads ending within the genomic window and a fourth number of the third plurality of cell-free nucleic acid molecules covering the genomic window and not ending within the genomic window. In some embodiments, the third number of the third plurality of cell-free nucleic acid molecules do not end within the genomic window. In some embodiments, determining whether the rate of cell-free nucleic acid molecules ending within the genomic window is above the first threshold comprises determining whether the first ratio is greater than a multiplicative factor times the reference ratio. In some embodiments, the sample type of the biological sample and the at least one first additional sample is selected from a group consisting of plasma, serum, cerebrospinal fluid, and urine. In some embodiments, the at least one first additional sample is from the subject and are obtained at a different time than the biological sample. In some embodiments, the first windows have a width of one genomic position, and wherein the relative abundance is computed by, for each genomic position of the first set of genomic positions, computing a corresponding number of the first plurality of cell-free nucleic acid molecules ending on the genomic position as part of determining that the first amount of the first plurality of cell-free nucleic acid molecules end on any one of the first set of genomic positions, computing a third number of the first plurality of cell-free nucleic acid molecules covering the genomic position and not ending on the genomic position as part of determining the second amount of the first plurality of cell-free nucleic acid molecules, and computing a first ratio of the corresponding number and the third number, computing a mean of the first ratios as the relative abundance. In some embodiments, the relative abundance is computed by, for each genomic position of the first set of genomic positions, computing a corresponding number of the first plurality of cell-free nucleic acid molecules ending within a first window comprising the genomic position as part of determining that the first amount of the first plurality of cell-free nucleic acid molecules end within one of the first windows, computing a third number of the first plurality of cell-free nucleic acid molecules ending within a second window comprising the genomic position, the second window larger than the first window; computing a first ratio of the corresponding number and the third number, and computing a mean of the first ratios as the relative abundance. In some embodiments, the second set of genomic positions and the first set of genomic positions do not overlap. In some embodiments, the second set of genomic positions comprises all genomic positions corresponding to an end of at least one of the first plurality of cell-free nucleic acid molecules. In some embodiments, analyzing one or more of the cell-free nucleic acid molecules comprises determining both genomic positions corresponding to both ends of the cell-free nucleic acid molecule. In some embodiments, the first set of genomic positions or the second set of genomic positions comprises between 600 and 10,000 genomic positions.

In some aspects, the present disclosure provides a method of analyzing a biological sample, including a mixture of cell-free nucleic acid molecules, to determine a level of pathology in a subject from which the biological sample is obtained, the mixture including nucleic acid molecules from the subject and potentially nucleic acid molecules from a pathogen. In some embodiments, the method comprises, for each of a plurality of nucleic acid molecules in the biological sample, measuring a size of the nucleic acid molecule. In some embodiments, the method comprises, for each of a plurality of nucleic acid molecules in the biological sample, determining that the nucleic acid molecule is from a reference genome, the reference genome corresponding to the pathogen. In some embodiments, the method comprises, for each of a plurality of nucleic acid molecules in the biological sample, determining a statistical value of a size distribution of the plurality of nucleic acid molecules from the reference genome. In some embodiments, the method comprises, for each of a plurality of nucleic acid molecules in the biological sample, determining the level of pathology in the subject by processing the statistical value against one or more cutoff values. In some embodiments, the statistical value is an average, mode, median, or mean of the size distribution. In some embodiments, the statistical value is a percentage of the plurality of nucleic acid molecules in the biological sample from the reference genome that are below a size threshold. In some embodiments, the statistical value is a ratio of a first amount the plurality of nucleic acid molecules in the biological sample from the reference genome that are within a first size range; and a second amount the plurality of nucleic acid molecules in the biological sample from the reference genome that are within a second size range that is different than the first size range. In some embodiments, the pathology is selected from the group consisting of bladder cancer, bone cancer, a brain tumor, breast cancer, cervical cancer, colorectal cancer, esophageal cancer, gastrointestinal cancer, hematopoietic malignancy, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, and thyroid cancer. In some embodiments, the level of pathology is selected from a group consisting of: an amount of tumor tissue in the subject, a size of the tumor in the subject, a stage of the tumor in the subject, a tumor load in the subject, and presence of tumor metastasis in the subject. In some embodiments, the pathogen compromises a virus. In some embodiments, the virus comprises EBV DNA, HPV DNA, HBV DNA, HCV nucleic acids, or fragments thereof. In some embodiments, the method further comprises obtaining template nucleic acid molecules from the biological sample to be analyzed. In some embodiments, the method further comprises preparing a sequencing library of analyzable nucleic acid molecules using the template nucleic acid molecules, the preparing of the sequencing library of analyzable nucleic acid molecules not comprising an operation of nucleic acid amplification of the template nucleic acid molecules. In some embodiments, the method further comprises sequencing the sequencing library of analyzable nucleic acid molecules to obtain a plurality of sequence reads corresponding to the first plurality of cell-free nucleic acid molecules. In some embodiments, analyzing the first plurality of cell-free nucleic acid molecules or the plurality of cell-free nucleic acid molecules comprises receiving, at the computer system, the plurality of sequence reads; and aligning, by the computer system, the plurality of sequence reads to the reference genome to determine genomic positions for the plurality of sequence reads. In some embodiments, the method further comprises providing a therapeutic intervention based on the level of pathology or performing imaging of the subject based on the level of pathology. In some embodiments, the cell-free nucleic acid molecules are deoxyribonucleic acid (DNA) molecules.

In some aspects, the present disclosure provides a computer product comprising a computer readable medium storing a plurality of instructions for controlling a computer system to perform operations of any of the methods above.

In some aspects, the present disclosure provides a system comprising the computer product above, and one or more processors for executing instructions stored on the computer readable medium.

In some aspects, the present disclosure provides a system comprising means for performing any of the methods above.

In some aspects, the present disclosure provides a system configured to perform any of the above methods.

In some aspects, the present disclosure provides a system comprising modules that respectively perform the steps of any of the above methods.

In some aspects, the present disclosure provides a method of analyzing a biological sample, including a mixture of cell-free nucleic acid molecules, to determine a level of pathology in a subject from which the biological sample is obtained, the mixture including nucleic acid molecules from the subject and potentially nucleic acid molecules from a pathogen. In some embodiments, the method comprises performing a first assay, wherein the first assay comprises analyzing a plurality of cell-free nucleic acid molecules from a biological sample of the subject to determine a first amount of the plurality of cell-free nucleic acid molecules aligning to a reference genome, the reference genome corresponding to the pathogen. In some embodiments, the method comprises performing a second assay. In some embodiments, the second assay comprises measuring a size of each of the plurality of nucleic acid molecules in the biological sample. In some embodiments, the second assay comprises determining a second amount of the plurality of nucleic acid molecules having a size within a given range and aligning to the reference genome. In some embodiments, the method comprises comparing the first amount to a first cutoff threshold. In some embodiments, the method comprises comparing the second amount to a second cutoff threshold. In some embodiments, the method comprises determining the level of pathology in the subject based on the first amount and the second amount. In some embodiments, the method further comprises enriching the sample for the plurality of cell-free nucleic acid molecules. In some embodiments, the method further comprises normalizing the second amount using a third amount of cell-free nucleic acid molecules having a size within the given range and aligning to an autosomal genome.

In some aspects, the present disclosure provides a method of analyzing a biological sample including a mixture of cell-free nucleic acid molecules to determine a level of pathology in a subject from which the biological sample is obtained, the mixture including nucleic acid molecules from the subject and potentially nucleic acid molecules from a pathogen. In some embodiments, the method comprises performing massively parallel sequencing on the cell-free nucleic acid molecules to generate sequence reads. In some embodiments, the method comprises determining an amount of the sequence reads that align to a reference genome of the pathogen. In some embodiments, the method comprises determining an amount of the cell-free nucleic acid molecules that have a size within a given range and align to a reference genome of the pathogen. In some embodiments, the method comprises using the amount of the sequence reads that align to a reference genome of the pathogen and the amount of the cell-free nucleic acid molecules that have a size within a given range and align to a reference genome of the pathogen to the determine the level of pathology in the subject. In some embodiments, the method further comprises determining a percentage of the sequence reads that align to a reference genome of the pathogen. In some embodiments, the method comprises comparing the percentage to a first cutoff value. In some embodiments, the pathogen compromises a virus. In some embodiments, the virus comprises EBV DNA, HPV DNA, HBV DNA, HCV nucleic acids, or fragments thereof. In some embodiments, the virus comprises EBV DNA or fragments thereof. In some embodiments, the level of pathology is selected from the group consisting of bladder cancer, bone cancer, a brain tumor, breast cancer, cervical cancer, colorectal cancer, esophageal cancer, gastrointestinal cancer, hematopoietic malignancy, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, and thyroid cancer. In some embodiments, the level of pathology comprises nasopharyngeal cancer. In some embodiments, the method further comprises determining a size ratio of a first proportion of the cell-free nucleic acid molecules that align to the reference genome of the pathogen with a size within the given range; and a second proportion of the cell-free nucleic acid molecules that align to a reference genome of the subject with a size within the given range. In some embodiments, the pathogen is EBV and the given range is from 80 bp to 110 bp. In some embodiments, the method further comprises determining a size index, wherein the size index is an inverse of the size ratio, and comparing the size index to a second cutoff value.

In some aspects, the methods of the present disclosure comprise detecting a tumor in a subject. In some embodiments, the method comprises obtaining a first biological sample from the subject. In some embodiments, the first biological sample comprises tumor-derived DNA. In some embodiments, the first biological sample comprises cell-free DNA. In some embodiments, the method comprises performing a first assay. In some embodiments, the first assay has sensitivity for a first set of markers. In some embodiments, the first set of markers is indicative of a tumor. In some embodiments, the first assay comprises measuring a first amount of the tumor-derived DNA from the first biological sample. In some embodiments, the first amount of the tumor-derived DNA corresponds to a copy number of the tumor-derived DNA. In some embodiments, the first amount of the tumor-derived DNA corresponds to a fragment size distribution of the tumor-derived DNA. In some embodiments, the first amount of the tumor-derived DNA corresponds to a fragmentation pattern of the tumor-derived DNA. In some embodiments, the first amount of the tumor-derived DNA corresponds to a methylation status of the tumor-derived DNA. In some embodiments, the first amount of the tumor-derived DNA corresponds to a mutational status of the tumor-derived DNA. In some embodiments, the first assay comprises generating a comparison of the first amount of tumor-derived DNA to at least one first calibration value. In some embodiments, the first assay comprises determining if the first biological sample includes the first set of markers indicative of the tumor. In some embodiments, the first assay comprises determining if the first biological sample includes the first set of markers indicative of the tumor, and the determining is based on the comparison of the first amount of tumor-derived DNA to the at least one first calibration value. In some embodiments, the method comprises performing a second assay. In some embodiments, the method comprises performing a second assay if it is determined that the first biological sample includes the first set of markers indicative of the tumor. In some embodiments, the second assay has a specificity for a second set of markers indicative of the tumor. In some embodiments, the second assay comprises measuring a second amount of tumor-derived DNA from a second biological sample. In some embodiments, the second amount of tumor-derived DNA corresponds to a fragment size distribution of the tumor-derived DNA. In some embodiments, the second amount of tumor-derived DNA corresponds to a fragmentation pattern of the tumor-derived DNA. In some embodiments, the second amount of tumor-derived DNA corresponds to a methylation status of the tumor-derived DNA. In some embodiments, the second amount of tumor-derived DNA corresponds to a mutational status of the tumor-derived DNA. In some embodiments, the second assay comprises generating a comparison of the second amount of DNA to at least one second calibration value. In some embodiments, the second assay comprises identifying the tumor in the subject. In some embodiments, the second assay comprises identifying the tumor in the subject, and the identifying is based on the comparison of the second amount of DNA to the at least one second calibration value. In some embodiments, the method comprises outputting a report. In some embodiments, the method comprises outputting a report, and the report is indicative of tumor in the subject. In some embodiments, the second amount of tumor-derived DNA corresponds to the fragment size distribution. In some embodiments, measuring the second amount includes the tumor-derived DNA and other DNA, thereby generating amounts of DNA fragments at the plurality of sizes. In some embodiments, the method comprises generating a comparison, and generating a comparison comprises calculating a first value of a first parameter. In some embodiments, the method comprises generating a comparison, and generating a comparison comprises calculating a first value of a first parameter providing a statistical measure of a size profile of DNA fragments in the second biological sample. In some embodiments, the method comprises generating a comparison, and generating a comparison comprises comparing the first value to at least one second calibration value. In some embodiments, obtaining the first biological sample is non-invasive. In some embodiments, the first biological sample comprises DNA derived from normal cells. In some embodiments, the second biological sample comprises DNA derived from normal cells. In some embodiments, the method further comprises obtaining the second biological sample. In some embodiments, the second biological sample comprises DNA derived from normal cells and tumor-derived DNA. In some embodiments, the method comprises obtaining the second biological sample, and obtaining the second biological sample is non-invasive. In some embodiments, the second biological sample is obtained at least about 1 week after obtaining the first biological sample. In some embodiments, the second biological sample is obtained at least about 2 weeks after obtaining the first biological sample. In some embodiments, the second biological sample is obtained at least about 3 weeks after obtaining the first biological sample. In some embodiments, the second biological sample is obtained at least about 4 weeks after obtaining the first biological sample. In some embodiments, the second biological sample is obtained at least about 5 weeks after obtaining the first biological sample. In some embodiments, the second biological sample is obtained at least about 6 weeks after obtaining the first biological sample. In some embodiments, the second biological sample is obtained at least about 7 weeks after obtaining the first biological sample. In some embodiments, the second biological sample is obtained at least about 8 weeks after obtaining the first biological sample. In some embodiments, the first biological sample and the second biological sample are the same sample. In some embodiments, the first set of markers and the second set of markers are the same set of markers. In some embodiments, the sensitivity of the first assay for the first set of markers is at least about 80%. In some embodiments, the first assay has a negative predictive value of at least about 80%. In some embodiments, the specificity of the second assay for the second set of markers is at least about 70%. In some embodiments, the second assay has a positive predictive value of at least about 10%. In some embodiments, the positive predictive value of the second assay is at least about 1.5-fold, at least about 2-fold, at least about 4-fold, at least about 10-fold, at least about 20-fold, at least about 50-fold, or at least about 100-fold greater than the positive predictive value of the first assay. In some embodiments, the method has a sensitivity of at least about 80%. In some embodiments, the method has a negative predictive value of at least about 80%. In some embodiments, the method has a specificity of at least about 70%. In some embodiments, the method has a positive predictive value of at least about 10%. In some embodiments, the method has a negative predictive value of at least about 95%. In some embodiments, the method of the present disclosure comprises determining if the first biological sample includes the first set of markers. In some embodiments, the first set of markers is indicative of the tumor. In some embodiments the method comprises determining if first biological sample includes the first set of markers, and the determining is performed within at most about 24 hours after performing the first assay. In some embodiments, the second assay is performed at least about 1 week after performing the first assay. In some embodiments, the tumor is benign. In some embodiments, the tumor is pre-cancerous. In some embodiments, the tumor is cancerous. In some embodiments, the tumor is nasal cancer. In some embodiments, the tumor is nasopharyngeal cancer. In some embodiments, the tumor is oral cancer. In some embodiments, the tumor-derived DNA comprises viral DNA or a fragment thereof. In some embodiments, the tumor is oropharyngeal cancer. In some embodiments, the tumor-derived DNA comprises tumor-derived Epstein-Barr Virus (EBV) DNA fragments. In some embodiments, the tumor-derived EBV DNA fragments comprise at least one BamHI-W sequence. In some embodiments, the tumor-derived EBV DNA fragments have a length of less than about 180 nucleotides. In some embodiments, at least one of the first biological sample and the second biological sample comprise virus-derived EBV DNA fragments having a length of at least about 180 nucleotides. In some embodiments, the methods of the present disclosure comprise detecting the virus-derived DNA. In some embodiments, the methods of the present disclosure comprise detecting the virus-derived DNA, and detection of the virus-derived DNA is a negative control for tumor-derived DNA. In some embodiments, the tumor is liver cancer. In some embodiments, the tumor is bladder cancer. In some embodiments, the tumor is bone cancer. In some embodiments, the tumor is a brain tumor. In some embodiments, the tumor is breast cancer. In some embodiments, the tumor is esophageal cancer. In some embodiments, the tumor is gastrointestinal cancer. In some embodiments, the tumor is a hematopoietic malignancy. In some embodiments, the tumor is leukemia. In some embodiments, the tumor is lung cancer. In some embodiments, the tumor is lymphoma. In some embodiments, the tumor is myeloma. In some embodiments, the tumor is ovarian cancer. In some embodiments, the tumor is prostate cancer. In some embodiments, the tumor is sarcoma. In some embodiments, the tumor is stomach cancer. In some embodiments, the tumor is thyroid cancer. In some embodiments, the first biological sample is whole blood, blood plasma, blood serum, urine, cerebrospinal fluid, buffy coat, or a combination thereof. In some embodiments, the second biological sample is whole blood, blood plasma, blood serum, urine, cerebrospinal fluid, buffy coat, or a combination thereof. In some embodiments, at least one of the first biological sample and the second biological sample is selected from the group consisting of whole blood, blood plasma, blood serum, urine, cerebrospinal fluid, buffy coat, and a combination thereof. In some embodiments, the tumor-derived DNA are substantially cell-free. In some embodiments, measuring the first amount of the tumor derived DNA comprises using real time polymerase chain reaction (PCR) to detect the copy number of tumor-derived DNA in the biological sample. In some embodiments, the tumor-derived DNA comprises Epstein-Barr Virus (EBV) DNA fragments. In some embodiments, the EBV DNA fragments comprise at least one BamHI-W sequence. In some embodiments, detecting the copy number of tumor-derived DNA comprises detecting the copy number of the at least one BamHI-W sequence. In some embodiments, the tumor is nasopharyngeal cancer, and the first calibration value is between zero and at most about 1,000,000 copies of BamHI-W sequence per milliliter of the biological sample. In some embodiments, the first calibration value is between zero and at most about 4,000 copies of BamHI-W sequence per milliliter of the biological sample. In some embodiments, the first calibration value is between about 20,000 and about 50,000 copies of BamHI-W sequence per milliliter of the biological sample. In some embodiments, the first calibration value corresponds to a copy number of DNA fragments derived from a control subject. In some embodiments, the first calibration value is obtained from a database. In some embodiments, measuring the first amount of the tumor derived DNA comprises using sequencing to detect one of the fragment size distribution or the fragmentation pattern of tumor-derived DNA in the biological sample. In some embodiments, the method of present disclosure comprises sequencing, and the sequencing is massively parallel sequencing. In some embodiments, measuring the first amount of the tumor derived DNA comprises using methylation-aware sequencing to detect the methylation status of tumor-derived DNA in the biological sample. In some embodiments, the tumor is nasopharyngeal cancer, and identifying the tumor in the subject further comprises performing an endoscopic examination of the nasopharynx in the subject. In some embodiments, identifying the tumor in the subject further comprises performing a magnetic resonance imaging examination on the subject. In some embodiments, the DNA fragments correspond to one or more predetermined regions of a genome. In some embodiments, the first parameter represents an abundance of short DNA fragments relative to an abundance of large DNA fragments. In some embodiments, the short DNA fragments have a smaller size than the large DNA fragments. In some embodiments, the second calibration value comprises a plurality of second calibration values. In some embodiments, each of the plurality of second calibration values corresponds to a fractional concentration of the tumor-derived DNA in a calibration sample. In some embodiments, each of the plurality of second calibration values is determined from a histogram corresponding to a different calibration sample of a plurality of calibration samples. In some embodiments, the histogram provides amounts of DNA fragments at a plurality of sizes. In some embodiments, at least a portion of each of the different calibration samples has different fractional concentrations of tumor-derived DNA. In some embodiments, the methods of the present disclosure comprise calculating the second calibration value. In some embodiments, calculating the second calibration value comprises, for each of the plurality of calibration samples, measuring the fractional concentration of tumor-derived DNA in the calibration sample. In some embodiments, calculating the second calibration value comprises, for each of the plurality of calibration samples, measuring amounts of DNA fragments at the plurality of sizes. In some embodiments, calculating the second calibration value comprises, for each of the plurality of calibration samples, calculating the second calibration value of the first parameter based on the amounts of DNA fragments at the plurality of sizes. In some embodiments, the methods of the present disclosure comprise determining a function that approximates the second calibration value of the plurality of second calibration values. In some embodiments, each of the plurality of second calibration values corresponds to a different fractional concentration of tumor-derived DNA. In some embodiments, the function is a linear function. In some embodiments, measuring the second amount of DNA fragments from the biological sample, corresponding to each of a plurality of sizes, comprises, for each of the DNA fragments, measuring a size of the DNA fragment. In some embodiments, measuring the size of the DNA fragment comprises performing sequencing of the DNA fragment to obtain sequence reads. In some embodiments, measuring the size of the DNA fragment comprises aligning the sequence reads to locations in a reference genome. In some embodiments, measuring the size of the DNA fragment comprises using the aligned locations to determine the size of the DNA fragment. In some embodiments, the methods of the present disclosure comprise sequencing, and the sequencing is paired-end sequencing. In some embodiments, a size of the plurality of sizes corresponds to a length. In some embodiments, a size of the plurality of sizes corresponds to a molecular mass. In some embodiments, a size of the plurality of sizes corresponds to a parameter that is proportional to the length. In some embodiments, a size of the plurality of sizes corresponds to a parameter that is proportional to a mass.

In some embodiments, methods and systems provided herein are not used for diagnostic purposes. In some aspects, the methods of the present disclosure comprise a non-diagnostic method for detecting a disease (e.g., a tumor) in a subject. In some embodiments, the non-diagnostic method comprises obtaining a first biological sample from the subject. In some embodiments, the first biological sample comprises tumor-derived DNA. In some embodiments, the first biological sample comprises cell-free DNA. In some embodiments, the non-diagnostic method comprises performing a first assay. In some embodiments, the first assay has a sensitivity for a first set of markers. In some embodiments, the first set of markers are indicative of a tumor. In some embodiments, the first assay comprises measuring a first amount of the tumor-derived DNA from the first biological sample. In some embodiments, the first amount of the tumor-derived DNA corresponds to a copy number of the tumor-derived DNA. In some embodiments, the first amount of the tumor-derived DNA corresponds to a fragment size distribution of the tumor-derived DNA. In some embodiments, the first amount of the tumor-derived DNA corresponds to a fragmentation pattern of the tumor-derived DNA. In some embodiments, the first amount of the tumor-derived DNA corresponds to a methylation status of the tumor-derived DNA. In some embodiments, the first amount of the tumor-derived DNA corresponds to a mutational status of the tumor-derived DNA. In some embodiments, the first assay comprises generating a comparison of the first amount of tumor-derived DNA to at least one first calibration value. In some embodiments, the first assay comprises determining if the first biological sample includes the first set of markers indicative of the tumor. In some embodiments, the first assay comprises determining if the first biological sample includes the first set of markers indicative of the tumor, and the determining is based on the comparison of the first amount of tumor-derived DNA to the at least one first calibration value. In some embodiments, the non-diagnostic method comprises performing a second assay. In some embodiments, the non-diagnostic method comprises performing a second assay if it is determined that the first biological sample includes the first set of markers indicative of the tumor. In some embodiments, the second assay has a specificity for a second set of markers indicative of the tumor. In some embodiments, the second assay comprises measuring a second amount of tumor-derived DNA from a second biological sample. In some embodiments, the second amount of tumor-derived DNA corresponds to a fragment size distribution of the tumor-derived DNA. In some embodiments, the second amount of tumor-derived DNA corresponds to a fragmentation pattern of the tumor-derived DNA. In some embodiments, the second amount of tumor-derived DNA corresponds to a methylation status of the tumor-derived DNA. In some embodiments, the second amount of tumor-derived DNA corresponds to a mutational status of the tumor-derived DNA. In some embodiments, the second assay comprises generating a comparison of the second amount of DNA to at least one second calibration value. In some embodiments, the second assay comprises identifying the tumor in the subject. In some embodiments, the second assay comprises identifying the tumor in the subject, and the identifying is based on the comparison of the second amount of DNA to the at least one second calibration value. In some embodiments, the non-diagnostic method comprises outputting a report. In some embodiments, the non-diagnostic method comprises outputting a report, and the report is indicative of tumor in the subject. In some embodiments, the second amount of tumor-derived DNA corresponds to the fragment size distribution. In some embodiments, measuring the second amount includes the tumor-derived DNA and other DNA, thereby generating amounts of DNA fragments at the plurality of sizes. In some embodiments, the non-diagnostic method comprises generating a comparison, and generating a comparison comprises calculating a first value of a first parameter. In some embodiments, the non-diagnostic method comprises generating a comparison, and generating a comparison comprises calculating a first value of a first parameter providing a statistical measure of a size profile of DNA fragments in the second biological sample. In some embodiments, the non-diagnostic method comprises generating a comparison, and generating a comparison comprises comparing the first value to at least one second calibration value. In some embodiments, obtaining the first biological sample is non-invasive. In some embodiments, the first biological sample comprises DNA derived from normal cells. In some embodiments, the second biological sample comprises DNA derived from normal cells. In some embodiments, the non-diagnostic method further comprises obtaining the second biological sample. In some embodiments, the second biological sample comprises DNA derived from normal cells and tumor-derived DNA. In some embodiments, the non-diagnostic method comprises obtaining the second biological sample, and obtaining the second biological sample is non-invasive. In some embodiments, the second biological sample is obtained at least about 1 week after obtaining the first biological sample. In some embodiments, the second biological sample is obtained at least about 2 weeks after obtaining the first biological sample. In some embodiments, the second biological sample is obtained at least about 3 weeks after obtaining the first biological sample. In some embodiments, the second biological sample is obtained at least about 4 weeks after obtaining the first biological sample. In some embodiments, the second biological sample is obtained at least about 5 weeks after obtaining the first biological sample. In some embodiments, the second biological sample is obtained at least about 6 weeks after obtaining the first biological sample. In some embodiments, the second biological sample is obtained at least about 7 weeks after obtaining the first biological sample. In some embodiments, the second biological sample is obtained at least about 8 weeks after obtaining the first biological sample. In some embodiments, the first biological sample and the second biological sample are the same sample. In some embodiments, the first set of markers and the second set of markers are the same set of markers. In some embodiments, the sensitivity of the first assay for the first set of markers is at least about 80%. In some embodiments, the first assay has a negative predictive value of at least about 80%, In some embodiments, the specificity of the second assay for the second set of markers is at least about 70%. In some embodiments, the second assay has a positive predictive value of at least about 10%. In some embodiments, the positive predictive value of the second assay is at least about 1.5-fold, at least about 2-fold, at least about 4-fold, at least about 10-fold, at least about 20-fold, at least about 50-fold, or at least about 100-fold greater than the positive predictive value of the first assay. In some embodiments, the non-diagnostic method has a sensitivity of at least about 80%. In some embodiments, the non-diagnostic method has a negative predictive value of at least about 80%. In some embodiments, the non-diagnostic method has a specificity of at least about 70%. In some embodiments, the non-diagnostic method has a positive predictive value of at least about 10%. In some embodiments, the non-diagnostic method has a negative predictive value of at least about 95%. In some embodiments, the non-diagnostic method of the present disclosure comprises determining if the first biological sample includes the first set of markers. In some embodiments, the first set of markers are indicative of the tumor. In some embodiments the non-diagnostic method comprises determining if first biological sample includes the first set of markers, and the determining is performed within at most about 24 hours after performing the first assay. In some embodiments, the second assay is performed at least about 1 week after performing the first assay. In some embodiments, the tumor is benign. In some embodiments, the tumor is pre-cancerous. In some embodiments, the tumor is cancerous. In some embodiments, the tumor is nasal cancer. In some embodiments, the tumor is nasopharyngeal cancer. In some embodiments, the tumor is oral cancer. In some embodiments, the tumor-derived DNA comprises viral DNA or a fragment thereof. In some embodiments, the tumor is oropharyngeal cancer. In some embodiments, the tumor-derived DNA comprises tumor-derived Epstein-Barr Virus (EBV) DNA fragments. In some embodiments, the tumor-derived EBV DNA fragments comprise at least one BamHI-W sequence. In some embodiments, the tumor-derived EBV DNA fragments have a length of less than about 180 nucleotides. In some embodiments, at least one of the first biological sample and the second biological sample comprise virus-derived EBV DNA fragments having a length of at least about 180 nucleotides. In some embodiments, the non-diagnostic methods of the present disclosure comprise detecting the virus-derived DNA. In some embodiments, the non-diagnostic methods of the present disclosure comprise detecting the virus-derived DNA, and detection of the virus-derived DNA is a negative control for tumor-derived DNA. In some embodiments, the tumor is liver cancer. In some embodiments, the tumor is bladder cancer. In some embodiments, the tumor is bone cancer. In some embodiments, the tumor is a brain tumor. In some embodiments, the tumor is breast cancer. In some embodiments, the tumor is esophageal cancer. In some embodiments, the tumor is gastrointestinal cancer. In some embodiments, the tumor is a hematopoietic malignancy. In some embodiments, the tumor is leukemia. In some embodiments, the tumor is lung cancer. In some embodiments, the tumor is lymphoma. In some embodiments, the tumor is myeloma. In some embodiments, the tumor is ovarian cancer. In some embodiments, the tumor is prostate cancer. In some embodiments, the tumor is sarcoma. In some embodiments, the tumor is stomach cancer. In some embodiments, the tumor is thyroid cancer. In some embodiments, the first biological sample is whole blood, blood plasma, blood serum, urine, cerebrospinal fluid, buffy coat, or a combination thereof. In some embodiments, the second biological sample is whole blood, blood plasma, blood serum, urine, cerebrospinal fluid, buffy coat, or a combination thereof. In some embodiments, at least one of the first biological sample and the second biological sample is selected from the group consisting of whole blood, blood plasma, blood serum, urine, cerebrospinal fluid, buffy coat, and a combination thereof. In some embodiments, the tumor-derived DNA are substantially cell-free. In some embodiments, measuring the first amount of the tumor derived DNA comprises using real time polymerase chain reaction (PCR) to detect the copy number of tumor-derived DNA in the biological sample. In some embodiments, the tumor-derived DNA comprises Epstein-Barr Virus (EBV) DNA fragments. In some embodiments, the EBV DNA fragments comprise at least one BamHI-W sequence. In some embodiments, detecting the copy number of tumor-derived DNA comprises detecting the copy number of the at least one BamHI-W sequence. In some embodiments, the tumor is nasopharyngeal cancer, and the first calibration value is between zero and at most about 1,000,000 copies of BamHI-W sequence per milliliter of the biological sample. In some embodiments, the first calibration value is between zero and at most about 4,000 copies of BamHI-W sequence per milliliter of the biological sample. In some embodiments, the first calibration value is between about 20,000 and about 50,000 copies of BamHI-W sequence per milliliter of the biological sample. In some embodiments, the first calibration value corresponds to a copy number of DNA fragments derived from a control subject. In some embodiments, the first calibration value is obtained from a database. In some embodiments, measuring the first amount of the tumor derived DNA comprises using sequencing to detect one of the fragment size distribution or the fragmentation pattern of tumor-derived DNA in the biological sample. In some embodiments, the non-diagnostic method of present disclosure comprises sequencing, and the sequencing is massively parallel sequencing. In some embodiments, measuring the first amount of the tumor derived DNA comprises using methylation-aware sequencing to detect the methylation status of tumor-derived DNA in the biological sample. In some embodiments, the tumor is nasopharyngeal cancer, and identifying the tumor in the subject further comprises performing an endoscopic examination of the nasopharynx in the subject. In some embodiments, identifying the tumor in the subject further comprises performing a magnetic resonance imaging examination on the subject. In some embodiments, the DNA fragments correspond to one or more predetermined regions of a genome. In some embodiments, the first parameter represents an abundance of short DNA fragments relative to an abundance of large DNA fragments. In some embodiments, the short DNA fragments have a smaller size than the large DNA fragments. In some embodiments, the second calibration value comprises a plurality of second calibration values. In some embodiments, each of the plurality of second calibration values corresponds to a fractional concentration of the tumor-derived DNA in a calibration sample. In some embodiments, each of the plurality of second calibration values is determined from a histogram corresponding to a different calibration sample of a plurality of calibration samples. In some embodiments, the histogram provides amounts of DNA fragments at a plurality of sizes. In some embodiments, at least a portion of each of the different calibration samples has different fractional concentrations of tumor-derived DNA. In some embodiments, the non-diagnostic methods of the present disclosure comprise calculating the second calibration value. In some embodiments, calculating the second calibration value comprises, for each of the plurality of calibration samples, measuring the fractional concentration of tumor-derived DNA in the calibration sample. In some embodiments, calculating the second calibration value comprises, for each of the plurality of calibration samples, measuring amounts of DNA fragments at the plurality of sizes. In some embodiments, calculating the second calibration value comprises, for each of the plurality of calibration samples, calculating the second calibration value of the first parameter based on the amounts of DNA fragments at the plurality of sizes. In some embodiments, the non-diagnostic methods of the present disclosure comprise determining a function that approximates the second calibration value of the plurality of second calibration values. In some embodiments, each of the plurality of second calibration values corresponds to a different fractional concentration of tumor-derived DNA. In some embodiments, the function is a linear function. In some embodiments, measuring the second amount of DNA fragments from the biological sample, corresponding to each of a plurality of sizes, comprises, for each of the DNA fragments, measuring a size of the DNA fragment. In some embodiments, measuring the size of the DNA fragment comprises performing sequencing of the DNA fragment to obtain sequence reads. In some embodiments, measuring the size of the DNA fragment comprises aligning the sequence reads to locations in a reference genome. In some embodiments, measuring the size of the DNA fragment comprises using the aligned locations to determine the size of the DNA fragment. In some embodiments, the non-diagnostic methods of the present disclosure comprise sequencing, and the sequencing is paired-end sequencing. In some embodiments, a size of the plurality of sizes corresponds to a length. In some embodiments, a size of the plurality of sizes corresponds to a molecular mass. In some embodiments, a size of the plurality of sizes corresponds to a parameter that is proportional to the length. In some embodiments, a size of the plurality of sizes corresponds to a parameter that is proportional to a mass.

Various embodiments are directed to applications (e.g., diagnostic applications) of the analysis of the fragmentation patterns and size of cell-free DNA, e.g., plasma DNA and serum DNA, including nucleic acids from pathogens, including viruses. Embodiments of one application can determine if a subject has a particular condition. For example, a method of present disclosure can determine if a subject has cancer or a tumor, or other pathology. Embodiments of another application can be used to assess the stage of a condition, or the progression of a condition over time. For example, a method of the present disclosure may be used to determine a stage of cancer in a subject, or the progression of cancer in a subject over time (e.g., using samples obtained from a subject at different times).

Embodiments of yet another application can determine a classification of a proportional contribution of a particular tissue type in a mixture of cell-free DNA from different tissue types. For example, specific percentages, range of percentages, or whether the proportional contribution is above a specified percentage can be determined as a classification. In one example, preferred ending positions for the particular tissue type can be identified, and a relative abundance of cell-free DNA molecules ending on the preferred ending positions can be used to provide the classification of the proportional contribution (e.g., a relative contribution from one tissue to another). In another example, an amplitude in a fragmentation pattern (e.g., number of cell-free DNA molecules ending at a genomic position) in a region specific to the particular tissue type can be used.

Other embodiments are directed to systems, portable consumer devices, and computer readable media associated with methods described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The novel features are set forth with particularity in the appended claims. A better understanding of the features and advantages will be obtained by reference to the following detailed description that sets forth illustrative embodiments, in which the principles are utilized, and the accompanying drawings (also "Figure" and "FIG." herein), of which:

FIG. 1 depicts a schematic showing Epstein-Barr virus (EBV) DNA fragments from a nasopharyngeal cancer (NPC) cell being deposited into the bloodstream of a subject.

FIG. 6A depicts a table with values for the sensitivity and specificity of a single assay in detecting NPC in a subject at various concentrations of plasma EBV DNA concentration.

FIG. 8A depicts a table with values for the sensitivity and specificity in detecting NPC in a subject at various concentrations of plasma EBV DNA concentration.

FIG. 11 depicts an exemplary timeline for performing a first assay to detect plasma EBV DNA concentration (e.g., at enrollment) and one or more follow-up tests (e.g., a second assay) at 4 weeks after enrollment. A second assay can be performed as early as 1 week after performing the first assay.

FIG. 17 depicts an illustration of preferred-end termination ratios (PETR).

FIG. 26 shows an illustration of asynchronous variation of $P_I$ for maternally and fetal-derived DNA in maternal plasma.

FIG. 29 shows an illustration of the amplitude of variation of $P_I$.

FIG. 35 is a flowchart of a method 1300 of analyzing a biological sample to determine a classification of a proportional contribution of the first tissue type according to embodiments of the present invention.

FIGS. 45A-45E show data regarding plasma DNA size distributions for fragments ending on the fetal-preferred ending positions and fragments ending on the maternal-preferred ending positions.

FIG. 63 shows the size distribution of sequenced plasma DNA fragments mapped to the EBV genome and human genome in 3 subjects having lymphoma (TBR1332, TBR1333, and TBR1551).

FIG. 86 shows the number of plasma HPV DNA fragments ending at different positions of the HPV genome.

FIG. 88 shows a flowchart of a method 5800 of analyzing a biological sample to determine a genotype of the first tissue type according to embodiments of the present invention.

FIG. 92A shows a proportion of reads mapped to EBV genome in plasma (%) for a validation set of 56 transiently positive samples, 44 persistently positive samples, and 29 samples from confirmed NPC subjects.

FIG. 94 shows the size distribution of sequenced plasma DNA fragments mapped to the HPV genome and human genome in three HPV subjects.

DETAILED DESCRIPTION OF THE INVENTION

Definitions

Figure 2:
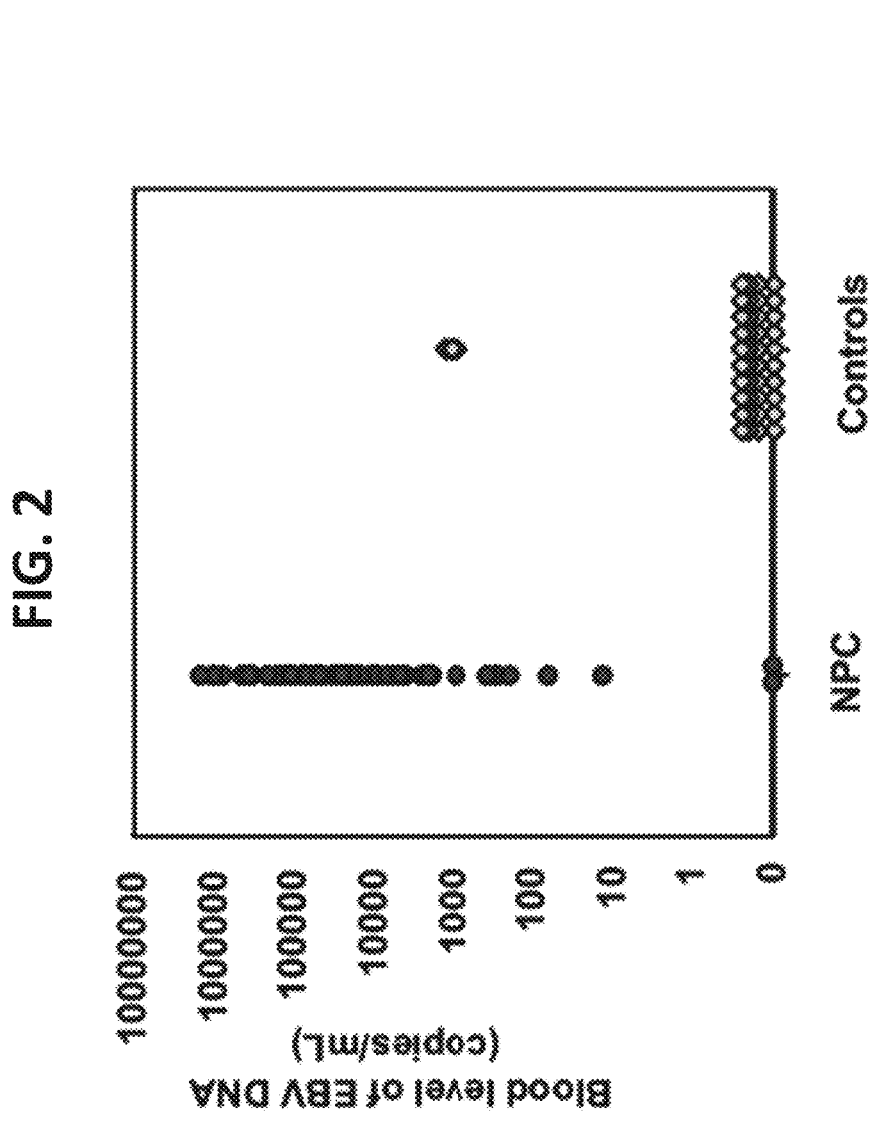
FIG. 2 depicts the concentration of plasma EBV DNA (copies/mL of plasma) in subjects with NPC and control subjects.

The term "true positive" (TP), as used in the present disclosure, can refer to a subject having a condition. "True positive" can refer to a subject that has a tumor, a cancer, a pre-cancerous condition (e.g., a precancerous lesion), a localized or a metastasized cancer, or a non-malignant disease. "True positive" can refer to a subject having a condition, and is identified as having the condition by an assay or method of the present disclosure.

The term "true negative" (TN), as used in the present disclosure, can refer to a subject that does not have a condition or does not have a detectable condition. True negative can refer to a subject that does not have a disease or a detectable disease, such as a tumor, a cancer, a pre-cancerous condition (e.g., a precancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

The term "false positive" (FP), as used in the present disclosure, can refer to a subject that does not have a condition. False positive can refer to a subject that does not have a tumor, a cancer, a pre-cancerous condition (e.g., a precancerous lesion), a localized or a metastasized cancer, a non-malignant disease, or is otherwise healthy. The term false positive can refer to a subject that does not have a condition, but is identified as having the condition by an assay or method of the present disclosure.

The term "false negative" (FN), as used in the present disclosure, can refer to a subject that has a condition. False negative can refer to a subject that has a tumor, a cancer, a pre-cancerous condition (e.g., a precancerous lesion), a localized or a metastasized cancer, or a non-malignant disease. The term false negative can refer to a subject that has a condition, but is identified as not having the condition by an assay or method of the present disclosure.

The terms "sensitivity" or "true positive rate" (TPR), as used in the present disclosure, can refer to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

The terms "specificity" or "true negative rate" (TNR), as used in the present disclosure, can refer to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity can characterize the ability of a method to correctly identify one or more markers indicative of cancer.

The term "ROC" or "ROC curve," as used in the present disclosure, can refer to a receiver operator characteristic curve. A ROC curve can be a graphical representation of the performance of a binary classifier system. For any given method, a ROC curve can be generated by plotting the sensitivity against the specificity at various threshold settings. The sensitivity and specificity of a method for detecting the presence of a tumor in a subject can be determined at various concentrations of tumor-derived DNA in the plasma sample of the subject. Furthermore, provided at least one of three parameters (e.g., sensitivity, specificity, and the threshold setting), a ROC curve can determine the value or expected value for any unknown parameter. The unknown parameter can be determined using a curve fitted to a ROC curve. For example, provided the concentration of tumor-derived DNA in a sample, the expected sensitivity and/or specificity of a test can be determined. The term "AUC" or "ROC-AUC" can refer to the area under a receiver operator characteristic curve. This metric can provide a measure of diagnostic utility of a method, taking into account both the sensitivity and specificity of the method.

A ROC-AUC can range from 0.5 to 1.0, where a value closer to 0.5 can indicate a method has limited diagnostic utility (e.g., lower sensitivity and/or specificity) and a value closer to 1.0 indicates the method has greater diagnostic utility (e.g., higher sensitivity and/or specificity). See, e.g., Pepe et al, "Limitations of the Odds Ratio in Gauging the Performance of a Diagnostic, Prognostic, or Screening Marker," Am. J. Epidemiol 2004, 159 (9): 882-890, which is entirely incorporated herein by reference. Additional approaches for characterizing diagnostic utility include using likelihood functions, odds ratios, information theory, predictive values, calibration (including goodness-of-fit), and reclassification measurements. Examples of the approaches are summarized, e.g., in Cook, "Use and Misuse of the Receiver Operating Characteristic Curve in Risk Prediction," *Circulation* 2007, 115: 928-935, which is entirely incorporated herein by reference.

"Negative predictive value" or "NPV" can be calculated by TN/(TN+FN) or the true negative fraction of all negative test results. Negative predictive value can be inherently impacted by the prevalence of a condition in a population and pre-test probability of the population intended to be tested. "Positive predictive value" or "PPV" can be calculated by TP/(TP+FP) or the true positive fraction of all positive test results. PPV can be inherently impacted by the prevalence of a condition in a population and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which is entirely incorporated herein by reference.

A "local maximum" can refer to a genomic position (e.g., a nucleotide) at which the largest value of the parameter of interest is obtained when compared with the neighboring positions or refer to the value of the parameter of interest at such a genomic position. As examples, the neighboring positions can range from 50 bp to 2000 bp. Examples for the parameter of interest include, but are not limited to, the number of fragments ending on a genomic position, the number of fragments overlapping with the position, or the proportion of fragments covering the genomic position that are larger than a threshold size. Many local maxima can occur when the parameter of interest has a periodic structure. A global maximum is a specific one of the local maxima. Similarly, a "local minimum" can refer to a genomic position at which the smallest value of the parameter of interest is obtained when compared with the neighboring positions or refer to the value of the parameter of interest at such a genomic position.

The term "mutation," as used herein, can refer to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation.

A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

The terms "control," "control sample," "reference," "reference sample," "normal," and "normal sample" can be used to describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

The phrase "healthy," as used herein, can refer to a subject possessing good health. A healthy subject can demonstrate an absence of any malignant or non-malignant disease. A "healthy individual" can have other diseases or conditions, unrelated to the condition being assayed, which can normally not be considered "healthy."

The term "sample," "biological sample" or "patient sample" can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

The term "fragment" (e.g., a DNA fragment), as used herein, can refer to a portion of a polynucleotide or polypeptide sequence that comprises at least 3 consecutive nucleotides. A nucleic acid fragment can retain the biological activity and/or some characteristics of the parent polynucleotide. In an example, nasopharyngeal cancer cells can deposit fragments of Epstein-Barr Virus (EBV) DNA into the blood stream of a subject, e.g., a patient. These fragments can comprise one or more BamHI-W sequence fragments, which can be used to detect the level of tumor-derived DNA in the plasma. The BamHI-W sequence fragment corresponds to a sequence that can be recognized and/or digested using the Bam-HI restriction enzyme. The BamHI-W sequence can refer to the sequence 5'-GGATCC-3'.

The terms "cancer" or "tumor" can refer to an abnormal mass of tissue wherein the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

The term "level of cancer" can refer to whether cancer exists (i.e., presence or absence), a stage of a cancer, a size of tumor, presence or absence of metastasis, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can comprise 'screening' or can comprise checking if someone, with suggestive features of cancer (e.g., symptoms or other positive tests), has cancer. A "level of pathology" can refer to level of pathology associated with a pathogen, where the level can be as described above for cancer. When the cancer is associated with a pathogen, a level of cancer can be a type of a level of pathology.

The term "assay" can refer to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

"Cancer-associated changes" or "cancer-specific changes" can include cancer-derived mutations (including single nucleotide mutations, deletions or insertions of nucleotides, deletions of genetic or chromosomal segments, translocations, inversions), amplification of genes, virus-associated sequences (e.g., viral episomes, viral insertions, viral DNA that is infected into a cell and subsequently released by the cell, and circulating or cell-free viral DNA), aberrant methylation profiles or tumor-specific methylation signatures, aberrant cell-free nucleic acid (e.g., DNA) size profiles, aberrant histone modification marks and other epigenetic modifications, and locations of the ends of cell-free DNA fragments that are cancer-associated or cancer-specific.

The term "random sequencing," as used herein can refer to sequencing whereby nucleic acid fragments sequenced have not been specifically identified or predetermined before the sequencing procedure. Sequence-specific primers to target specific gene loci are not required. In some embodiments, adapters are added to the end of a nucleic acid fragment, and primers for sequencing are attached (e.g., hybridized) to the adapters. Thus, any fragment can be sequenced with the same primer, e.g., that attaches to a same universal adapter, and thus the sequencing can be random. Massively parallel sequencing can include using random sequencing.

A "sequence read" (or "sequencing read") can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

The term "sequencing depth" can refer to the number of times a locus is covered by a sequence read aligned to the locus. The locus can be as small as a nucleotide, or as large as a chromosome arm, or as large as an entire genome. Sequencing depth can be expressed as "Yx", e.g., 50×, 100×, etc., where "Y" refers to the number of times a locus is covered with a sequence read. Sequencing depth can also be applied to multiple loci, or the whole genome, in which case Y can refer to the mean number of times a loci or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

The term "sequencing breadth" can refer to what fraction of a particular reference genome (e.g., human reference genome) or part of the genome has been analyzed. The denominator of the fraction can be a repeat-masked genome, and thus 100% can correspond to all of the reference genome minus the masked parts. A repeat-masked genome can refer to a genome in which sequence repeats are masked (e.g., sequence reads align to unmasked portions of the genome). Any parts of a genome can be masked, and thus one can focus on any particular part of a reference genome. Broad sequencing can refer to sequencing and analyzing at least 0.1% of the genome.

A "methylome" can be a measure of an amount of DNA methylation at a plurality of sites or loci in a genome. The methylome can correspond to all of a genome, a substantial part of a genome, or relatively small portion(s) of a genome. A "tumor methylome" can be a methylome of a tumor of a subject (e.g., a human). A tumor methylome can be determined using tumor tissue or cell-free tumor DNA in plasma. A tumor methylome can be one example of a methylome of interest. A methylome of interest can be a methylome of an organ that can contribute nucleic acid, e.g., DNA into a bodily fluid (e.g., a methylome of brain cells, a bone, lungs, heart, muscles, kidneys, etc.). The organ can be a transplanted organ.

A "plasma methylome" can be the methylome determined from plasma or serum of an animal (e.g., a human). A plasma methylome can be an example of a cell-free methylome since plasma and serum can include cell-free DNA. A plasma methylome can be an example of a mixed methylome since it can be a mixture of tumor/patient methylome. A "cellular methylome" can be a methylome determined from cells (e.g., blood cells or tumor cells) of a subject, e.g., a patient. A methylome of blood cells can be called a blood cell methylome (or blood methylome).

The "methylation index" for each genomic site (e.g., a CpG site) can refer to the proportion of sequence reads showing methylation at the site over the total number of reads covering that site. The "methylation density" of a region can be the number of reads at sites within a region showing methylation divided by the total number of reads covering the sites in the region. The sites can have specific characteristics, (e.g., the sites can be CpG sites). The "CpG methylation density" of a region can be the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of unconverted cytosines (which can correspond to methylated cytosine) at CpG sites as a proportion of all CpG sites covered by sequence reads mapped to the 100-kb region. This analysis can also be performed for other bin sizes, e.g., 50-kb or 1-Mb, etc. A region can be an entire genome or a chromosome or part of a chromosome (e.g., a chromosomal arm). A methylation index of a CpG site can be the same as the methylation density for a region when the region only includes that CpG site. The "proportion of methylated cytosines" can refer the number of cytosine sites, "C's," that are shown to be methylated (for example unconverted after bisulfite conversion) over the total number of analyzed cytosine residues, i.e., including cytosines outside of the CpG context, in the region. The methylation index, methylation density and proportion of methylated cytosines are examples of "methylation levels."

A "methylation profile" (also called methylation status) can include information related to DNA methylation for a region. Information related to DNA methylation can include a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes can refer to the addition of a methyl group to position 5 of the heterocyclic ring of cytosine (i.e., to produce 5-methylcytosine) among CpG dinucleotides. Methylation of cytosine can occur in cytosines in other sequence contexts, for example 5'-CHG-3' and 5'-CHH-3', where H is adenine, cytosine or thymine. Cytosine methylation can also be in the form of 5-hydroxymethylcytosine. Methylation of DNA can include methylation of non-cytosine nucleotides, such as N6-methyladenine.

The terms "size profile" and "size distribution" can relate to the sizes of DNA fragments in a biological sample. A size profile can be a histogram that provides a distribution of an amount of DNA fragments at a variety of sizes. Various statistical parameters (also referred to as size parameters or just parameter) can distinguish one size profile to another. One parameter can be the percentage of DNA fragment of a particular size or range of sizes relative to all DNA fragments or relative to DNA fragments of another size or range.

The term "about" or "approximately" can mean within an acceptable error range for the particular value as determined by one of ordinary skill in the art, which can depend in part on how the value is measured or determined, i.e., the limitations of the measurement system. For example, "about" can mean within 1 or more than 1 standard deviation, per the practice in the art. "About" can mean a range of ±20%, ±10%, ±5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

An "informative cancer DNA fragment" or an "informative DNA fragment" can correspond to a DNA fragment bearing or carrying any one or more of the cancer-associated or cancer-specific change or mutation, or a particular ending-motif (e.g., a number of nucleotides at each end of the DNA fragment having a particular sequence).

An "ending position" or "end position" (or just "end") can refer to the genomic coordinate or genomic identity or nucleotide identity of the outermost base, i.e., at the extremities, of a cell-free DNA molecule, e.g., plasma DNA molecule. The end position can correspond to either end of a DNA molecule. In this manner, if one refers to a start and end of a DNA molecule, both can correspond to an ending position. In some cases, one end position is the genomic coordinate or the nucleotide identity of the outermost base on one extremity of a cell-free DNA molecule that is detected or determined by an analytical method, e.g., massively parallel sequencing or next-generation sequencing, single molecule sequencing, double- or single-stranded DNA sequencing library preparation protocols, polymerase chain reaction (PCR), or microarray. In some cases, such in vitro techniques can alter the true in vivo physical end(s) of the cell-free DNA molecules. Thus, each detectable end can represent the biologically true end or the end is one or more nucleotides inwards or one or more nucleotides extended from the original end of the molecule e.g., 5' blunting and 3' filling of overhangs of non-blunt-ended double stranded DNA molecules by the Klenow fragment. The genomic identity or genomic coordinate of the end position can be derived from results of alignment of sequence reads to a human reference genome, e.g., hg19. It can be derived from a catalog of indices or codes that represent the original coordinates of the human genome. It can refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment). The term "genomic position" is not limited to nucleotide positions within a genome (e.g., the haploid set of chromosomes in a gamete or microorganism, or in each cell of a multicellular organism).

A "preferred end" (or "recurrent ending position") can refer to an end that is more highly represented or prevalent (e.g., as measured by a rate) in a biological sample having a physiological or pathological (disease) state (e.g., cancer) than a biological sample not having such a state or than at different time points or stages of the same pathological or physiological state, e.g., before or after treatment. A preferred end can have an increased likelihood or probability for being detected in the relevant physiological or pathological state relative to other states. The increased probability can be compared between the pathological state and a non-pathological state, for example in patients with and without a cancer and quantified as likelihood ratio or relative probability. The likelihood ratio can be determined based on the probability of detecting at least a threshold number of preferred ends in the tested sample or based on the probability of detecting the preferred ends in patients with such a condition than patients without such a condition. Examples for the thresholds of likelihood ratios include but are not limited to 1.1, 1.2, 1.3, 1.4, 1.5, 1.6, 1.8, 2.0, 2.5, 3.0, 3.5, 4.0, 4.5, 5, 6, 8, 10, 20, 40, 60, 80 and 100. Such likelihood ratios can be measured by comparing relative abundance values of samples with and without the relevant state. Because the probability of detecting a preferred end in a relevant physiological or disease state can be higher, such preferred ending positions can be seen in more than one individual with that same physiological or disease state. With the increased probability, more than one cell-free DNA molecule can be detected as ending on a same preferred ending position, even when the number of cell-free DNA molecules analyzed is far less than the size of the genome. Thus, the preferred or recurrent ending positions can also referred to as the "frequent ending positions." A quantitative threshold generally requires that ends be detected at least multiple times (e.g., 3, 4, 5, 6, 7, 8, 9, 10, 15, 20, or 50) within the same sample or same sample aliquot to be considered as a preferred end. A relevant physiological state can include a state when a person is healthy, disease-free, or free from a disease of interest. Similarly, a "preferred ending window" can correspond to a contiguous set of preferred ending positions.

A "relative abundance" can refer to a ratio of a first amount of nucleic acid fragments having a particular characteristic (e.g., a specified length, ending at one or more specified coordinates/ending positions, or aligning to a particular region of the genome) to a second amount nucleic acid fragments having a particular characteristic (e.g., a specified length, ending at one or more specified coordinates/ending positions, or aligning to a particular region of the genome). In one example, relative abundance may refer to a ratio of the number of DNA fragments ending at a first set of genomic positions to the number of DNA fragments ending at a second set of genomic positions. In some aspects, a "relative abundance" can be a type of separation value that relates an amount (one value) of cell-free DNA molecules ending within one window of genomic position to an amount (other value) of cell-free DNA molecules ending within another window of genomic positions. The two windows can overlap, but can be of different sizes. In other implementations, the two windows can not overlap. Further, the windows can be of a width of one nucleotide, and therefore be equivalent to one genomic position.

A "rate" of nucleic acid molecules (e.g., DNA or RNA) ending on a position can relate to how frequently a nucleic acid molecule ends on the position. The rate can be based on a number of nucleic acid molecules that end on the position normalized against a number of nucleic acid molecules analyzed. The rate can be based on a number of nucleic acid molecules that end on the position normalized against a number of nucleic acid molecules that end on a different position. The rate can be based on a number of nucleic acid molecules from a first sample that end on the position normalized against a number of nucleic acid molecules from a second sample (e.g., a reference sample) that end on the position. The rate can be based on a number of nucleic acid molecules from a first sample that end on a first set of positions (e.g., genomic positions) normalized against a number of nucleic acid molecules from a second sample (e.g., a reference sample) that end on a second set of positions. Accordingly, the rate can correspond to a frequency of how many nucleic acid molecules end on a position, and in some cases does not relate to a periodicity of positions having a local maximum in the number of nucleic acid molecules ending on the position.

A "calibration sample" can correspond to a biological sample whose tissue-specific nucleic acid fraction is known or determined via a calibration method, e.g., using an allele specific to the tissue. As another example, a calibration sample can correspond to a sample from which preferred ending positions can be determined. A calibration sample can be used for both purposes.

A "calibration data point" can include a "calibration value" and a measured or known proportional distribution of the nucleic acid of interest (i.e., DNA of particular tissue type). The calibration value can be a relative abundance as determined for a calibration sample, for which the proportional distribution of the tissue type can be known. The calibration data points can be defined in a variety of ways, e.g., as discrete points or as a calibration function (also called a calibration curve or calibration surface). The calibration function can be derived from additional mathematical transformation of the calibration data points.

The term "classification" can refer to any number(s) or other characters(s) that are associated with a particular property of a sample. For example, a "+" symbol (or the word "positive") can signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

A "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Overview

Analysis of circulating, cell-free DNA can be a non-invasive and easily accessible way to screen cancer, make a cancer diagnosis, a prognostic determination for a cancer, and provide guidance for cancer treatment. However, cell-free tumor-derived DNA can be difficult to detect because it can have a low concentration in the blood. A high sensitivity test can be useful for assessing a disease when its result is negative, since the probability of misdiagnosing those who have the disease is relatively low. However, a positive result in a test with high sensitivity is not necessarily useful for ruling in disease, as sensitivity does not consider false positives, of which there can be many. Similarly, a high specificity test can be useful for assessing a disease when its result is positive, since the probability of misdiagnosing those who do not have the disease is low. However, an increase in the specificity of an assay can result in an increase in false negatives (e.g., incorrectly identifying subjects who actually have a disease as not having the disease).

The present disclosure provides methods for increasing the positive predictive value (e.g., precision) for screening a subject for a condition, e.g., cancer, and for reducing a false positive rate. The positive predictive value can correspond to a ratio of subjects who are actually positive for a condition (true positives) to subjects identified as having the condition (true positives+false positives). In particular, methods of the present disclosure can include performing a first assay with a high sensitivity and low positive predictive value, followed by a second, high specificity assay for those samples that are positive in the first assay, thereby increasing the positive predictive value of the overall screen. For example, the positive predictive value (PPV) for the first assay can be less than 4%, but the overall PPV for a method can increase to 11% (e.g., by a factor of between 2 and 3) after performing a second assay. Increasing the positive predictive value for a cancer screen can help correctly identify subjects who have cancer, and can reduce the pool of subjects subjected to additional expensive and/or invasive assays.

Figure 22:
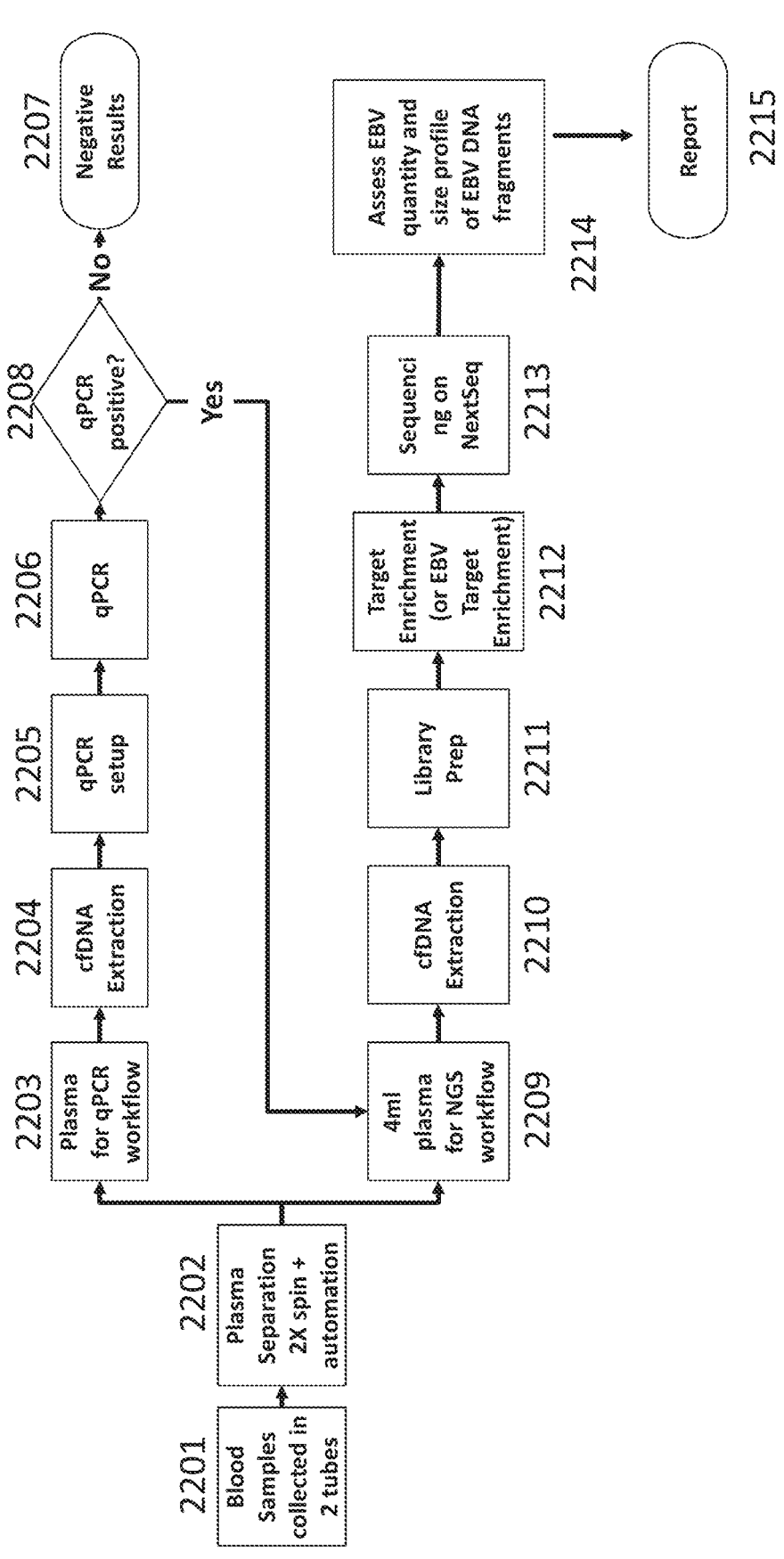
FIG. 22 depicts an flow chart of an exemplary method of the present disclosure comprising performing a first qPCR assay, and potentially performing a second next-generation sequencing (NGS)-based assay.

In some embodiments, a first assay can comprise an assay that can be relatively inexpensive, such as a quantitative polymerase chain reaction (qPCR)-based assay, to detect the presence and/or an amount and/or copy number of cell-free tumor-derived nucleic acid, e.g., DNA, e.g., Epstein-Barr virus (EBV) DNA, in a biological sample, e.g. plasma, from a subject. In some embodiments, a second assay can comprise a massively parallel sequencing assay (or next-generation sequencing (NGS)-based assay), for example, to analyze EBV nucleic acid quantity (e.g., percentage of sequence reads that align to an EBV reference genome) and/or a size profile of EBV nucleic acid fragments (e.g., size ratio of a proportion of EBV nucleic fragments in a given size range (e.g., 80 bp-110 bp) to a proportion of autosomal nucleic acid molecules of the given size range) of cell-free tumor-derived nucleic acid, e.g., DNA, from a biological sample, e.g., plasma, from the subject. The sample used in the first assay and the second assay can be the same sample (e.g., a plasma sample); in some cases, a portion of the sample is banked, e.g., until results of the first assay are known, and the banked portion of the sample is then used for the second assay. The following disclosure provides examples of methods and types of assays that can be used as a first assay and/or the second assay, (and/or third, fourth, fifth, etc. assay), on cell-free nucleic acid (e.g., DNA) from a biological sample, e.g., plasma, to assess (e.g., screen, detect, diagnose, or prognose) cancer. FIG. 22 illustrates an embodiment of a method provided herein.

The methods of the present disclosure generally relate to detecting a cancer or a tumor in a subject. The subject can be any human patient, such as a cancer patient, a patient at risk for cancer, or a patient with a family or personal history of cancer. In some cases, the subject is in a particular stage of cancer treatment. In some cases, the subject can have or be suspected of having cancer. In some cases, the subject is asymptomatic to cancer. In some cases, whether the subject has cancer is unknown.

Subjects

Where relevant in the description herein, a subject can have any type of cancer or tumor. In an example, a subject can have nasopharyngeal cancer, or cancer of the nasal cavity. In another example, a subject can have oropharyngeal cancer, or cancer of the oral cavity. Non-limiting examples of cancer can include adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, hepatocellular carcinoma, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The term 'lymphoma' can refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' can refer to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, a patient can have a cancer that is not breast cancer.

Examples of cancer include cancers that cause solid tumors as well as cancers that do not cause solid tumors. Furthermore, any of the cancers mentioned herein can be a primary cancer (e.g., a cancer that is named after the part of the body where it first started to grow) or a secondary or metastatic cancer (e.g., a cancer that has originated from another part of the body).

A subject at risk of cancer can be at risk because of a particular condition such as a pre-cancerous condition. Pre-cancerous conditions include but are not limited to actinic keratosis, Barrett's esophagus, atrophic gastritis, ductal carcinoma in situ, dyskeratosis congenita, sideropenic dysphagia, lichen planus, oral submucous fibrosis, solar elastosis, cervical dysplasia, leukoplakia, and erythroplakia). In some cases, a patient can be at risk of cancer because of cell or tissue dysplasia (e.g., an abnormal change in cell number, abnormal change in cell shape, abnormal change in cell size, or abnormal change in cell pigmentation). A subject that is at risk of cancer can be a patient that was exposed to a carcinogenic agent. Such patients can include patients with exposure to known or probable carcinogens (e.g., acetyl aldehyde, asbestos, or tobacco products), or patients exposed to ionizing radiation (e.g., gamma radiation, beta-radiation, X-radiation, or ultraviolet radiation). In some cases, a patient at risk of cancer is at risk because of a family history of cancer.

In some embodiments, a method of the present disclosure can detect a tumor or cancer in a subject, wherein the tumor or cancer has a geographic pattern of disease. In an example, a subject can have an EBV-related cancer (e.g., nasopharyngeal cancer), which can be prevalent in South China (e.g., Hong Kong SAR). In another example, subject can have an HPV-related cancer (e.g., oropharyngeal cancer), which can be prevalent in the United States and Western Europe. In yet another example, a subject can have a Human T-lymphotrophic virus-1 (HTLV-1)-related cancer (e.g., adult T-cell leukemia/lymphoma), which can be prevalent in southern Japan, the Caribbean, central Africa, parts of South America, and in some immigrant groups in the southeastern United States.

Both DNA and RNA viruses have been shown to be capable of causing cancer in humans. In some embodiments, a subject can have a cancer caused by a virus (e.g., an oncovirus). In some embodiments, a subject can have a cancer, and the cancer can be detectable using viral DNA. In some embodiments, a subject can have cancer, and the cancer can be detectable using tumor-derived viral DNA. In some embodiments, a subject can have a cancer, and the cancer can be detectable using tumor-derived viral DNA, or a fragment thereof, in cell-free sample obtained from the subject (e.g., a blood sample, a plasma sample, or a serum sample). A person having skill in the art will appreciate that a virus can have multiple viral strains (e.g., related viruses that can differ in their genetic makeup). For example, a subject can have oral, oropharyngeal, cervical cancer, penile, anal, vaginal, or vulvar cancer caused by (or associated with) infection by a Human papilloma virus (HPV), which can include more than 150 related viruses. Infection with the Epstein-Barr virus (EBV) can also increase a subject's risk of developing nasal cancer, nasopharyngeal cancer, lymphomas (e.g., Burkitt lymphoma or Hodgkin lymphoma), or stomach cancer. In yet another example, infection with the Hepatitis B virus (HBV) or Hepatitis C virus can cause chronic infections, which can increase a subject's chance of developing liver cancer. Non-limiting examples of viruses that can cause, or be associated with, cancer in a subject include HPV, EBV, HBV, HCV, Human immunodeficiency virus (e.g., associated with Kaposi sarcoma, cervical cancer, non-Hodgkin lymphoma, anal cancer, Hodgkin disease, lung cancer, oral cancer, oropharyngeal cancer, skin cancer, and liver cancer), human herpes virus 8 (e.g., associated with Kaposi sarcoma, blood cancer, primary effusion lymphoma, and Castleman disease), Human T-lymphotrophic virus-1 (e.g., associated with lymphocytic leukemia, non-Hodgkin lymphoma, and adult T-cell leukemia/lymphoma), and Merkel cell polyomavirus (e.g., associated with skin cancers such as Merkel cell carcinoma). In some embodiments, a non-human subject (e.g., a primate) can have cancer, and the cancer can be detectable using tumor-derived viral DNA. For example, infection with Simian virus 40 (SV40) can increase a subject's risk of developing mesothelioma, brain tumor, bone cancer, and lymphoma.

A subject from whom a sample is taken, or is treated by any of the methods or compositions described herein can be of any age and can be an adult, infant or child. In some cases, the subject, e.g., patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old). A particular class of subjects, e.g., patients that can benefit from a method of the present disclosure is subjects, e.g., patients over the age of 40. Another particular class of subjects, e.g., patients that can benefit from a method of the present disclosure is pediatric patients, who can be at higher risk of chronic heart symptoms. Furthermore, a subject, e.g., patient from whom a sample is taken, or is treated by any of the methods or compositions described herein, can be male or female.

Any of the methods disclosed herein can also be performed on a non-human subject, such as a laboratory or farm animal, or a cellular sample derived from an organism disclosed herein. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish. A sample can be obtained from a subject invasively (e.g., surgical means) or non-invasively (e.g., a blood draw, a swab, or collection of a discharged sample).

Performance Metrics

In some embodiments, methods of the present disclosure comprise performing two assays or more assays (e.g., a first assay and a second assay). The second assay can be performed to improve the sensitivity, specificity, negative predictive value and/or positive predictive value of the first assay or overall method. In some embodiments, methods of the present disclosure comprise performing an assay (e.g., a first assay and/or a second assay) having a sensitivity and/or specificity for a marker or set of markers indicative of a tumor. The sensitivity of an assay can refer to the number of true positives divided by the sum of the number of true positives and false negatives. Sensitivity can characterize the ability of an assay or method to correctly identify a proportion of the population that truly has a condition. In some embodiments, an assay can have a sensitivity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% for a set of markers indicative of a tumor.

For example, a method of the present disclosure can comprise a first assay, and the first assay can have a sensitivity for a first set of markers indicative of a tumor of at least about 80%. In some embodiments, the sensitivity of an assay can be within a range (e.g., between about 75% and about 85%, between about 65% and about 95%, between about 60% and about 100%, between about 10% and about 25%, between about 90% and about 100%).

Alternatively, a first assay can have a sensitivity or PPV that is lower than that of an overall test (e.g., one that involves the use of more than one assay).

In one example, a first assay in a method has a sensitivity of up to 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%.

In some embodiments, a method of the present disclosure can comprise one or more assays, and the method can have a sensitivity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting a tumor in a subject). Thus, the combined sensitivity of two or more assays can result in any of the above sensitivities.

For example, a method for screening cancer can involve performing a first assay to screen for individuals who have cancer, the true positives (TP). The screen can capture more false positives (FP) (individuals that do not have cancer) than would otherwise be desired. This can result in a low positive predictive value (PPV). However, a second assay performed on the same or new samples from the TP and FP individuals that has a lower false positive rate, can increase the PPV of the overall test.

The specificity of an assay can refer to the number of true negatives divided by the sum of the number of true negatives and false positives. Specificity can characterize the ability of an assay or method to correctly identify a proportion of the population that truly does not have a condition.

In some embodiments, an assay can have a specificity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% for a set of markers indicative of a tumor.

For example, a method of the present disclosure can comprise a first assay, and the first assay can have a specificity for a marker or first set of markers indicative of a tumor of at least about 80%. In some embodiments, the specificity of an assay can be within a range (e.g., between about 75% and about 85%, between about 65% and about 95%, between about 60% and about 100%, between about 10% and about 25%, between about 90% and about 100%).

In one example, a first assay in a method has a specificity of up to 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, a method of the present disclosure can comprise one or more assays, and the method can have a specificity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting that a subject does not have a tumor). Thus, the combined sensitivity of two or more assays can result in any of the above sensitivities.

The negative predictive value of an assay can refer to the probability that subjects with a negative screening test truly don't have the disease, and can be inherently impacted by the prevalence of a condition in a population.

In some embodiments, an assay can have a negative predictive value of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In a particular example, a method of the present disclosure can comprise a second assay, and the second assay can have a negative predictive value of at least about 70%. In some embodiments, the negative predictive value of an assay can fall within a range (e.g., between about 65% and about 75%, between about 55% and about 65%, between about 60% and about 100%, between about 10% and about 25%, between about 90% and about 100%).

In one example, an assay, such as a first assay has a negative predictive value that is up to %, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, a method of the present disclosure can comprise one or more assays, and the method can have a negative predictive value of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting that a subject does not have a tumor).

In some embodiments, the negative predictive value of a method can fall within a range (e.g., between about 80% and about 90%, between about 90% and about 100%, between about 70% and about 80%, between about 10% and about 25%, between about 25% and about 50%).

The positive predictive value of an assay can refer to the probability that subjects with a positive screening test truly have the disease, and it can be inherently impacted by the prevalence of a condition in a population.

In some embodiments, an assay can have a positive predictive value of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In a particular example, a method of the present disclosure can comprise a second assay, and the second assay can have a positive predictive value of at least about 70%.

In some embodiments, an assay (e.g., a first assay) can have a positive predictive value of at most about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. After the first assay is performed, one or more additional assays can be performed on the positives (true positives and false positives) to increase the overall positive predictive value of the test. The increase in PPV is preferably at least 2 fold, 3 fold, 4 fold, 5 fold, 7.5 fold, 10 fold, or 20 fold. The increase in PPV can be about 4 fold to about 10 fold, about fold to about 10 fold, or about 5 fold to about 15 fold, or about 5 fold to about 20 fold.

For example, a first assay can have a positive predictive value of at most about 4%, whereas a second assay can have a positive predictive value of at least about 11%. In some embodiments, the positive predictive value of an assay can fall within a range (e.g., between about 65% and about 75%, between about 90% and about 100%, between about 70% and about 80%, between about 10% and about 25%, between about 25% and about 50%). For example, a first assay can have a positive predictive value of between about 3% and 5%, whereas a second assay can have a positive predictive value of between about 10% and 15%.

In some embodiments, a method of the present disclosure can comprise one or more assays, and the overall method can have a positive predictive value of at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting that a subject does not have a tumor).

In some embodiments, the positive predictive value of the overall method can fall within a range (e.g., between about 15% and about 30%, about 20% and about 40%, about 20% and about 50%, about 30% and about 50%, about 50% and about 70%, about 60% and about 70%, about 80% and about 90%, between about 90% and about 100%, between about 70% and about 80%, between about 10% and about 25%, between about 25% and about 50%).

Where the method comprises a first assay and a second assay, the positive predictive value of the second assay can be at least, or at least about 1.1-fold, 1.2-fold, 1.3-fold, 1.4-fold, 1.5-fold, 2-fold, 2.5-fold, 3-fold, 3.5-fold, 4-fold, 4.5-fold, 5-fold, 6-fold, 7-fold, 8-fold, 9-fold, 10-fold, 15-fold, 20-fold, 25-fold, 30-fold, 35-fold, 40-fold, 45-fold, 50-fold, 75-fold, 100-fold, or more than 100-fold greater than the positive predictive value of the first assay. Alternatively, or in addition to, the positive predictive value of the overall method (e.g., two or more assays) can be at least 1.1-fold, 1.2-fold, 1.3-fold, 1.4-fold, 1.5-fold, 2-fold, 2.5-fold, 3-fold, 3.5-fold, 4-fold, 4.5-fold, 5-fold, 6-fold, 7-fold, 7.5-fold, 8-fold, 9-fold, 10-fold, 15-fold, 20-fold, 25-fold, 30-fold, 35-fold, 40-fold, 45-fold, 50-fold, 75-fold, 100-fold, greater than the positive predictive value of the first assay, or a single assay of the method, alone.

For example, the positive predictive value of the second assay can be 4-fold greater than the positive predictive value of the first assay. In some embodiments, the positive predictive value of the second assay can greater than the positive predictive value of the first assay, and the value for the fold-change in positive predictive value can fall within a range. For example, the positive predictive value of the second assay can be about 2-fold to 6-fold greater than the positive predictive value of the first assay. In another example, the positive predictive value of the second assay can be about 3.8-fold to about 4.2 fold greater than the positive predictive value of the first assay.

An screen or an assay can have a false positive rate, which can be about, or less than 01.%, 0.25%, 0.5%, 0.75%, 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Performing one or more additional assays can reduced the false positive rate for an overall screen or method about, or at least 1.1-fold, 1.2-fold, 1.3-fold, 1.4-fold, 1.5-fold, 2-fold, 2.5-fold, 3-fold, 3.5-fold, 4-fold, 4.5-fold, 5-fold, 6-fold, 7-fold, 7.5-fold, 8-fold, 9-fold, 10-fold, 13-fold, 15-fold, 20-fold, 25-fold, 30-fold, 35-fold, 40-fold, 45-fold, 50-fold, 75-fold, or 100-fold. The false positive rate for an overall screen or method involving two more assays (e.g., 2, 3, 4, 5, 6, 7, 8, 9, or 10 assays) can be about, or less than 01.%, 0.2%, 0.25%, 0.3%, 0.4%, 0.5%, 0.6%, 0.7%, 0.75%, 0.8%, 0.9%, 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Positive and negative likelihood ratios (LR+ and LR−, respectively) can quantify the change in the certainty of the "diagnosis" conferred by test results. More specifically, the likelihood ratios can transform the pretest odds to the posttest odds of a given (positive or negative) diagnosis. A high positive likelihood ratio and/or a low negative likelihood ratio can describe an assay or method of the present disclosure having a very good ability to predict the true disease status of a subject. A completely non-informative assay can have positive and negative likelihood ratios equal to 1 (i.e., does not transform the pre-test odds substantially). In some instances, a positive likelihood ratio of 10 or more and a negative likelihood ratio of 0.1 or less can represent informative tests. In some embodiments, the positive likelihood ratio of an assay or method of the present disclosure can be at least about 0.1, 0.5, 1, 2, 3, 4, 5, 6, 7, 8, 9, or 10. In some embodiments, the positive likelihood ratio of an assay or method can fall within a range (e.g., between about 5 and about 8). In some embodiments, the negative likelihood ratio of an assay or method of the present disclosure can be at most about 10, 9, 8, 7, 6, 5, 4, 3, 2, 1, 0.5, or 0.1. In some embodiments, the negative likelihood ratio of an assay or method can fall within a range (e.g., between about 0.1 and about 0.5).

Timing

In some embodiments, a method provided herein can comprise two or more assays (e.g., a first assay and a second assay). In a particular example, a first assay for a first marker or a first set of markers can have a sensitivity indicative of a tumor, and the second assay for a second marker or second set of markers can have a specificity indicative of a tumor. The first marker and the second marker can be the same or different. The first set of markers and the second set of markers can be the same or different. The first assay and the second assay can be the same or different.

A second assay can be performed hours, days, or weeks after the first assay. In one embodiment, a second assay can be performed immediately after the first assay. In other embodiments, a second assay can be performed within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after the first assay. In a particular example, the second assay can be performed within 2 weeks of the first sample. Generally, a second assay can be used to improve the specificity with which a tumor can be detected in a patient. The time between performing the first assay and the second assay can be determined experimentally. In some embodiments, the method can comprise 2 or more assays, and both assays use the same sample (e.g., a single sample is obtained from a subject, e.g., a patient, prior to performing the first assay, and is preserved for a period of time until performing the second assay). For example, two tubes of blood can be obtained from a subject at the same time. A first tube can be used for a first assay. The second tube can be used only if results from the first assay from the subject are positive. The sample can be preserved using any method known to a person having skill in the art (e.g., cryogenically). This preservation can be beneficial in certain situations, for example, in which a subject can receive a positive test result (e.g., the first assay is indicative of cancer), and the patient can rather not wait until performing the second assay, opting rather to seek a second opinion.

The time between obtaining a sample and performing an assay can be optimized to improve the sensitivity and/or specificity of the assay or method. In some embodiments, a sample can be obtained immediately before performing an assay (e.g., a first sample is obtained prior to performing the first assay, and a second sample is obtained after performing the first assay but prior to performing the second assay). In some embodiments, a sample can be obtained, and stored for a period of time (e.g., hours, days or weeks) before performing an assay. In some embodiments, an assay can be performed on a sample within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after obtaining the sample from the subject.

The time between performing an assay (e.g., a first assay or a second assay) and determining if the sample includes a marker or a set of markers indicative of the tumor can be varied. In some instances, the time can be optimized to improve the sensitivity and/or specificity of the assay or method. In some embodiments, determining if the sample includes a marker or a set of markers indicative of a tumor can occur within at most 0.1 hour, 0.5 hours, 1 hour, 2 hours, 4 hours, 8 hours, 12 hours, 24 hours, 2 days, 3 days, 4 days, 5 days, 6 days, 1 week, 2 weeks, 3 weeks, or 1 month of performing the assay.

Assays

The following illustrates various assays that can be used in the methods of the present disclosure. Any of the following assays can be used as a first assay, second assay, third assay, etc. or a combination of any of the above. For example, the first assay can be a qPCR assay and the second assay can be a NGS assay (e.g., any assay that performs a next-generation sequencing assay). Examples of NGS assays include fragmentation assays and mutational assays. In other examples, the first assay is a single marker assay (e.g., presence of an EBV locus) and the second assay is a multi-marker assay.

1. EBV Detection Assay

In some embodiments, a first assay or a second assay can comprise a qPCR assay to measure an amount of tumor-associated DNA in a sample. While examples and embodiments have been provided herein, additional techniques and embodiments related to, e.g., copy number and NPC, can be found in PCT AU/2011/001562, filed Nov. 30, 2011, which is entirely incorporated herein by reference. NPC is closely associated with EBV infection. In southern China, the EBV genome can be found in the tumor tissues in almost all NPC patients. The plasma EBV DNA derived from NPC tissues has been developed as a tumor marker for NPC (Lo et al. Cancer Res 1999; 59: 1188-1191). In particular, a real-time quantitative PCR assay can be used for plasma EBV DNA analysis targeting the BamHI-W fragment of the EBV genome.

There can be about six to twelve repeats of the BamHI-W fragments in each EBV genome 5 and there can be approximately 50 EBV genomes in each NPC tumor cell (Longnecker et al. Fields Virology, 5th Edition, Chapter 61 "Epstein-Barr virus"; Tierney et al. J Virol. 2011; 85: 12362-12375). In other words, there can be on the order of 300-600 (e.g., about 500) copies of the PCR target in each NPC tumor cell. This high number of target per tumor cell can explain why plasma EBV DNA is a highly sensitive marker in the detection of early NPC.

Figure 1:
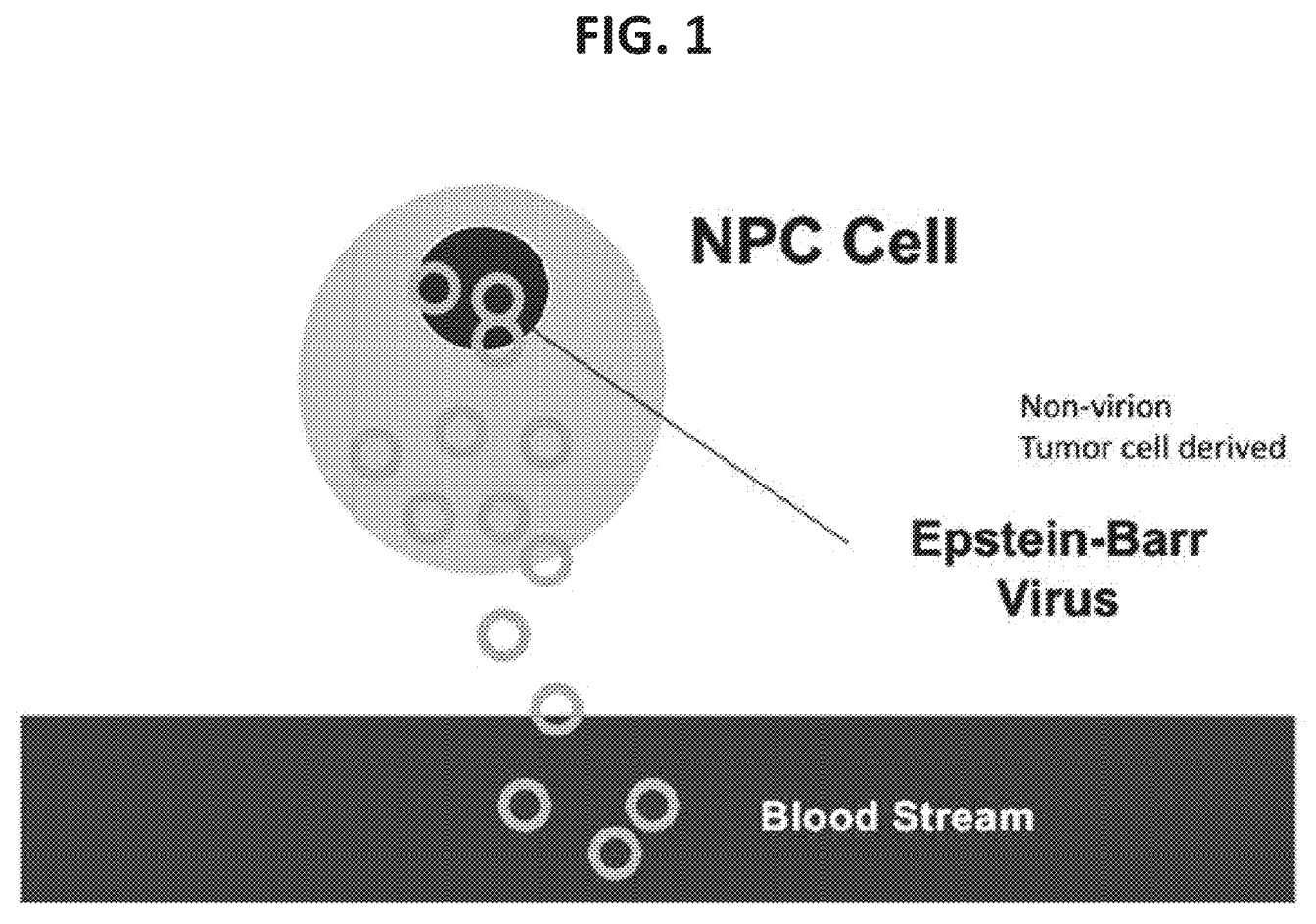
Figure 3:
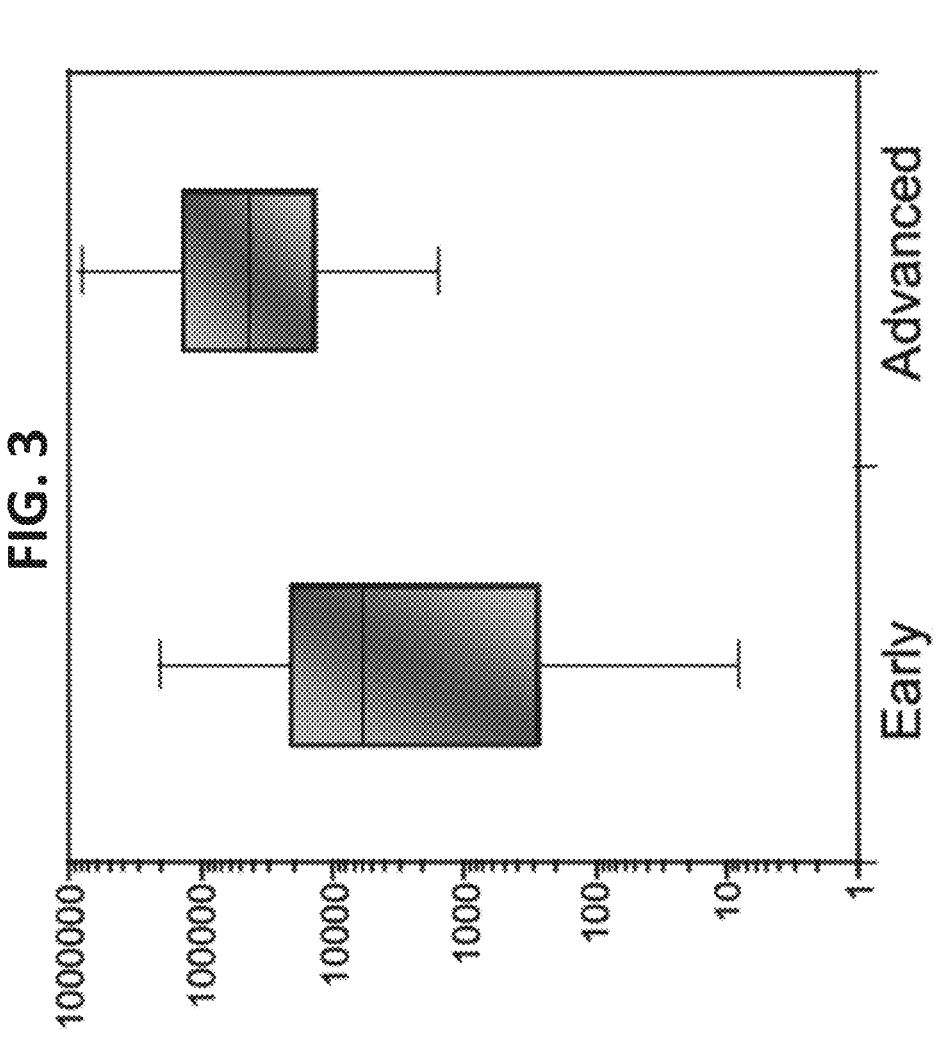
FIG. 3 depicts the concentration of plasma EBV DNA (copies/mL of plasma) in subjects with early stage NPC and advanced stage NPC.

As shown in FIG. 1, NPC cells can deposit fragments of the EBV DNA into the bloodstream of a subject. This tumor marker can be useful for the monitoring (Lo et al. Cancer Res 1999; 59: 5452-5455) and prognostication (Lo et al. Cancer Res 2000; 60: 6878-6881) of NPC. As shown in FIG. 2, cell-free EBV DNA was detectable in the plasma of 96% (55 of 57) of nasopharyngeal carcinoma (NPC) patients (median concentration, 21058 copies/ml) and 7% (3 of 43) of controls (median concentration, 0 copies/ml). Furthermore, as shown in FIG. 3, this test plasma cell-free EBV DNA levels in advanced NPC cases (median, 47,047 copies/ml; interquartile range, 17,314-133,766 copies/ml) were significantly higher than those in early-stage NPC cases (median, 5,918 copies/ml; interquartile range, 279-20,452 copies/ml; Mann-Whitney rank-sum test, P<0.001). More recent studies have shown that plasma EBV DNA analysis using real-time PCR can be useful for the detection of early NPC in asymptomatic subjects and can be useful for the screening of NPC (Chan et al. *Cancer* 2013; 119:1838-1844). In a population study with 1,318 participants, plasma EBV DNA levels were measured to investigate whether

US 12,692,553 B2

45

Figure 4:
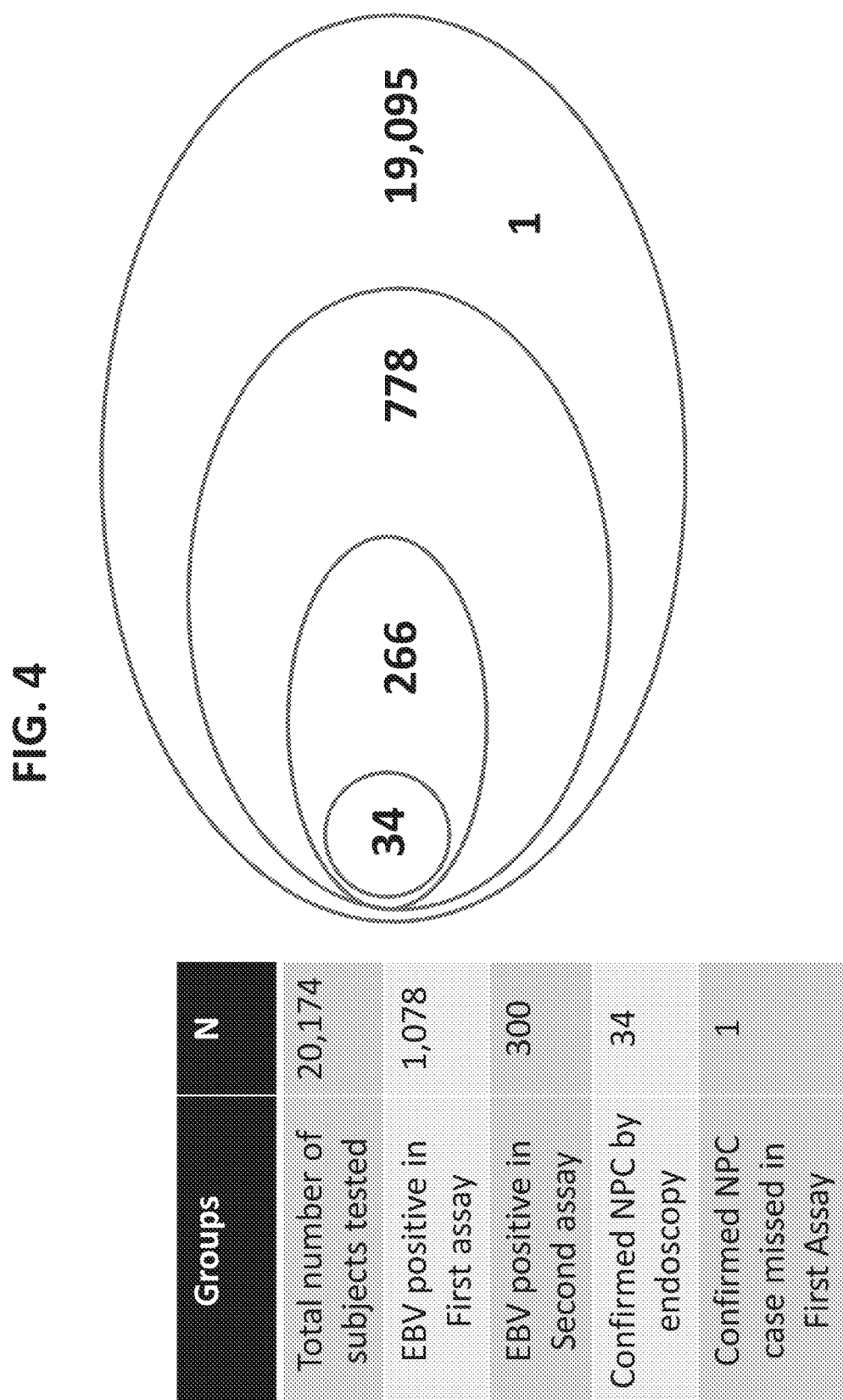
FIG. 4 depicts the population study on 20,174 subjects using single assay or two assays approach.
Figure 5:
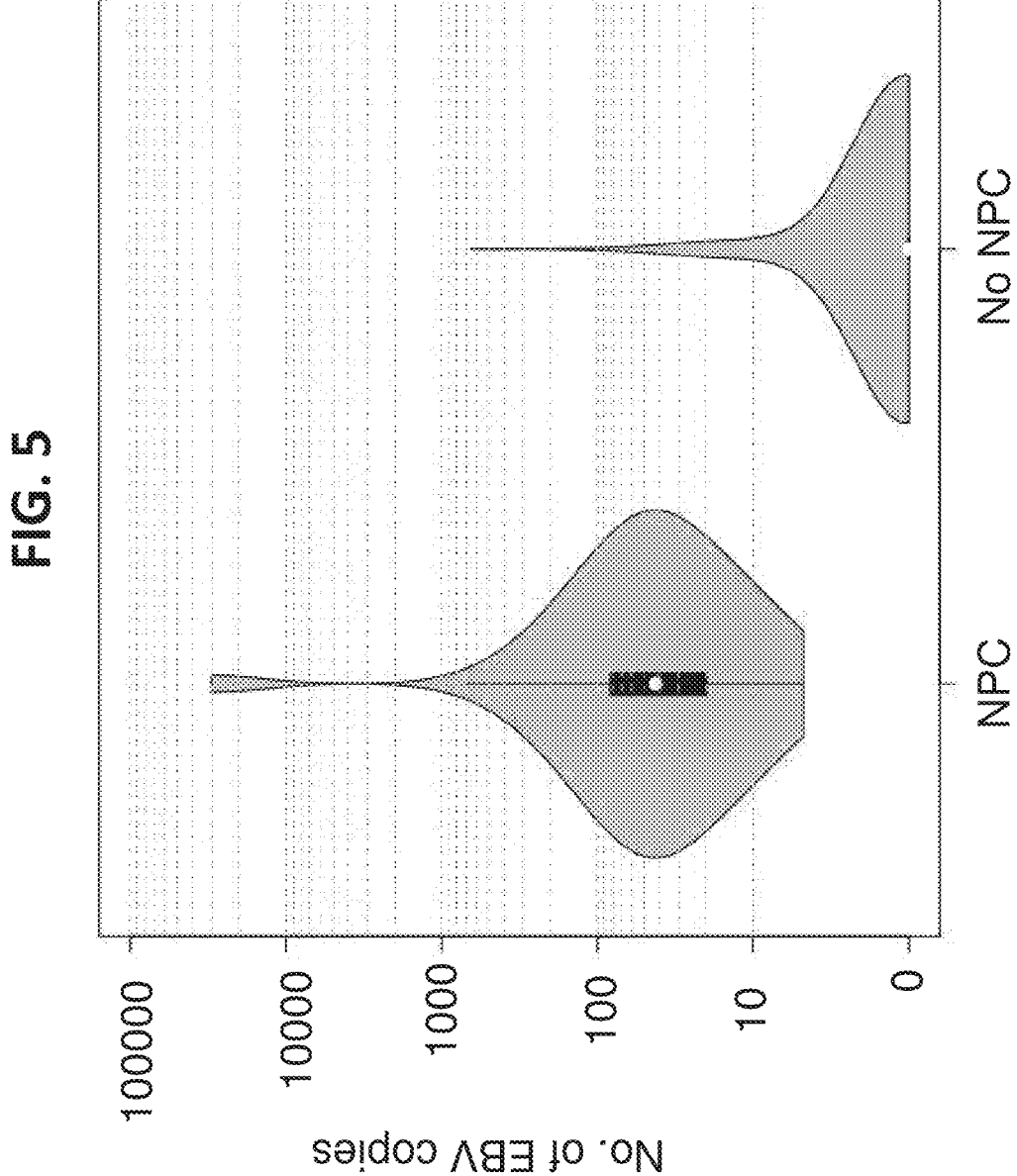
FIG. 5 depicts a violin plot of the concentration of plasma EBV DNA (copies/mL of plasma) in subjects with NPC and subjects not having NPC.
Figure 6B:
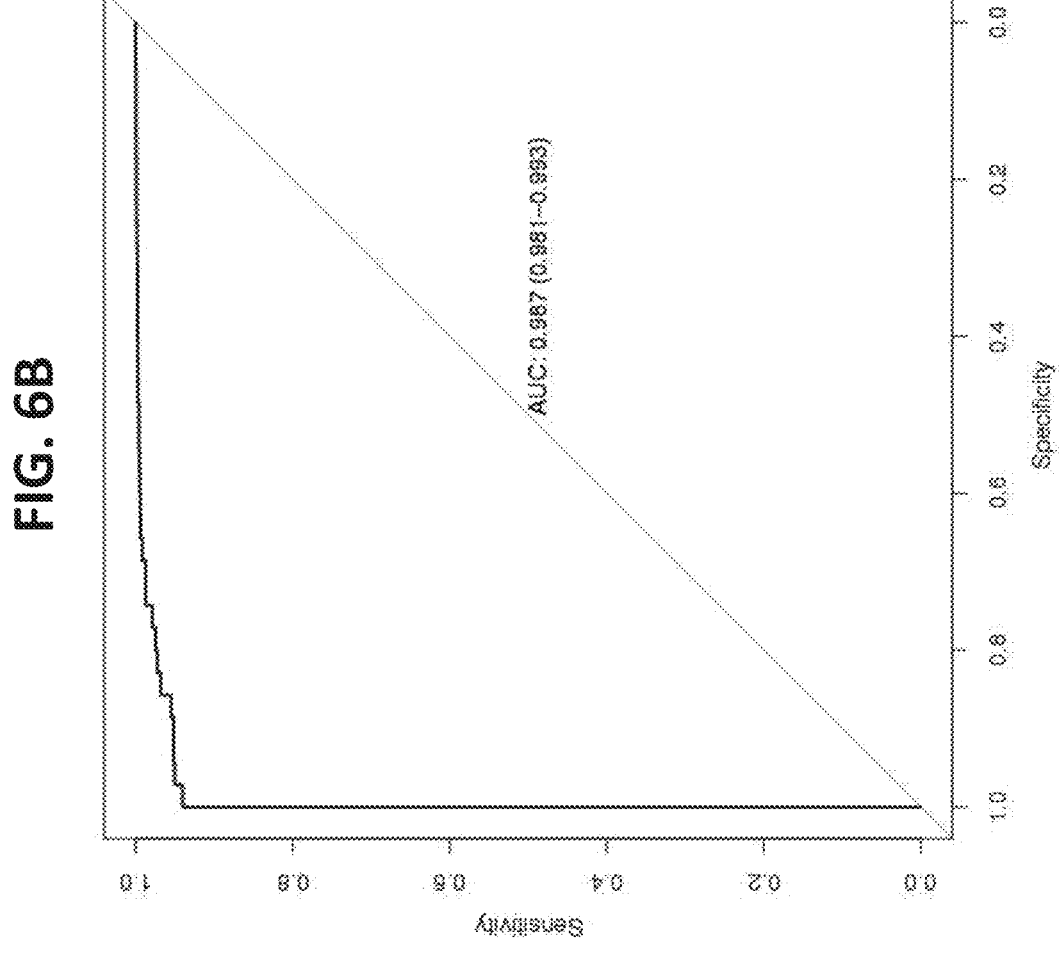
FIG. 6B depicts a ROC curve, corresponding to the values in the table in FIG. 6A, plotting the sensitivity against the specificity at various cutoff values of plasma EBV DNA concentration (copies/mL of plasma).
Figure 7:
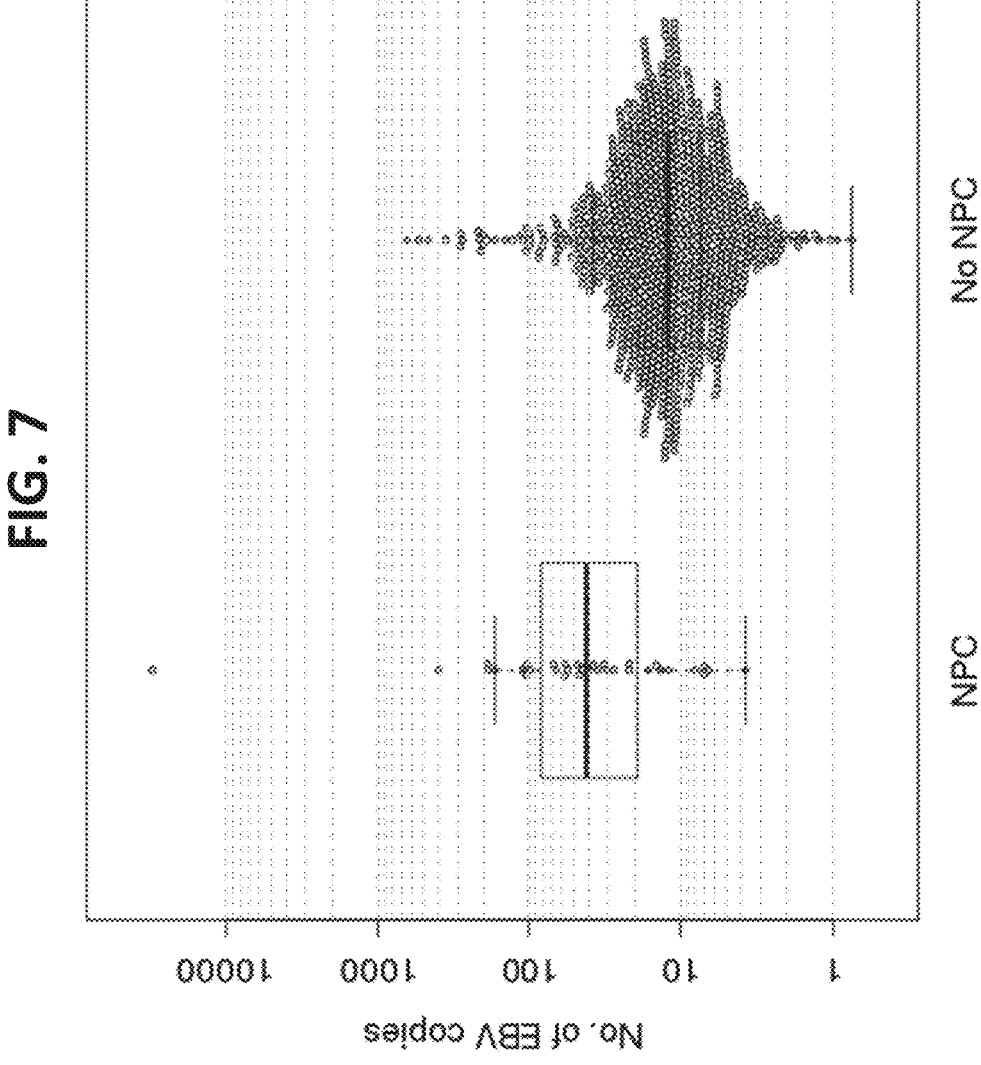
FIG. 7 depicts the concentration of plasma EBV DNA (copies/mL of plasma) in subjects with NPC and subjects who falsely tested positive (FP) for NPC (No NPC) in a first assay and a second assay.
Figure 9:
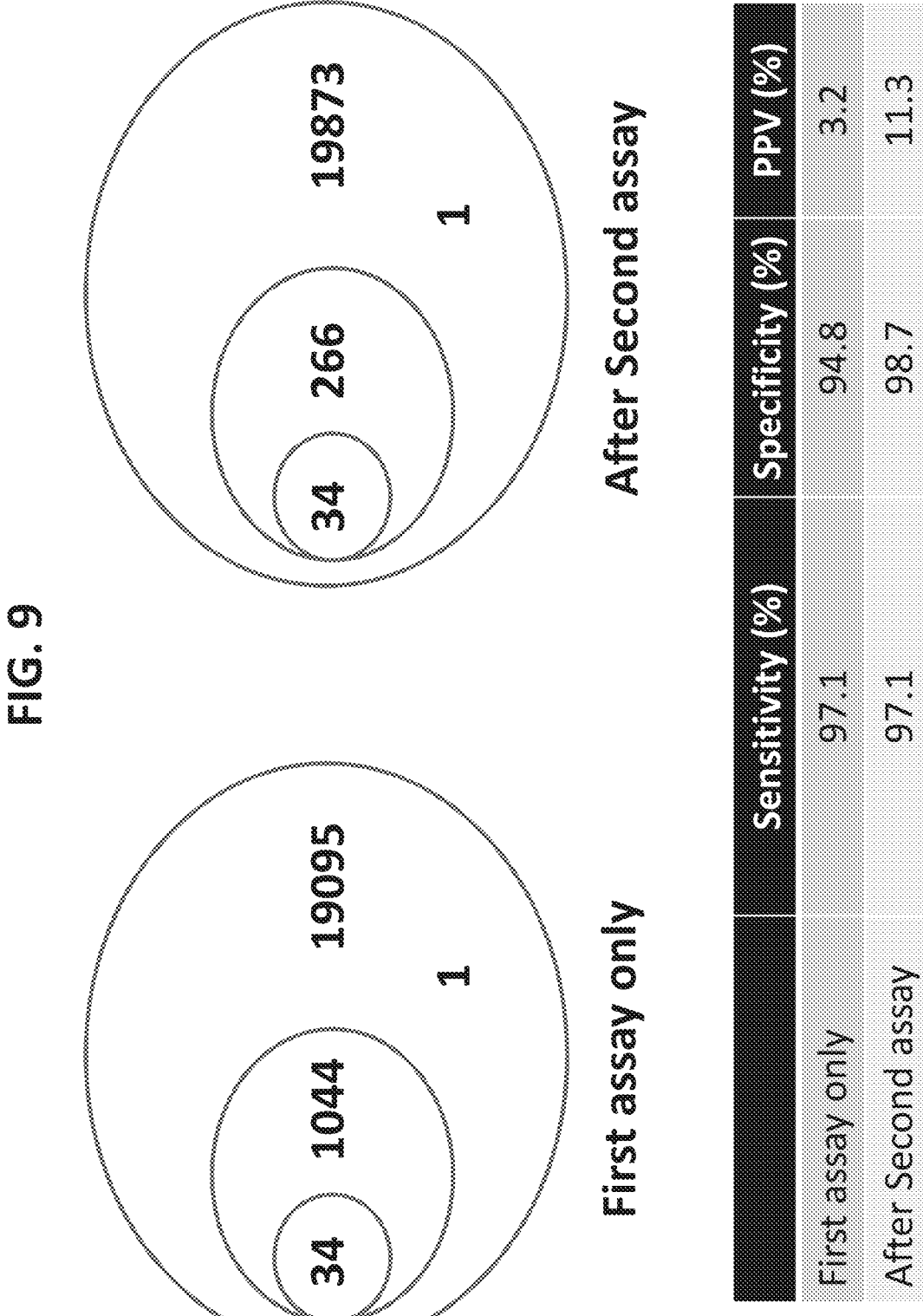
FIG. 9 depicts the specificity, sensitivity, and positive predictive value of a test comprising a single assay or two assays.

EBV DNA copy number can be useful for NPC surveillance. 69 participants (5.2%) had detectable levels of plasma EBV DNA, of 3 participants ultimately were clinically diagnosed, using nasal endoscopy and magnetic resonance imaging, as having NPC. Thus, the positive predictive value of a single plasma EBV DNA test in this study is about 4%, calculated as the number of patients truly having NPC (n=3) divided by the sum of number of patients truly having NPC and the number of patients falsely identified as having NPC (n=66). A much larger population study with about 20,174 patients was performed. The results of this study are shown in FIG. 4, which depicts the results of 20,174 patients in the NPC study using a first assay and a second assay. Based on the study parameters, if the subject was tested positive in a first assay, the second assay can be performed on the same subject between 2-6 week later. Subjects, who tested positive in the second assay, were sent to nasal endoscopy or MRI assessment. FIG. 5 depicts a violin plot of the plasma concentration of EBV DNA in participants ultimately diagnosed as having NPC (NPC; n=34) and participants not having NPC (no NPC; n=20,140) at the enrollment of the study. These results show that the plasma EBV DNA concentrations at enrollment were significantly higher in the NPC patients compared with those without NPC (P<0.001, Student t-test). FIG. 6A depicts a table showing the sensitivity and specificity of plasma EBV DNA analysis with real-time qPCR for NPC based on different cutoffs for the plasma EBV DNA for this larger population study. FIG. 6B. depicts a ROC curve, corresponding to the values provided in FIG. 6A, with an AUC of 0.987. The ROC-AUC can provide a measure of diagnostic utility of a method, taking into account both the sensitivity and specificity of the method. Generally, ROC-AUC ranges from 0.5 to 1.0, where a value closer to 0.5 indicates the method has limited diagnostic utility (e.g., lower sensitivity and/or specificity) and a value closer to 1.0 indicates the method has greater diagnostic utility (e.g., higher sensitivity and/or specificity). While the test exhibits relatively high sensitivity and specificity across a broad range of cutoff values for EBV DNA concentration, because the prevalence of NPC in the population is low, the single EBV test has a low positive predictive value, thereby limiting diagnostic utility. FIG. 9 depicts the change in test sensitivity, specificity and PPV values for the single assay test and the two assay test. Subjects who were positive in first EBV assay can be retested again after 2-6 weeks later. Of the participants that had detectable levels of plasma EBV DNA in the first assay (n=1078), about 300 participants exhibited persistently elevated levels of plasma EBV DNA (e.g., participants again tested positive in a second assay). FIG. 7 depicts the copy number (e.g., copies/mL of plasma) of EBV DNA fragments in the plasma of subjects ultimately diagnosed as having nasopharyngeal cancer (NPC), and subjects falsely testing positive for nasopharyngeal cancer in a second assay (No NPC). The positive predictive value of a method comprising a first assay and a second assay is about 11%, calculated as the number of patients truly having NPC (n=34) divided by the sum of number of patients truly having NPC and the number of patients falsely identified as having NPC (e.g., about 266 participants). In other words, the positive predictive value of the second assay is about 4-fold greater than the positive predictive value of the first assay. Improvements in positive predictive value can be significant, particularly with respect to patients having a cancer with a low incidence in the population, in that the improved PPV can directly reduce patient burden (e.g., follow-up costs and psychological burden) as a result of false positive results. Additional

Figure 8B:
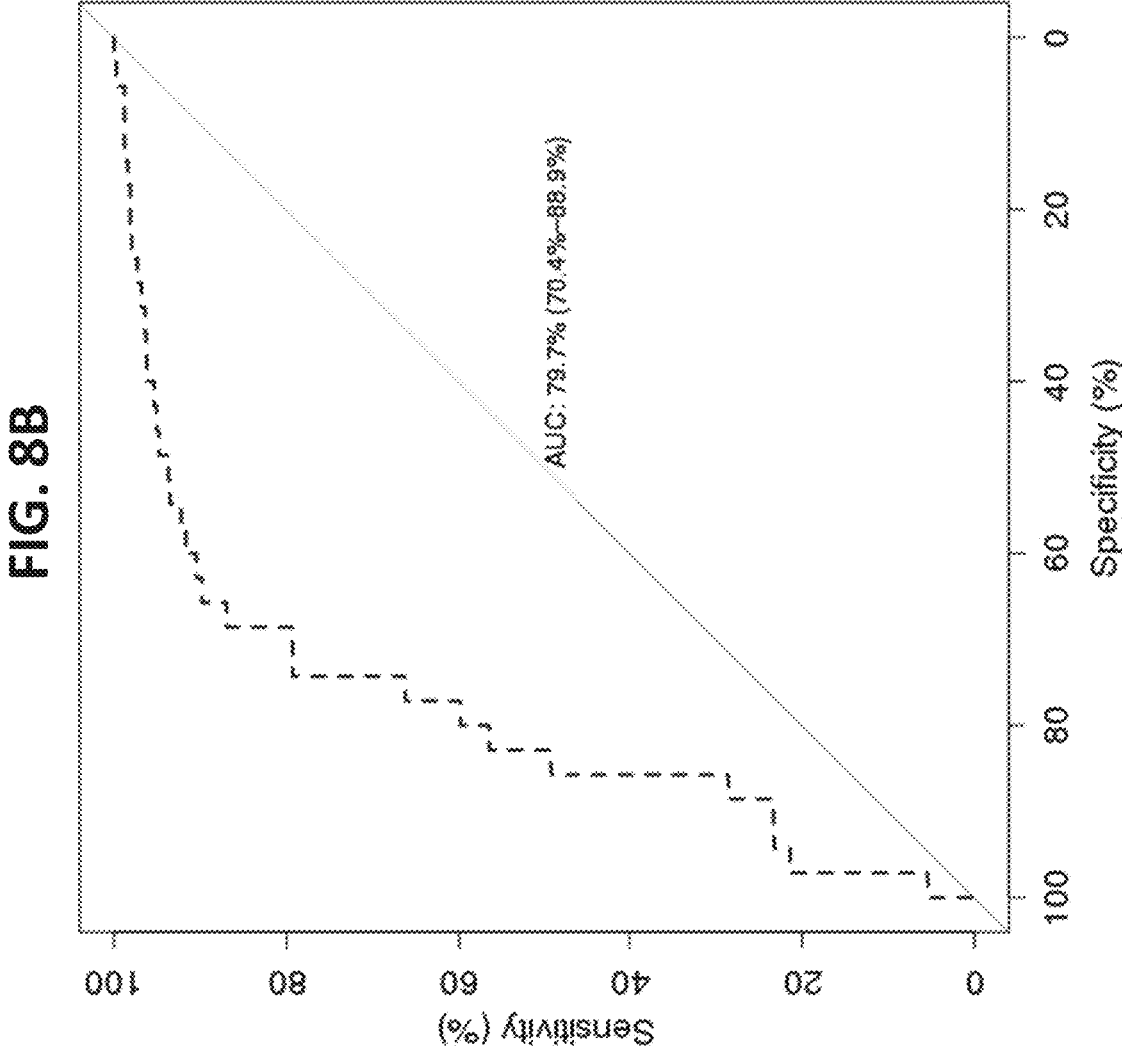
FIG. 8B depicts a ROC curve, corresponding to the values in the table in FIG. 8A, plotting the sensitivity against the specificity at various cutoff values of plasma EBV DNA concentration (copies/mL of plasma).
Figure 10:
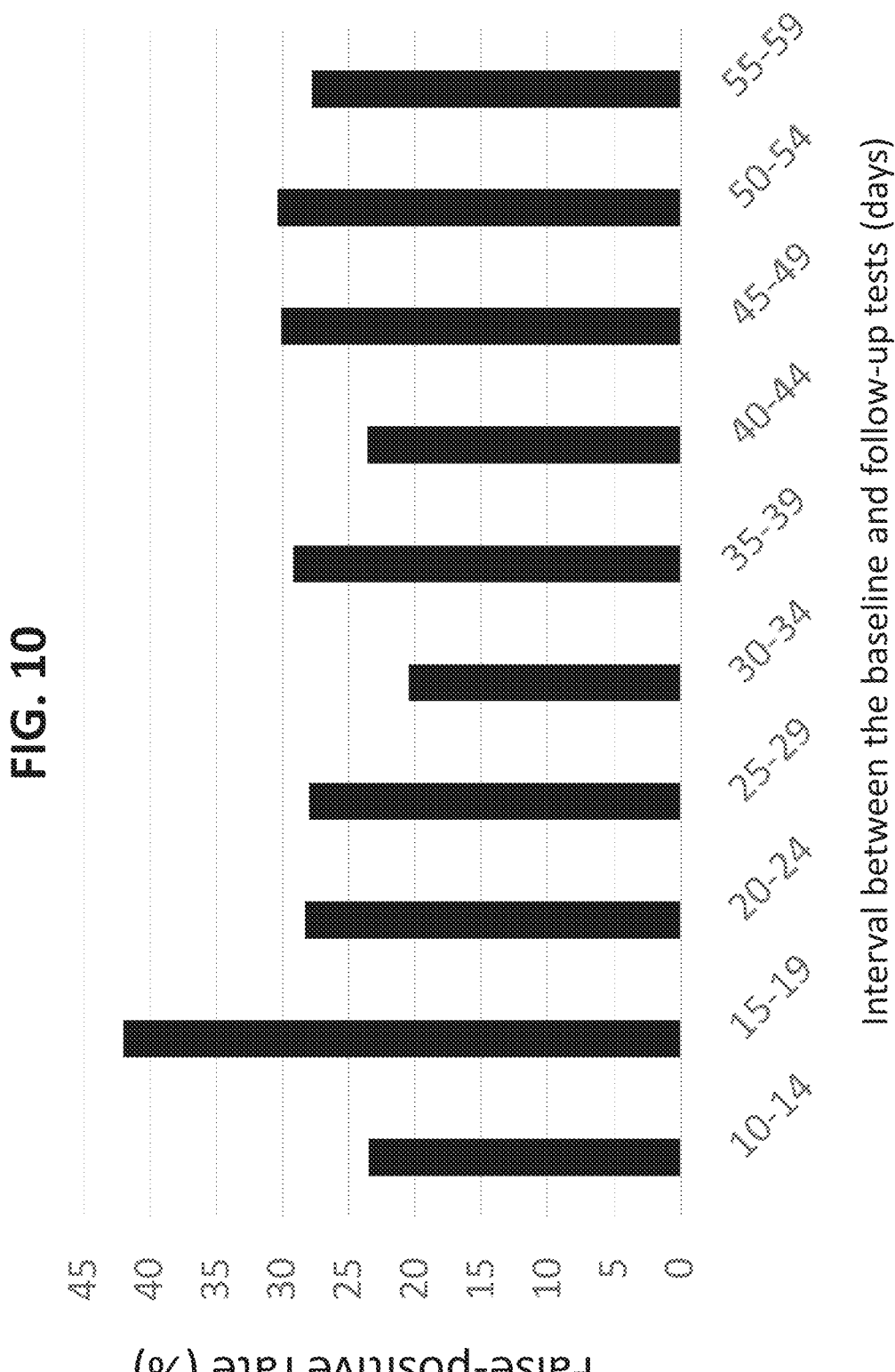
FIG. 10 depicts the false positive rate of a second assay (e.g., follow-up test), performed in subjects that are positive for a first assay (e.g., baseline), at various time intervals after performing the first assay.
Figure 11:
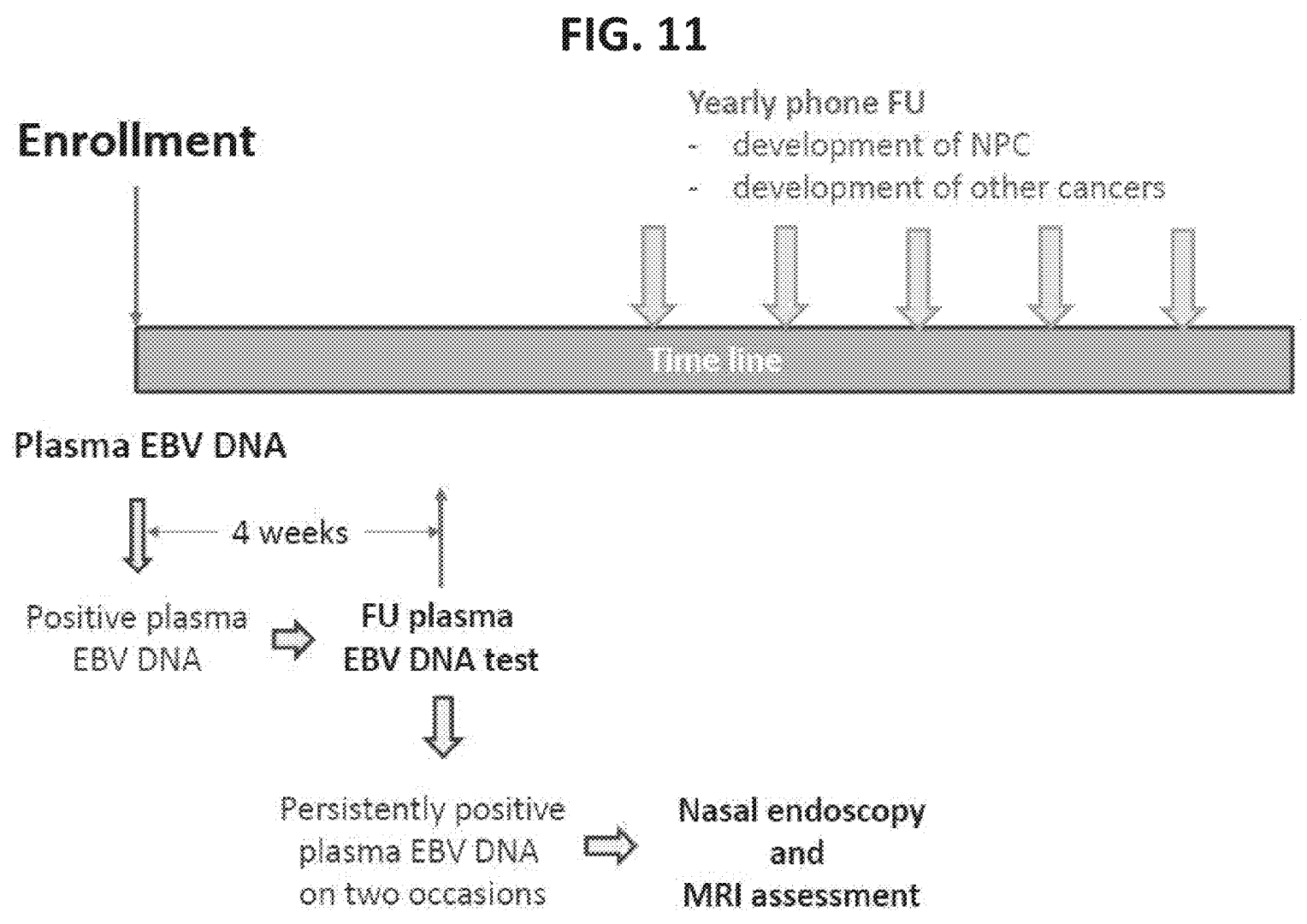

46 analysis of the EBV DNA between 34 NPC subjects and EBV assay positive subjects were performed to further reduce the group of 300 subjects positive in second test. FIG. 8A depicts a table showing the sensitivity and specificity of plasma EBV DNA analysis with real-time qPCR for NPC based on different cutoffs for the plasma EBV DNA. FIG. 8B. depicts an ROC curve, corresponding to the values provided in FIG. 8A, with an AUC of 0.797. This analysis indicates that there can be no level of EBV DNA that can be used to improve specificity without substantial loss in sensitivity. Therefore, only a second EBV assay performed on the same subject within 2-6 weeks can reduce the number of subjects who can be sent for nasal endoscopy or MRI assessment (e.g., from 1078 subjects to 300 subjects). Analysis of interval between first and second EBV assays were used to assess if it can be used for specificity improvement. As shown in FIG. 10, a follow-up (e.g., a second assay) plasma EBV DNA analysis using real-time qPCR at various intervals after the first assay showed a relatively constant false-positive rate over time, suggesting that the follow-up test can be performed as early as 1 to 2 weeks following the first assay, and that a second assay with a higher specificity than the plasma EBV DNA test can be used to improve positive predictive value. FIG. 11 depicts an exemplary timeline for performing a first assay (e.g., at enrollment) and a second assay (e.g., at 4 weeks after the first assay, or as early as 1-2 weeks after the first assay). In some embodiments, methods of the present disclosure can also comprise nasal endoscopy or MRI assessment to confirm results from the first assay and/or second assay.

Figure 12:
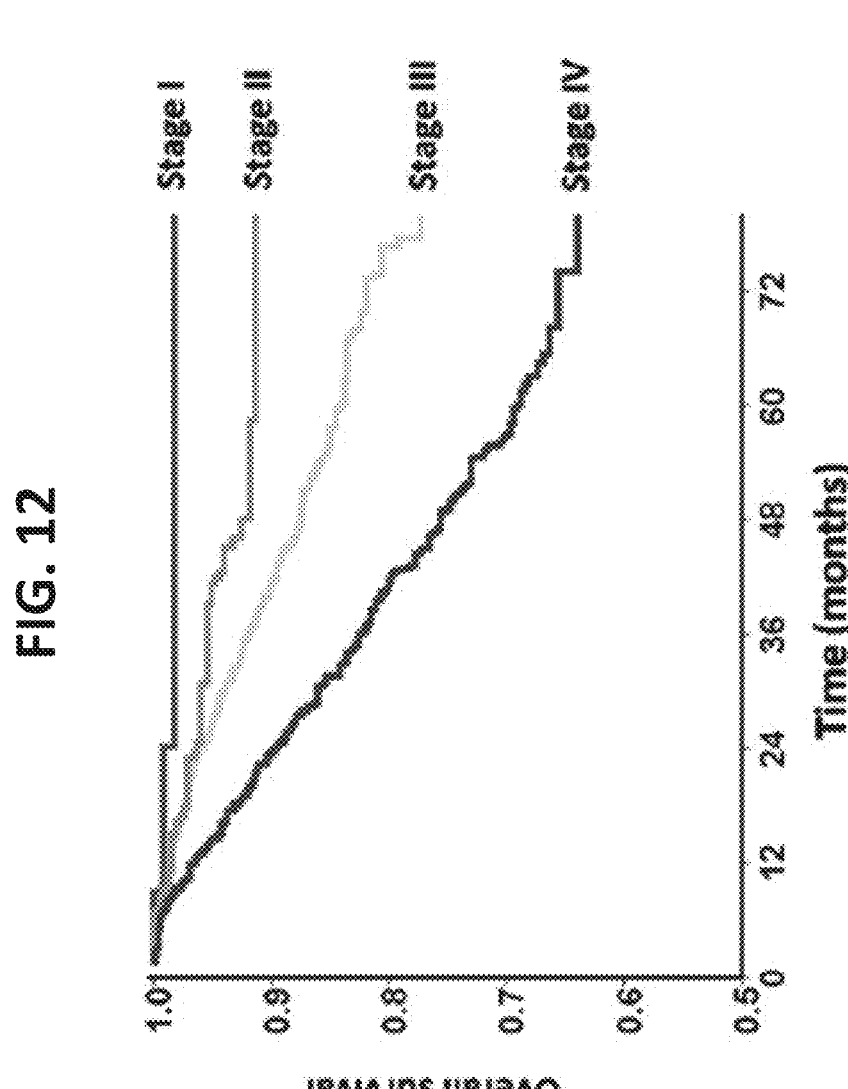
FIG. 12 depicts overall survival of subjects with various stages of NPC over time.
Figure 13:
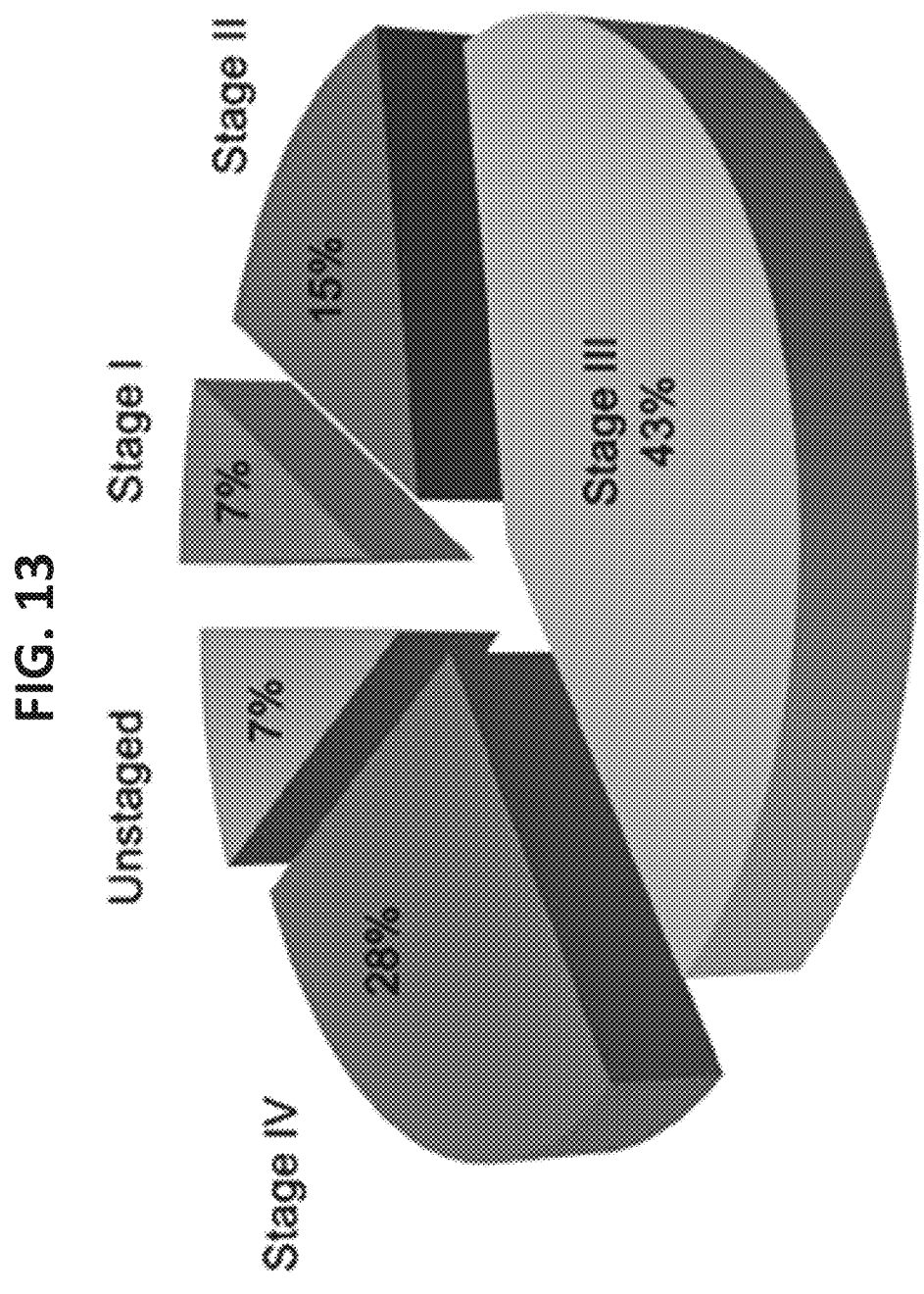
FIG. 13 depicts the stage distribution of NPC in Hong Kong subjects.

The methods of the present disclosure can be particularly useful in the early detection of cancer and/or downstaging of cancer. In some instances, downstaging can refer to any process of screening for cancer using methods for early detection of a disease. FIGS. 12 and 13 depict the overall survival of NPC patients at various stages of cancer, and the stage distribution of NPC in Hong Kong, respectively. In some embodiments, methods of the present disclosure can be useful in reducing the number of patients that reach a higher stage of cancer, thereby increasing their overall survival probability.

In some embodiments, a first assay can comprise plasma EBV DNA analysis (e.g., using real-time PCR). In some embodiments, determining if a biological sample includes a first set of markers indicative of cancer requires generating a comparison of the first amount of tumor-derived DNA to at least one first calibration value. In some embodiments, a calibration value can be 0 copies/mL (e.g., copies of EBV DNA). In some embodiments, a calibration value can be as many as 10,000,000 copies/mL of plasma. In some embodiments, a calibration value can be about 1 copy/mL, 5 copies/mL, 10 copies/mL, 50, 100, 1000, 10000, 100000, 500000, 1M or 10M copies/mL. In an example, the calibration value for a first assay (e.g., a plasma EBV DNA analysis) can be between 0 and 1M copies/mL. In another example, the calibration value for a first assay (e.g., a plasma EBV DNA analysis) can be between 0 and 4000 copies/mL. In yet another example, the calibration value for a first assay (e.g., a plasma EBV DNA analysis) can be between 20000 and 50000 copies/mL. In some embodiments, the calibration value can be used to determine whether or not a subject has a condition (e.g., NPC). In another embodiment, the calibration value can be used to determine whether a subject has early stage NPC or late stage NPC.

In some embodiments, an assay (e.g., a first assay or a second assay) can comprise performing a next generation sequencing (NGS) or massively parallel sequencing to measure a property of cell-free DNA in the sample. Not many cancers have clear mutational or other markers for identifying that cancer exists or is highly likely to be present in an individual. And, even if such markers do exist, there are generally few such known markers that are unique for a specific cancer. Thus, it can be difficult to detect cancer in plasma or other such sample with cell-free DNA, where such mutational markers can not be in high concentration. In such samples where a cancer-specific marker does not exist, alternative methods can be used to determine a plasma concentration of tumor-derived DNA or copy-number. For example, after obtaining a sample at least a portion of a plurality of the nucleic acid molecules contained in the biological sample can be sequenced. The portion sequenced can represent a fraction of the human genome. In one embodiment, the nucleic acid molecules are fragments of respective chromosomes. One end (e.g., 35 base pairs (bp)), both ends, or an entire fragment can be sequenced. All of the nucleic acid molecules in the sample can be sequenced, or just a subset can be sequenced.

In one embodiment, the sequencing is done using massively parallel sequencing. Massively parallel sequencing, such as that achievable on the 454 platform (Roche) (see e.g., Margulies, M. et al. 2005 *Nature* 437, 376-380), Illumina Genome Analyzer (or Solexa platform) or SOLiD System (Applied Biosystems) or the Helicos True Single Molecule DNA sequencing technology (see e.g., Harris T D et al. 2008 Science, 320, 106-109), the single molecule, real-time (SMRT™) technology of Pacific Biosciences, and nanopore sequencing (see e.g., Soni G V and Meller A. 2007 Clin Chem 53: 1996-2001), can allow the sequencing of many nucleic acid molecules isolated from a specimen at high orders of multiplexing in a parallel fashion (see e.g., Dear *Brief Funct Genomic Proteomic* 2003; 1: 397-416). Each of these platforms can sequence clonally expanded or even non-amplified single molecules of nucleic acid fragments.

As a high number of sequencing reads, in the order of hundreds of thousands to millions or even possibly hundreds of millions or billions (e.g., 100,000, 1,000,000 (1M), 10M, 100M, 1000M, or more reads), are generated from each sample in each run, the resultant sequenced reads can form a representative profile of the mix of nucleic acid species in the original specimen. Due to the large sampling of sequences from each specimen, the number of identical sequences, such as that generated from the sequencing of a nucleic acid pool at several folds of coverage or high redundancy, can also be a good quantitative representation of the count of a particular nucleic acid species or locus in the original sample.

Based on the sequencing (e.g., data from the sequencing), an amount of a chromosome, DNA fragment, or nucleic acid (e.g., the clinically relevant nucleic acid) can be determined. In an example, the amount can be determined from sequences identified as originating from the chromosome. A bioinformatics procedure can then be used to locate each of these DNA sequences to the human genome. A proportion of such sequences can be discarded from subsequent analysis because they are present in the repeat regions of the human genome, or in regions subjected to inter-individual variations, e.g., copy number variations. An amount of the chromosome of interest and of one or more other chromosomes can thus be determined. There are a number of ways of determining the amounts of the chromosomes, including but not limited to counting the number of sequenced tags, the number of sequenced nucleotides (basepairs) or the accumulated lengths of sequenced nucleotides (basepairs) originating from particular chromosome(s) or chromosomal regions.

2. HPV Detection Assay

A qPCR assay can be used in a way similar to that described herein for EBV to measure amount of tumor-associated HPV DNA in a sample. Such analysis can be especially useful for screening of cervical cancer (CC) and head and neck squamous cell carcinoma (HNSCC). In one example, the qPCR assay targets a region (e.g., 200 nucleotides) within the polymorphic L1 region of the HPV genome. More specifically, contemplated herein is the use of qPCR primers that selectively hybridize to sequences that encode one or more hypervariable surface loops in the L1 region.

Alternatively, HPV sequences can be detected and quantified using sequencing techniques. For example, cfDNA fragments can be sequenced and aligned to the HPV genome and quantified.

| Groups | Sample IDs | Fragment mapped to HPV genomes | Percentage of fragments mapped to HPV genomes (%) |
|---|---|---|---|
| Healthy controls | EN086 | 0 | 0 |
| | GC038 | 0 | 0 |
| | ER022 | 0 | 0 |
| | BP065 | 0 | 0 |
| | FF159 | 0 | 0 |
| Nasopharyngeal carcinoma (NPC) patients | TBR1358 | 0 | 0 |
| | TBR1390 | 0 | 0 |
| | TBR1379 | 0 | 0 |
| | TBR1378 | 0 | 0 |
| Chronic hepatitis B virus (HBV) carriers | GM2192F | 0 | 0 |
| | GM2910F | 0 | 0 |
| | GM6421F | 0 | 0 |
| Hepatocellular carcinoma (HCC) patients | TBR_1330 | 0 | 0 |
| | TBR_1386 | 0 | 0 |
| | TBR_1428 | 0 | 0 |
| Cervical cancer (CC) patients | C-819 | 1489 | 0.00731 |
| | C-822 | 1720 | 0.0132 |
| | C-877 | 6773 | 0.03177 |
| | C-788 | 7992 | 0.06083 |
| | C-801 | 2127 | 0.04563 |
| | C-803 | 1316 | 0.01504 |
| Head and Neck Squamous cell carcinoma (HNSCC) patients | TBR_1067 | 53 | 0.00009 |
| | TBR_1019 | 3287 | 0.00642 |

Figure 86:
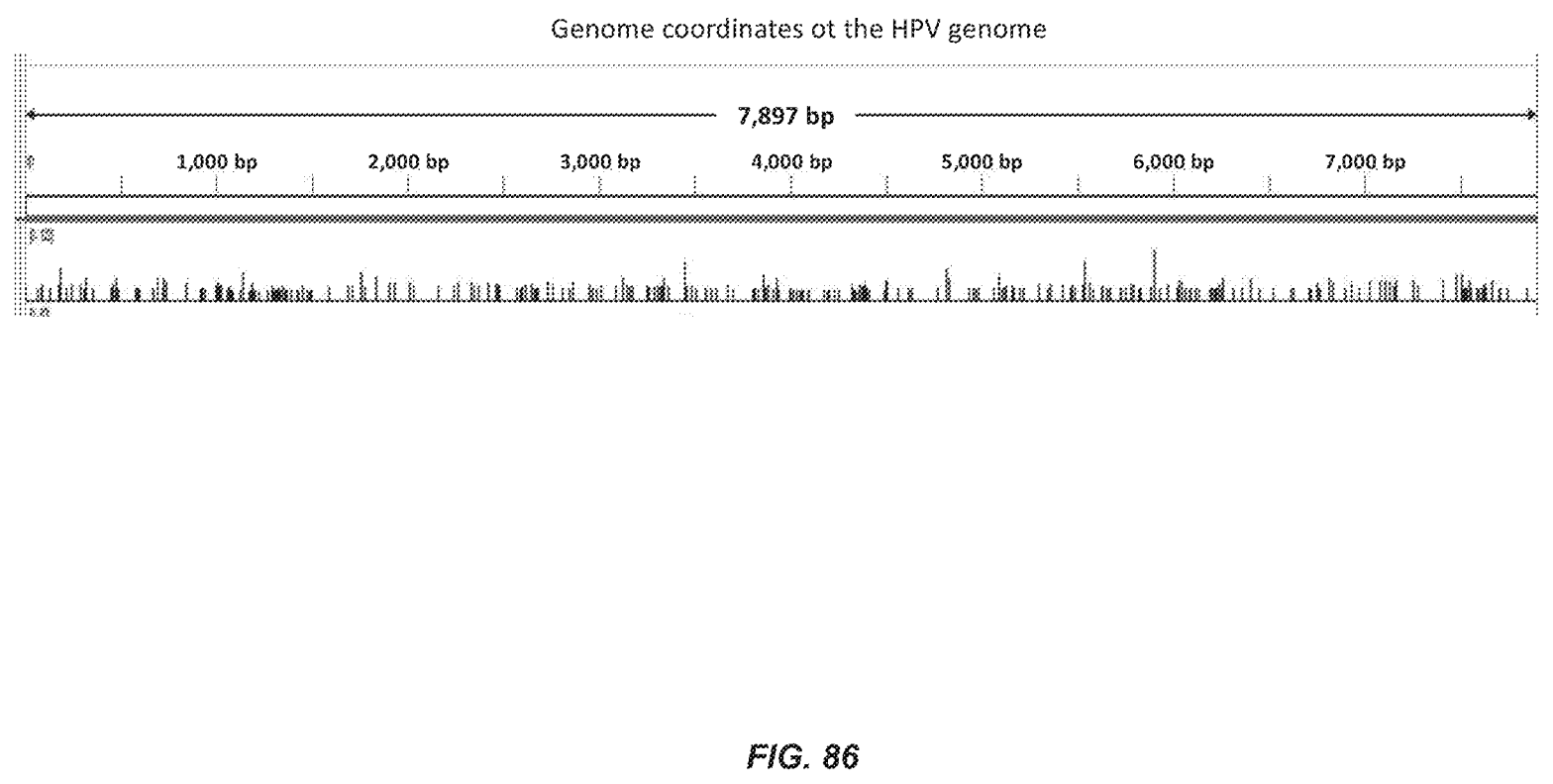
Figure 95:
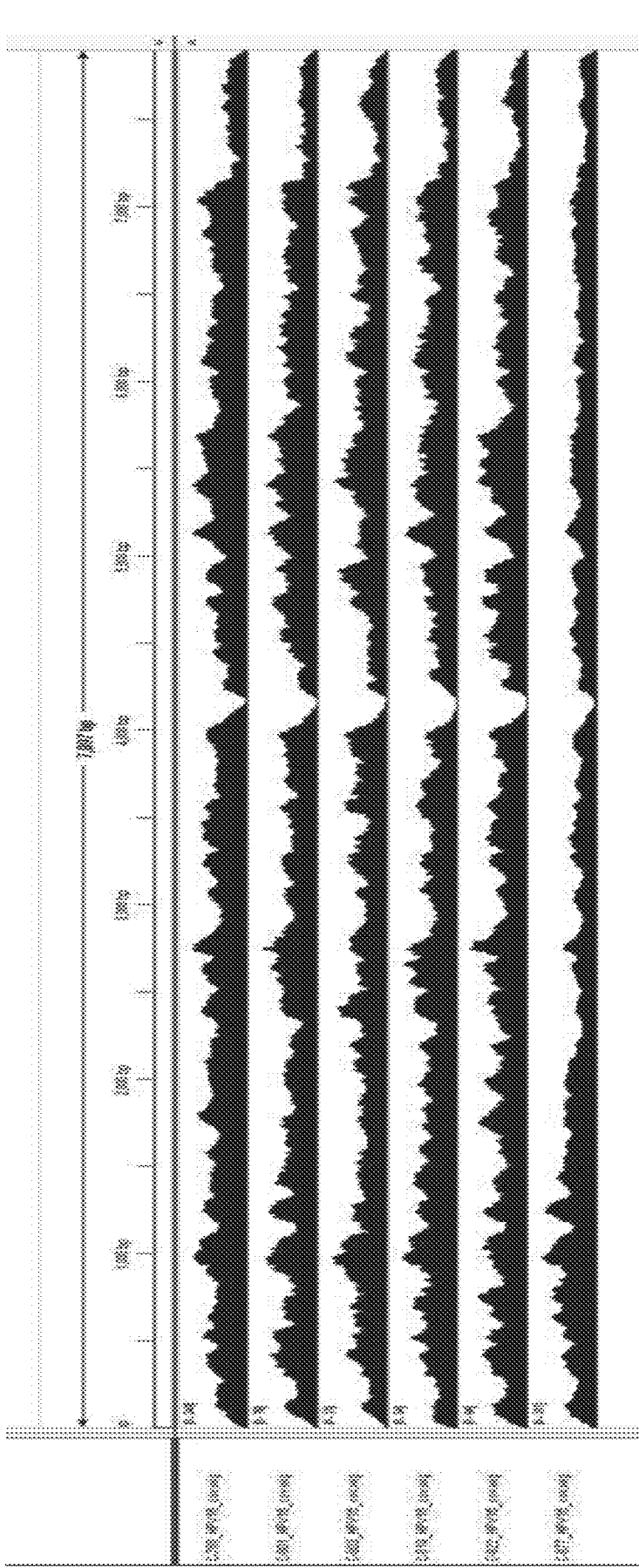
FIG. 95 shows the frequency of plasma DNA fragments ending on each nucleotide in the HPV genome for 6 subjects.

Plasma samples from 23 individuals without cancer (healthy controls or chronic HBV carriers) or with various cancers (NPC, HCC, CC, HNSCC) were analyzed by targeted sequencing using the capture probe design as shown in Table 2. The sequence reads were aligned to the HPV genome and counted. The data show that plasma DNA fragments derived from HPV are detectable in plasma of patients with HPV-related CC or HNSCC but not in any of the other patient groups. The amount of plasma HPV DNA fragments can be expressed in terms of absolute number detected from the amount of sequencing performed or be expressed as a proportion to the amount of other non-HPV derived sequence reads. First, the presence of the amount of plasma HPV DNA sequences above a threshold established from healthy individuals or individuals without HPV-related cancers can provide evidence for the presence of the HPV-related cancer. In this analysis, CC and HNSCC are the HPV-related cancers while NPC and HCC are the non-HPV related cancers. In this analysis, a cutoff>0 fragments mapped to HPV or >0% reads mapped to HPV was used. Other methods to establish reference values or cutoffs based on data from individuals without HPV-related cancers, including ROC analysis, >90$^{th}$ percentile, >99$^{th}$ percentile, >2 standard deviations or >3 standard deviations above the mean, for example, can be used. Second, the difference in range of abundance of plasma HPV DNA sequences in a sample can be reflective of the stage of the HPV-related cancer. Third, the difference in the order of magnitude of the plasma HPV DNA sequences can be reflective of cancers of different tissue origin. For example, Table 1 shows that the amounts of plasma HPV DNA sequences are generally higher in samples of CC patients than those of HNSCC patients. Fourth, as shown in FIG. 94 and FIG. 95, the size profile and fragmentation patterns, respectively, of the plasma HPV DNA sequences can allow one to distinguish those with HPV-related cancer and individuals without cancer but with detectable plasma HPV DNA due to other benign conditions. The size profile and fragmentation patterns of the plasma HPV DNA sequences can further allow one to distinguish between HPV-related cancers of different tissue origin, for example CC and HNSCC (FIG. 86). Fifth, sequence variants among the plasma HPV DNA sequences can allow one to determine the serotype or genotype of HPV and further provide evidence for the high likelihood of the cancer diagnosis. For example, CC is typically associated with HPV types 16 and HPV type 18

3. Methylation Detection Assay

Figure 19:
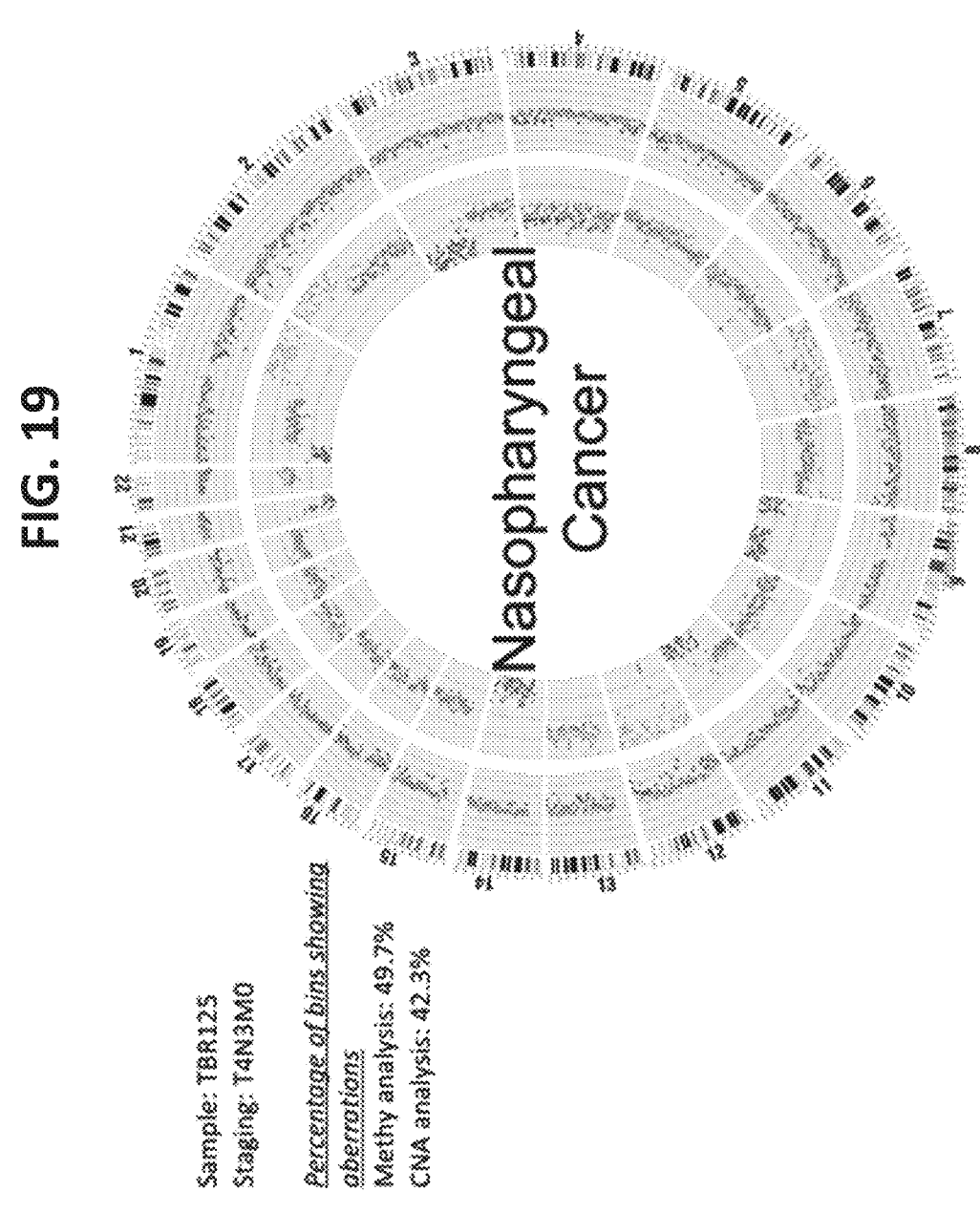
FIG. 19 depicts a chromosome ideogram showing arm-level z-score analysis to detect copy number and/or methylation aberrations in a pre-operative (inner ring) and post-operative (outer ring) plasma sample of a subject.

In another embodiment, an assay (e.g., first assay or a second assay) can comprise performing methylation-aware sequencing, or sequencing cell-free nucleic acid molecules to determine a methylation status at one or more genomic locations. While examples and embodiments have been provided herein, additional techniques and embodiments related to, e.g., determining a methylation status, can be found in PCT AU/2013/001088, filed Sep. 20, 2013, which is entirely incorporated herein by reference. Qualitative changes in the methylation profile can be reflected among the plasma methylome data. As shown in FIG. 19, for example, plasma DNA molecules originating from genes that are hypermethylated only in cancer cells can show hypermethylation in plasma of a cancer patient when compared with plasma DNA molecules originating from the same genes but in a sample of a healthy control. Because aberrant methylation occurs in most cancers, the methods herein described can be applied to the detection of all forms of malignancies with aberrant methylation, for example, malignancies in, but not limited to, the lung, breast, colorectum, prostate, nasopharynx, stomach, testes, skin, nervous system, bone, ovary, liver, hematologic tissues, pancreas, uterus, kidney, lymphoid tissues, etc. The malignancies can be of a variety of histological subtypes, for example, carcinomas, adenocarcinomas, sarcomas, fibroadenocarcinoma, neuroendocrine, undifferentiated.

Tumor-derived DNA molecules can be distinguished from the background non-tumor-derived DNA molecules because the overall short size profile of tumor-derived DNA can be accentuated for DNA molecules originating from loci with tumor-associated aberrant hypomethylation which can have an additional effect on the size of the DNA molecule. Also, tumor-derived plasma DNA molecules can be distinguished from the background non-tumor-derived plasma DNA molecules using multiple characteristic features that are associated with tumor DNA, including but not limited to single nucleotide variants, copy number gains and losses, translocations, inversions, aberrant hyper- or hypo-methylation and size profiling. As all of these changes can occur independently, the combined use of these features can provide additive advantage for the sensitive and specific detection of cancer DNA in plasma.

The methylation densities of the pre-operative plasma DNA can be lower than those of the non-malignant tissues in the cancer patient. This can result from the presence of DNA from the tumor tissue which was hypomethylated. This lower plasma DNA methylation density can be used as a biomarker for the detection and monitoring of cancer. For cancer monitoring, if a cancer is progressing, then there can be an increased amount of cancer-derived DNA in plasma with time. In this example, an increased amount of circulating cancer-derived DNA in plasma can lead to a further reduction in the plasma DNA methylation density on a genome wide level.

Conversely, if a cancer responds to treatment, then the amount of cancer-derived DNA in plasma can decrease with time. In this example, a decrease in the amount of cancer-derived DNA in plasma can lead to an increase in the plasma DNA methylation density. For example, if a lung cancer patient with epidermal growth factor receptor mutation has been treated with a targeted therapy, e.g., tyrosine kinase inhibition, then an increase in plasma DNA methylation density can signify a response. Subsequently, the emergence of a tumor clone resistant to tyrosine kinase inhibition can be associated with a decrease in plasma DNA methylation density which can indicate a relapse.

Plasma methylation density measurements can be performed serially and the rate of change of such measurements can be calculated and used to predict or correlate with clinical progression or remission or prognosis. For selected genomic loci which are hypermethylated in cancer tissues but hypomethylated in normal tissues, e.g., the promoter regions of a number of tumor suppressor genes, the relationship between cancer progression and favorable response to treatment can be opposite to the patterns described above.

Plasma methylation density values beyond, for example lower than, a defined cutoff based on the reference values can be used to assess if a subject's plasma has tumor DNA or not. To detect the presence of hypomethylated circulating tumor DNA, the cutoff can be defined as lower than the 5th or 1st percentiles of the values of the control population, or based on a number of standard deviations, for example, 2 or 3 standard deviations (SDs), below the mean methylation density values of the controls, or based on determining a multiple of the median (MoM). For hypermethylated tumor DNA, the cutoff can be defined as higher than the 95th or 99th percentile of the values of the control population, or based on a number of standard deviations, for example, 2 or 3 SDs, above the mean methylation density values of the controls, or based on determining a multiple of the median (MoM). In one embodiment, the control population can be matched in age to the test subject. The age matching does not need to be exact and can be performed in age bands (e.g., 30 to 40 years, for a test subject of 35 years).

To assess if a tested subject is having cancer, the result of the tested subject can be compared to the values of a reference group. In one embodiment, the reference group can comprise of a number of healthy subjects. In another embodiment, the reference group can comprise of subjects with non-malignant conditions, for example, chronic hepatitis B infection or cirrhosis. The difference in the methylation densities between the tested subject and the reference group can then be quantified.

In one embodiment, a reference range can be derived from the values of the control group. Then deviations in the result of the tested subject from the upper or lower limits of the reference group can be used to determine if the subject has a tumor. This quantity can be affected by the fractional concentration of tumor-derived DNA in the plasma and the difference in the level of methylation between malignant and nonmalignant tissues. Higher fractional concentration of tumor-derived DNA in plasma can lead to larger methylation density differences between the test plasma sample and the controls. A larger degree of difference in the methylation level of the malignant and non-malignant issues can also be associated with larger methylation density differences between the test plasma sample and the controls. In yet another embodiment, different reference groups are chosen for test subjects of different age ranges.

In one embodiment, the mean and SD of the methylation densities of the four control subjects can be calculated for each 1 Mb bin. Then for corresponding bins, the difference between the methylation densities of the HCC patient and the mean value of the control subjects can be calculated. In one embodiment, this difference can then be divided by the SD of the corresponding bin to determine the z-score. In other words, the z-score represents the difference in methylation densities between the test and control plasma samples expressed as a number of SDs from the mean of the control subjects. A z-score>3 of a bin indicates that the plasma DNA of the HCC patient is more hypermethylated than the control subjects by more than 3 SDs in that bin whereas a z-score of <–3 in a bin indicates that the plasma DNA of the HCC patient is more hypomethylated than the control subjects by more than 3 SDs in that bin.

The cutoff values of the number of bins can be determined using statistical methods. For example, approximately 0.15% of the bins can be expected to have a zscore of <–3 based on a normal distribution. Therefore, the cutoff number of bins can be 0.15% of the total number of bins being analyzed. In other words, if a plasma sample from a subject shows more than 0.15% of bins with z-scores<–3, there can be a source of hypomethylated DNA in plasma, namely cancer.

In yet another embodiment, the cutoff number can be determined by receiver operator characteristic (ROC) curve analysis by analyzing a number of cancer patients and individuals without cancer. To further validate the specificity of this approach, a plasma sample from a patient seeking medical consultation for a non-malignant condition (C06) was analyzed. 1.1% of the bins had a z-score of <–3. In one embodiment, different thresholds can be used to classify different levels of disease status. A lower percentage threshold can be used to differentiate healthy status from benign conditions and a higher percentage threshold to differentiate benign conditions from malignancies.

In other embodiments, other methods can be used to survey the methylation level of plasma DNA. For example, the proportion of methylated cytosine residues over the total content of cytosine residues can be determined using mass spectrometry (see e.g., M. L. Chen et al. 2013 *Clin Chem*; doi: 10.1373/clinchem.2012.193938) or massively parallel sequencing. However, as most cytosine residues can not be in the CpG dinucleotide context, the proportion of methylated cytosine among total cytosine residuals can be relatively small when compared to methylation levels estimated in the context of CpG dinucleotides. The methylation level of the tissue and plasma samples obtained from the HCC patient as well as the four plasma samples obtained from the four healthy controls can be determined. The methylation levels can be measured in the context of CpGs, any cytosines, in 5'-CHG-3' and 5'-CHH-3' contexts using the genome-wide massively parallel sequencing data. H refers to adenine, thymine or cytosine residues.

In other embodiments, the methylation status of the plasma DNA can be determined by methods using antibodies against methylated cytosine, for example, methylated DNA immunoprecipitation (MeDIP). In yet another embodiment, the level of 5-hydroxymethylcytosine in plasma DNA can be determined. In this regard, a reduction in the level of 5-hydroxymethylcytosine can be an epigenetic feature of certain cancer, e.g., melanoma (see e.g., C. G. Lian, et al. 2012 *Cell;* 150: 1135-1146).

In another embodiment, this approach can be applied to other types of cancers. The plasma samples from 2 patients with adenocarcinoma of the lung (CL1 and CL2), 2 patients with nasopharyngeal carcinoma (NPC1 and NPC2), 2 patients with colorectal cancer (CRC1 and CRC2), 1 patient with metastatic neuroendocrine tumor (NE1) and 1 patient with metastatic smooth muscle sarcoma (SMS1) can be analyzed. The plasma DNA of these subjects can be bisulfite-converted and sequenced using the Illumina HiSeq2000 platform for 50 bp at one end. The four healthy control subjects can be used as a reference group for the analysis of these 8 patients. 50 bp of the sequence reads at one end can be used. The whole genome can be divided into 1 Mb bins. The mean and SD of methylation density can be calculated for each bin using the data from the reference group. Then the results of the 8 cancer patients can be expressed as z-scores which represent the number of SDs from the mean of the reference group. A positive value can indicate that the methylation density of the test case is lower than the mean of the reference group, and vice versa.

4. Fragment Assays

In another embodiment, an assay (e.g., first assay or a second assay) can comprise performing an assay, e.g., next generation sequencing assay, to analyze nucleic acid fragments, e.g., fragments of EBV DNA.

Factors affecting the fragmentation pattern of cell-free DNA (e.g., plasma DNA) and the applications, including those in molecular diagnostics, of the analysis of cell-free DNA fragmentation patterns are described. Various applications can use a property of a fragmentation pattern to determine a proportional contribution of a particular tissue type, to determine a genotype of a particular tissue type (e.g., fetal tissue in a maternal sample or tumor tissue in a sample from a cancer patient), and/or to identify preferred ending positions for a particular tissue type, which may then be used to determine a proportional contribution of a particular tissue type. In some embodiments, the preferred ending positions for a particular tissue can also be used to measure the absolute contribution of a particular tissue type in a sample, e.g. in number of genomes per unit volume (e.g. per milliliter).

Examples of a classification of a proportional contribution include specific percentages, range of percentage, or whether the proportional contribution is above a specified percentage can be determined as a classification. For determining the classification of a proportional contribution, some embodiments can identify preferred ending positions corresponding to a particular tissue type (e.g., fetal tissue or tumor tissue). Such preferred ending positions can be determined in various ways, e.g., by analyzing a rate at which cell-free DNA molecules end on genomic positions, comparisons such rates to other samples (e.g., not having a relevant condition), and comparisons of sets of genomic positions with high occurrence rates of ends of cell-free DNA molecules for different tissues and/or different samples differing in a condition. A relative abundance of cell-free DNA molecules ending at the preferred ending positions relative to cell-free DNA molecules ending at other genomic positions can be compared to one or more calibration values determined from one or more calibration biological samples whose proportional contribution of the particular tissue type are known. Data provided herein shows a positive relationship between various measures of relative abundance and a proportional contribution of various tissues in a sample.

For determining the classification of a proportional contribution, some embodiments can use an amplitude in a fragmentation pattern (e.g., number of cell-free DNA molecules ending at a genomic position). For example, one or more local minima and one or more local maxima can be identified by analyzing the numbers of cell-free DNA molecules that end at a plurality of genomic positions. A separation value (e.g., a ratio) of a first number of cell-free DNA molecules at one or more local maxima and a second number of cell-free DNA molecules at one or more local minima is shown to be positively related to a proportional contribution of the particular tissue type.

In some embodiments, a concentration of the tissue of interest can be measured in relation to the volume or weight of the cell-free DNA samples. For example, quantitative PCR can be used to measure the number of cell-free DNA molecules ending at one or more preferred ends in a unit volume or unit weight of the extracted cell-free DNA sample. Similar measurements can be made for calibration samples, and thus the proportional contribution can be determined as a proportional contribution, as the contribution is a concentration per unit volume or unit weight.

For determining a genotype of a particular tissue type (e.g., fetal tissue or tumor tissue) in a mixture of cell-free DNA from different tissue types, some embodiments can identify a preferred ending position for the particular tissue type. For each cell-free DNA molecule of a set of cell-free DNA molecules ending on the preferred ending position, a corresponding base occurring at the preferred ending position or within the rest of the fragment can be determined. The corresponding bases can be used to determine the genotype at the preferred ending position, e.g., based on percentages of different bases seen. In various implementations, a high percentage of just one base (e.g., above 90%) can indicate the genotype is homozygous for the base, while two bases having similar percentages (e.g., between 30-70%) can lead to a determination of the genotype being heterozygous.

To identify preferred ending positions, some embodiments can compare a local maximum for left ends of cell-free DNA molecules to a local maximum for right ends of cell-free DNA molecules. Preferred ending positions can be identified when corresponding local maximum are sufficiently separated. Further, amounts of cell-free DNA molecules ending on a local maximum for left/right end can be compared to an amount of cell-free DNA molecules for a local maximum with low separation to determine a proportional contribution of a tissue type.

In the description below, an overview of fragmentation and techniques is first described, followed by specifics of fragmentation patterns and examples of quantification thereof, and further description relating to determining a proportional contribution, identifying preferred ending positions, and determining a genotype.

I. Overview of Fragmentation and Techniques

In this disclosure, we show that there exists a non-random fragmentation process of cell-free DNA. The non-random fragmentation process takes place to some extent in various types of biological samples that contain cell-free DNA, e.g. plasma, serum, urine, saliva, cerebrospinal fluid, pleural fluid, amniotic fluid, peritoneal fluid, and ascitic fluid. Cell-free DNA occurs naturally in the form of short fragments. Cell-free DNA fragmentation refers to the process whereby high molecular weight DNA (such as DNA in the nucleus of a cell) are cleaved, broken, or digested to short fragments when cell-free DNA molecules are generated or released.

Not all cell-free DNA molecules are of the same length. Some molecules are shorter than others. It has been shown that cell-free DNA, such as plasma DNA, is generally shorter and less intact than cellular DNA. Cell-free DNA also has poor intact probability or poorer integrity within open chromatin domains, including around transcription start sites, and at locations between nucleosomal cores, such as at the linker positions (Straver et al Prenat Diagn 2016, 36:614-621). Each different tissue may have its characteristic gene expression profile which in turn may be regulated by various approaches, including chromatin structure and nucleosomal positioning. Thus, cell-free DNA patterns of intact probability or integrity at certain genomic locations, such as that of plasma DNA, are signatures or hallmarks of the tissue origin of those DNA molecules. Similarly, when a disease process, e.g. cancer, alters the gene expression profile and function of the genome of a cell, the cell-free DNA intact probability profile derived from the cells with disease would be reflective of those cells. The cell-free DNA profile, hence, would provide evidence for or are hallmarks of the presence of the disease.

Some embodiments further enhance the resolution for studying the profile of cell-free DNA fragmentation. Instead of just summating reads over a stretch of nucleotides to identify regions with higher or lower intact probability or integrity, we studied the actual ending positions or termini of individual cell-free DNA molecules, especially plasma DNA molecules. Remarkably, our data reveal that the specific locations of where cell-free DNA molecules are cut are non-random. High molecular weight genomic tissue DNA that are sheared or sonicated in vitro show DNA molecules with ending positions randomly scattered across the genome. However, there are certain ending positions of cell-free DNA molecules that are highly represented within a sample, such as plasma. The number of occurrence or representation of such ending positions is statistically significantly higher than expected by chance alone. These data bring our understanding of cell-free DNA fragmentation one step beyond that of regional variation of integrity (Snyder et al Cell 2016, 164: 57-68). Here we show that the process of cell-free DNA fragmentation is orchestrated even down to the specific nucleotide position of cutting or cleavage. We termed these non-random positions of cell-free DNA ending positions as the preferred ending positions or preferred ends.

In the present disclosure, we show that there are cell-free DNA ending positions that commonly occur across individuals of different physiological states or disease states. For example, there are common preferred ends shared by pregnant and non-pregnant individuals, shared by a pregnant and a cancer patient, shared with individuals with and without cancer. On the other hand, there are preferred ends that mostly occur only in pregnant women, only in cancer patients, or only in non-pregnant individuals without cancer. Interestingly, these pregnancy-specific or cancer-specific or disease-specific ends are also highly represented in other individuals with comparable physiological or disease state. For example, preferred ends identified in the plasma of one pregnant woman are detectable in plasma of other pregnant women. Furthermore, the quantity of a proportion of such preferred ends correlated with the fetal DNA fraction in plasma of other pregnant women. Such preferred ends are indeed associated with the pregnancy or the fetus because their quantities are reduced substantially in the post-delivery maternal plasma samples. Similarly, in cancer, preferred ends identified in the plasma of one cancer patient are detectable in plasma of another cancer patient. Furthermore, the quantity of a proportion of such preferred ends correlated with the tumor DNA fraction in plasma of other cancer patients. Such preferred ends are associated with cancer because their quantities are reduced following treatment of cancer, e.g. surgical resection.

There are a number of applications or utilities for the analysis of cell-free DNA preferred ends. They can provide information about the fetal DNA fraction in pregnancy and hence the health of the fetus. For example, a number of pregnancy-associated disorders, such as preeclampsia, preterm labor, intrauterine growth restriction (IUGR), fetal chromosomal aneuploidies and others, have been reported to be associated with perturbations in the fractional concentration of fetal DNA, namely fetal DNA fraction, or fetal fraction, compared with gestational age matched control pregnancies. The cell-free plasma DNA preferred ends associated with cancer reveals the tumor DNA fraction or fractional concentration in a plasma sample. Knowing the tumor DNA fraction provides information about the stage of cancer, prognosis and aid in monitoring for treatment efficacy or cancer recurrence. The profile of cell-free DNA preferred ends would also reveal the composition of tissues contributing DNA into the biological sample containing cell-free DNA, e.g. plasma. One may therefore be able to identify the tissue origin of cancer or other pathologies, e.g. cerebrovascular accidents (i.e. stroke), organ manifestations of systemic lupus erythematosus.

A catalog of preferred ends relevant to particular physiological states or pathological states can be identified by comparing the cell-free DNA profiles of preferred ends among individuals with different physiological or pathological states, e.g. non-pregnant compared with pregnant samples, cancer compared with non-cancer samples, or profile of pregnant woman without cancer compared with profile of non-pregnant cancer patients. Another approach is to compare the cell-free DNA profiles of preferred ends at different time of a physiological (e.g. pregnancy) or pathological (e.g. cancer) process. Examples of such time points include before and after pregnancy, before and after delivery of a fetus, samples collected across different gestational ages during pregnancy, before and after treatment of cancer (e.g. targeted therapy, immunotherapy, chemotherapy, surgery), different time points following the diagnosis of cancer, before and after progression of cancer, before and after development of metastasis, before and after increased severity of disease, or before and after development of complications.

In addition, the preferred ends can be identified using genetic markers that are relevant for a particular tissue. For example, cell-free DNA molecules containing a fetal-specific SNP allele would be useful for identifying fetal-specific preferred ends in a sample such as maternal plasma. Vice versa, plasma DNA molecules containing a maternal-specific SNP allele would be useful for identifying maternal-specific preferred ends in maternal plasma. Plasma DNA molecules containing a tumor-specific mutation can be used to identify preferred ends associated with cancer. Plasma DNA molecules containing either a donor or recipient-specific SNP allele in the context of organ transplantation are useful for identifying preferred ends of the transplanted or non-transplanted organ. For example, the SNP alleles specific to the donor would be useful for identifying preferred ends representative of the transplanted organ.

A preferred end can be considered relevant for a physiological or disease state when it has a high likelihood or probability for being detected in that physiological or pathological state. In other embodiments, a preferred end is of a certain probability more likely to be detected in the relevant physiological or pathological state than in other states. Because the probability of detecting a preferred end in a relevant physiological or disease state is higher, such preferred or recurrent ends (or ending positions) would be seen in more than one individual with that same physiological or disease state. The high probability would also render such preferred or recurrent ends to be detectable many times in the same cell-free DNA sample or aliquot of the same individual. In some embodiments, a quantitative threshold may be set to limit the inclusion of ends that are detected at least a specified number of times (e.g., 5, 10, 15, 20, etc.) within the same sample or same sample aliquot to be considered as a preferred end.

After a catalog of cell-free DNA preferred ends is established for any physiological or pathological state, targeted or non-targeted methods can be used to detect their presence in cell-free DNA samples, e.g. plasma, or other individuals to determine a classification of the other tested individuals having a similar health, physiologic or disease state. The cell-free DNA preferred ends can be detected by random non-targeted sequencing. The sequencing depth would need to be considered so that a reasonable probability of identifying all or a portion of the relevant preferred ends can be achieved.

For example, capture probes may be designed to cover the whole EBV genome, the whole hepatitis B virus (HBV) genome, the whole human papillomavirus (HPV) genome and/or multiple genomic regions in the human genome (including regions on chr1, chr2, chr3, chr5, chr8, chr15 and chr22). To efficiently capture viral DNA fragments from plasma, more probes hybridizing to viral genomes than human autosomal regions of interest may be used. In one embodiment, for whole viral genomes, on average 100 hybridizing probes covering each region with ~200 bp in size (e.g., 100× tiling capturing probes). For the regions of interest of human genome, we designed on average 2 hybridizing probes covering each region with ~200 bp in size (e.g., 2× tiling capturing probes). The capture probes may be designed according to Table 2.

Alternatively, hybridization capture of loci with high density of preferred ends can be performed on the cell-free DNA samples to enrich the sample with cell-free DNA molecules with such preferred ends following but not limited to detection by sequencing, microarray, or the PCR. Yet, alternatively, amplification based approaches can be used to specifically amplify and enrich for the cell-free DNA molecules with the preferred ends, e.g. inverse PCR, rolling circle amplification. The amplification products can be identified by sequencing, microarray, fluorescent probes, gel electrophoresis and other standard approaches known to those skilled in the art.

TABLE 2

| Design of capture probes for targeted sequencing | | | |
| --- | --- | --- | --- |
| | | Length (bp) | Targeted capture design |
| Autosomes | chr1 | 29,382,851 | 2x tiling |
| | chr2 | 819,161 | capturing |
| | chr3 | 25,981,149 | probes |
| | chr5 | 2,339,138 | |
| | chr8 | 21,438,698 | |
| | chr15 | 767,847 | |
| | chr22 | 327,728 | |
| Viral | EBV | 170,771 | 100x tiling |
| targets | HBV | 3,216 | capturing |
| | HPV16 | 7,855 | probes |
| | HPV18 | 7,789 | |
| | HPV31 | 7,791 | |
| | HPV33 | 7,744 | |
| | HPV35 | 7,813 | |
| | HPV39 | 7,734 | |
| | HPV45 | 7,784 | |
| | HPV51 | 7,674 | |
| | HPV52 | 7,820 | |
| | HPV56 | 7,814 | |
| | HPV58 | 7,705 | |
| | HPV66 | 7,806 | |
| | HPV68 | 7,751 | |
| | HPV70 | 7,884 | |

In practice, one end position can be the genomic coordinate or the nucleotide identity of the outermost base on one extremity of a cell-free DNA molecule that is detected or determined by an analytical method, such as but not limited to massively parallel sequencing or next-generation sequencing, single molecule sequencing, double- or single-stranded DNA sequencing library preparation protocols, PCR, other enzymatic methods for DNA amplification (e.g. isothermal amplification) or microarray. Such in vitro techniques may alter the true in vivo physical end(s) of the cell-free DNA molecules. Thus, each detectable end may represent the biologically true end or the end is one or more nucleotides inwards or one or more nucleotides extended from the original end of the molecule. For example, the Klenow fragment is used to create blunt-ended double-stranded DNA molecules during DNA sequencing library construction by blunting of the 5' overhangs and filling in of the 3' overhangs. Though such procedures may reveal a cell-free DNA end position that is not identical to the biological end, clinical relevance can still be established. This is because the identification of the preferred being relevant or associated with a particular physiological or pathological state can be based on the same laboratory protocols or methodological principles that would result in consistent and reproducible alterations to the cell-free DNA ends in both the calibration sample(s) and the test sample(s). A number of DNA sequencing protocols use single-stranded DNA libraries (Snyder et al Cell 2016, 164: 57-68). The ends of the sequence reads of single-stranded libraries may be more inward or extended further than the ends of double-stranded DNA libraries.

The genome identity or genomic coordinate of the end position can be derived from results of alignment of sequence reads to a human reference genome, e.g. hg19. It can be derived from a catalog of indices or codes that represent the original coordinates of the human genome. While an end is the nucleotide at one or both extremities of a cell-free DNA molecule, the detection of the end can be done through the recognition of other nucleotide or other stretches of nucleotides on the plasma DNA molecule. For example, the positive amplification of a plasma DNA molecule with a preferred end detected via a fluorescent probe that binds to the middle bases of the amplicon. For instance, an end can be identified by the positive hybridization of a fluorescent probe that binds to some bases on a middle section of a plasma DNA molecule, where the fragment size known. In this way, one can determine the genomic identity or genomic coordinate of an end by working out how many bases are external to the fluorescent probe with known sequence and genomic identity. In other words, an end can be identified or detected through the detection of other bases on the same plasma DNA molecule. An end can be a position or nucleotide identity on a cell-free DNA molecule that is read by but not limited to target-specific probes, mini-sequencing, and DNA amplification.

II. Fragmentation Patterns of Plasma DNA

For the analysis of the fragmentation pattern of maternal plasma DNA, we sequenced the plasma DNA from a pregnant woman recruited from the Department of Obstetrics and Gynaecology at a gestational age of 12 weeks (Lo et al. Sci Transl Med 2010; 2(61):61ra91). Plasma DNA obtained from the mother was subjected to massively parallel sequencing using the Illumina Genome Analyzer platform. Other massively parallel or single molecule sequencers can be used. Paired-end sequencing of the plasma DNA molecules was performed. Each molecule was sequenced at each end for 50 bp, thus totaling 100 bp per molecule. The two ends of each sequence were aligned to the reference human genome (Hg18 NCBI.36) using the SOAP2 program (Li R et al. Bioinformatics 2009, 25:1966-7). DNA was also extracted from the buffy coat samples of the father and mother, and the CVS sample. These DNA samples were genotyped using the Affymetrix Genome-Wide Human SNP Array 6.0 system.

A. Example Quantifying of Fragmentation

To reflect the fragmentation patterns, intact probability ($P_I$) can be determined for each nucleotide for the genome based on the sequencing results of the maternal plasma DNA.

$$P_I = \frac{N_z}{N_T}$$

where $N_z$ is the number of full length sequenced reads covering at least z nucleotides (nt) on both sides (5' and 3') of the target nucleotide; and $N_T$ is the total number of sequenced reads covering the target nucleotide.

The value of $P_I$ can reflect the probability of having an intact DNA molecule centered at a particular position with a length of twice the value of z plus 1 (2z+1). The higher the value of intact probability ($P_I$), the less likely is the plasma DNA being fragmented at the particular nucleotide position. To further illustrate this, the definition of intact probability is illustrated in FIG. 23.

Figure 23:
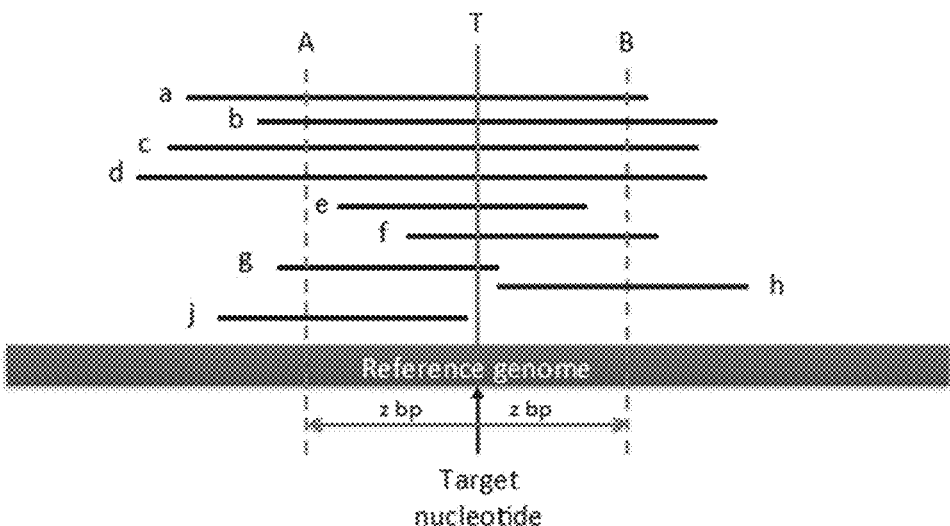
FIG. 23 shows an illustrative example for the definition of intact probability ($P_I$) according to embodiments of the present invention.

FIG. 23 shows an illustrative example for the definition of intact probability ($P_I$). T is the position of the target nucleotide at which PI is calculated for. A and B are two positions at z nucleotides (nt) upstream (5') and z nt downstream (3') of T, respectively. The black lines labeled from a to j represent sequenced plasma DNA fragments from the maternal plasma. Fragments a to d cover all the three positions A, B and T. Therefore, the number of fragments covering at least z nt on both sides (5' and 3') of the target nucleotide ($N_z$) is 4. In addition, fragments e, f and g also cover the position T, but they do not cover both positions A and B. Therefore, there are a total of 7 fragments covering position T ($N_T$=7). Fragments h and j cover either A or B but not T. These fragments are not counted in $N_z$ or $N_T$. Therefore, the PI in this particular example is 4/7 (57%).

In one embodiment, PI can be calculated using 25 as the value of z. Thus, the intact plasma DNA fragments would be defined as fragments covering at least 25 nt upstream of the target position to 25 nt downstream of the target position. In other embodiments, other values of z can be used, for example, but not limited to, 10, 15, 20, 30, 35, 40, 45, 50, 55, 60, 65, 70, 75 and 80.

PI is an example of a relative abundance of cell-free DNA molecules ending within a window of genomic positions. Other metrics can be used, e.g., the reciprocal of PI, which would have an opposite relationship with the probability of having an intact DNA molecule. A higher value of the reciprocal of PI would indicate a higher probability of being an ending position or an ending window. Other examples are a p-value for a measured number of ending DNA fragments vs. an expected number of ending DNA fragments, a proportion of DNA fragments ending out of all aligned DNA fragments, or a proportion of preferred end termination ratio (PETR), all of which are described in more detail below. All such metrics of a relative abundance measure a rate at which cell-free DNA fragments end within a window, e.g., with a width of 2z+1, where z can be zero, thereby causing the window to be equivalent to a genomic position.

B. Periodicity of Fragmentation Pattern

Certain regions of the genome are prone to a higher rate (frequency) of breakage of a chromosomal region in a particular tissue, and thus have a higher rate of cell-free DNA fragments ending within a window in the region. A plot of the relative abundance shows a fragmentation pattern, which can have a periodic structure. The periodic structure shows positions of maximum ending positions (high cleavage) and positions of minimum ending positions (low cleavage). When using PI, a maximum value corresponds to a window of low cleavage, as PI measures an intact probability as opposed to a cleavage probability (ending position probability), which have an inverse relationship to each other.

Figures 24A, 24B:
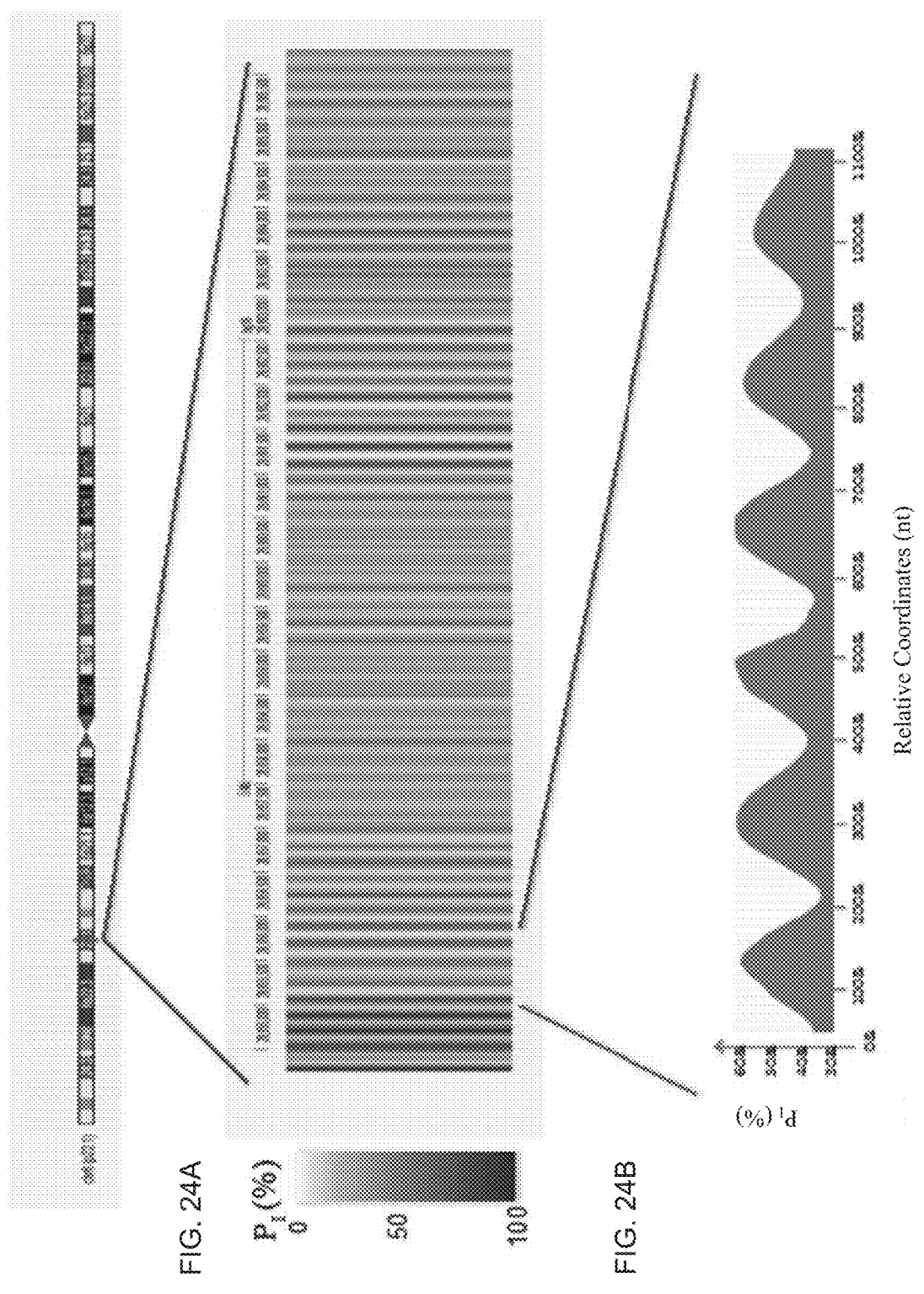
FIGS. 24A and 24B show variation in $P_I$ across a segment on chromosome 6 using 25 as the value of z, according to embodiments of the present invention.

FIGS. 24A and 24B show variation in PI across a segment on chromosome 6 using 25 as the value of z, according to embodiments of the present invention. In FIG. 24A, the variation in PI is presented in different intensities of grey as shown in the key on the left side. In FIG. 24B, the variation in PI is visualized in a shorter segment. The x-axis is the genomic coordinate in nucleotides (nt) and the y-axis is the $P_I$. The variation in $P_I$ has an apparent periodicity of around 180 bp.

C. Synchronous Variation in $P_I$ for Maternal and Fetal DNA in Maternal Plasma

While $P_I$ varies across the genome with a periodicity of approximately 180 bp, we further investigated if the variation in $P_I$ would be synchronous for fetal and maternally derived plasma DNA molecules. Synchronous variation means that the peaks (maxima) and troughs (minima) of PI occur at the same relative nucleotide positions throughout the genome or at a sufficiently high proportion of the genome. The threshold for defining the sufficiently high proportion can be adjusted for specific applications, for example, but not limited to, >20%, >25%, >30%, >35%, >40%, >45%, >50%, >55%, >60%, >65%, >70%, >75%, >80%, >85%, >90% and >95%. The two figures below (FIG. 25 and FIG. 26) show two possible relationships between the variations in $P_I$ for the maternally and fetal-derived DNA in maternal plasma.

Figure 25:
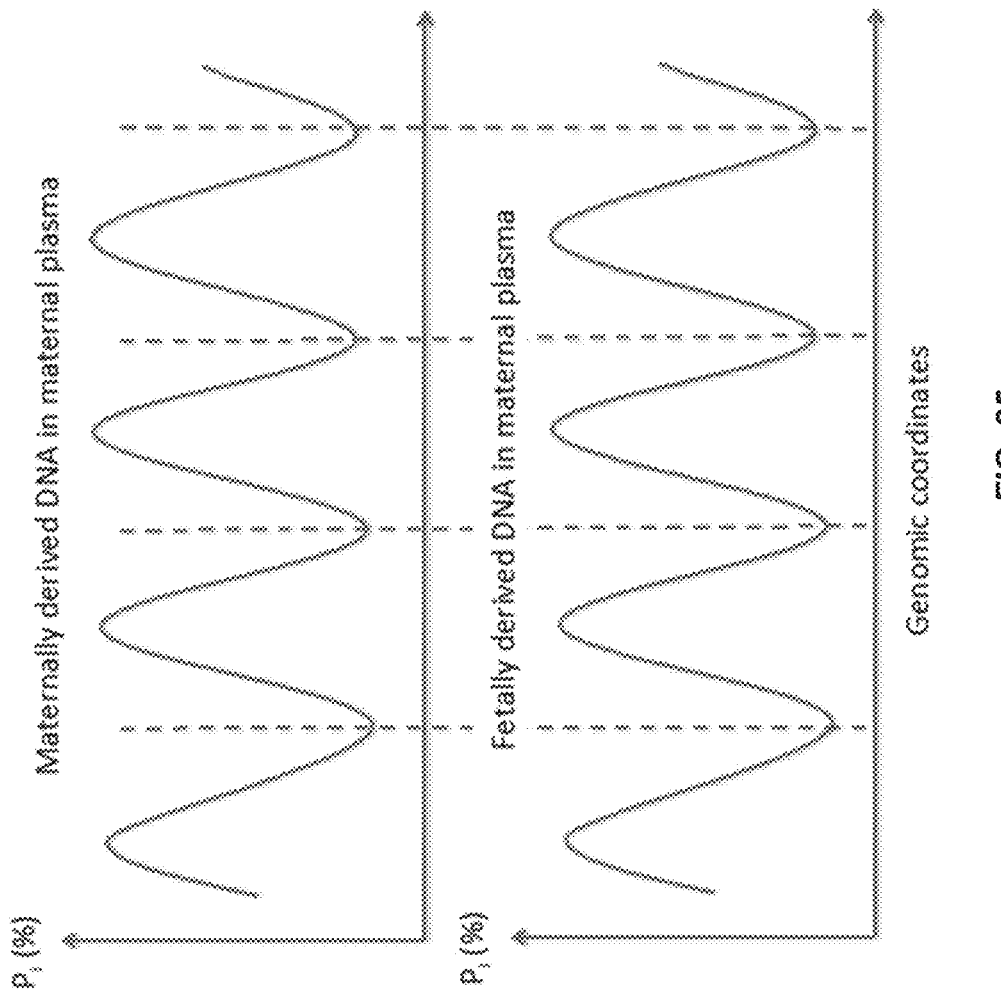
FIG. 25 shows the illustration of the synchronous variation of $P_I$ for maternally and fetal-derived DNA in maternal plasma.

FIG. 25 shows the illustration of the synchronous variation of $P_I$ for maternally and fetal-derived DNA in maternal plasma. The peaks and troughs of PI occur at the same relative positions for the maternal and fetal DNA across the genome or in most part of the genome. If there was synchronous variation in a region, then fetal-derived DNA and maternally-derived DNA would have the same fragmentation pattern, thereby hindering use of a periodicity of a fragmentation pattern in the region as a signature of one of the tissue types.

FIG. 26 shows an illustration of asynchronous variation of PI for maternally and fetal derived DNA in maternal plasma. The peaks and troughs for PI for maternal and fetal DNA do not have a constant relative relationship across the genome. At Region I, the peaks of PI for the maternal DNA coincide with the peak for the fetal DNA. At Region II, the peaks of PI for the maternal DNA coincide with the trough for the fetal DNA. At Regions III and IV, the peaks of PI for the maternal DNA are in-between the peaks and troughs of the fetal DNA. If the variation was not synchronous, such a difference in the fetal and maternal fragmentation patterns can be used as a signature to identify DNA that is likely from the fetus or the mother. Further, such a difference can be used to determine a proportional contribution of fetal or maternal tissue, as is described in more detail below. For example, DNA fragments ending at one of the peaks in region II is more likely fetal DNA, and the relative abundance of DNA fragments ending at such a peak compared to other genomic positions would increase with increasing fetal DNA fraction.

Figure 27:
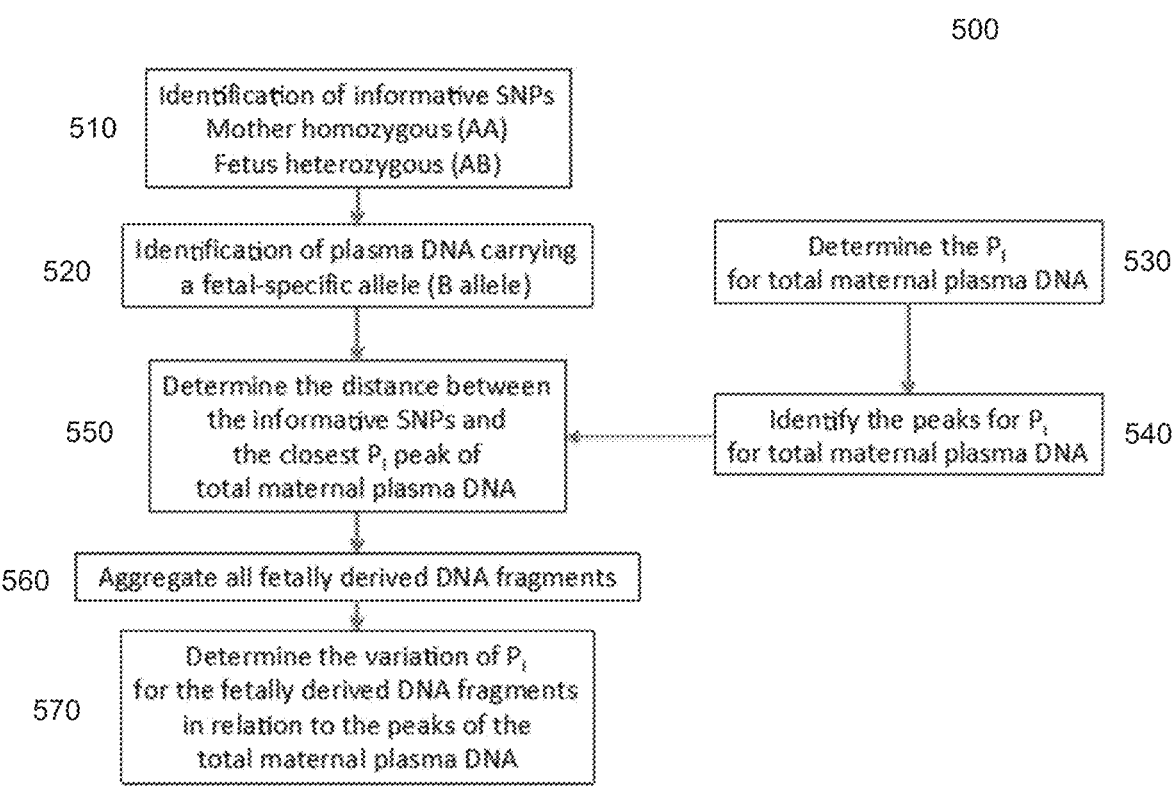
FIG. 27 is a flowchart showing an analysis on whether maternal and fetal DNA molecules are synchronous in the variation in $P_I$.

FIG. 27 is a flowchart showing an analysis 500 on whether maternal and fetal DNA molecules are synchronous in the variation in PI. Analysis 500 investigates if the variation in PI is synchronous between maternally and fetal-derived DNA in maternal plasma. Analysis 500 can use a computer system. Although analysis 500 was performed using sequencing, as described above, other techniques may be used, e.g., as described herein.

At block 510, analysis 500 identifies SNPs where the pregnant woman is homozygous (AA) and the fetus is heterozygous (AB). These SNPs are termed informative SNPs. The B allele is the fetal-specific allele. Such informative SNPs can be identified by analyzing a maternal sample that is only or predominantly of maternal origin. For example, the buffy coat of a blood sample can be used, as the white blood cells would be predominantly from the mother. Genomic positions where only one nucleotide appears (or a high percentage of one nucleotide, e.g., above 80%, which may depend on the fetal DNA fraction) can be identified as being homozygous in the mother. The plasma can be analyzed to identify positions homozygous in the mother where a sufficient percentage of DNA fragments are identified that have another allele identified.

At block 520, plasma DNA molecules having the fetal-specific allele B were identified. These DNA molecules can be identified as corresponding to fetal tissue as a result of allele B being identified.

At block 530, the value of PI was determined for the cell-free DNA in the maternal plasma. These values for PI include fetal and maternal DNA. The value for PI for a given genomic position was obtained by analyzing the sequence reads aligned to that genomic position of a reference genome.

At block 540, the peaks for PI were determined by analyzing the output of block 530. The peaks can be identified in various ways, and each peak may be restricted to just one genomic position or allowed to correspond to more than one genomic position. We observed that PI varies across the whole genome for the mostly maternally-derived DNA in maternal plasma in a sinusoid-like pattern with a periodicity of approximately 180 bp.

At block 550, a distance between the informative SNPs and the closest PI (block 540) for the total maternal plasma were determined. We identified the position of the SNP relative to the nearest peak of PI variation for the total plasma DNA which was predominantly derived from the pregnant woman herself.

At block 560, all of the fetal-derived DNA fragments were aggregated. All the detected plasma DNA fragments carrying a fetal-specific allele were aggregated for the calculation of the PI for fetal-derived DNA. PI was then calculated for the aggregated fetal-derived DNA fragments with reference to the position of the nearest PI peak for the total maternal plasma DNA. The calculation of the PI for fetal-derived DNA was performed in a similar manner as the calculation of the PI for the total maternal plasma DNA.

At block 570, a variation of PI for the fetal-derived DNA fragments was determined in relation to the peaks in PI for the total maternal plasma DNA. The variation is shown in FIG. 28.

Figure 28:
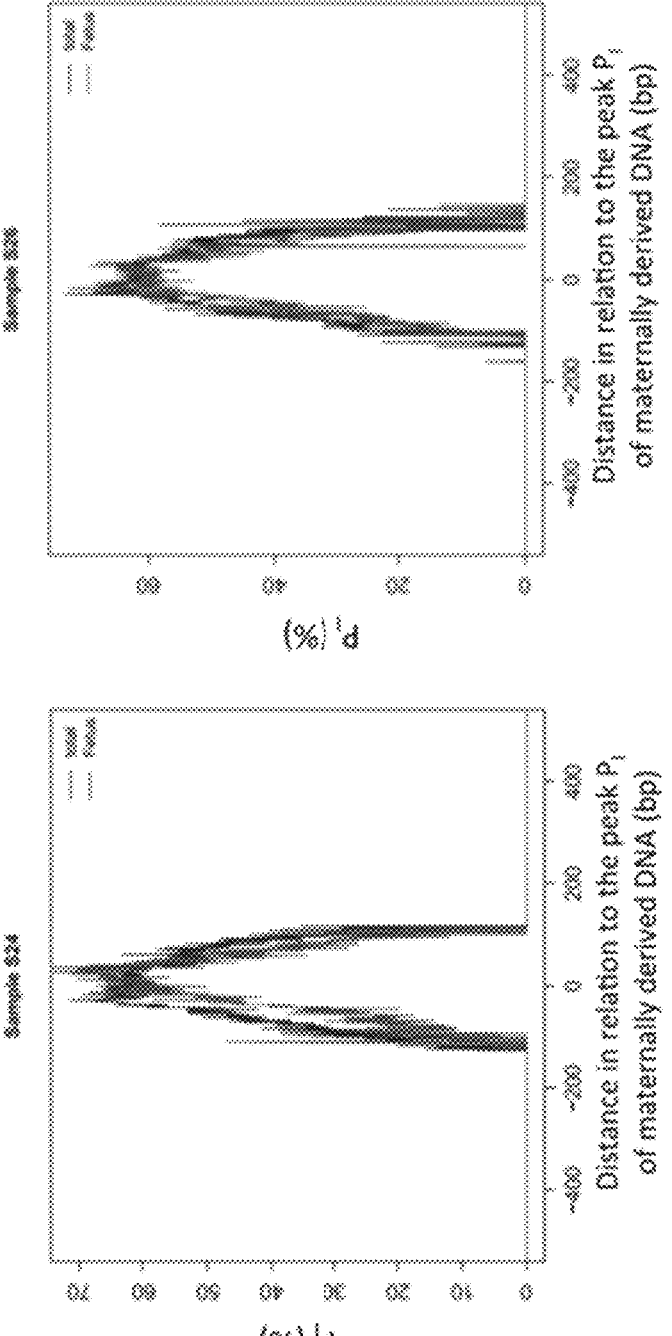
FIG. 28 shows an analysis of two maternal plasma samples (S24 and S26) for the variation of $P_I$ for maternally (red/grey) and fetal (blue/black) derived DNA fragments in maternal plasma.

FIG. 28 shows an analysis of two maternal plasma samples (S24 and S26) for the variation of PI for fetal-derived (red/grey) and total (blue/black) DNA fragments in the maternal plasma samples. The vertical axis shows PI as a percentage. The horizontal axis shows the distance in base pairs (bp) between the informative SNP and the closest peak in PI.

The total values include contributions from fetal and maternal DNA. The total values are aggregated across all peaks PI. As can be seen, the closer the SNP is to the peak PI higher the value for PI. In fact, for the fetal-derived DNA fragments, the peak PI was located at about position 0. Thus, the PI peaked at about the same position for the maternally and fetal-derived DNA fragments. From these data, we conclude that the variations of PI for maternally and fetal-derived DNA are synchronous.

Although the fragmentation patterns appear to be synchronous, the description below shows that other properties besides a periodicity can be used to distinguish the fragmentation patterns, thereby allowing a signature for a particular tissue type to be determined. For example, a difference in amplitude of the peaks and troughs for certain genomic regions has been found, thereby allowing certain positions within those regions to be used in determining a tissue-specific fragmentation pattern.

D. Factors Affecting the Variation of the Fragmentation Patterns of Plasma DNA

In previous studies, it was shown that the fragmentation of plasma DNA was not random close to the TSS (Fan et al. PNAS 2008; 105:16266-71). The probability of any plasma DNA ending on a specific nucleotide would vary with the distance to the TSS with a periodicity of approximately the size of nucleosomes. It was generally believed that this fragmentation pattern is a consequence of apoptotic degradation of the DNA. Therefore, the size of plasma DNA generally resembles the size of DNA associated with a histone complex.

In previous studies, it was also shown that the size of plasma DNA generally resembles the size of DNA associated with a nucleosome (Lo et al. Sci Transl Med 2010; 2(61):61ra91). It is believed that plasma DNA is generated through the apoptotic degradation of cellular DNA (nuclear DNA and mitochondrial DNA). This view is further supported by the lack of this nucleosomal pattern in circulating mitochondrial DNA as mitochondrial DNA is not associated with histones in cells. Although it was shown that the nucleotide position that a plasma DNA fragment ends is not random close to transcriptional start sites (Fan et al. PNAS 2008; 105:16266-71), the exact mechanism governing the fragmentation patterns of plasma DNA is still unclear.

Recently, it has further been shown that the size of plasma DNA would be different in regions with different sequence contexts (Chandrananda et al. BMC Med Genomics 2015; 8:29). The latter data also support the previous hypothesis that cell-free DNA fragments are more likely to start and end on nucleosome linker regions, rather than at nucleosomal cores. These findings are consistent with our finding of the nucleotide-to-nucleotide variation in intact probability as discussed in previous sections. Here, we further hypothesize that the amplitude of the variation in the intact probability would vary across different genomic regions. This region-to-region variation in the fragmentation variability has not been adequately explored or quantified in any previous studies. The following figures illustrate the concept of local and regional variation in PI.

FIG. 29 shows an illustration of the amplitude of variation of PI. In the previous sections, we have demonstrated that there is sinusoidal-like pattern of variation in PI on a short stretch of DNA. Here we further analyze the amplitude of the variation across larger genomic regions. The amplitude of variation refers to the difference in PI between the highest peak and trough variation of PI at a particular region with specified size. In one embodiment, the size of a particular region can be 1000 bp. In other embodiments, other sizes, for example but not limited to 600 bp, 800 bp, 1500 bp, 2000 bp, 3000 bp, 5000 bp and 10000 bp, can be used.

As shown in FIG. 29, the amplitude of region 1 is higher than the amplitude in region 2. This behavior is seen in the data below. If such occurrences of high amplitudes occur at different genomic regions for different tissues, then a measurement of amplitude can be used to determine a proportional contribution of a tissue type when analyzing a region where the amplitude differs between the tissue types. For example, if the amplitude is different for different tissue types, then the proportional contribution would vary proportionally with an increasing amount of DNA from a particular tissue type (e.g., fetal tissue or tumor tissue). Accordingly, a measure of the amplitude would correspond to a particular proportional contribution. Embodiments can use calibration data from samples where the proportional contribution is measured via another technique (e.g., by analysis of alleles, methylation signatures, degree of amplification/deletion) as are described in U.S. Patent Publication Nos. 2009/0087847, 2011/0276277, 2011/0105353, 2013/0237431, and 2014/0100121, each of which is entirely incorporated herein by reference.

In our sequencing data, we observed that the amplitude of variation in PI varied across different genomic regions. We hypothesize that the amplitude of variation of PI is related to the accessibility of the chromatin to degradation during apoptosis. Thus, we investigated the possible relationship between the amplitude of variation and DNase hypersensitivity sites in the genome. In a previous study, it was observed that the fragmentation pattern of plasma DNA is affected by its relative position to the TSS. In our analysis, we investigated the relative importance of TSS and DNase hypersensitivity sites on the effect of the fragmentation patterns of plasma DNA. Other sites where the amplitude corresponds to the tissue being tested can be used. One example of such a type of site is one that is identified using the Assay for Transposase-Accessible Chromatin with high throughput sequencing (ATAC-Seq) (Buenrostro et al. Nat Methods 2013; 10: 1213-1218). Another example of such a type of site is one that is identified using micrococcal nuclease (MNase).

We compared the amplitude of $P_I$ variation in two types of genomic regions:
  i. Regions that are TSS but not DNase hypersensitivity sites; and
  ii. Regions that are DNase hypersensitivity sites but not TSS.

The coordinates of the TSS and the DNase hypersensitivity sites were retrieved from the ENCODE database (genome.ucsc.edu/ENCODE/downloads.html).

The $P_I$ patterns around TSS and DNase I sites were profiled using the following approach.
  1) The upstream and downstream 2 kb regions around targeted reference sites were retrieved.
  2) Then the absolute genomic coordinates were re-scaled according to the distance to a reference site. For example, if a particular window with 60 bp in size is 50 bp from a reference site in an upstream direction, it will be marked as −50. Otherwise if a particular window with 60 bp in size is 50 bp from reference site in a downstream direction, it will be marked as +50.
  3) The $P_I$ value in a particular window with the same rescaled new coordinates will be recalculated using the count of intact fragments and all fragments which are overlapped with the said window.

Figure 30B:
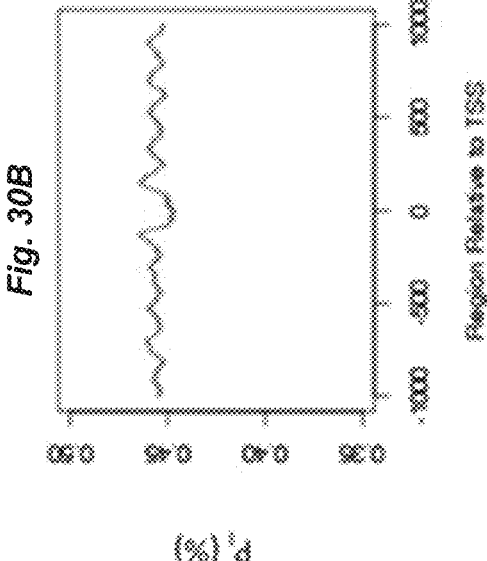
FIG. 30B shows patterns of $P_I$ variation at regions that are TSS but not DNase hypersensitivity sites.
Figure 30A:
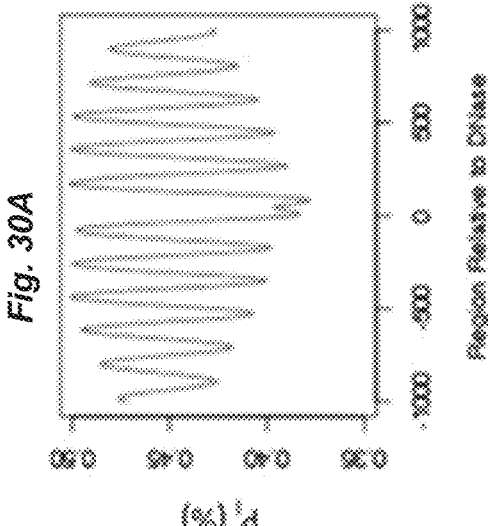
FIG. 30A shows patterns of $P_I$ variation at regions that are DNase hypersensitivity sites but not TSS.

FIG. 30A shows patterns of $P_I$ variation at regions that are DNase hypersensitivity sites but not TSS. FIG. 30B shows patterns of $P_I$ variation at regions that are TSS but not DNase hypersensitivity sites. As shown, the amplitude of variation is much higher in regions that are DNase hypersensitivity sites but not TSS, than those which are TSS but not DNase hypersensitivity sites. These observations suggest that one factor influencing the fragmentation pattern of plasma DNA is the relative position of a region subjected to fragmentation to DNase hypersensitivity sites.

III. Using Peaks and Troughs to Determine Proportion of Tissue

Having demonstrated that the relative position to the DNase hypersensitivity sites is an important factor governing the fragmentation pattern of plasma DNA, we investigated if this observation can be translated into clinical applications. It has been observed that the profiles of DNase hypersensitivity sites are different in different types of tissues. The profiles correspond to genomic locations of the sites; locations of DNase hypersensitivity sites are different for different tissues. Thus, we reason that the plasma DNA released from different types of tissues would exhibit tissue-specific fragmentation patterns. In a similar manner, other regions where the amplitude for a region varies from tissue to tissue can be used.

A. Example for DNase Hypersensitivity Sites

Figure 31:
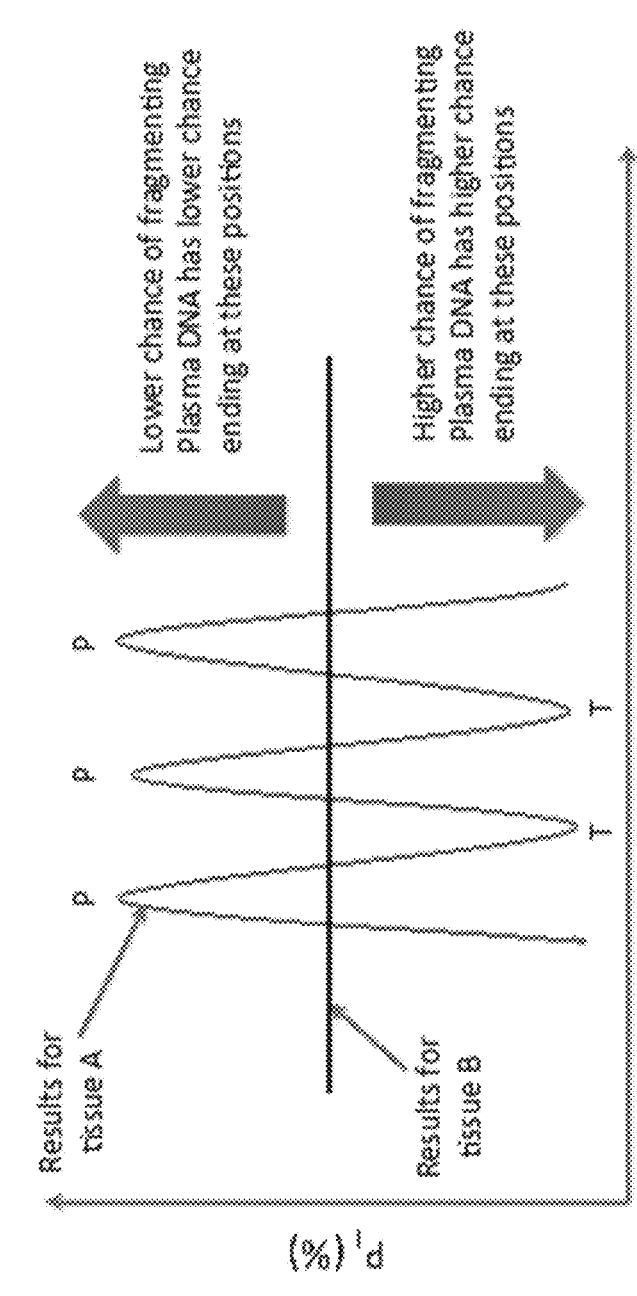
FIG. 31 shows an illustration of the principle for the measurement of the proportion of DNA released from different tissues.

FIG. 31 shows an illustration of the principle for the measurement of the proportion of DNA released from different tissues. Plasma DNA derived from tissue A has a lower probability of fragmenting at nucleotide positions with high PI (peaks, denoted by P). Therefore, the ends of plasma DNA derived from tissue A has a lower probability of being located at these nucleotide positions. In contrast, the ends of plasma DNA derived from tissue A has a higher probability of being located at nucleotide positions with low PI (troughs, denoted by T). On the other hand, as this site is not a DNase hypersensitivity site for tissue B, the amplitude of PI variation is low for plasma DNA derived from tissue B. Therefore, the probability of plasma DNA from tissue B ending on the positions P and positions T would be similar, at least relative to the amount of variation seen for tissue A.

We define the fragment end ratio at regions that are DNase hypersensitivity sites of tissue A ($FR_A$) as follows:

$$FR_A = \frac{N_T}{N_P}$$

where $N_T$ is the number of plasma DNA fragments ending on nucleotide positions of the troughs of $P_I$ and $N_P$ is the number of plasma DNA fragments ending on nucleotide positions of the peaks of $P_I$. $FR_A$ is an example of a separation value, and more specifically an example of relative abundance of DNA fragments ending on the trough relative to ending on the peak. In other embodiments, separate ratios of neighboring troughs (local minimum) and peaks (local maximum) can be determined, and an average of the separate ratios can be determined.

For tissue A, $FR_A$ would be larger than 1 because $N_T$ would be larger than $N_P$. For tissue B, $FR_A$ would be approximately 1 because NT and NP would be similar. Therefore, in a mixture containing the plasma DNA derived from both tissues A and B, the value of $FR_A$ would have a positive correlation with the proportional contribution of tissue A. In practice, $FR_A$ for tissue B does not need to be 1. As long as $FR_A$ for tissue B is different from the $FR_A$ for tissue A, the proportional contribution of the two types of tissues can be determined from $FR_A$.

In such regions, the high variation in likelihood for DNA fragments to end at the troughs will result in a higher number of DNA fragments ending at such positions than ending at the peaks (Note that for different defined relative abundance values, a higher likelihood may occur for the peaks). When more DNA fragments are from tissue type A, the larger the difference will be in the number of DNA fragments ending at the troughs and the peaks. Thus, as the proportional contribution of tissue A increases, the larger will be the separation between the number of DNA fragments ending on a trough and the number of DNA fragments ending on a peak. This separation value corresponds to the high amplitude in the likelihood function shown in FIG. 31 for tissue A.

B. Relationship Between Relative Abundance and Proportional Contribution

Figure 32:
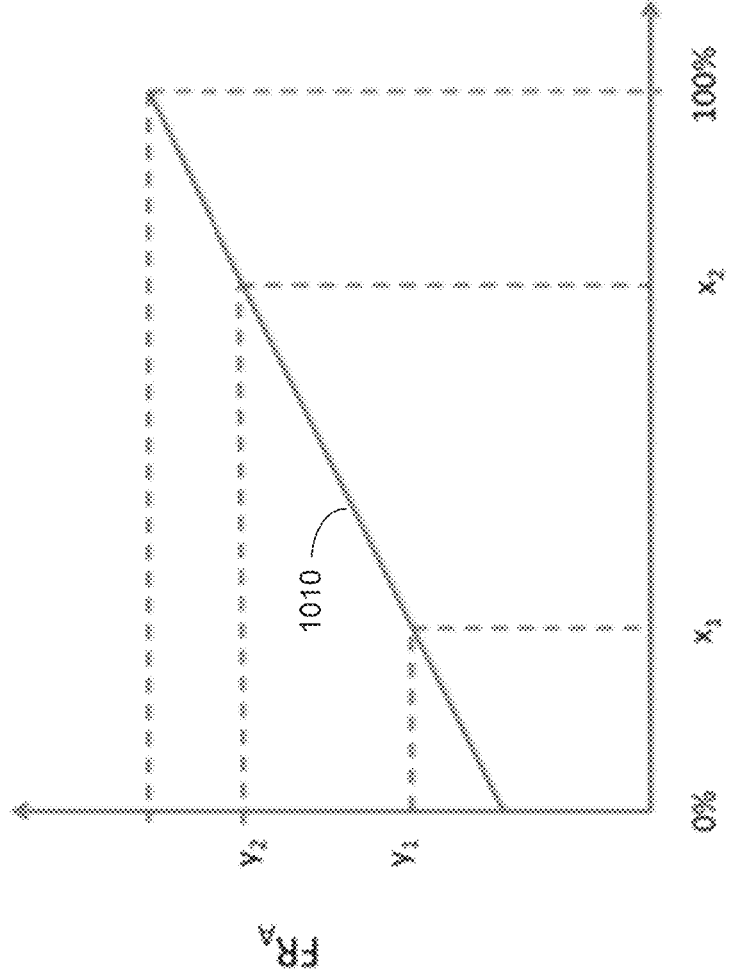
FIG. 32 shows the relationship between $FR_A$ and the proportional contribution of tissue A to DNA in a mixture determined by analysis of two or more calibration samples with known proportional concentrations of DNA from tissue A.

FIG. 32 shows the relationship between $FR_A$ and the proportional contribution of tissue A to DNA in a mixture determined by analysis of two or more calibration samples with known proportional concentrations of DNA from tissue A. In the example shown, two samples with proportional contribution of tissue A of $x_1$ and $x_2$ are analyzed. The $FR_A$ values of the two samples were determined as $y_1$ and $y_2$, respectively. The relationship between $FR_A$ and the proportional contribution of A can be determined based on the values of $x_1$, $x_2$, $y_1$ and $y_2$.

The values y1 and y2 are examples of calibration values. The data points (x1,y1) and (x2,y2) are examples of calibration data points. The calibration data points can be fit to a function to obtain a calibration curve 1010, which may be linear. When a new $FR_A$ (or other relative abundance value) is measured for a new sample, the new $FR_A$ can be compared to at least one of the calibration values to determine a classification of the proportional contribution of the new sample. The comparison to the calibration value can be made in various ways. For example, the calibration curve can be used to find the proportional contribution x corresponding to the new $FR_A$. As another example, the new $FR_A$ can be compared to calibration value y1 of a first calibration data point to determine whether the new sample as a proportional contribution greater or less than x1.

In other embodiments, a mixture containing more than two types of tissues can be analyzed similarly for the proportional contribution of tissues A as long as the $FR_A$ of other tissues is relatively constant. Such methods are practically useful for the analysis of different clinical scenarios, for example but not limited to cancer detection, transplantation monitoring, trauma monitoring, infection and prenatal diagnosis.

In one embodiment, the fractional concentration of the affected tissue in the plasma of a cancer patient can be determined. For example, in a patient with liver cancer, the fractional contribution of the liver DNA can be determined via the analysis of the liver-specific open chromatin regions, e.g., DNase hypersensitivity sites. In one embodiment, this can be done using DNase-Seq (Boyle et al. Cell 2008; 132: 311-322; Madrigal et al. Front Genet 2012; 16: 123-131). In another embodiment, this can be performed by Formaldehyde-Assisted Isolation of Regulatory Elements (FAIRE)-Seq (Giresi et al. Genome Res 2007; 17: 877-885). In yet another embodiment, this can be performed by ATAC-Seq (Buenrostro et al. Nat Methods 2013; 10: 1213-1218). The $FR_{liver}$ can be determined at these sites and compared with normal healthy subjects. At the liver-specific DNase hypersensitivity sites, the variation in in PI between peak and trough regions would be mainly contributed from the liver. Through the comparison with a calibration curve similar to FIG. 32, the contribution of the liver can be determined. The value of $FR_{liver}$ of the tested case can be compared with a range of the contribution of the liver in the healthy subjects. Other regions that have a high variation in amplitude in the likelihood function of DNA fragments ending at a genomic position among various tissues of a mixture can be used. Examples of such other regions are described in more detail in later sections.

Similarly, the contribution of the transplanted organ in a patient who has received organ transplantation can be determined by this method. In previous studies, it was shown that patients with rejection would lead to an increased release of DNA from the transplanted organ resulting in an elevated concentration of the DNA from the transplanted organ in plasma. The analysis of FR of the transplanted organ would be a useful way for the detection and monitoring of organ rejection. The regions used for such analysis can vary depending on which organ is transplanted.

In another embodiment, this method can be used for the determination of fetal DNA concentration in maternal plasma. In maternal plasma, the DNA molecules carrying the fetal genotypes are actually derived from the placenta. Thus, if we focus on the DNase hypersensitivity sites that are specific for the placenta but not present in the blood cells, we would be able to determine the proportional contribution of the placenta to the plasma DNA through the analysis of the $FR_{placenta}$.

Figure 33:
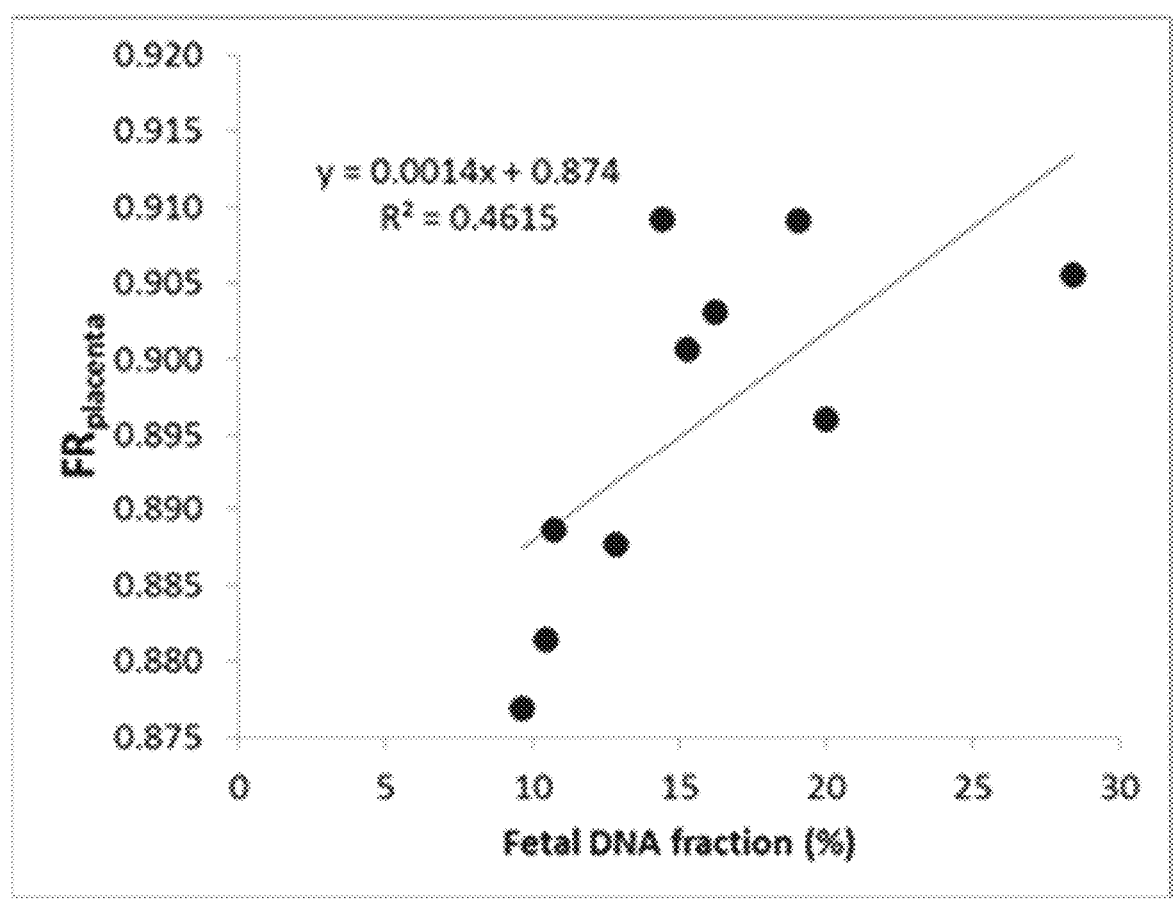
FIG. 33 shows a correlation between $FR_{placenta}$ and fetal DNA percentage in maternal plasma.

FIG. 33 shows a correlation between $FR_{placenta}$ and fetal DNA percentage in maternal plasma according to embodiments of the present invention. The vertical axis corresponds to $FR_{placenta}$ as determined using one or more local maxima and local minima that are located in one or more DNase hypersensitivity sites. The horizontal axis is fetal DNA fraction measured using a separate measurement technique. As can be seen, the value of $FR_{placenta}$ is correlated with fetal DNA fraction. In this example, the fetal DNA fraction was determined based on the proportion of fetal-specific allele at SNPs that the mother was homozygous and the fetus was heterozygous. Thus, the fetal DNA percentage can be estimated using $FR_{placenta}$ based on the sequencing results of maternal plasma DNA.

Alternatively, as the two key components in the maternal plasma are placenta-derived DNA and the DNA derived from blood cells (a different tissue type), we reasoned that $FR_{blood}$ would be negatively correlated with the fractional concentration of fetal DNA in the blood plasma. Thus, DNase hypersensitivity sites specific for blood cells were identified and $FR_{blood}$ was determined.

Figure 34:
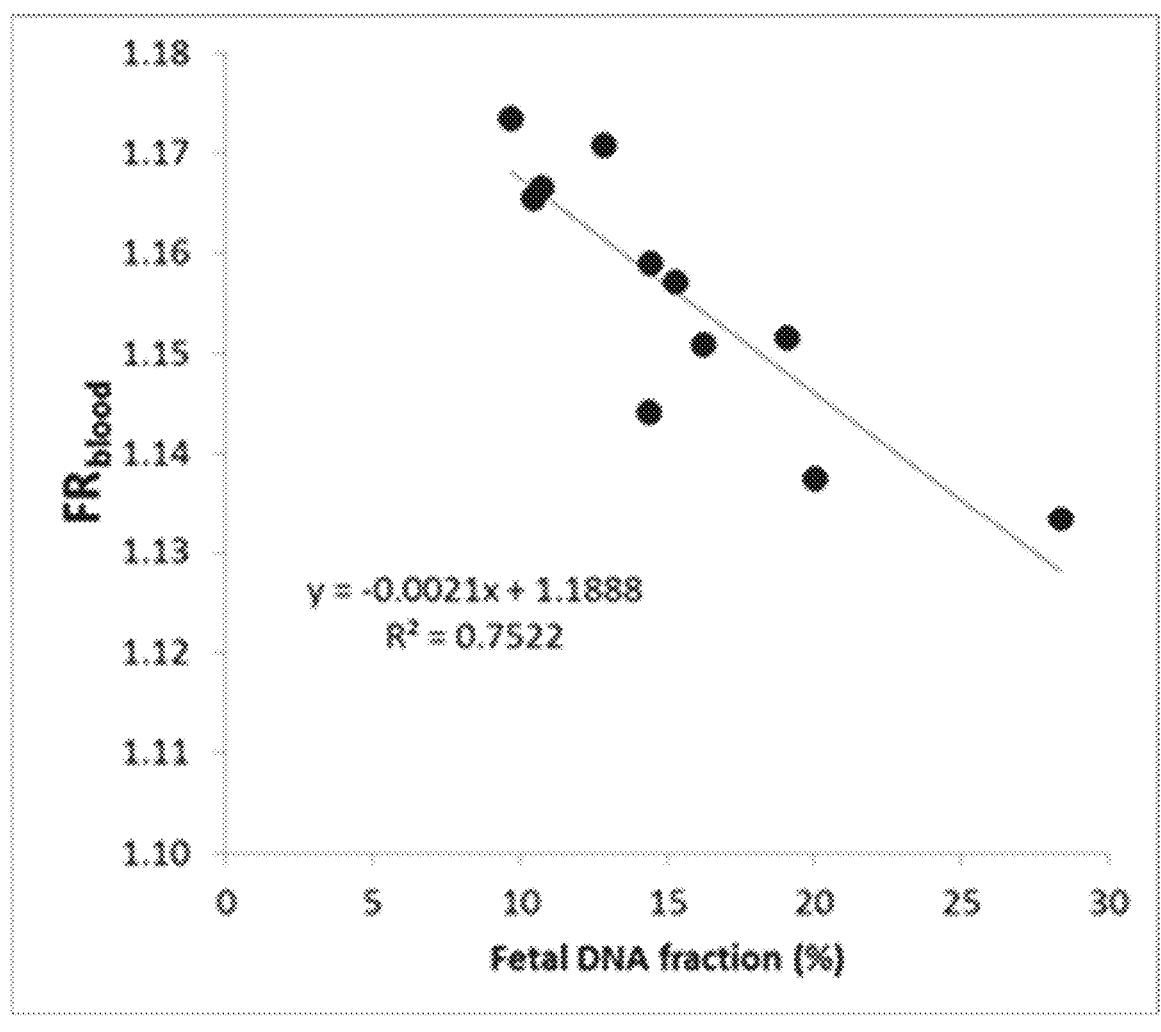
FIG. 34 shows a correlation between $FR_{blood}$ and fetal DNA concentration in maternal plasma.

FIG. 34 shows a correlation between $FR_{blood}$ and fetal DNA concentration in maternal plasma. The vertical axis corresponds to $FR_{blood}$ as determined using one or more local maxima and local minima that are located in one or more DNase hypersensitivity sites. The horizontal axis is fetal DNA fraction measured based on the proportion of fetal-specific alleles in maternal plasma. A negative correlation can be observed between $FR_{blood}$ and fetal DNA percentage. Thus, the fetal DNA percentage can be estimated using $FR_{blood}$ based on the sequencing results of maternal plasma DNA. Accordingly, a genomic region can have a fragmentation pattern specific to multiple tissue types, e.g., positive correlation(s) for some tissue(s) and negative correlation(s) for other tissue(s).

C. Method Using Maxima and Minima

FIG. 35 is a flowchart of a method 1300 of analyzing a biological sample to determine a classification of a proportional contribution of the first tissue type according to embodiments of the present invention. The biological sample includes a mixture of cell-free DNA molecules from a plurality of tissues types that includes the first tissue type. As with other methods described herein, method 1300 can use a computer system. The first tissue type (e.g., liver tissue or fetal tissue) can be selected based on the specific subject. For example, if the subject previously had liver cancer, then screening can be performed to check whether the liver cancer has returned, which would result in an increase in the proportional contribution from liver tissue. Such a selection criteria applies to other methods described herein.

At block 1310, at least one genomic region having a fragmentation pattern specific to the first tissue type is identified. As an example, the at least one genomic region can include one or more DNase hypersensitivity sites. Each of the at least one genomic region having a fragmentation pattern specific to the first tissue type can include one or more first tissue-specific alleles in at least one additional sample, e.g., as will be described in section VI. As another example, the at least one genomic region can include one or more ATAC-seq or micrococcal nuclease sites. The first tissue type can correspond to a particular organ or even to a particular cancer of the organ.

At block 1320, a plurality of cell-free DNA molecules from the biological sample are analyzed. The analyzing of a cell-free DNA molecule includes determining a genomic position (ending position) in a reference genome corresponding to at least one end of the cell-free DNA molecule. Thus, two ending positions can be determined, or just one ending position of the cell-free DNA molecule.

The ending positions can be determined in various ways, as described herein. For example, the cell-free DNA molecules can be sequenced to obtain sequence reads, and the sequence reads can be mapped (aligned) to the reference genome. If the organism was a human, then the reference genome would be a reference human genome, potentially from a particular subpopulation. As another example, the cell-free DNA molecules can be analyzed with different probes (e.g., following PCR or other amplification), where each probe corresponds to a genomic location, which may cover the at least one genomic region.

A statistically significant number of cell-free DNA molecules can be analyzed so as to provide an accurate determination the proportional contribution from the first tissue type. In some embodiments, at least 1,000 cell-free DNA molecules are analyzed. In other embodiments, at least 10,000 or 50,000 or 100,000 or 500,000 or 1,000,000 or 5,000,000 cell-free DNA molecules, or more, can be analyzed.

At block 1330, a first set of first genomic positions is identified. Each first genomic position has a local minimum of ends of cell-free DNA molecules corresponds to the first genomic position. Multiple neighboring genomic positions can be defined as a local extremum (maximum or minimum), and thus a local maximum is not limited to just one position.

In some embodiments, a ratio can be determined for each of a plurality of genomic positions. A first amount of cell-free DNA molecules that end at the genomic position and extend at least a specified number of nucleotides to both sides of the genomic position can be determined, e.g., as described for FIG. 23. A second amount of cell-free DNA molecules that are located at the genomic position can be used with the first amount to determine the ratio. A plurality of local minima and a plurality of local maxima can be identified in the ratios, e.g., by stepping through the ratio values to identify one or more contiguous genomic positions occurring at each of the extremum (maximum or minimum).

At block 1340, a second set of second genomic positions is identified. Each second genomic position having a local maximum of ends of cell-free DNA molecules corresponds to the second genomic position. The second set can be identified in a similar manner as the first set.

At block 1350, a first number of cell-free DNA molecules ending on any one of the first genomic positions in any one of the at least one genomic region is determined. The first number can be determined in various ways, e.g., as a sum across all first genomic positions. As another example, separate amount can be determined at each genomic position. Thus, determining the first number of cell-free DNA molecules can include determining a first amount of cell-free DNA molecules ending on each first genomic position, thereby determining a plurality of first amounts.

At block 1360, a second number of cell-free DNA molecules ending on any one of the second genomic positions in any one of the at least one genomic region is determined. The second number can be determined in a similar manner as the first number. Thus, determining the second number of cell-free DNA molecules can include determining a second amount of cell-free DNA molecules ending on each second genomic position, thereby determining a plurality of second amounts.

At block 1370, a separation value using the first number and the second number is computed. The separation value can be computed in various ways, e.g., by a ratio of the first number and the second number, as described in section III.A. In another implementation using multiple maxima and minima, an amount at each such genomic position can be determined. Computing the separation value can include determining a plurality of separate ratios, each separate ratio of one of the plurality of first amounts and one of the plurality of second amounts. The separation value can be determined using the plurality of separate ratios, e.g., a mean or median of the separate ratios.

At block 1380, the classification of the proportional contribution of the first tissue type is determined by comparing the separation value to one or more calibration values determined from one or more calibration samples whose proportional contributions of the first tissue type are known.

D. Amplification-Free Analysis

The analysis of the cell-free DNA molecules in block 1310 can be amplification free. When using PCR, the sequencing depth (i.e. the number of sequence reads covering a particular nucleotide or ending on the particular nucleotide in a reference genome) does not directly reflect how many plasma DNA molecules covering that particular nucleotide are analyzed. This is because one plasma DNA molecule can generate multiple replicates during the PCR process, and multiple sequence reads can originate from a single plasma DNA molecule. This duplication problem would become more important with i) a higher number of PCR cycles for amplifying the sequencing library; ii) an increased sequencing depth, and iii) a smaller number of DNA molecules in the original plasma sample (e.g. a smaller volume of plasma).

In addition, the PCR operation introduces further errors (Kinde et al. Proc Natl Acad Sci USA 2011; 108: 9530-9535) because the fidelity of a DNA polymerase is not 100%, and occasionally, an erroneous nucleotide would be incorporated into the PCR daughter strand. If this PCR error occurs during the early PCR cycles, clones of daughter molecules showing the same error would be generated. The fractional concentration of the erroneous base may reach such a high proportion among other DNA molecules from the same locus that the error would be misinterpreted, e.g., as a fetal-derived or tumor-derived mutation. Examples of PCR-free protocols include: Berry Genomics (investor.illumina-.com/mobile.view?c=121127&v=203&d=1&id=1949110); Illumina (www.illumina.com/products/truseq-dna-pcr-free-sample-prep-kits.html), and various single molecule sequencing techniques. Further details of an amplification-free analysis can be found in PCT Application No. PCT/CN2016/073753.

Accordingly, some embodiments can include obtaining template DNA molecules from the biological sample to be analyzed; preparing a sequencing library of analyzable DNA molecules using the template DNA molecules, the preparation of the sequencing library of analyzable DNA molecules not including an operation of DNA amplification of the template DNA molecules; sequencing the sequencing library of analyzable DNA molecules to obtain a plurality of sequence reads corresponding to the first plurality of cell-free DNA molecules. Analyzing the first plurality of cell-free DNA molecules can include receiving, at the computer system, the plurality of sequence reads and aligning, by the computer system, the plurality of sequence reads to the reference genome to determine genomic positions for the plurality of sequence reads.

IV. Relative Abundance of Left and Right Nucleotides

Figure 36:
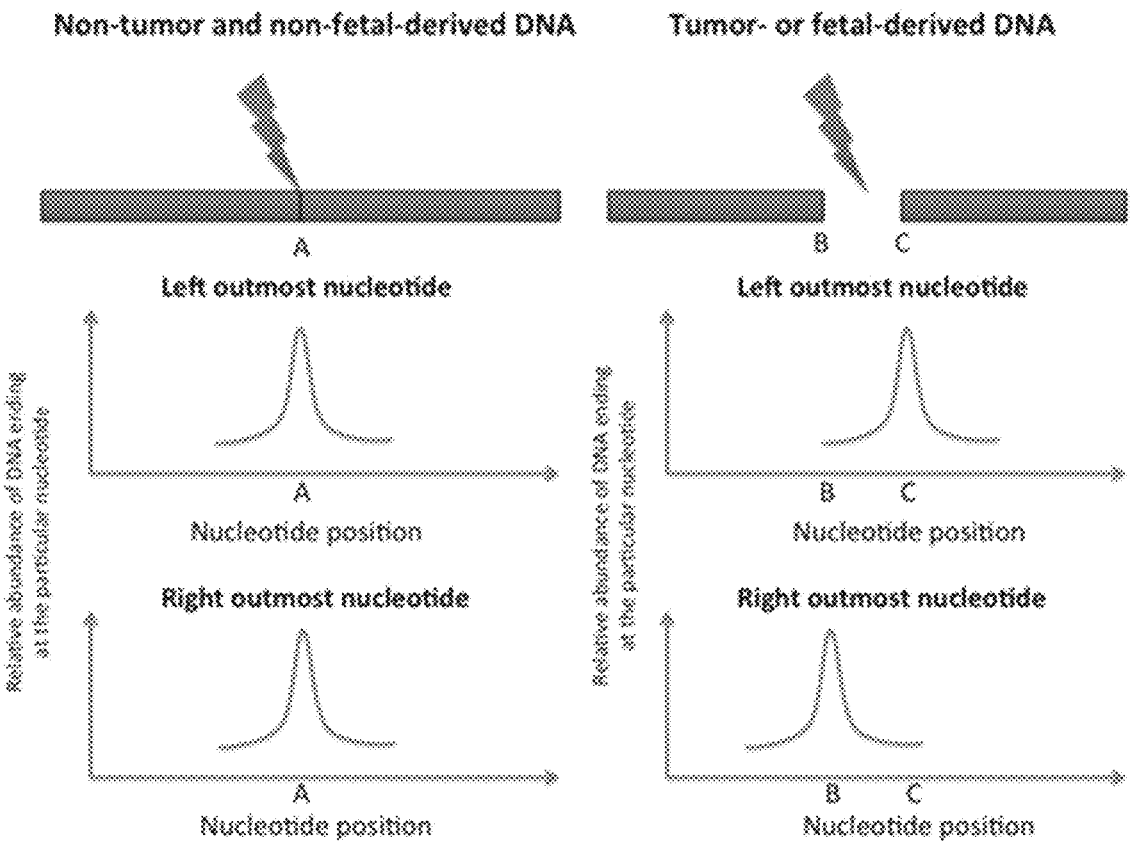
FIG. 36 shows an illustration of the principle of a difference for where circulating DNA fragments for tumor or fetal-derived DNA.

FIG. 36 shows an illustration of the principle of a difference for where circulating DNA fragments for tumor or fetal-derived DNA. In previous studies, it has been shown that the size of the circulating DNA closely resembles the size of nucleosomal DNA. The major peak of 166 bp in the size distribution of plasma DNA represents the DNA associated with the core of the histone complex together with the linker DNA connecting two successive histones complex.

It has also been observed that the size distributions of fetal- and tumor-derived DNA molecules are shorter than those for the non-tumor- and non-fetal-derived DNA in the plasma of cancer patients and pregnant women (Lo et al. Sci Transl Med 2010; 2(61):61ra91 and Jiang et al. Proc Natl Acad Sci USA 2015; 112:E1317-25). For the size distribution of tumor- and fetal-derived DNA in plasma, the peak of 166 bp is diminished and a peak at 144 bp is more prominent. The 144 bp peak is likely to be due to the degradation of the ~20 bp linker DNA that connects two successive histones complex.

For the illustration of the principle of this method, we use the scenario of a cancer patient as an example. The same principle can then be applied for other scenarios, including the analysis of circulating fetal DNA in maternal plasma in pregnancy, and the analysis of the plasma of patients who have received transplantation. Embodiments can analyze the ends of the plasma DNA molecules, denoted as the left and right ends in the FIG. 36.

When DNA from non-malignant tissues are fragmented and released into the plasma, the connecting ends of the two molecules would both be located at nucleotide position A. In other words, for the molecule on the right side, the left outermost nucleotide is just next to the nucleotide position A. For the molecule on the left side, the right outermost nucleotide is also just next to the nucleotide position A. When the relative abundance of molecules ending at a particular nucleotide is plotted against the nucleotide coordinate, the peaks abundance of the ends would be at position A for the left and right outermost nucleotides mapping to this region. For DNA molecules derived from tumor cells, a 20 bp fragment would be removed from the molecules after the fragmentation process.

As a result, there would be a gap of 20 bp between the left side of the molecule on the right and the right side of the molecule on the left. When the relative abundance of molecules ending at a particular nucleotide is plotted against the nucleotide coordinate, the peaks for the right outermost nucleotide (located at B) and the peak for the left outermost nucleotide (located at C) would be separated by 20 bp. Therefore, the ratio between the abundance of molecules ending on nucleotide positions B and C and the abundance of molecules ending on position A would represent the fractional concentration of tumor-derived DNA in the plasma sample.

The same principle can be applied for the quantification of DNA species that have differential size distribution, for example, but not limited to, the measurement of fetal DNA in the plasma of pregnant women and the measurement of DNA from a transplanted organ.

Figure 37:
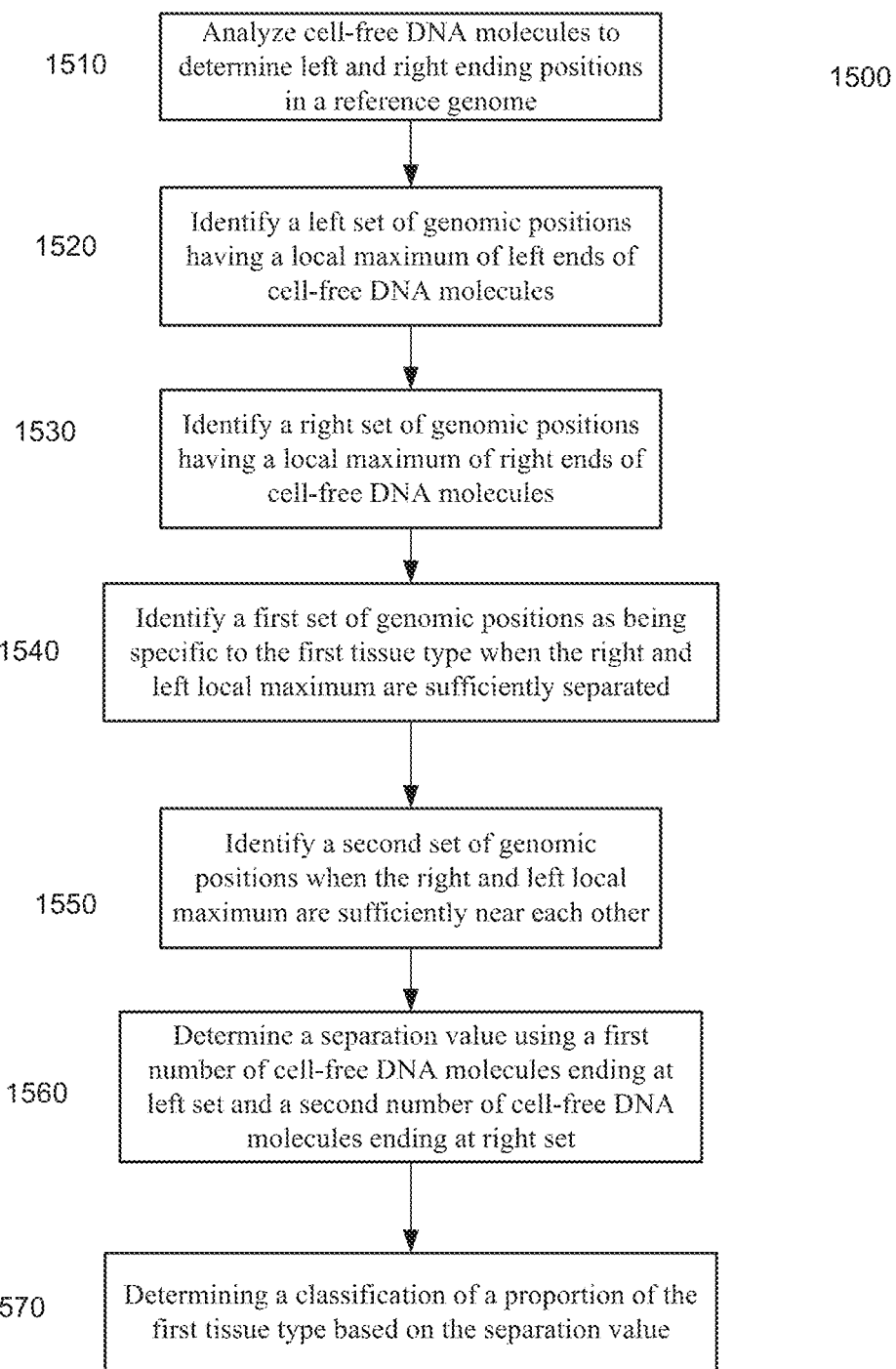
FIG. 37 is a flowchart of a method of analyzing a biological sample including a mixture of cell-free DNA molecules from a plurality of tissues types that includes a first tissue type.

FIG. 37 is a flowchart of a method 1500 of analyzing a biological sample including a mixture of cell-free DNA molecules from a plurality of tissues types that includes a first tissue type. Portions of method 1500 can be used to implement block 1310 and other blocks identifying preferred ending positions.

At block 1510, cell-free DNA molecules are analyzed to determine left and right ending positions in a reference genome. Block 1510 may be performed in a similar manner as block 1320. In block 1510, a first plurality of cell-free DNA molecules from the biological sample of a subject can be analyzed, where each of the first plurality of cell-free DNA molecules has a left end and a right end. A left ending position in the reference genome corresponding to the left end of the cell-free DNA molecule can be determined, e.g., by aligning (mapping) a sequence read of the DNA fragment to the reference genome or via a probe whose position is known in the reference genome. The left end can refer to either end, depending on the coordinate system chosen for defining the reference genome. Similarly, a right ending position in the reference genome corresponding to the right end of the cell-free DNA molecule can be determined. The two ending positions can be determined in two separate alignment operations, e.g., if the two ends have separate sequence reads.

At block 1520, a left set of left genomic positions is identified. Each genomic position of the left set has a local maximum of left ends of the first plurality of cell-free DNA molecules corresponding to one of the left set of genomic positions. The left set can be determined in a similar manner as described for maxima for method 1300.

At block 1530, a right set of right genomic positions is identified. Each genomic position of the right set has a local maximum of right ends of the first plurality of cell-free DNA molecules corresponding to one of the right set of genomic positions. The right set can be determined in a similar manner as described for maxima for method 1300.

At block 1540, a first set of genomic positions is identified as being specific to the first tissue type. All or a portion of the left genomic positions of the left set can be compared to all or a portion of the right genomic positions of the right set to identify the first set of genomic positions where a distance from a left genomic position to a nearest right genomic position is greater than a first threshold distance of genomic positions (e.g., nucleotides) in the reference genome. Examples of the first threshold distance are 5, 6, 7, 8, 9, 10, 15, and 20 nucleotides.

At block 1550, a second set of genomic positions is identified. All or a portion of the left genomic positions of the left set can be compared to all or a portion of the right genomic positions of the right set to identify the second set of genomic positions where a distance from a left genomic position to a nearest right genomic position is less than a second threshold distance of genomic position in the reference genome. Examples of the second threshold distance are 2, 3, 4, and 5 genomic positions (e.g., nucleotides).

At block 1560, a separation value is determined using a first number of the first plurality of cell-free DNA molecules ending at one of the left set of genomic positions and a second number of the first plurality of cell-free DNA molecules ending at one of the right set of genomic positions. A separation value (e.g., a relative abundance value) can be determined between the first number and the second number.

In one embodiment, pairs of the first set of genomic positions and the second set of genomic positions are identified. The pairs can be of positions that are nearest to each other. For each of one or more of the pairs, a first amount of cell-free DNA molecules ending at the first genomic position can be determined, and a second amount of cell-free DNA molecules ending at the first genomic position can be determined. The first amounts of cell-free DNA molecules correspond to the first number of the plurality of cell-free DNA molecules and the second amounts of cell-free DNA molecules correspond to the second number of the plurality of cell-free DNA molecules. For example, the first amounts can sum to the first number and the second amounts can sum to the second number, and the separation value can be determined directly from the first number and the second number. As another example, the separation value can be determined from a plurality of ratios, each including the first amount and the second amount for one the pairs. In various implementations, an average or median of the ratios can be used as the separation value. The respective first and second amounts of the pairs can be used in other ways to determine individual separation values used to determine the total separation value.

At block 1570, the classification of the proportional contribution of the first tissue type is determined by comparing the separation value to one or more calibration values determined from one or more calibration samples whose proportional contributions of the first tissue type are known. Block 1570 can be performed in a similar manner as other determination of proportional contributions.

In various embodiments, both the left and right sets can be used as the first set of genomic positions; just the left set can be used; just the right set can be used; or some from the left set and some from the right set can be used. For the whole set of left positions, there is a subset of left positions that has a corresponding right set of positions separated from the subset of left positions by a threshold number of nucleotides. Therefore, it is possible to use the subset of left positions or the corresponding subset of right positions to make the calculation.

V. Use of Tissue-Specific Ending Positions

The fragmentation patterns of circulating DNA derived from cancer cells, placental cells and cell types can be different. The coordinate of the terminal nucleotides at one or both ends of a circulating DNA fragment can be used for predicting if the DNA fragment carrying a putative mutation is actually derived from a tumor. Cancer-specific and pregnancy-specific ending positions can be identified in plasma DNA fragments.

A. Cancer Example Using Hepatocellular Carcinoma (HCC)

To illustrate the feasibility of this approach, the sequencing data of the plasma DNA for a patient with hepatocellular carcinoma (HCC) and a pregnant woman were analyzed. For illustration purposes, the analysis was focused on chromosome 8. The same approach can be applied to the whole genome or any other chromosomes.

The coordinates of the terminal nucleotides at both ends of each sequenced plasma DNA fragment was determined. Then, the number of fragments ending on each nucleotide on chromosome 8 was counted. The top 1 million nucleotides that had the highest number of DNA fragments ending on them were determined for the HCC case and the pregnant woman. The top one million can be viewed as being above a threshold.

Figure 38:
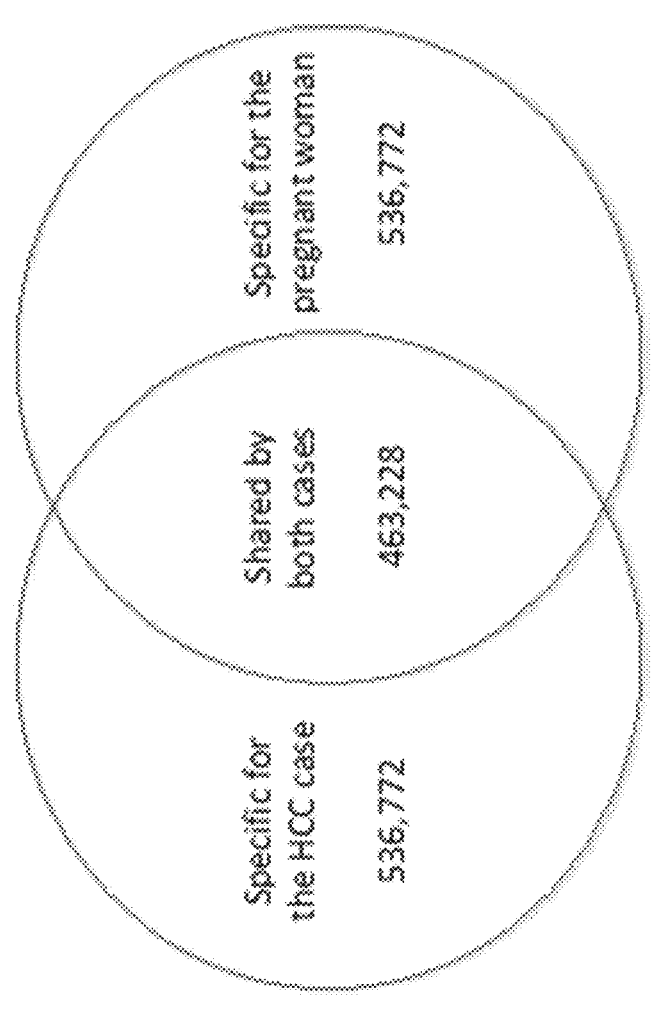
FIG. 38 is a Venn diagram showing the number of frequent endings sites that are specific for the hepatocellular carcinoma (HCC) case, specific for the pregnant woman and shared by both cases.

FIG. 38 is a Venn diagram showing the number of frequent endings sites that are specific for the HCC case, specific for the pregnant woman and shared by both cases. The coordinates of the 536,772 nucleotides that were the most frequent ending positions specific for the HCC case is shown in Appendix A. The coordinates of the 536,772 nucleotides that were the most frequent ending positions specific for the pregnant woman are listed in Appendix B. The coordinates of the 463,228 nucleotides that were the most frequent ending positions shared by the two cases are omitted.

We reason that plasma DNA fragments with terminal nucleotide ending exactly at the 536,772 HCC-specific ending positions would be more likely to be derived from the tumor. Based on this assumption, the number of sequenced plasma DNA fragments that ended on the HCC-specific ending positions can be used to indicate the presence or absence of HCC or other cancers having the same plasma DNA fragmentation pattern. In another embodiment, this parameter can also be used for reflecting the level of cancer, for example but not limited to the size of the tumor, the stage of the cancer, tumor load and the presence of metastasis.

In yet another embodiment, the number of fragments ending on the HCC-specific ending positions can be correlated with the fractional concentration of cancer-derived DNA in the plasma for samples with known tumor DNA fraction in plasma. The tumor DNA fraction in plasma can be determined by, for example but not limited to, quantify-ing the cancer mutations in plasma or magnitude of the copy number aberrations in plasma DNA (Chan et al. Clin Chem 2013; 59:211-24). This correlation can be used as a calibration curve (FIG. 23). For patients with unknown tumor DNA fraction in plasma, the amount of DNA fragments ending on the HCC-specific ending positions can be determined. Then, the tumor DNA fraction in plasma can be determined based on the calibration curve and the amount of DNA fragments ending on the HCC-specific ending positions. In one implementation, the amount of DNA fragments ending on the HCC specific ending positions can be normalized to the total number of DNA fragments sequenced, the total number of alignable reads or the number of DNA fragments aligned to certain chromosomal regions. Thus, the proportion of sequenced DNA fragments ending on cancer-specific positions can be used as a parameter.

Figure 39:
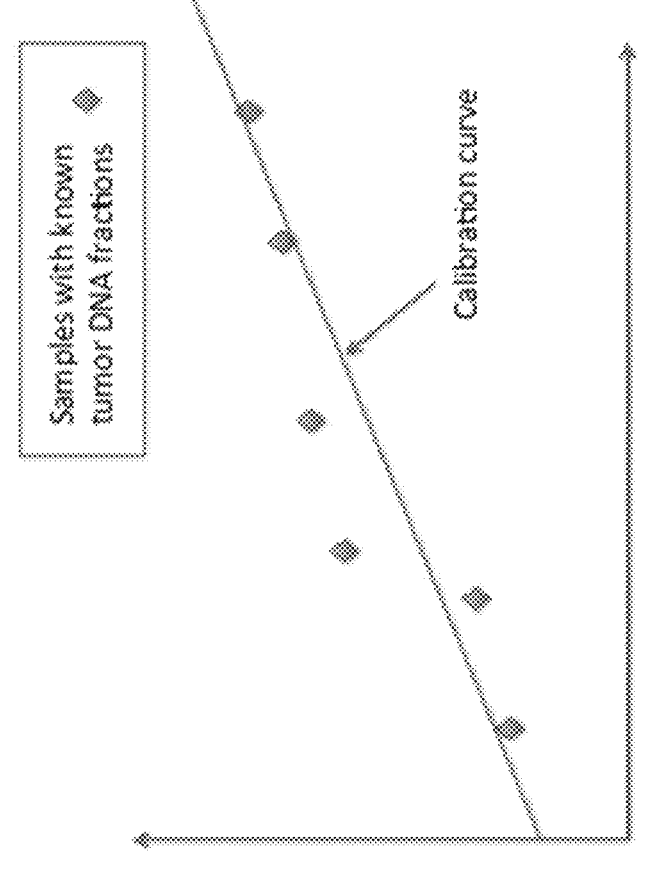
FIG. 39 shows a calibration curve showing the relationship between the proportion of sequenced DNA fragments ending on cancer-specific ending positions and tumor DNA fraction in plasma for cancer patients with known tumor DNA fractions in plasma.

FIG. 39 shows a calibration curve showing the relationship between the proportion of sequenced DNA fragments ending on cancer-specific ending positions and tumor DNA fraction in plasma for cancer patients with known tumor DNA fractions in plasma. This conceptual diagram shows a correlation of the calibration curve between tumor DNA fraction and the proportion of sequence DNA fragments ending on the cancer-specific ending positions. A calibration curve can be determined by fitting the data points determined from calibration samples, whose tumor DNA fraction was determined via other techniques.

In another embodiment of this invention, the plasma DNA fragmentation patterns for patients suffering from different types of cancers can be determined. The overlapping ends of these cancer patients can be considered as cancer-specific ends whereas the ending positions for individual cancer types can be considered as specific for a particular cancer type. For any individual suspected of having a cancer, the sequenced plasma DNA fragments can first be compared with the cancer-specific ending positions to determine the likelihood of the individual having a cancer. If the individual is likely to have a cancer, the sequenced fragments can be analyzed for the cancer type-specific ending positions to determine the most likely cancer an individual is suffering from.

In another embodiment of this invention, the ending positions of DNA derived from different organs can be determined and can be used to determine the relative contributions (or other proportional contribution) of DNA from different organs into plasma.

B. Fetal Example

In another embodiment, this approach can be used for determining the fetal DNA fraction in a maternal plasma sample. A calibration curve can be established by correlation the proportion of sequenced plasma DNA fragments ending on the pregnancy-specific ending positions is first determined and the fetal DNA fractions for a number of maternal plasma samples with known fetal DNA fraction. The fetal DNA fractions can be determined by a number of methods, for example but not limited to determining of the fetal specific alleles in the sample, the quantification of targets on chromosome Y for male pregnancies and the analysis of fetal-specific methylation markers. For a pregnant plasma sample with unknown fetal DNA fraction, the proportion of sequenced plasma DNA fragments ending on the pregnancy-specific ending positions can be determined. Using on this information, the fetal DNA fraction in the tested plasma DNA sample can be determined based on the calibration curve.

C. Kit for Use of Preferred Ending Positions

In some embodiments, a kit is provided for analyzing DNA in a biological sample containing a mixture of cell-free DNA molecules of a plurality of tissue types. The kit can comprise one or more oligonucleotides for specifically hybridizing to at least a section of a genomic region listed in Appendices A and B. In one embodiment, the kit includes one or more oligonucleotides for specifically hybridizing to at least a section of a genomic region listed in Appendix A for use in testing a subject for HCC. In another embodiment, the kit includes one or more oligonucleotides for specifically hybridizing to at least a section of a genomic region listed in Appendix B for use in testing a pregnant female, e.g., to determine a fetal DNA fraction in a maternal biological sample from the pregnant female.

VI. Ending Position Analysis Using Polymorphisms

In some embodiments, the regions having a tissue-specific fragmentation pattern can be identified using tissue-specific alleles. For example, a fetal-specific allele can be identified by analyzing a maternal plasma sample and comparing detected alleles to alleles detected in a maternal-only sample, as is described herein. Genomic positions that have a high rate of fetal DNA molecules ending on them relative to the rate for tissue exhibiting a shared allele (i.e., shared with the fetus and the mother) can be identified as having a fetal tissue-specific fragmentation pattern. These fetal preferred ending positions may or may not be DNase hypersensitivity sites, thereby showing that various genomic regions may have tissue-specific amplitudes for the fragmentation patterns, and embodiments are not limited to DNase hypersensitivity sites. A similar analysis can be made for a sample from a subject being screened for a tumor.

A. Fetal Example

Preferred ending positions can be obtained by analyzing a plasma DNA from a pregnant woman. The fetal- and maternal-derived plasma DNA fragments can be differentiated through polymorphism-based methods. Fragments carrying fetal- and maternal-specific alleles can be used for determining the preferred ending positions of the fetal-derived and maternal-derived DNA.

A pregnant woman with a male singleton pregnancy was recruited for this study at 38 weeks of gestation from the Department of Obstetrics and Gynecology, Prince of Wales Hospital, Hong Kong, with informed consent. Blood samples were centrifuged at 1,600 g for 10 min at 4° C. The plasma portion was harvested and re-centrifuged at 16,000 g for 10 min at 4° C. to remove the blood cells. The blood cell portion was re-centrifuged at 2,500 g, and any residual plasma was removed. DNA from the blood cells and that from maternal plasma was extracted with the blood and body fluid protocol of the QIAamp DNA Blood Mini Kit and the QIAamp DSP DNA Blood Mini Kit (Qiagen), respectively. DNA from the placenta was extracted with the QIAamp DNA Mini Kit (Qiagen) according to the manufacturer's tissue protocol. The sequencing libraries were sequenced using the Illumina TruSeq PCR-free library preparation protocol. The paired-end sequencing data were analyzed using the Short Oligonucleotide Alignment Program 2 (SOAP2) in the paired-end mode (Li et al. Bioinformatics 2009; 25:1966-1967). The paired-end reads were aligned to the non-repeat-masked reference human genome (Hg19). Up to 2 nucleotide mismatches were allowed for the alignment of each end. The genomic coordinates of these potential alignments for the 2 ends were then analyzed to determine whether any combination would allow the 2 ends to be aligned to the same chromosome with the correct orientation, spanning an insert size≤600 bp, and mapping to a single location in the reference human genome. The maternal plasma sample was sequenced to a depth of 270× coverage of a haploid human genome. The maternal blood cells, paternal blood cells and umbilical cord blood cells were sequenced to 40×, 45× and 50× haploid human genome coverage, respectively, using the same sequencing protocol.

To this end, recurrent end sequences in maternal plasma DNA were analyzed.

1. Identification of Fetal-Specific Ending Positions

Figure 40:
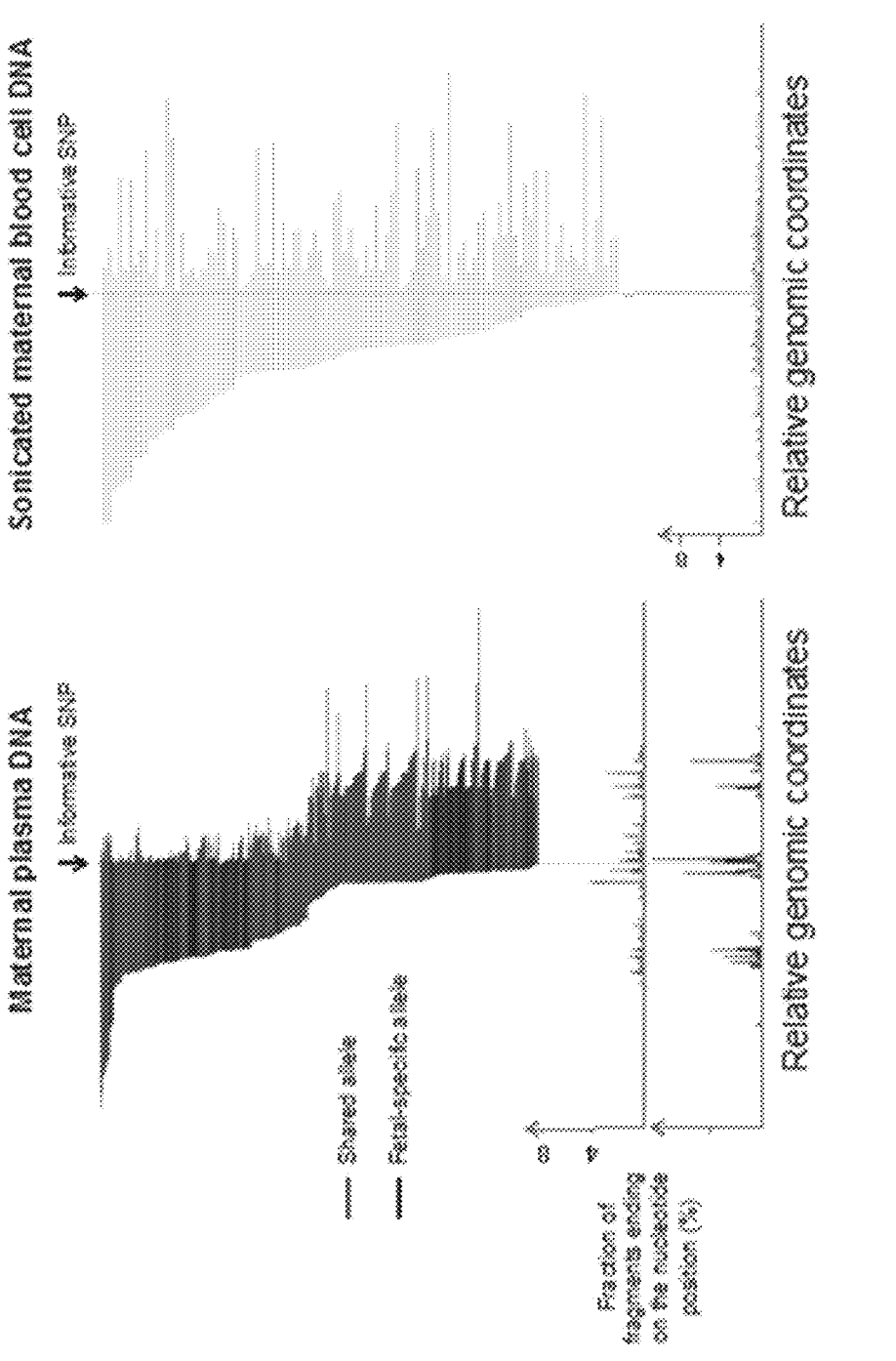
FIG. 40 shows an illustrative example of the non-random fragmentation patterns of plasma DNA carrying a fetal-specific allele and an allele shared by the mother and the fetus.

With the performance of very high sequencing depth of the maternal plasma DNA sample using a non-PCR-amplified library, we investigated if there may be sites in the maternal and fetal genomes that would be preferentially cleaved in the generation of plasma DNA. To demonstrate this effect, informative SNP loci that the mother was homozygous (genotype denoted as AA) and the fetus was heterozygous (genotype denoted as AB) were identified. In this illustrative example, the B allele would be fetal-specific and the A allele would be shared by the mother and the fetus. A representative example is shown in FIG. 40. As a control, the sequencing results of a DNA sample obtained from blood cells and artificially fragmented using sonication are shown.

A non-random fragmentation pattern was observed in the plasma DNA. For the plot of the probability of being an end of DNA fragments, three peaks were observed for each of the two groups of fragments carrying the fetal-specific and the allele shared by the mother. These peaks represent the hotspots for the end positions of fetal- and maternal-derived DNA in maternal plasma, respectively. The positions of the peaks largely overlapped between these two groups. In contrast, the fragmentation pattern for the sonicated DNA appears to be random and the fragment-end probability is similar across the region.

FIG. 40 shows an illustrative example of the non-random fragmentation patterns of plasma DNA carrying a fetal-specific allele and an allele shared by the mother and the fetus. On the upper part of the figure, each horizontal line represents one sequenced DNA fragment. The ends of the DNA fragments represent the ending position of the sequenced read. The fragments are sorted according to the coordinate of the left outermost nucleotide (smallest genomic coordinate). On the lower part of figure, the percentage of fragments ending on a particular position is shown. The X-axis represents the genomic coordinates and the SNP is located at the center indicated by the dotted line.

We further searched for coordinates that had an increased probability of being an ending position for plasma DNA fragments. We focused our search based on fragments covering the informative SNPs so that the fragments carrying fetal-specific alleles and alleles shared by the mother and the fetus can be evaluated separately. We determined if certain locations within the human genome had a significantly increased probability of being an ending position of plasma DNA fragments using a Poisson probability function. For the analysis of SNPs that the mother was homozygous (genotype AA) and the fetus was heterozygous (genotype AB), the A allele would be the "shared allele" and the B allele would be the fetal-specific allele. The number of sequenced reads carrying the shared allele and the fetal-specific allele would be counted. In the size distribution of plasma DNA, a peak would be observed at 166 bp for both the fetal-derived and maternally-derived DNA. If the fragmentation of the plasma DNA is random, the two ends would be evenly distributed across a region 166 bp upstream and 166 downstream of the informative SNP.

Figure 41:
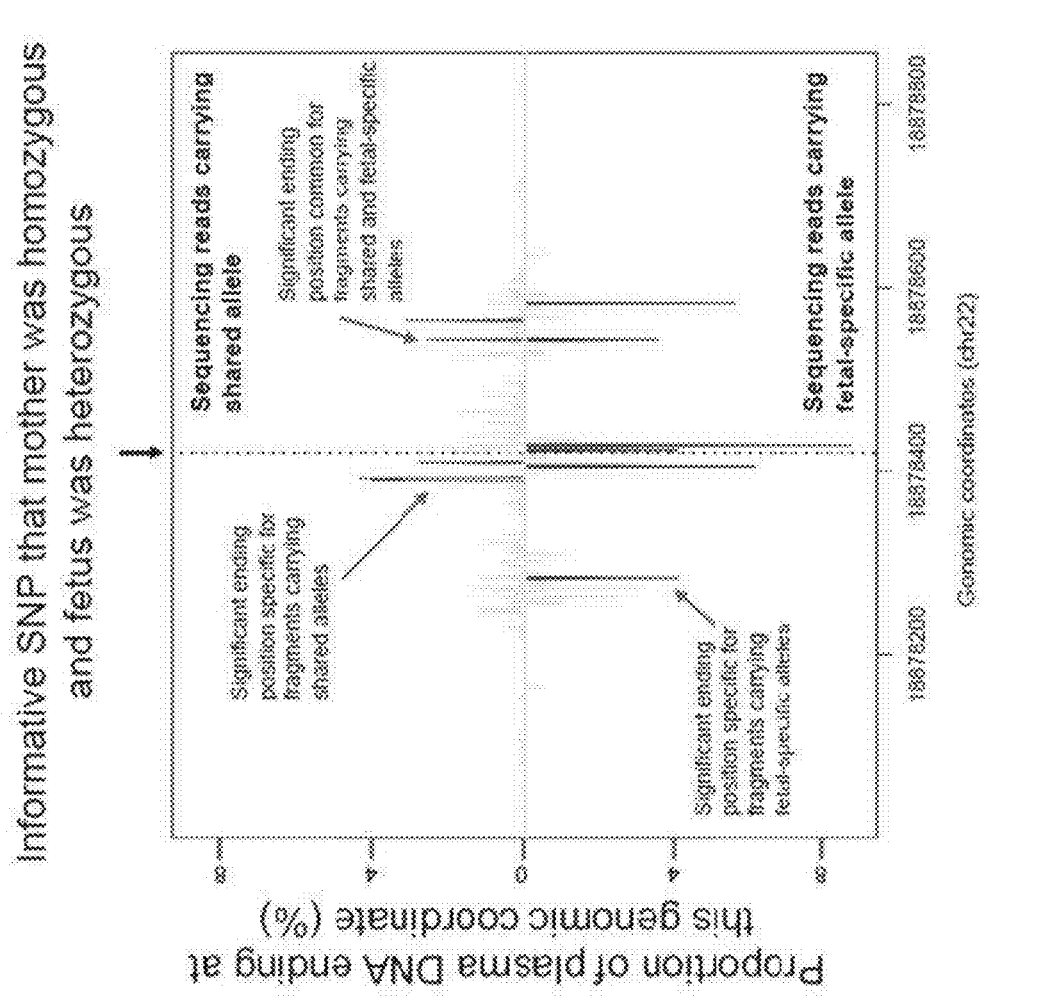
FIG. 41 shows a plot of probability a genomic coordinate being an ending position of maternal plasma DNA fragments across a region with an informative single nucleotide polymorphism (SNP).

A p-value can be calculated to determine if a particular position has significantly increased probability for being an end for the reads carrying the shared allele or the fetal-specific allele based on Poisson probability function.

$$p-\text{value} = \text{Poisson}(N_{actual}, N_{predict})$$

where Poisson( ) is the Poisson probability function; $N_{actual}$ is the actual number of reads ending at the particular nucleotide; and $N_{predict}$ is the total number of reads divided by 166. A p-value of <0.01 was used as a cutoff to define preferred ending positions for the reads carrying the fetal-specific allele or the shared allele. Statistically significant ending positions were determined for DNA fragments carrying the shared allele and the fetal-specific allele independently (FIG. 41). Other probability distributions can be used, e.g., binomial distribution, negative binomial distribution, and normal distribution.

FIG. 41 shows a plot of probability a genomic coordinate being an ending position of maternal plasma DNA fragments across a region with an informative SNP. Results for nucleotide positions with a significantly increased probability of being an end of plasma DNA fragments carrying a shared allele and a fetal-specific allele are shown in red/grey (above 0) and blue/black (below 0), respectively. The X-axis represents the genomic coordinates and the mutation is located at the center indicated by the dotted line. As shown, there are coordinates that have a high rate of occurrence of ending positions for just the fetal-specific allele, for just the shared allele, and some are common to both.

We identified a total of 4,131 (Set A) and 10,021 (Set B) nucleotide positions with a significantly increased chance of being an end of plasma DNA fragments carrying fetal-specific alleles and shared alleles, respectively. Set C was the overlapping set and contained 4,258 nucleotide positions (FIG. 25). These ending positions were obtained from regions spanning totally 1.42 Mb and covering 4,303 SNPs. Thus, the preferred ending positions for fetal-specific fragments accounted for 0.29% of the analyzed regions. There were 24,500, 22,942 and 31,925 plasma DNA fragments carrying fetal-specific alleles ending on Set A, Set B and Set C positions, respectively. There were 27,295, 158,632 and 87,804 plasma DNA fragments carrying shared alleles ending on Set A, Set B and Set C positions, respectively. The number or prevalence of preferred ending positions are expected to be much higher and occur at other genomic coordinates.

The polymorphism-based approach as described here only identifies preferred ending positions that are associated with an informative SNP for this fetal-maternal pair. Thus, the identified preferred ends would represent a subset of such ends in the genome. We have developed approaches that are not polymorphism-based to identify the preferred ends. Indeed, many more preferred ending approaches were identified using the non-polymorphism based approaches. Please refer to other experiments described below.

Figure 42:
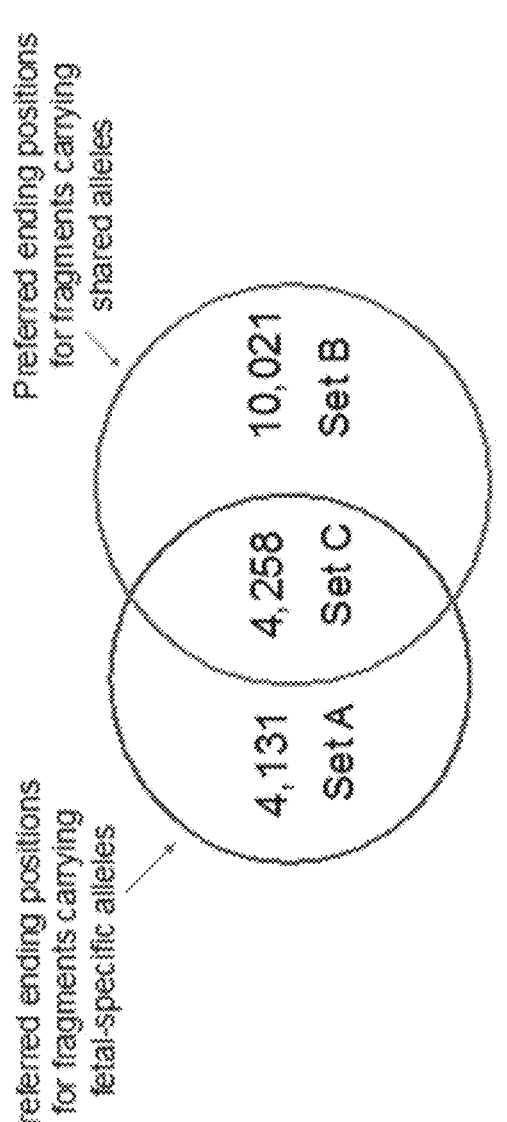
FIG. 42 shows an analysis of ending positions for plasma DNA fragments across SNPs that were homozygous in the mother and heterozygous in the fetus.

FIG. 42 shows an analysis of ending positions for plasma DNA fragments across SNPs that were homozygous in the mother and heterozygous in the fetus. Set A included preferred ending positions for fragments carrying fetal-specific alleles. Set B included preferred ending positions for fragments carrying shared alleles. Set C included preferred ending positions for both types of plasma DNA fragments.

Using the same principle, we further analyzed the ending positions for maternally derived DNA fragments across SNPs that were heterozygous in the mother (genotype AB) and homozygous in the fetus (genotype AA). We identified a total of 7,527 (Set X) and 18,829 (Set Y) nucleotide positions with significantly increased chance of being an ending position for plasma DNA fragments carrying fetal-specific alleles and shared alleles, respectively. Set Z is the overlapping set and contained 10,534 positions (FIG. 26). These ending positions were obtained from regions spanning totally 3.1 Mb and covering 9,489 SNPs. Thus, the preferred ending positions for maternal-specific fragments accounted for 0.24% of the analyzed regions for this pair of mother and fetus. There were 69,136, 82,413 and 121,607 plasma DNA fragments carrying maternal-specific alleles ending on Set X, Set Y and Set Z positions, respectively. There were 46,554, 245,037 and 181,709 plasma DNA fragments carrying shared alleles ending on Set X, Set Y and Set Z positions, respectively. Again, this analysis focuses on plasma DNA molecules that cover at least on informative SNP, the identified preferred ends only represent a subset of such non-random ends throughout the genome.

Figure 43:
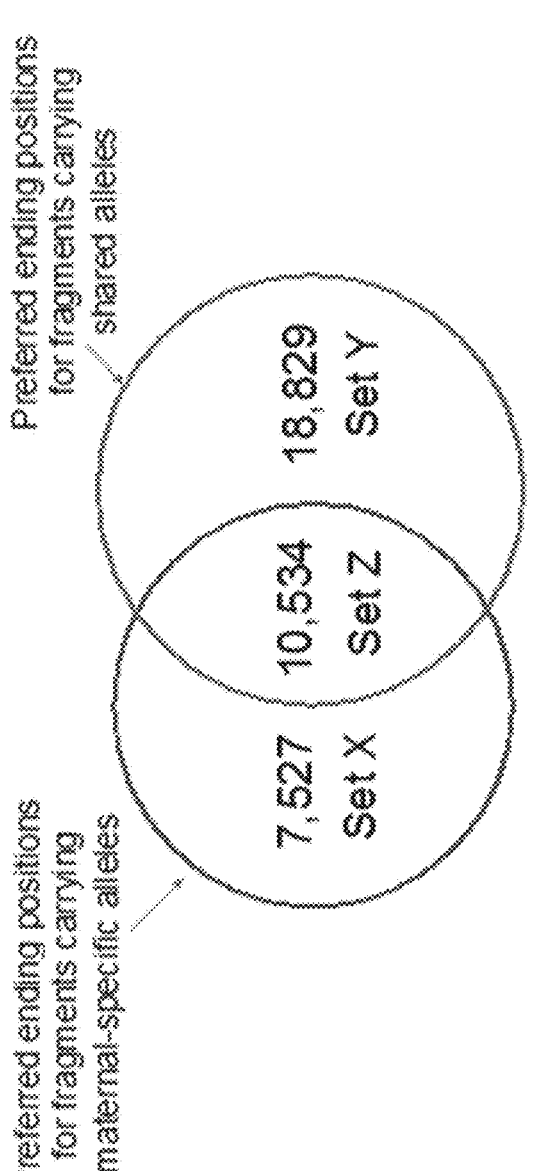
FIG. 43 shows an analysis of ending positions for plasma DNA fragments across SNPs that were homozygous in the fetus and heterozygous in the mother.

FIG. 43 shows an analysis of ending positions for plasma DNA fragments across SNPs that were homozygous in the fetus and heterozygous in the mother. Set X included preferred ending positions for fragments carrying maternal-specific alleles. Set Y included preferred ending positions for fragments carrying shared alleles. Set Z included preferred ending positions for both types of plasma DNA fragments.

2. Using Recurrent Ending Positions to Deduce Fetal DNA Fraction

After the identification of recurrent ending positions for plasma DNA fragments derived from the mother and the fetus, we reasoned that the relative abundance of plasma DNA ending on these sets of nucleotide positions would reflect the fetal DNA fraction. To confirm this, we sequenced the plasma DNA of 26 first trimester pregnant (10~13 weeks) women each carrying a male fetus. The median mapped read count was 16 million (range: 12-22 million). The proportion of sequenced reads aligning to chromosome Y was used for calculating the actual fetal DNA fraction in each plasma sample. A positive correlation can be observed between the relative abundance (denoted as F/M ratio) of plasma DNA with recurrent fetal (Set A) and maternal (Set X) ends and the fetal DNA fraction (R=0.63, P=0.0004, Pearson correlation, FIG. 44). It is interesting that while the preferred ending positions were identified based on informative SNPs for one pair of fetus and mother and only represented a subset of such ends in the genome, the identified ends were also relevant for other pregnancies and the correlation with fetal fraction was achieved even with just this subset of preferred ends.

Figure 44:
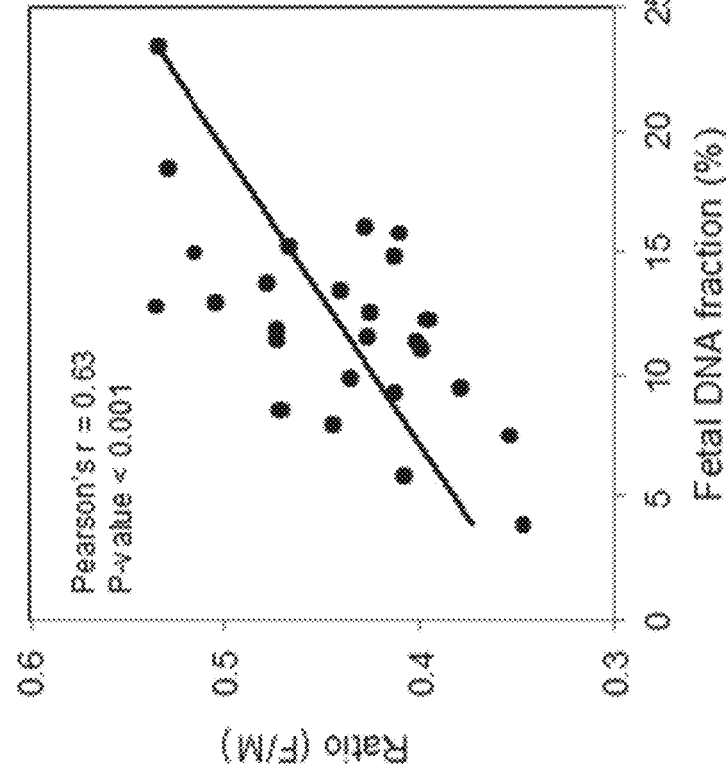
FIG. 44 shows a correlation between the relative abundance (Ratio (F/M)) of plasma DNA molecules with recurrent fetal (Set A) and maternal (Set X) ends and fetal DNA fraction.

FIG. 44 shows a correlation between the relative abundance (Ratio (F/M)) of plasma DNA molecules with recurrent fetal (Set A) and maternal (Set X) ends and fetal DNA fraction. Each of the data points can correspond to a respective calibration sample, and thus be considered calibration data points. The line fitting the calibration data points is an example of a calibration function.

Other sets can be used besides Set A and Set X. For example, a ratio (or other relative abundance or a function of a ratio) can be taken of Set A relative to Set C and Set A relative to Set B. As another example, a ratio can be taken of Set X and Set Z or a ratio between Set X and Set Y, which would provide a maternal DNA fraction, which can be assumed to be an inverse of the fetal DNA fraction. In such an example, the maternal tissue can be a first tissue type whose proportional contribution is determined, even if implicitly.

3. Use of Size

Size distribution of plasma DNA fragments ending on the fetal-specific ending positions provides further evidence that the positions are fetal-specific. To further support Set A and Set X positions were preferred ending sites for fetal-derived and maternal-derived DNA fragments, respectively, we compared the size distributions of plasma DNA ending on these two sets of positions. For the sample that these positions were derived from, the size distribution was shorter for fragments ending on Set A positions was shorter than those ending on Set X positions (FIG. 45A).

FIG. 45A shows plasma DNA size distributions for fragments ending on the fetal-preferred ending positions (Set A) (in blue/black) and fragments ending on the maternal-preferred ending positions (Set X) (in red/grey). Shorter size distribution was observed for fragments ending on Set A positions compared with those ending on Set X positions. FIG. 45B shows the cumulative plot for the size distributions for the two sets of fragments. FIG. 45C shows the difference in the cumulative frequencies of the two sets of fragments ($\Delta S$) against fragment size. FIG. 45D shows $\Delta S$ against size with shifting of the Set A and Set X end positions to positions with larger genomic coordinates by zero to 5 bp. FIG. 45E shows $\Delta S$ against size with shifting of the Set A and Set X ending positions by zero to 5 bp in a reverse direction (positions with smaller genomic coordinates).

To further quantify the difference in the size distribution, the cumulative frequencies of the two curves are plotted (FIG. 45B). The difference in the two curves, represented by $\Delta S$, are plotted in FIG. 45C. We observed that the maximum difference was observed at 166 bp. This is consistent with the previous reports that the maximal difference between fetal- and maternal-derived DNA could be observed at 166 bp (Yu et al. Proc Natl Acad Sci USA. 2014; 111:8583-8). The present findings suggested that there was an enrichment of fetal-derived DNA for fragments ending on the fetal-preferred ending positions (Set A) compared with those ending on maternal-preferred ending positions (Set X).

We further investigated the specificity of these ending positions by shifting the Set A and Set X ending positions by 1 to 5 bp upstream or downstream the genome. The $\Delta S$ values are plotted against size with the shifting of Set A and Set X ending positions in both directions (FIGS. 45D and 45E). Positive numbers of the shift represent the shifting to a position with a larger genomic coordinate (FIG. 45D) and negative numbers of the shift represent the shifting to a position with a smaller genomic coordinate (FIG. 45E). The shifting of the fetal- and maternal-preferred positions even by 1 bp would significantly reduce the size difference between DNA fragments ending on these two sets of positions ($\Delta S$). The shifting of 5 bp almost completely eliminated the size difference. These results suggested that the reads ending at those alternative positions were not as fetal- or maternal-specific than the reads ending at those preferred ending positions identified by our algorithm. These data further support our interpretation that plasma or cell-free DNA molecules fragment or are cleaved very precisely at those preferred end positions. In other words, there the non-random cell-free DNA fragmentation process is precise down to the level of specific nucleotides.

Then, we analyzed the pooled sequenced reads from the 26 first trimester plasma samples used for fetal DNA fraction analysis. Shorter size distribution was observed for fragments ending on Set A positions compared with those ending on Set X positions (FIG. 24A).

Figures 46A, 46B, 46C, 46D, 46E:
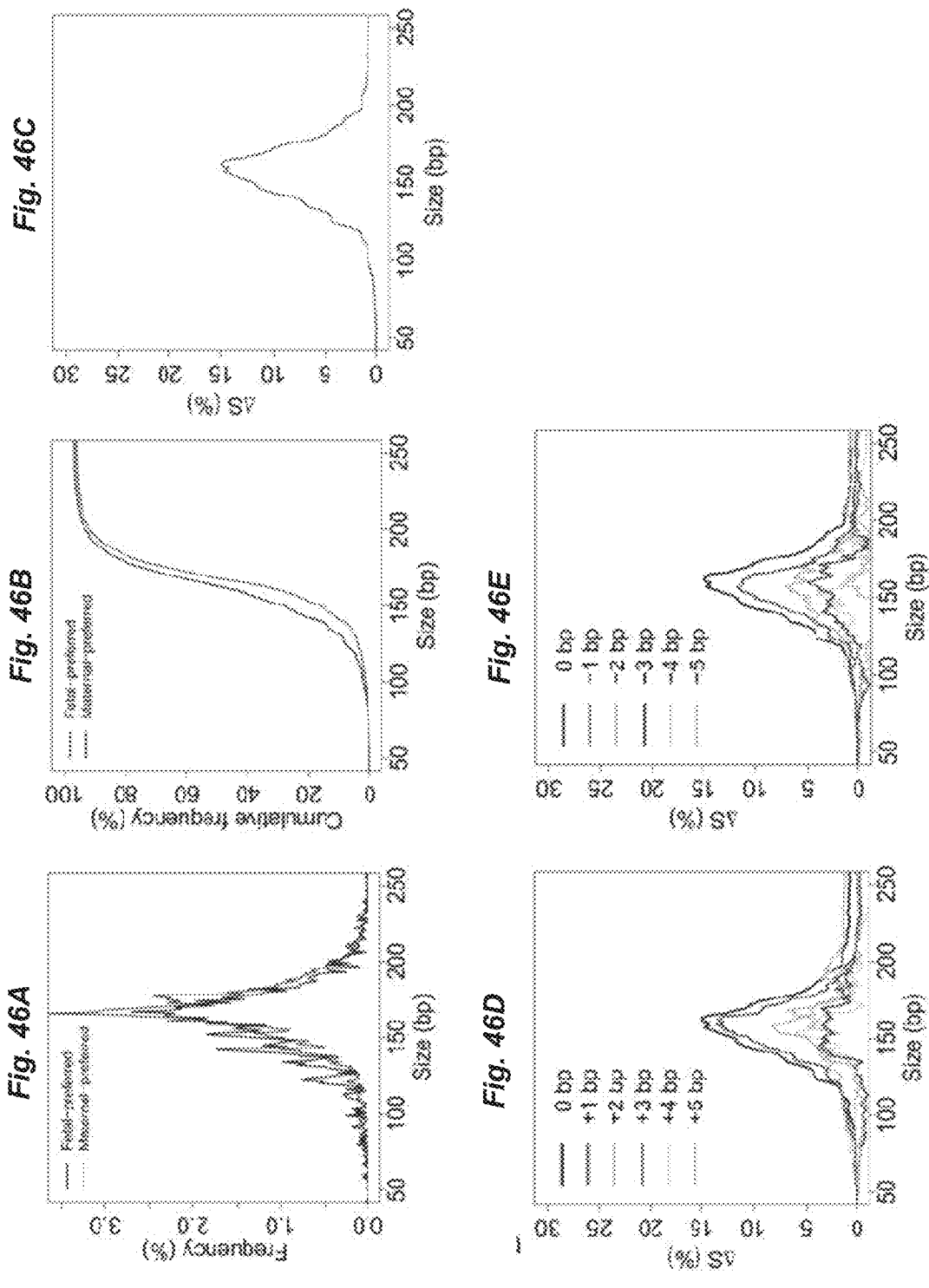
FIGS. 46A-46E show data regarding plasma DNA size distributions in a pooled plasma DNA sample from 26 first trimester pregnant women for fragments ending on the fetal-preferred ending positions and fragments ending on the maternal-preferred ending positions.

FIG. 46A shows plasma DNA size distributions in a pooled plasma DNA sample from first trimester pregnant women for fragments ending on the fetal-preferred ending positions (Set A) (in blue/black) and fragments ending on the maternal-preferred ending positions (Set X) (in red/grey). Shorter size distribution was observed for fragments ending on Set A positions compared with those ending on Set X positions. FIG. 46B shows the cumulative plot for the size distributions for the two sets of fragments. FIG. 46C shows the difference in the cumulative frequencies of the two sets of fragments ($\Delta S$) against fragment size. FIG. 46D shows $\Delta S$ against size with shifting of the Set A and Set X positions by zero to 5 bp (larger genomic coordinates). FIG. 46E shows $\Delta S$ against size with shifting of the Set A and Set X positions by zero to 5 bp in a reverse direction (smaller genomic coordinates). The size difference between the plasma DNA fragments ending on the two sets of positions ($\Delta S$) would reduce with the shifting of these positions, indicating that these positions would be precise to a single nucleotide level.

B. Cancer Example

The same strategy can also be applied for the analysis of preferred ending positions for cancer-derived fragments. In this example, we sequenced the plasma (220× coverage), buffy coat (48×) and tumor tissue (45×) of a patient suffering from hepatocellular carcinoma (HCC). The mutational profile of the patient was obtained by comparing the genotypes of the tumor tissue and the buffy coat. To determine the preferred ending positions for cancer-derived plasma DNA fragments, we analyzed the plasma DNA fragments carrying the cancer mutations. As shown in FIGS. 46A-46E, the fragmentation pattern of plasma DNA in the HCC patient is not random. Certain nucleotide positions have increased probability of being an end of a plasma DNA fragments.

1. Identification of Cancer-Specific Ending Positions

Figure 47:
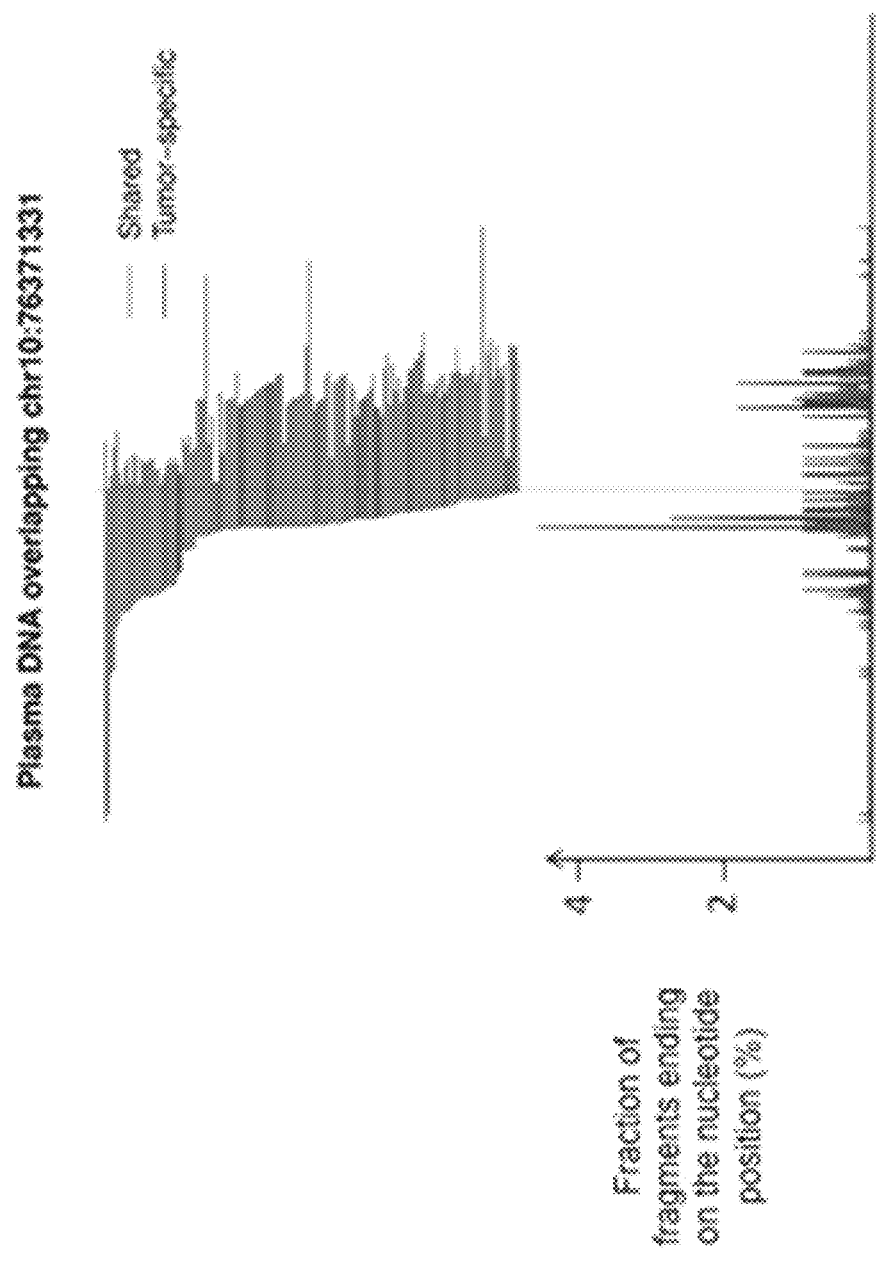
FIG. 47 shows an illustrative example of the non-random fragmentation patterns of plasma DNA of the HCC patient.

FIG. 47 shows an illustrative example of the non-random fragmentation patterns of plasma DNA of the HCC patient. On the upper part of the figure, each horizontal line represents one sequenced DNA fragment. The red/grey and blue/black lines represent DNA fragments carrying the wild-type and mutant alleles, respectively. The ends of the DNA fragments represent the ending position of the sequenced read. The fragments are sorted according to the coordinate of the left outermost nucleotide (smallest genomic coordinate). On the lower part of figure, the percentage of fragments ending on a particular position is shown. The X-axis represents the genomic coordinates and the mutation is located at the center indicated by the dotted line.

We identified genomic positions that have increased probability of being an end of plasma DNA fragments carrying mutant alleles and wildtype alleles using Poisson probability distribution function as described previously. A p-value of 0.01 was used as the threshold. The reverse is also true, as described in PCT Application No. PCT/CN2016/073753, namely when a plasma DNA molecule with a specific end is identified, the SNP allele or mutation on the molecule is more likely to be cancer-derived, disease-associated or pregnancy-associated, depending which set of ends was used in the plasma DNA data interpretation.

Figure 48:
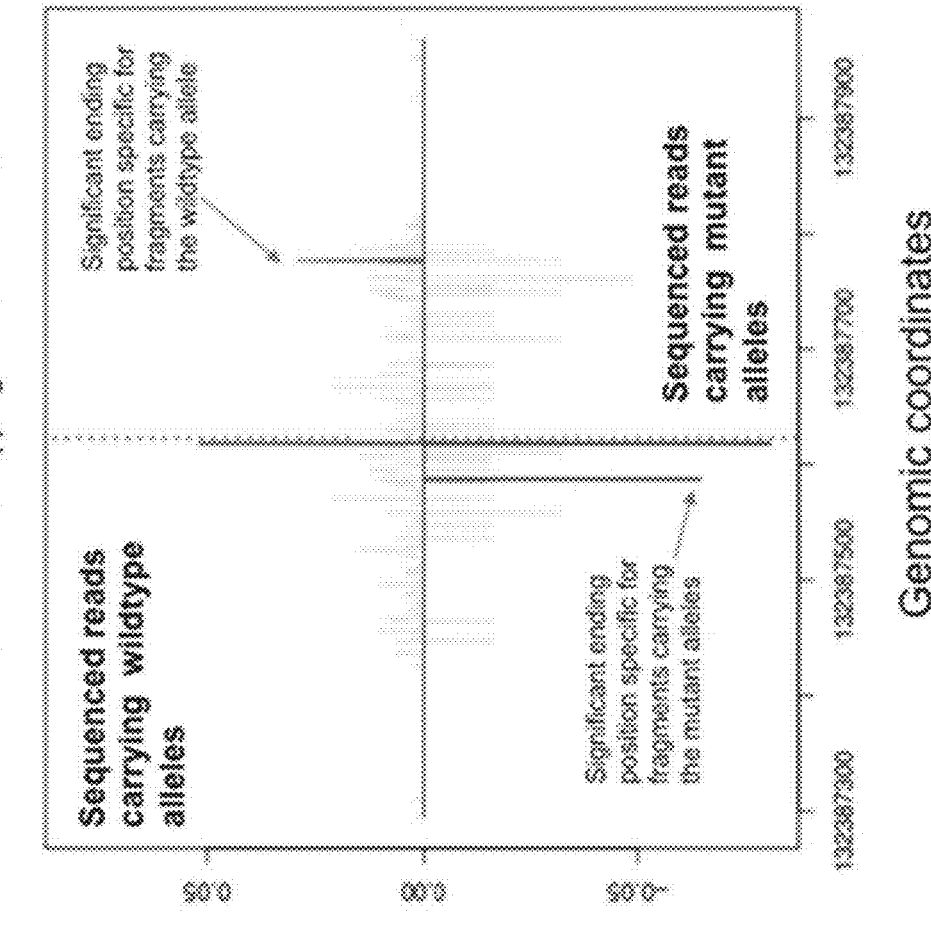
FIG. 48 is a plot of probability a genomic coordinate being an ending position of plasma DNA fragments across a region with a mutation site.

FIG. 48 is a plot of probability a genomic coordinate being an ending position of plasma DNA fragments across a region with a mutation site. Results for nucleotide positions with a significantly increased probability of being an end of plasma DNA fragments carrying a wildtype allele and a mutant allele are shown in red/grey and blue/black, respectively. The X-axis represents the genomic coordinates and the mutation is located at the center indicated by the dotted line. As shown, there are coordinates that have a high rate of occurrence of ending positions for just the mutant-specific allele, for just the wildtype allele, and some are common to both.

Figure 49A:
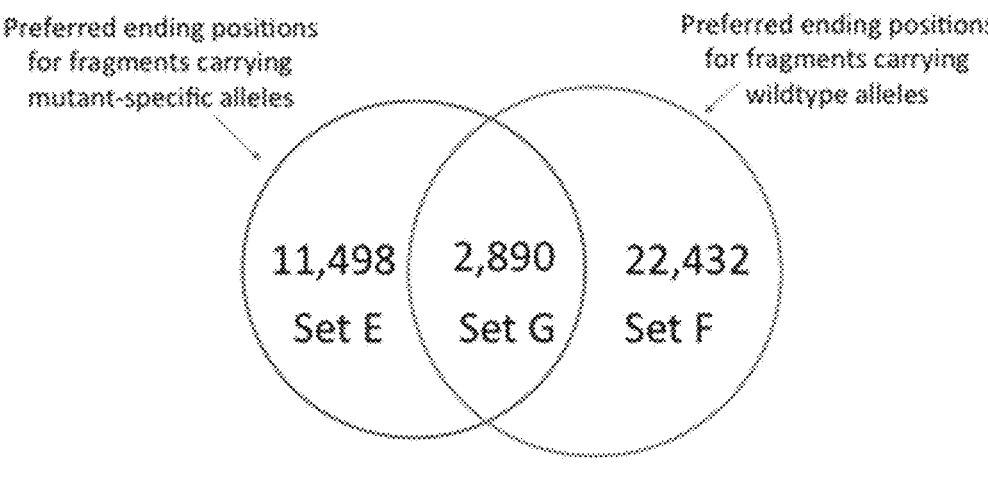
FIG. 49A shows an analysis of ending positions for plasma DNA fragments across genomic positions where mutations were present in the tumor tissue.

FIG. 49A shows an analysis of ending positions for plasma DNA fragments across genomic positions where mutations were present in the tumor tissue. Set E included preferred ending positions for fragments carrying mutant alleles. Set F included preferred ending positions for fragments carrying wildtype alleles. Set G included preferred ending positions for both types of plasma DNA fragments.

2. Using Recurrent Ending Positions to Deduce Tumor DNA Fraction

As Set E positions were preferred ending sites for cancer-derived DNA and Set F positions were preferred ending sites for background DNA predominantly derived from non-tumor tissues, we hypothesize that the ratio between the fragments ending on these two set of positions would correlate with the DNA derived from the tumor. Thus, we analyzed the plasma of 71 HCC patients whose plasma contained at least 1% of tumor-derived DNA. These patients were previously analyzed for copy number aberrations in plasma DNA and the tumor DNA fractions were estimated by the magnitude of the copy number aberrations. (Jiang et al. Proc Natl Acad Sci USA. 2015; 112:E1317-25). The ratio between the fragments ending on these two sets of positions ($Ratio_{M/WT}$) is defined as:

$$Ratio_{M/WT} = \frac{No. \text{ of plasma } DNA \text{ fragments ending on Set } E \text{ positions}}{No. \text{ of plasma } DNA \text{ fragments ending on Set } F \text{ positions}}$$

Figure 49B:
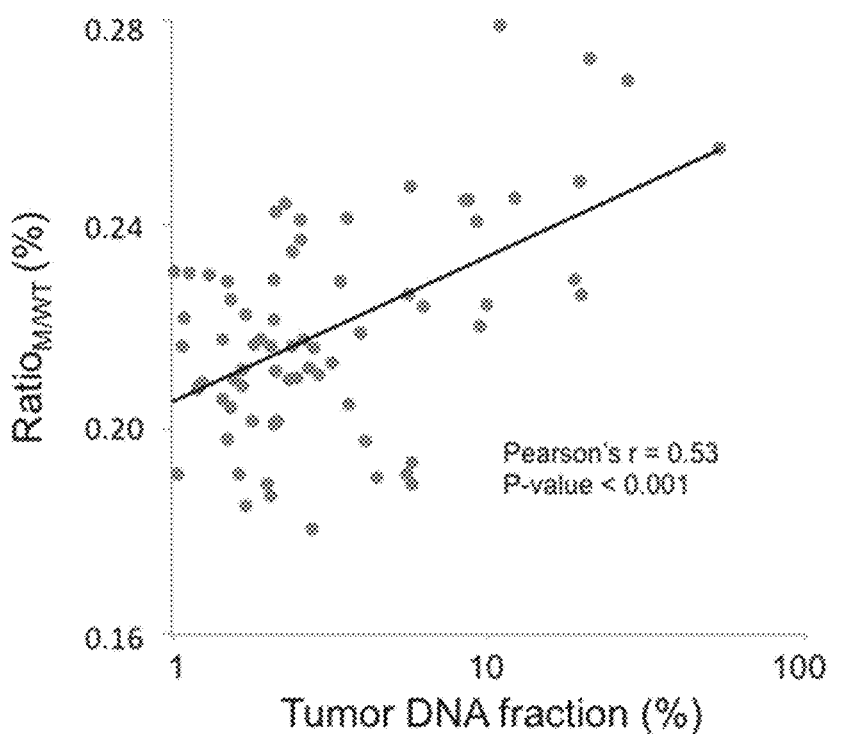
FIG. 49B shows a correlation between Ratio$_{M/WT}$ and tumor DNA fraction in the plasma of 71 HCC patients.

FIG. 49B shows a correlation between $Ratio_{M/WT}$ and tumor DNA fraction in the plasma of 71 HCC patients. A positive correlation between $Ratio_{M/WT}$ and the tumor DNA fraction in plasma was observed (r=0.53, p<0.001, Pearson correlation). These results suggest that the number of fragments ending on these cancer-preferred ending positions would be useful for predicting the amount of tumor-derived DNA in the plasma of cancer patients.

Some embodiments can increase the number of accessible informative cancer DNA fragments by the combined detection of a variety of cancer-specific or cancer-associated changes, for example, single nucleotide mutations, in combination with cancer-specific or cancer-associated DNA methylation signatures (e.g. location of 5-methycytosine and hydroxymethylation), cancer-specific or cancer-associated short plasma DNA molecules, cancer-specific or cancer-associated histone modification marks, and cancer-specific or cancer-associated plasma DNA end locations. Certain cancer-specific or cancer-associated changes may be used as filtering criteria in identifying mutations.

VII. Polymorphism-Independent End Position Analysis

In other embodiments, the preferred ending positions can be obtained by (A) comparing the ending positions of plasma DNA fragments from different individuals or (B) comparing the ending positions of plasma DNA fragments of samples from one individual taken at different time points.

A. Comparison Between the Preferred Ending Positions in Subjects Suffering from Different Pathological and Physiological Conditions 1. Use of Exclusive Sets Above Threshold Based on Poisson distribution probability function, we have identified genomic positions that had increased probability of being ending positions of plasma fragments for the pregnant woman and the HCC patient described in the previous sections. In this analysis, the null hypothesis is that all plasma DNA fragments would be fragmented randomly so that each genomic position would have an equal probability of being the end of plasma DNA fragments. The plasma DNA fragments were assumed to be 166 bp in size on average. The p-value was calculated as $$p\text{-value} = Poisson\,(N_{actual}, N_{predict})$$

where Poisson ( ) is the Poisson probability function; $N_{actual}$ is the actual number of reads ending at the particular nucleotide; and $$N_{predict} = \frac{Total \text{ number of reads}}{3 \times 10^9 \times 166},$$

the $3 \times 10^9$ in the denominator represents the number of nucleotides in a genome.

The p-value was adjusted using the Benjamini and Hochberg correction (Bejamini et al. Journal of the Royal Statistical Society, 1995; 57:289-300) so as to achieve an expected false-discovery rate (FDR) of <1%.

Figure 50A:
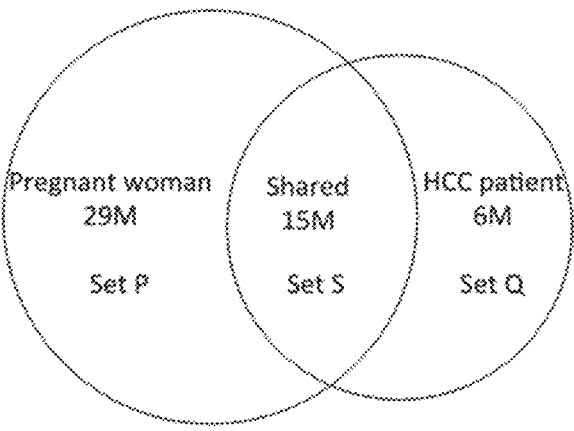
FIG. 50A shows the number of preferred ending positions for the plasma DNA of the pregnant woman and the HCC patient. Set P contained 29 million ending positions which were preferred in the pregnant woman.

FIG. 50A shows the number of preferred ending positions for the plasma DNA of the pregnant woman and the HCC patient. Set P contained 29 million ending positions which were preferred in the pregnant woman. Set Q contained 6 million ending positions which were preferred in the HCC patient. Set S is the overlapping set and contained 15 million ending positions.

We hypothesize that the fragments ending on the HCC preferred ending positions (Set Q) would be enriched for cancer-derived DNA when compared with those fragments ending on the pregnancy preferred ending positions (Set P). Thus, we calculated the $Ratio_{HCC/Preg}$ as $$Ratio_{HCC/Preg} = \frac{No. \text{ of plasma } DNA \text{ fragments ending on Set } Q \text{ positions}}{No. \text{ of plasma } DNA \text{ fragments ending on Set } P \text{ positions}}$$

and correlated this ratio with the tumor DNA fraction in the 71 HCC patients mentioned above.

Figure 50B:
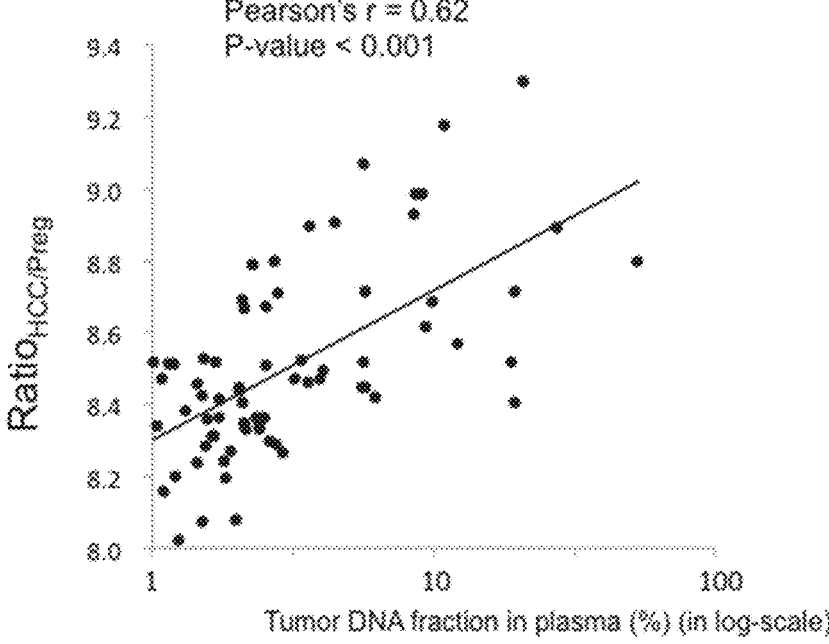
FIG. 50B shows a positive correlation was observed between Ratio$_{HCC/Preg}$ and tumor DNA fraction in plasma for the 71 HCC patients.

FIG. 50B shows a positive correlation was observed between $Ratio_{HCC/Preg}$ and tumor DNA fraction in plasma for the 71 HCC patients. These results suggest that the number or proportion of fragments ending on the preferred ending sites of a specific condition can be useful for detecting the condition or to quantify the amount of DNA released from the diseased organ.

2. Use of Set of Genomic Positions with Higher Ending Rate

Figure 51A:
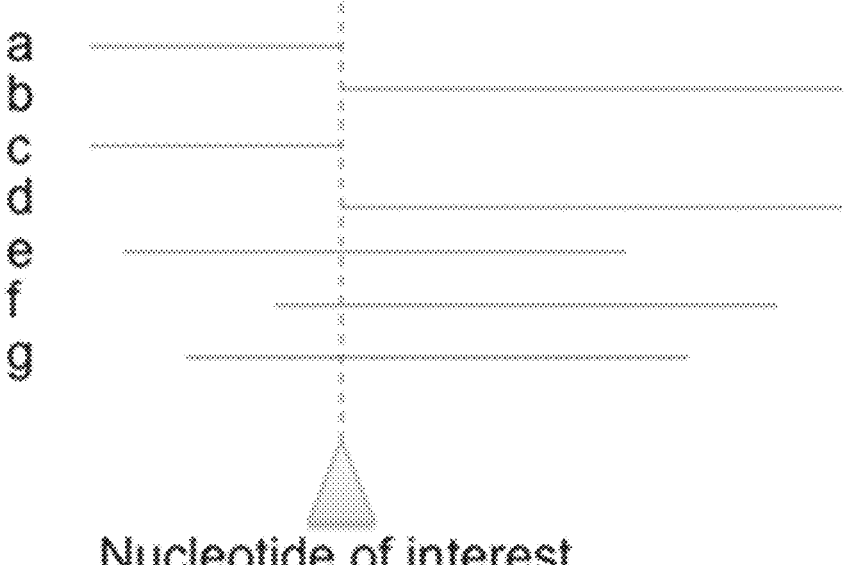
FIG. 51A shows an illustration of the concept of preferred end termination ratio (PETR). Each line represents one plasma DNA fragment.

In another embodiment, the preferred ending sites can be identified by determining the ratio between the number of fragments ending on such a position and the number of fragments covering the position but not ending on it. FIG. 51A illustrates the calculation of preferred end termination ratio (PETR).

$$PETR = \frac{No. \text{ of } DNA \text{ fragments end on the nucleotide}}{No. \text{ of } DNA \text{ fragments covering the nucleotide but not ned on it}}$$

FIG. 51A shows an illustration of the concept of PETR. Each line represents one plasma DNA fragment. These fragments are labeled as a to g. Fragments a, b, c and d terminated on the nucleotide of interest. Fragments e, f and g cover the nucleotide of interest but do not end on such position. In this illustrative example, PETR equals to 4/3, i.e. 1.33. In other embodiments, the denominator can be the number of DNA fragments covering the nucleotide, regardless of whether the DNA fragment ends on the position.

The calculation of PETR can be used to identify nucleotide positions that are preferred ends in individuals suffering from different disease conditions. The following example demonstrates the utility of PETR. The plasma samples of the previously mentioned HCC patient and a subject with chronic hepatitis B virus (HBV) infection but without a cancer (HBV carrier) were compared. The plasma DNA samples of the HBV carrier was sequenced to 215× haploid genome coverage. PETR was calculated for each genomic position for each subject. 7,350,067 genomic positions (Set H) were identified as having PETR at least 4 folds higher in the HCC patient compared with the HBV carrier. These positions had at least 4-fold increased chance of being an end of plasma DNA fragments in the HCC patient compared with the HBV carrier. Other fold differences can be used, e.g., 1.5 fold, 2 fold, and 3 fold.

Plasma samples from 11 independent HCC patients were further sequenced to a much lower sequencing depth. A mean of 28 million sequenced reads were obtained from these 11 plasma samples. The mean PETR at the 7,350,067 Set H positions were calculated for each of these 11 HCC patients and correlated with the tumor DNA fraction in plasma. The tumor DNA fraction in plasma was calculated based on the magnitude of the copy number aberrations in plasma as previously described (Chan et al. Proc Natl Acad Sci USA. 2015; 112:E1317-25).

Figure 51B:
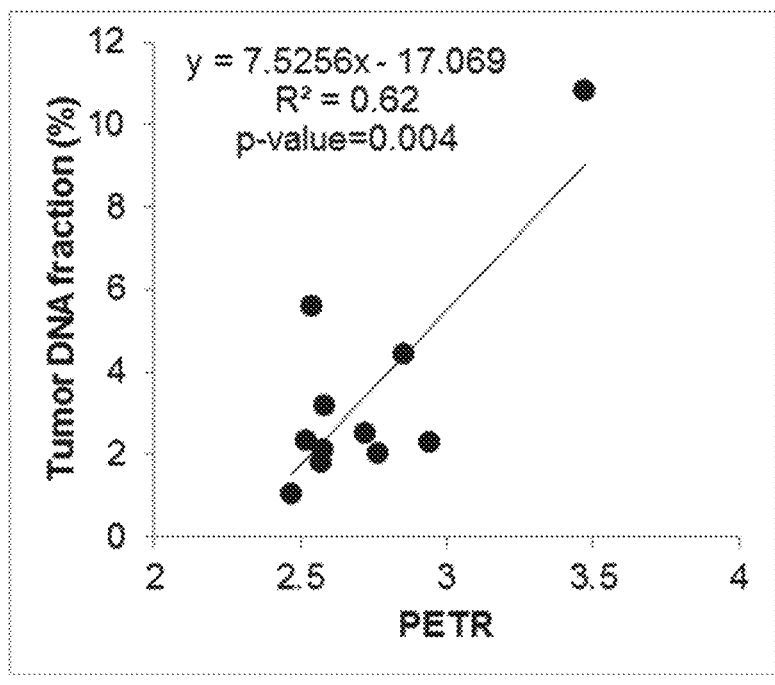
FIG. 51B shows a correlation between tumor DNA fraction in plasma with PETR at the Set H positions in 11 HCC patients.

FIG. 51B shows a correlation between tumor DNA fraction in plasma with PETR at the Set H positions in 11 HCC patients. A positive correlation between the two parameters can be observed suggesting that the average PETR at the HCC-preferred (Set H) positions would be useful to indicate the amount of tumor DNA in the plasma.

3. Confirmation of Ending Position being Liver-Related

To show that the preferred ending positions present in the HCC plasma DNA sample or in the HBV plasma DNA sample were liver-related, we searched for their presence in plasma samples collected from patients before and after surgical removal of HCC. The data are shown in Table 3. The pre- and post-surgical samples were sequenced to 17× and 20× haploid genomic coverages, respectively.

TABLE 3

|  | HCC-preferred ending sites | HBV-preferred ending sites |
|---|---|---|
| Pre-surgery preferred ending sites in HCC 1 | 92 | 16 |
| Post-surgery preferred ending sites in HCC 1 | 5 | 4 |

Table 3 shows HCC-preferred ending positions and HBV-preferred ending positions in plasma sample collected before and after surgery to remove the liver tumor in the patient with HCC.

As can be seen in Table 3, there are reductions the number of both HCC- and HBV-preferred ending positions. The HBV data suggest that the majority of the preferred ending positions are liver-derived and their reduction is due to the reduction in the liver cell mass after surgery. There is therefore reduced release of liver-derived cell-free DNA molecules into plasma. It is interesting to note that there are more than 5-fold more HCC-preferred ending positions in the pre-surgical sample that disappeared post-surgically. Some of the preferred ends that showed post-surgical disappearance are liver-derived. Given the observation that many more HCC-preferred ends than the HBV-preferred ends were detected in the same pre-surgical sample suggests that the majority of those ends are HCC-specific and are not just generically liver-associated.

There are a number of applications that can be derived from these data. The data indicate that the detection of cell-free DNA or plasma DNA preferred ends can be used for cancer treatment monitoring. For example, the post-surgical reduction in the preferred ends indicates the success of the surgical removal of the HCC. If the tumor was not removed completely or successfully, the amount or quantity of plasma DNA preferred ends would not show a substantial reduction after the surgery. This is because the remaining tumor or metastatic foci would be a source for continued release of cell-free DNA or plasma DNA with the HCC-preferred ending positions. The data show that treatment monitoring based on the analysis of cell-free DNA preferred ends can be achieved at relatively shallow sequencing depth.

The data also show that tissue-associated or cancer associated plasma DNA preferred ending positions can be used to identify the tissue of pathology, including the tissue that is harboring the cancer. For example, one can use multiple sets of cell-free DNA preferred ends that are derived from different organs. One would then be able to determine the relative amounts of cell-free DNA originating from various tissues. Thus, this can serve as an approach for cell-free DNA tissue deconvolution. The tissue shown by this approach to have the most deviation (significantly increased or significantly reduced) from reference values established from control samples would be the organ or tissue with the pathology (e.g. inflammation or viral infection just like in the chronic hepatitis B virus carrier) or cancer.

Figure 52:
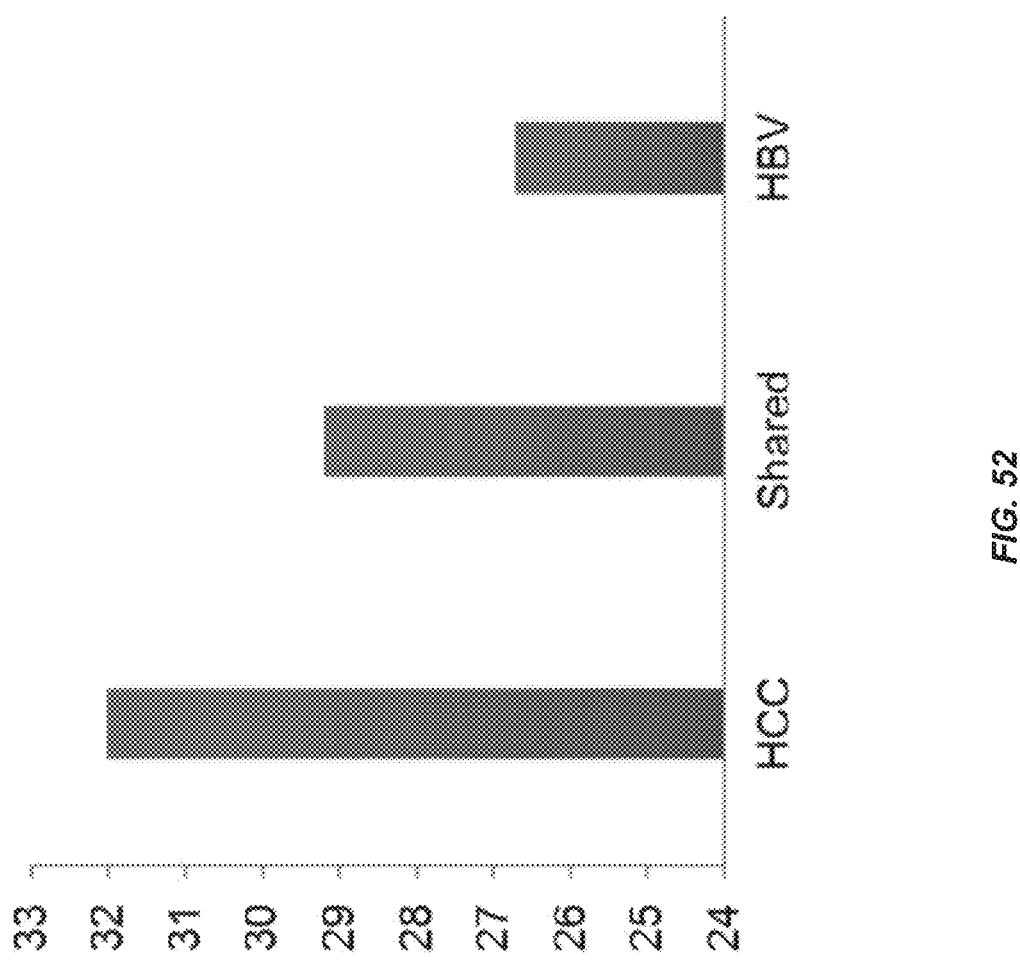
FIG. 52 shows a proportion of short DNA (<150 bp) detected among plasma DNA molecules ending with HCC-preferred ends, HBV-preferred ends or the shared ends.

Another piece of evidence to support that the plasma DNA HCC-preferred ends are cancer- or HCC-specific, we studied the size profile of plasma DNA molecules showing the HCC- or HBV-preferred ends (FIG. 52).

FIG. 52 shows a proportion of short DNA (<150 bp) detected among plasma DNA molecules ending with HCC-preferred ends, HBV-preferred ends or the shared ends. FIG. 52 shows that plasma DNA molecules exhibiting the HCC-preferred ends are generally much shorter (high proportion of short DNA) than those showing HBV-preferred ends. Jiang et al (Jiang et al. Proc Natl Acad Sci USA. 2015; 112:E1317-25) previously used another approach to show that tumor-derived plasma DNA molecules are shorter than the background non-tumor DNA. Because the plasma DNA molecules with the HCC-preferred ends are much shorter, they are highly likely to be tumor-derived. Thus, one may improve the chance of detecting the plasma DNA molecules with the HCC-preferred ends at even lower sequencing depth, by enriching the sample with short DNA, for example.

4. Window-Based Ending Rate

Figure 53A:
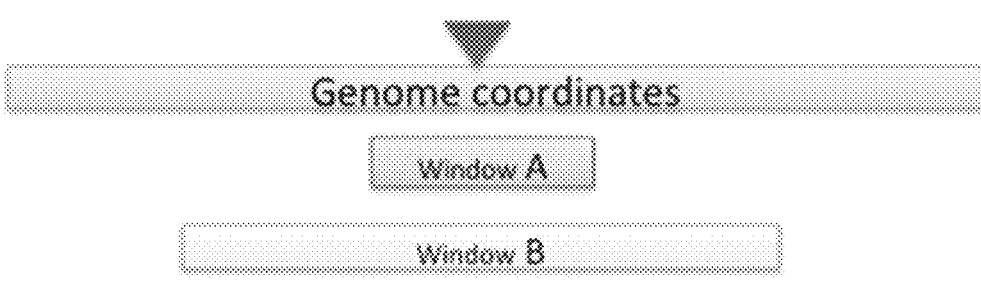
FIG. 53A shows an illustration of the principle of w-PETR. The value of w-PETR is calculated as the ratio between the number of DNA fragments ending within Window A and Window B.

In another embodiment, the HCC-preferred positions can be extended to include the neighboring nucleotides. FIG. 53A illustrates this method. The window-based PETR (w-PETR) ratio between the numbers of fragments ending within Window A and those ending within Window B would be determined. The size of Window A and Window B can be adjusted to achieve the desired performance. The performance of difference window sizes can be obtained experimentally. The size of Window A can be set, for example but not limited to 5 bp, 6 bp, 7 bp, 8 bp, 9 bp, 10 bp, 15 bp, 20 bp, 25 bp and 30 bp. The size of Window B would be larger than that of Window A and can be set, for example but not limited to 20 bp, 25 bp, 30 bp, 40 bp, 50 bp, 60 bp, 70 bp, 80 bp, 100 bp, 120 bp, 140 bp, 160 bp, 180 bp and 200 bp. In the follow illustrative example, the sizes of Window A and Window B were set as 20 bp and 150 bp, respectively.

FIG. 53A shows an illustration of the principle of w-PETR. The value of w-PETR is calculated as the ratio between the number of DNA fragments ending within Window A and Window B. Window A is larger and can be of width one when standard PETR is implemented. Window B is shown to be larger. Both windows are shown as being centered at the preferred ending position, but other positioning of the windows can be used. In some embodiments, window A can correspond to a preferred ending window.

Figure 53B:
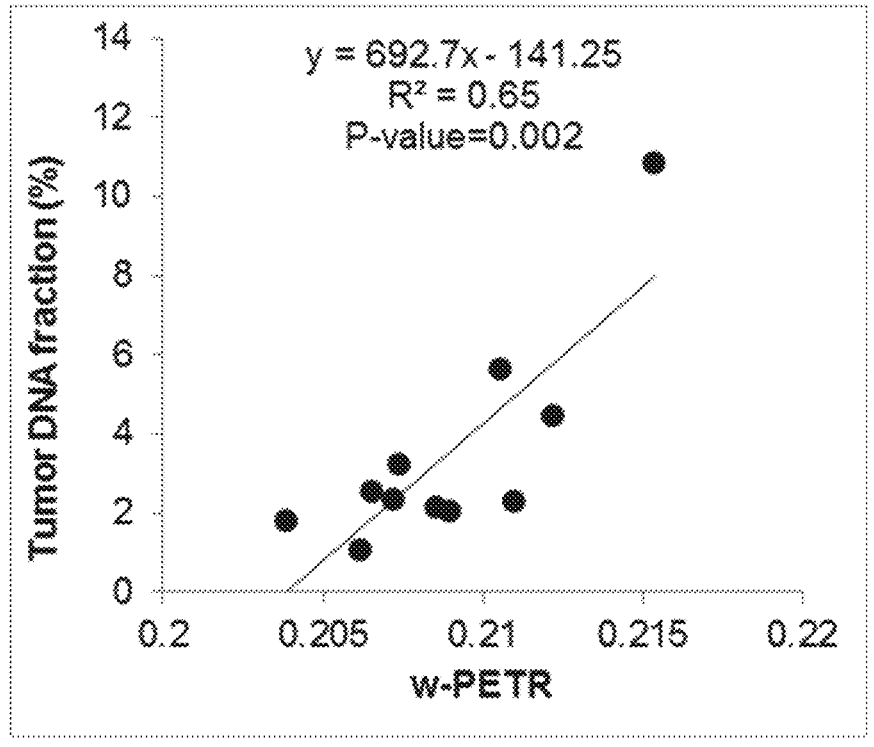
FIG. 53B shows a correlation between tumor DNA fraction and the value of w-PETR in the 11 HCC patients.

FIG. 53B shows a correlation between tumor DNA fraction and the value of w-PETR in the 11 HCC patients. These results suggest that w-PETR would be useful to determine the amount of tumor-derived DNA in the plasma of cancer patients.

5. Use of Highest Ending Positions Per Sample

Figure 54:
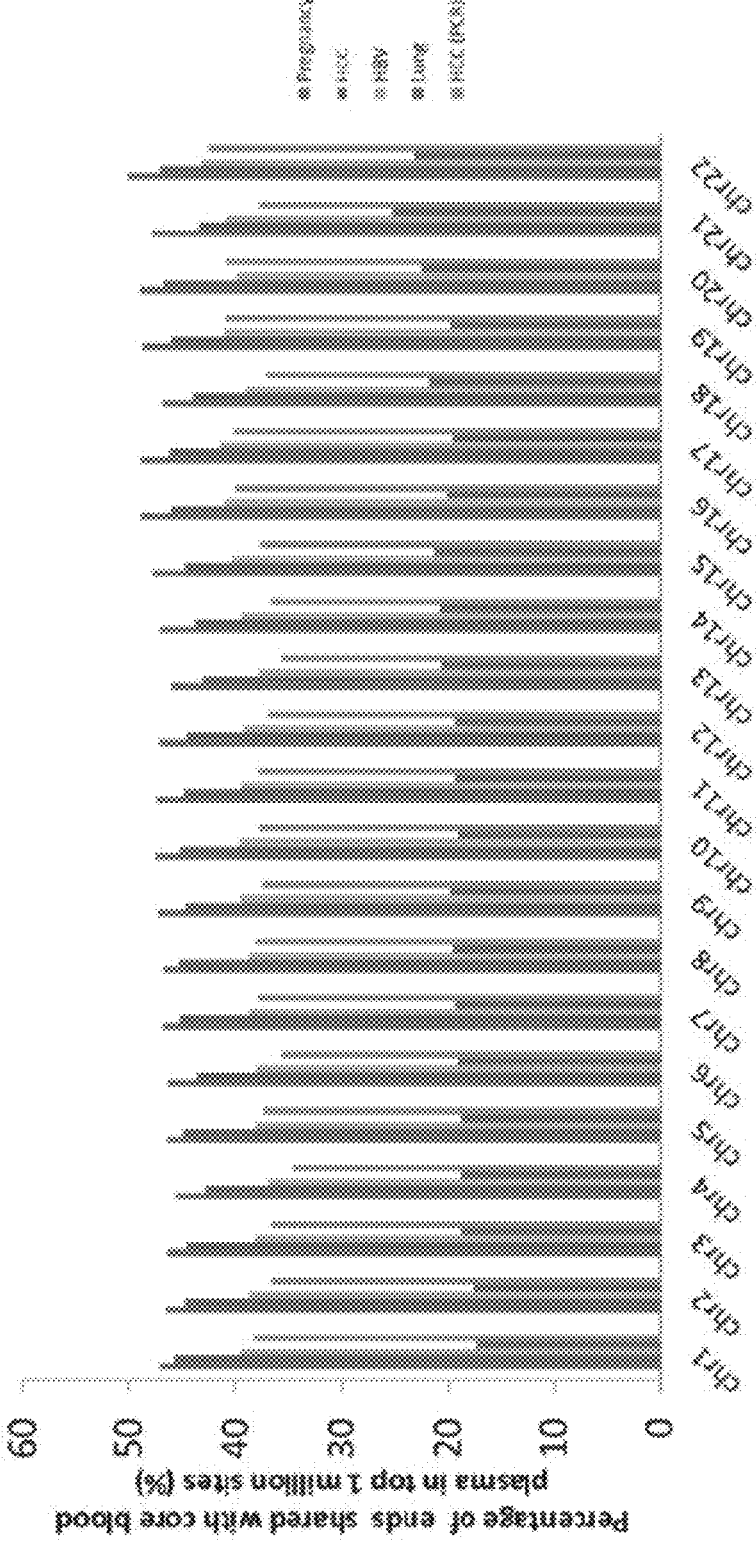
FIG. 54 shows the proportion of commonly shared preferred ending positions detected in plasma samples of each of the studied sample when compared with a cord blood plasma sample (210× haploid genome coverage).

We compared the top 1 million most frequently represented cell-free DNA ending positions between data from a pregnant woman, one chronic hepatitis B virus carrier (HBV), one lung cancer patient and two HCC patients. For the HCC patients, the sequencing library for one case (HCC) was prepared using a PCR-free protocol and the other sample (HCC (PCR) was prepared using a PCR-based protocol. All other samples are prepared using a PCR-free protocol. FIG. 54 shows the proportion of commonly shared preferred ending positions detected in plasma samples of each of the studied sample when compared with a cord blood plasma sample (210× haploid genome coverage).

FIG. 54 shows the proportion of commonly shared preferred ending positions detected in plasma samples of each of the studied sample when compared with a cord blood plasma sample (210× haploid genome coverage). Percentages are shown for the autosomes for each of pregnancy, HCC, HBV, lung cancer, and HCC detected using PCR.

The high level of commonality again supports the concept that plasma DNA fragmentation is not a random process. The HCC and HCC(PCR) data show that preferred ending position analysis can be performed using either library preparation protocols with or without PCR. It is interesting to note that there is still a proportion of plasma DNA molecules not showing common ends. The non-common ends are the preferred ends representative of the physiological state, e.g. pregnancy, the fetus or the placenta for the sample; or disease status, e.g. cancer. A more detailed comparison of the plasma DNA preferred ends is shown in FIG. 55.

Figure 55:
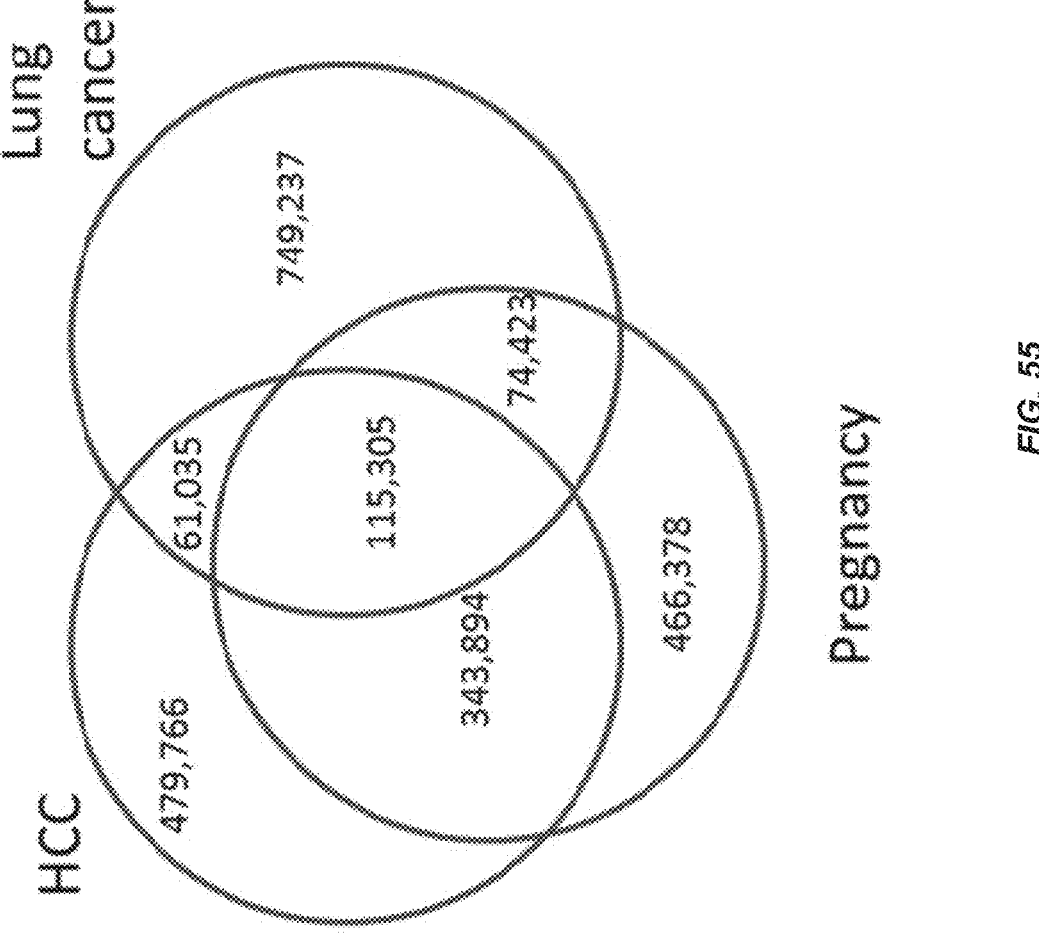
FIG. 55 shows a Venn diagram showing the number of preferred ending positions commonly observed in two or more samples as well as those that were only observed in any one sample.

FIG. 55 shows a Venn diagram showing the number of preferred ending positions commonly observed in two or more samples as well as those that were only observed in any one sample. Plasma DNA of lung cancer patient was sequenced at 175× haploid genome coverage.

It is noteworthy from FIG. 55 that 115,305 preferred ends are common across all three samples. These are likely to be derived from the major source of background plasma DNA, e.g., blood cells. The analysis also show that there were 61,035 preferred ending positions observed in the plasma samples of the HCC patient and the lung cancer patient. These preferred ends may be common to a number of cancers. Thus, they are cancer-derived. Whereas, there are ends that were only detected in the plasma DNA molecules of the HCC patient (479, 766 ends) or the lung cancer patient (749, 237 ends) but not both. These preferred ends therefore show a higher level of specificity. They are specific for a particular cancer tissue type. Based on the same rationale, one may be able to use similar mining strategies to identify ends specific for cancers of a particular organ and of a particular histology type. Plasma DNA molecules exhibiting the different classes of ends can be used for various applications. For example, one may aim to detect the HCC- or lung cancer-specific ends for the direct detection or screening of the specific cancer type. One may use the ends common to the HCC and lung cancer samples to detect or screen for cancer in general. One may use the most generic common ends as a denominator for normalization of the amount of disease-associated preferred ends detected. The generic common ends can also be detected for the purpose of screening for the sign of any disease (such as a general health screen). Positive findings for such a test can serve as an alert to visit a medical practitioner for more detailed investigation.

B. Comparison Between the Preferred Ending Positions Between Samples Collected from the Sample Individual but at Different Time Points The preferred ending positions of a particular condition can also be obtained by comparing the fragment ends of samples collected at different time points. For example, in a cancer patient, one plasma sample can be collected at the time of diagnosis and the other sample can be collected after treatment (e.g. after surgical resection of the tumor). The difference in the ending positions can potentially reflect the absence of the contribution of the cancer-derived DNA in the latter or the bodily response to the cancer. In another example, comparison can be made between the plasma samples collected from a pregnant woman taken before and after delivery of the fetus.

In the following example, the plasma samples collected from 8 pregnant women were analyzed. For each pregnant woman, a plasma samples was collected before delivery. In 6 of the women, an additional plasma sample was collected at the time of delivery. Multiple samples were collected from the eight pregnant women at 6 hours after delivery onwards and a total of 28 post-delivery plasma samples were collected. The plasma DNA samples were sequenced to an average depth of 6.49× haploid genome coverage. The sequenced reads for the samples collected before delivery and at the time of delivery were pooled together for PETR analysis and these reads would be referred as "pre-delivery reads". The sequenced reads for the samples collected at hours after delivery or later were pooled for PETR analysis and these reads would be referred as "post-delivery" reads. To identify the nucleotide positions that were preferred ends for pregnancy, positions with PETR at least 4 folds higher in the "pre-delivery" reads compared with "post-delivery" reads were retrieved. A total of 45,281 sites were identified.

An independent cohort of 8 first trimester pregnant women each carrying a male fetus was recruited and their plasma DNA was sequenced. A median of 20 million sequenced reads were obtained from these plasma DNA samples. The mean PETR values for the 45,281 sites was determined for each of the 8 pregnant women and these values were correlated with the fetal DNA fraction in plasma that was estimated from the proportion of reads aligning to the Y chromosome (Chiu et al. BMJ 2011; 342:c7401).

Figure 56A:
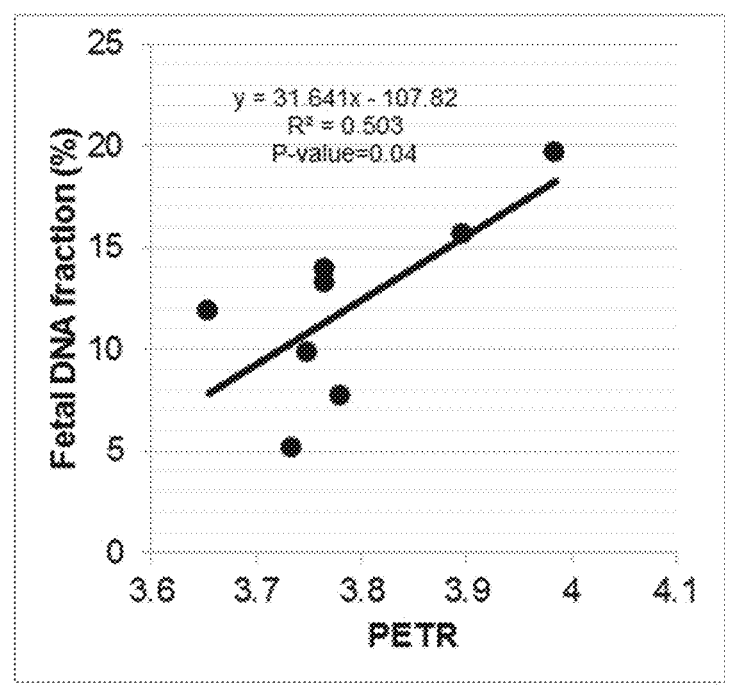
FIG. 56A shows a correlation between fetal DNA fraction in plasma and average PETR on the set of positions identified through the comparison between "pre-delivery" and "post-delivery" plasma DNA samples.

FIG. 56A shows a correlation between fetal DNA fraction in plasma and average PETR on the set of positions identified through the comparison between "pre-delivery" and "post-delivery" plasma DNA samples. These results suggest that the set of positions identified would be preferred for fetal-derived DNA and PETR analysis would be useful for quantifying fetal DNA in maternal plasma.

Similar to the approach described previously, we have applied the w-PETR analysis to this set of pregnancy-preferred positions. The size of Window A and Window B were set as 20 bp and 150 bp, respectively. In other embodiments, other window sizes can be used.

Figure 56B:
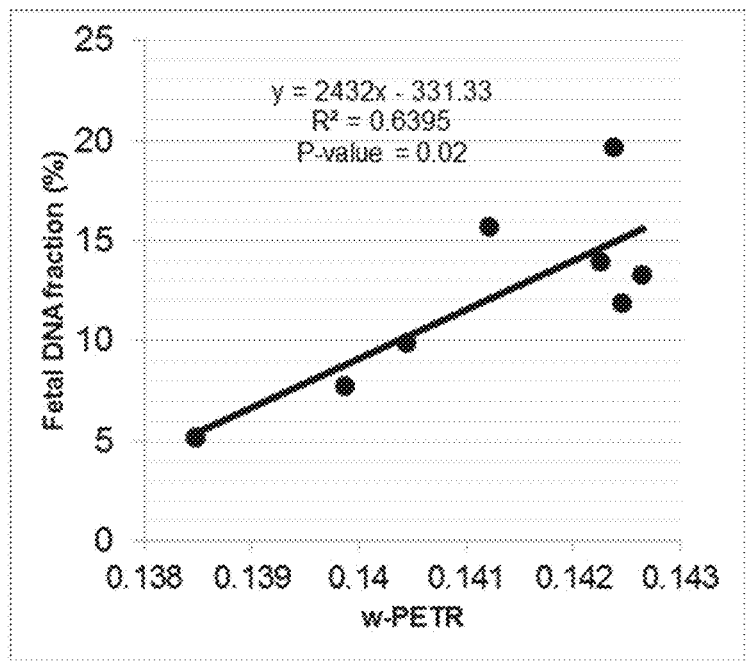
FIG. 56B shows a correlation between fetal DNA fraction in plasma and average w-PETR on the set of positions identified through the comparison between "pre-delivery" and "post-delivery" plasma DNA samples.

FIG. 56B shows a correlation between fetal DNA fraction in plasma and average w-PETR on the set of positions identified through the comparison between "pre-delivery" and "post-delivery" plasma DNA samples. These results suggest w-PETR analysis on these pregnancy-preferred positions would be useful for quantifying fetal DNA in maternal plasma.

C. Common End Points Among Same Condition

Figures 57A, 57B:
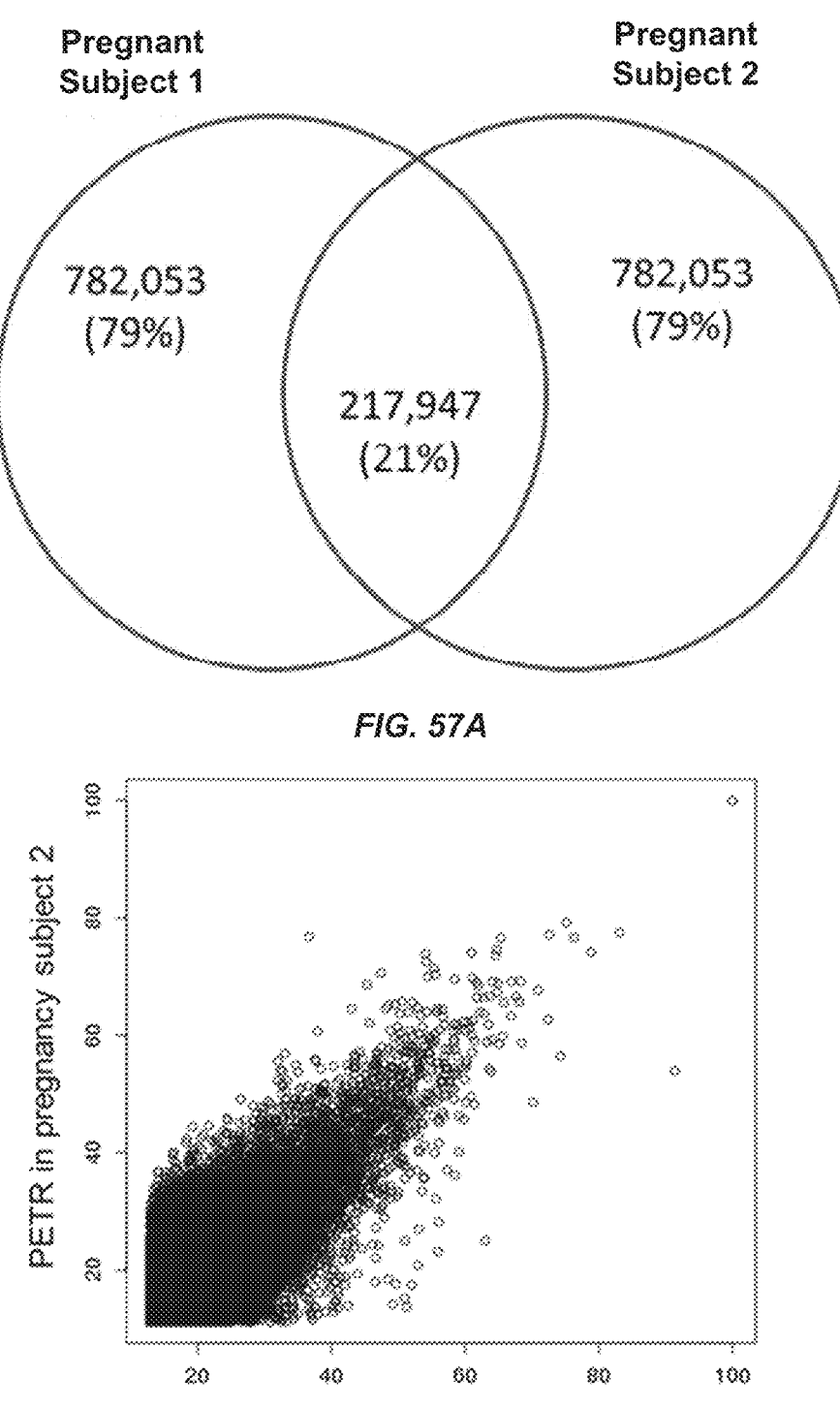
FIG. 57A shows the top 1 million most frequently observed plasma DNA preferred ending positions among two pregnant women at 18 weeks (pregnant subject 1) and 38 weeks of gestation (pregnant subject 2).
FIG. 57B shows a comparison of the PETR values of the top 1 million most frequently observed preferred ending positions in plasma of two pregnant women.

We compared the top 1 million most frequently observed preferred ending positions in plasma of two pregnant women (FIG. 57A).

FIG. 57A shows the top 1 million most frequently observed plasma DNA preferred ending positions among two pregnant women at 18 weeks (pregnant subject 1) and 38 weeks of gestation (pregnant subject 2). The data show that these women shared 217, 947 preferred ends. Given both women are pregnant, these ends are derived from the fetus, the placenta or organs that have increased cell-death (generation of plasma DNA) during pregnancy. These markers are therefore most useful for the monitoring of the pregnancy or the well-being of the fetus.

We calculated the PETR value for this sample set. Interestingly, a correlation (Pearson'r=0.52, p-value<0.0001) between the PETR values of the plasma DNA molecules in the two maternal plasma samples was observed (FIG. 57B).

FIG. 57B shows a comparison of the PETR values of the top 1 million most frequently observed preferred ending positions in plasma of two pregnant women. The high degree of correlation once again indicates that plasma DNA fragmentation is highly orchestrated. Some ending sites are more "preferred" than others. Interestingly, even among the top 1 million "most preferred" sites, there is a relatively wide dynamic range of PETR. If one was to choose several or a subset of preferred ends for targeted detection, e.g. to test for disease, one should choose those commonly shared among the disease group of interest, ideally not observed or are less prevalent in the control group without disease and particularly those ending positions with very high PETR.

VIII. Methods Using Tissue-Specific Ending Positions

Figure 58:
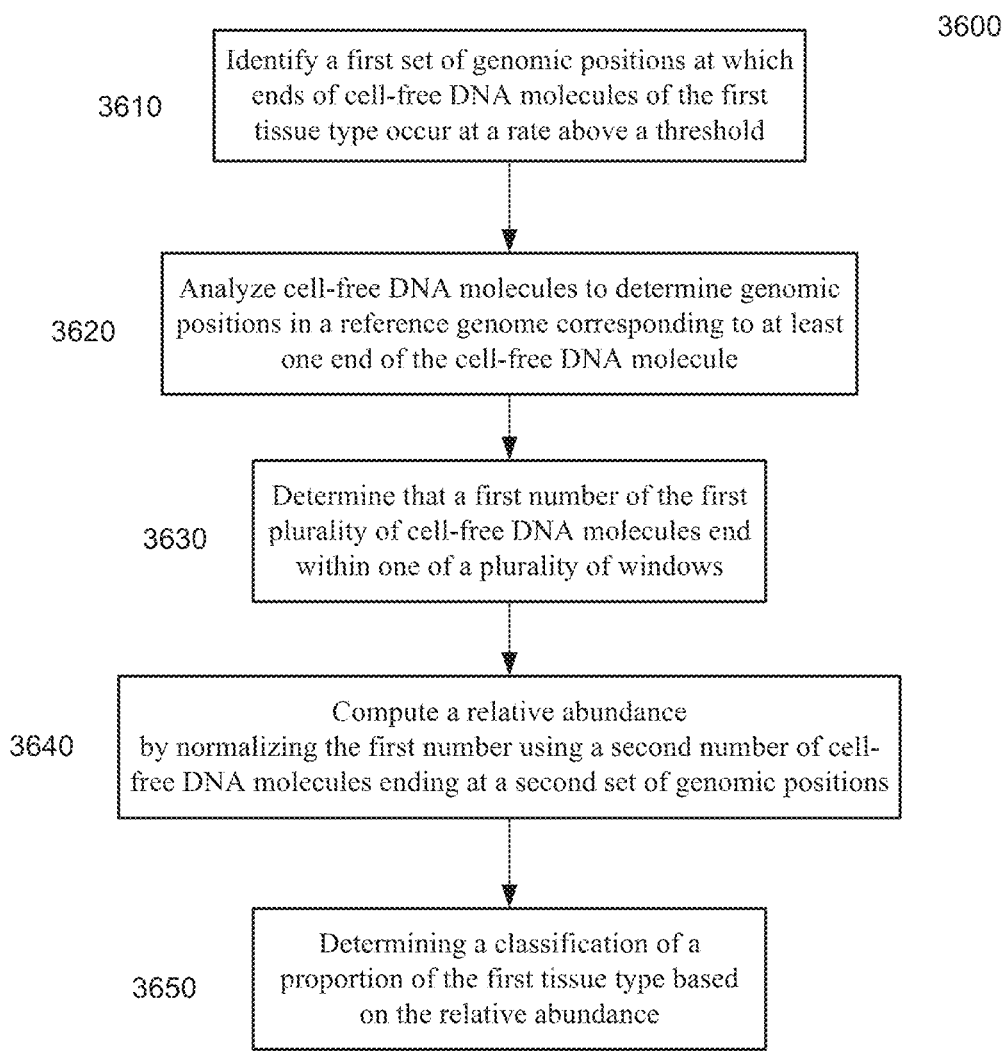
FIG. 58 is a flowchart of a method of analyzing a biological sample to determine a classification of a proportional contribution of the first tissue type in a mixture according to embodiments of the present invention.

FIG. 58 is a flowchart of a method 3600 of analyzing a biological sample to determine a classification of a proportional contribution of the first tissue type in a mixture according to embodiments of the present invention. The biological sample includes a mixture of cell-free DNA molecules from a plurality of tissues types that includes a first tissue type.

At block 3610, a first set of genomic positions at which ends of cell-free DNA molecules of the first tissue type occur at a rate above a threshold is identified. Further details about block 3610 in section X.B, as well as for other blocks performing identification of preferred ending positions. Details of other blocks of other methods can also be found in section X.

At block 3620, a first plurality of cell-free DNA molecules from the biological sample of a subject is analyzed. Analyzing a cell-free DNA molecule includes determining a genomic position in a reference genome corresponding to at least one end of the cell-free DNA molecule. Block 3620 can be performed in a similar manner as other blocks for analyzing cell-free DNA molecules, e.g., block 1320.

At block 3630, it is determined that a first number of the first plurality of cell-free DNA molecules end within one of a plurality of windows. The determination is performed based on the analyzing of the first plurality of cell-free DNA molecules. Each window includes at least one of the first set of genomic positions.

At block 3640, a relative abundance of the first plurality of cell-free DNA molecules ending within one of the plurality of windows is computed. The relative abundance can be determined by normalizing the first number of the first plurality of cell-free DNA molecules using a second number of cell-free DNA molecules. The second number of cell-free DNA molecules includes cell-free DNA molecules ending at a second set of genomic positions. In some aspects, the second set of genomic positions can be outside of the plurality of windows including the first set of genomic positions.

As described for FIG. 49A, the second set of genomic positions can be such that ends of cell-free DNA molecules of a second tissue type occur at a rate above the threshold in the at least one additional sample, where the second tissue type has a plurality of second tissue-specific alleles in the at least one additional sample. The second set of genomic positions can be determined using cell-free DNA molecules of the least one additional sample that include at least one of the plurality of second tissue-specific alleles. As Set G can be excluded from both set used to determine FIG. 49B, genomic positions at which ends of cell-free DNA molecules having a shared allele between the first tissue type and the second tissue type occur at a second rate above the threshold can be excluded from the first set of genomic positions and excluded from the second set of genomic positions. In some aspects, the second set of genomic positions can be determined using a reference sample (e.g., a sample from a healthy subject). In some aspects, the second set of genomic positions can be determined using the relative abundance of ending positions of cell-free DNA molecules from the reference sample. In one example, the first set of genomic positions can be determined from a biological sample from a subject suspected of having NPC using the relative abundance of EBV DNA fragment ending positions, and the second set of genomic positions can be determined from a reference (e.g., control) sample using the relative abundance of EBV DNA fragment ending positions. In some embodiments, the EBV DNA in each of the biological sample and the reference sample may be derived from the same tissue type or different tissue types.

At block 3650, the classification of the proportional contribution of the first tissue type is determined by comparing the relative abundance to one or more calibration values determined from one or more calibration samples whose proportional contributions of the first tissue type are known.

If the proportional contribution is high, further action can be performed, such as a therapeutic intervention or imaging of the subject (e.g., if the first tissue type corresponds to a tumor). For example, an investigation can use imaging modalities, e.g. computed tomography (CT) scan or magnetic resonance imaging (MRI), of the subject (entire subject or a specific part of the body (e.g. the thorax or abdomen), or specifically of the candidate organ) can be performed to confirm or rule out the presence of a tumor in the subject. If presence of a tumor is confirmed, treatment can be performed, e.g., surgery (by a knife or by radiation) or chemotherapy.

Treatment can be provided according to determined level of cancer, the identified mutations, and/or the tissue of origin. For example, an identified mutation (e.g., for polymorphic implementations) can be targeted with a particular drug or chemotherapy. The tissue of origin can be used to guide a surgery or any other form of treatment. And, the level of cancer can be used to determine how aggressive to be with any type of treatment, which may also be determined based on the level of cancer.

IX. Molecular Characteristics of Viral DNA in Plasma

Viral infections are implicated in a number of pathological conditions. For example, EBV infection is closely associated with NPC and natural killer (NK) T-cell lymphoma and infectious mononucleosis. HBV infection and hepatitis C virus (HCV) infection are associated with increased risks of developing HCC. In some aspects, the present disclosure provides methods for detecting and differentiating different conditions associated with viral infections by analyzing the levels and molecular features of circulating viral DNA. This may advantageously provide for the detection or screening of various pathological conditions using a cell-free sample from a subject, in some cases even when the subject is not displaying a given pathological condition. This may also enable monitoring of a progression or regression of the given pathological condition with time, in some cases during or following treatment. As examples, the nucleic acids of the pathogen found in the sample (e.g., plasma or serum) may be: (1) released from tumor tissues; (2) released from a non-cancer cell, e.g. rest B cells carrying EBV; and (3) contained in a virion.

A. Analysis of Concentration/Proportion of EBV and Association to NPC

The pathogenesis of NPC is closely associated with EBV infection. In endemic areas of NPC, e.g. South China, almost all NPC tumor tissues harbor EBV genomes. In this regard, plasma EBV DNA has been established as a biomarker for NPC (Lo et al. Cancer Res 1999; 59:1188-91). It has been shown that plasma EBV DNA is useful for detecting residual disease in NPC subjects after curative-intent treatment (Lo et al. Cancer Res 1999; 59:5452-5 and Chan et al. J Natl Cancer Inst 2002; 94:1614-9). The plasma EBV DNA in NPC subjects has been shown to be short DNA fragments of less than 200 bp and is thus unlikely to have derived from intact virion particles (Chan et al. Cancer Res 2003, 63:2028-32).

To investigate if plasma EBV DNA is useful for the screening of early NPC in asymptomatic individuals, we have screened 20,174 subjects without symptoms of NPC using plasma EBV DNA analysis. Subjects with detectable plasma EBV DNA were retested in approximately 4 weeks later with a follow-up plasma EBV DNA analysis. Subjects with persistently positive results on the two serial analyses were further investigated with nasal endoscopic examination and magnetic resonance imaging (MRI) of the nasopharynx. Out of the 20,174 subjects recruited, 1,112 were positive for plasma EBV DNA at enrollment. Among them, 309 were persistently positive on the follow-up test. Within the cohort of subjects who were persistently positive for EBV DNA in plasma, 34 were subsequently confirmed of having NPC after being investigated with nasal endoscopic examination and MRI. These results showed that the retesting of the subjects with initial positive plasma EBV DNA results can differentiate NPC subjects from those with transiently positive results and substantially reduce the proportion of subjects requiring the more invasive and costly investigations, namely endoscopy and MRI. However, the sequential testing of plasma EBV DNA requires the collection of an additional blood sample from subjects with initial positive results, which can present logistical challenges. In this application, we describe a method for differentiating NPC subjects from non-NPC subjects with detectable plasma EBV DNA based on the analysis of plasma EBV DNA fragmentation patterns. This method can also be applied for the analysis of other types of cancers associated with viral infection.

To analyze the cell-free viral DNA in plasma, targeted sequencing with capture enrichment with specifically designed capture probes was used. These capture probes covered the whole EBV genome, the whole HBV genome, the whole HPV genome and multiple genomic regions in the human genome (including regions on chr1, chr2, chr3, chr5, chr8, chr15 and chr22). For each plasma sample analyzed, DNA was extracted from 4 mL plasma using the QIAamp DSP DNA blood mini kit. For each case, all extracted DNA was used for the preparation of the sequencing library using the KAPA library preparation kit. Twelve cycles of PCR amplification were performed on the sequencing library using the KAPA PCR amplification kit. The amplification products were captured using the SEQCAP-EZ kit (Nimblegen) using the custom-designed probes covering the viral and human genomic regions stated above. After target capturing, 14 cycles of PCR amplification were performed and the products were sequenced using the Illumina Next-Seq platform. For each sequencing run, four to six samples with unique sample barcodes were sequenced using the paired-end mode. Each DNA fragments would be sequenced 75 nucleotides from each of the two ends. After sequencing, the sequenced reads would be mapped to an artificially combined reference sequence which consists of the whole human genome (hg19), the whole EBV genome, the whole HBV genome and the whole HPV genome. Sequenced reads mapping to unique position in the combined genomic sequence would be used for downstream analysis. The median number of uniquely mapped reads is 53 million (range: 15~141 million).

TABLE 4

| Type of samples | Number of samples |
|---|---|
| Non-NPC subjects with detectable plasma EBV DNA at enrollment to the study but undetectable plasma EBV DNA approximately four weeks later. For these subjects, the samples collected at enrollment were analyzed. These subjects are denoted as "transiently positive". | 5 |
| Non-NPC subjects with persistently detectable plasma EBV DNA at enrollment and approximately four weeks later. For these subjects, the samples collected at enrollment were analyzed. These subjects are denoted as "persistently positive". | 9 |
| NPC subjects | 6 |
| EBV-positive lymphoma subjects (two with NK T-cell lymphoma and one with Hodgkin lymphoma) | 3 |
| Subject with infectious mononucleosis | 1 |

Table 4 shows the number of different types of samples analyzed. In the initial analysis (Cohort 1), six subjects presenting with symptoms compatible with NPC, including neck lumps, hearing loss and epistaxis were recruited from the ear-nose and throat (ENT) clinic. The NPC subjects in cohort 1 have advanced disease. We determined if the concentration of plasma EBV DNA determined by real-time PCR and massively parallel sequencing would be useful for differentiating NPC subjects and those with false-positive plasma EBV DNA without a cancer.

Figures 59A, 59B:
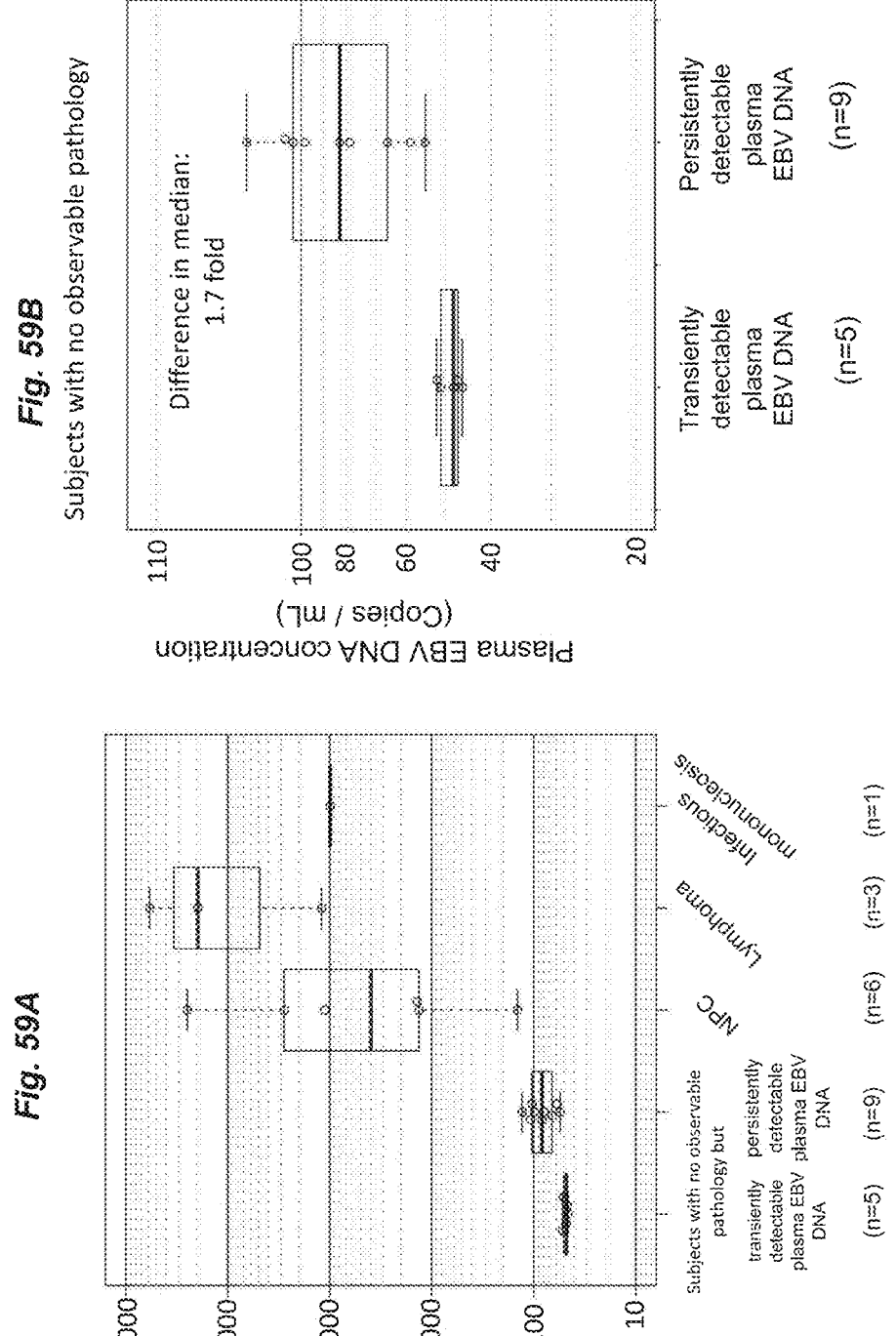
FIGS. 59A and 59B show plasma EBV DNA concentrations measured by real-time PCR for different groups of subjects.

FIG. 59A shows plasma EBV DNA concentrations measured by real-time PCR for different groups of subjects. As shown in FIG. 59A, plasma EBV DNA concentrations were higher in subjects with NPC, lymphoma and infectious mononucleosis compared with those with detectable plasma EBV DNA but without any observable pathology. As shown in FIG. 59B, for those subjects with detectable plasma EBV DNA at enrollment but without any observable pathology, the plasma EBV DNA concentration measured at enrollment was higher in the subjects with persistently positive results compared with those who would become negative in the follow-up test (i.e. with transiently detectable plasma EBV DNA) (p=0.002, Mann-Whitney test).

Figures 60A, 60B:
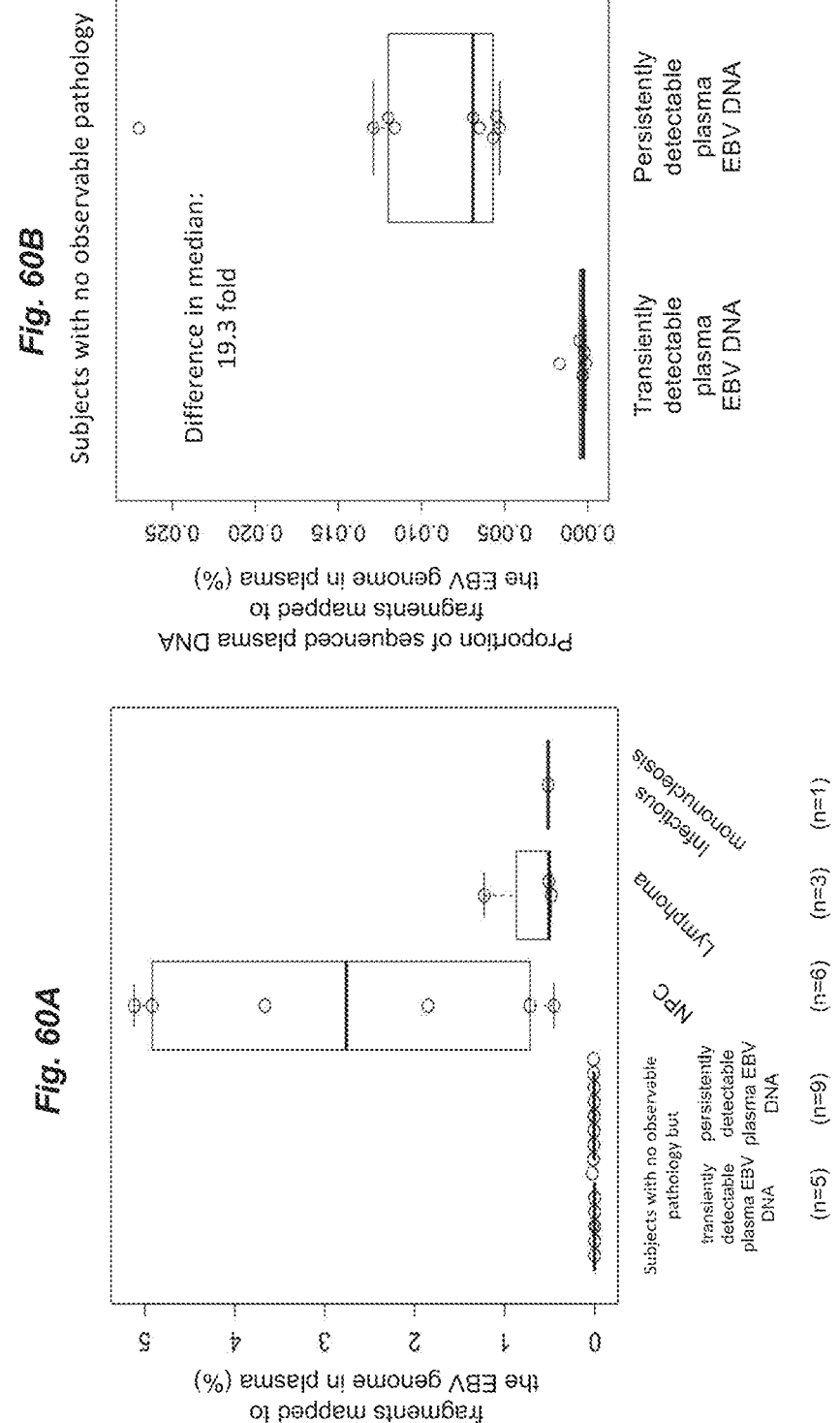
FIGS. 60A and 60B show the proportion of sequenced plasma DNA fragments mapped to the EBV genome for different groups of subjects.

FIGS. 60A and 60B show the proportion of sequenced plasma DNA fragments mapped to the EBV genome in plasma for different groups of subjects. As shown in FIG. 60A, using massively parallel sequencing following target capture, the proportions of reads uniquely mapped to the EBV genome were higher in subjects with NPC, lymphoma and infectious mononucleosis compared with those with detectable plasma EBV DNA at enrollment but without any observable pathology. As shown in FIG. 60B, for those subjects with detectable plasma EBV DNA at enrollment but without any observable pathology, the proportion of reads mapped to the EBV genome measured at enrollment was higher in the subjects with persistently positive results compared with those who would become negative in the follow-up test (i.e. with transiently detectable plasma EBV DNA) (p=0.002, Mann-Whitney test). The difference between subjects with transiently and persistently positive results is greater using the measurement of the proportion of reads uniquely mapped to the EBV genome compared with the concentration of plasma EBV DNA measured using real-time PCR (19.3 folds vs 1.7 folds).

Elevated plasma EBV DNA is associated with NPC. Previous studies compared NPC cases and healthy controls who are mostly negative for plasma EBV DNA. FIGS. 59A, 59B, 60A, and 60B provide a quantitative comparison between NPC cases and the non-NPC cases who are false-positive for plasma EBV DNA. Techniques described below allow for increased accuracy in discriminating between subjects with a pathology and those without, thereby reducing false-positives. In the context of EBV DNA, the term "false-positive" can mean that the subject has detectable plasma EBV DNA but the subject does not have nasopharyngeal cancer (an example of a pathology associated with the pathogen). The presence of plasma EBV DNA is true, but the identification of the associated pathology (e.g., NPC) may be false.

B. Size Analysis of EBV DNA Fragments

Figure 61:
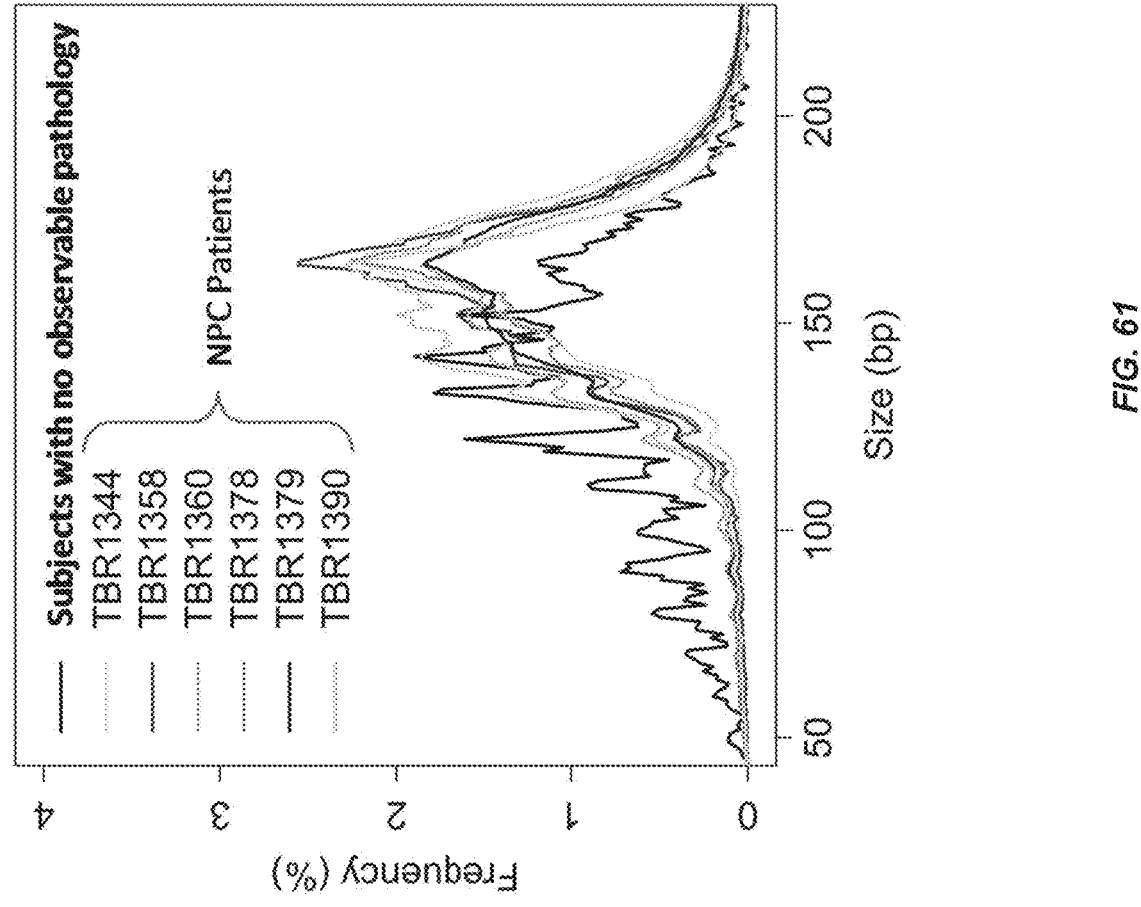
FIG. 61 shows the size distribution of EBV DNA fragments in a pooled sample from normal subjects and 6 subjects having nasopharyngeal cancer (e.g., TBR1344, TBR1358, TBR1360, TBR1378, TBR1379, and TBR1390).

FIG. 61 shows the size distribution of EBV DNA fragments in a normal subject and 6 subjects having NPC (TBR1344, TBR1358, TBR1360, TBR1378, TBR1379, and TBR1390). Using paired-end sequencing, the size of each plasma EBV DNA fragment was deduced based on the coordinates of the outermost nucleotide on each of the two ends of the sequenced EBV DNA fragment. The size profiles of plasma EBV DNA fragments for NPC subjects and those with no observable pathology are shown. The sequenced EBV DNA fragments from all the cases of this group were pooled together to plot an aggregated size profile for these subjects. The plasma EBV DNA size distribution of the subjects without any observable pathology is on the left side of the size distribution plots of the NPC subjects, indicating that the size distribution of sequenced plasma EBV DNA fragments is shorter in subjects without any observable pathology compared with NPC subjects. These results suggest that the size profile of plasma EBV DNA fragments as measured by massively parallel sequencing analysis can be used to differentiate subjects with NPC and with false-positive plasma EBV DNA results. In a previous study, it has been shown that plasma EBV DNA are short fragments in NPC subjects (Chan et al. Cancer Res. 2003; 63:2028-32). However, in that previous study, no information was provided regarding the difference in the size distribution of plasma EBV DNA fragments between subjects with NPC and those with false-positive plasma EBV DNA results.

Figure 62:
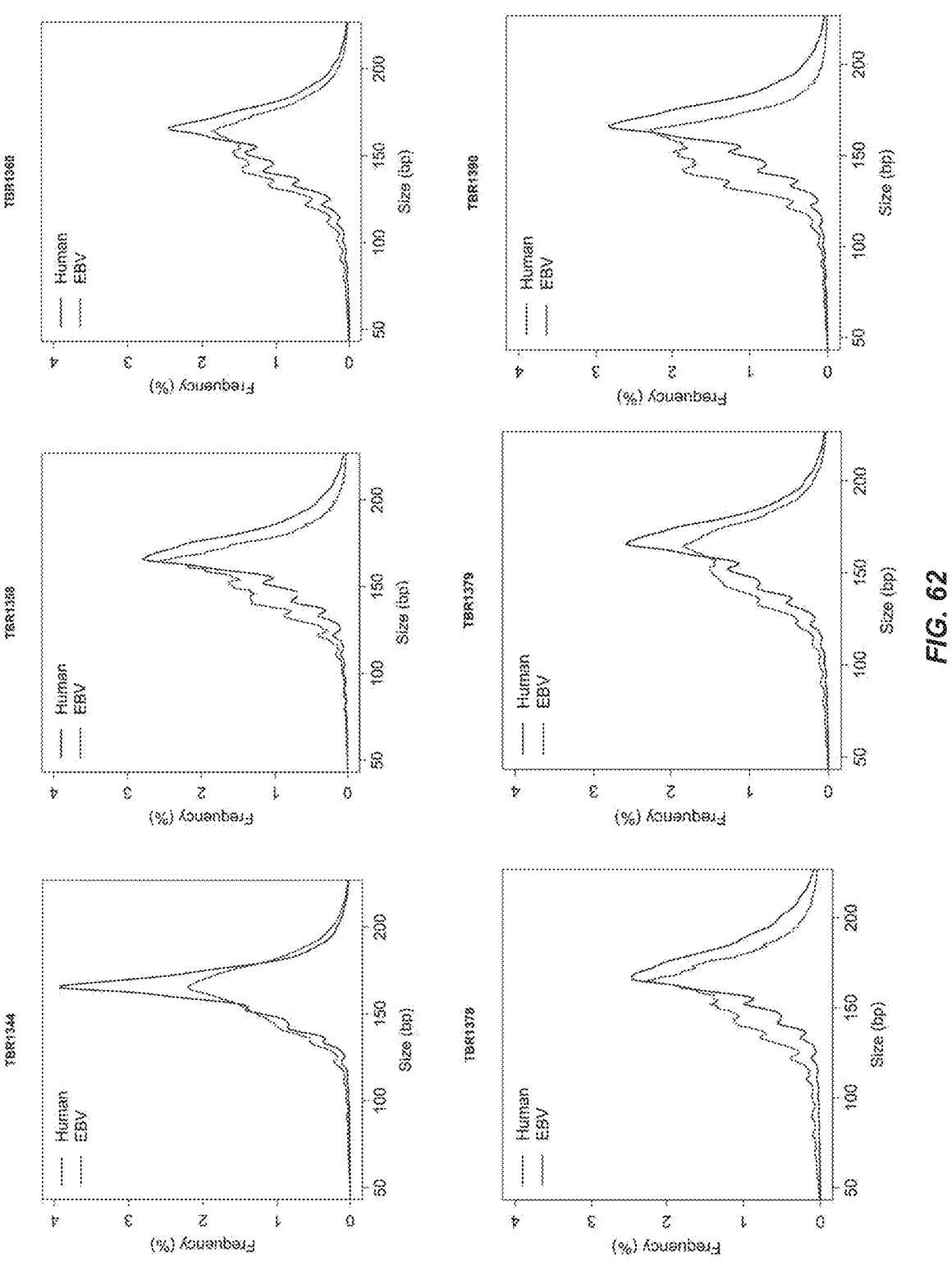
FIG. 62 shows the size distribution of sequenced plasma DNA fragments mapped to the EBV genome and human genome in 6 subjects having nasopharyngeal cancer (e.g., TBR1344, TBR1358, TBR1360, TBR1378, TBR1379, and TBR1390).

FIG. 62 shows the size distribution of sequenced plasma DNA fragments mapped to the EBV genome and human genome in 6 subjects having NPC (TBR1344, TBR1358, TBR1360, TBR1378, TBR1379, and TBR1390). For each subject, the size distribution of the plasma EBV DNA fragments is shorter than that of fragments mapped to the human genome. This observation is consistent with the findings of previous reports that the size distribution of plasma DNA derived from tumor cells is shorter that DNA fragments derived from non-tumor cells (Jiang et al. Proc Natl Acad Sci USA. 2015; 112:E1317-25) because the plasma EBV DNA fragments in NPC subjects are derived from the tumor cells (Chan et al. Clin Chem. 2005; 51:2192-5) and the plasma DNA fragments mapped to the human genome are derived from both tumor and non-tumor cells.

FIG. 63 shows the size distribution of sequenced plasma DNA fragments mapped to the EBV genome and human genome in 3 subjects having lymphoma (TBR1332, TBR1333, and TBR1551). For each of the three lymphoma subjects, the size distribution of the plasma EBV DNA fragments is shorter than that of fragments mapped to the human genome.

Figure 64:
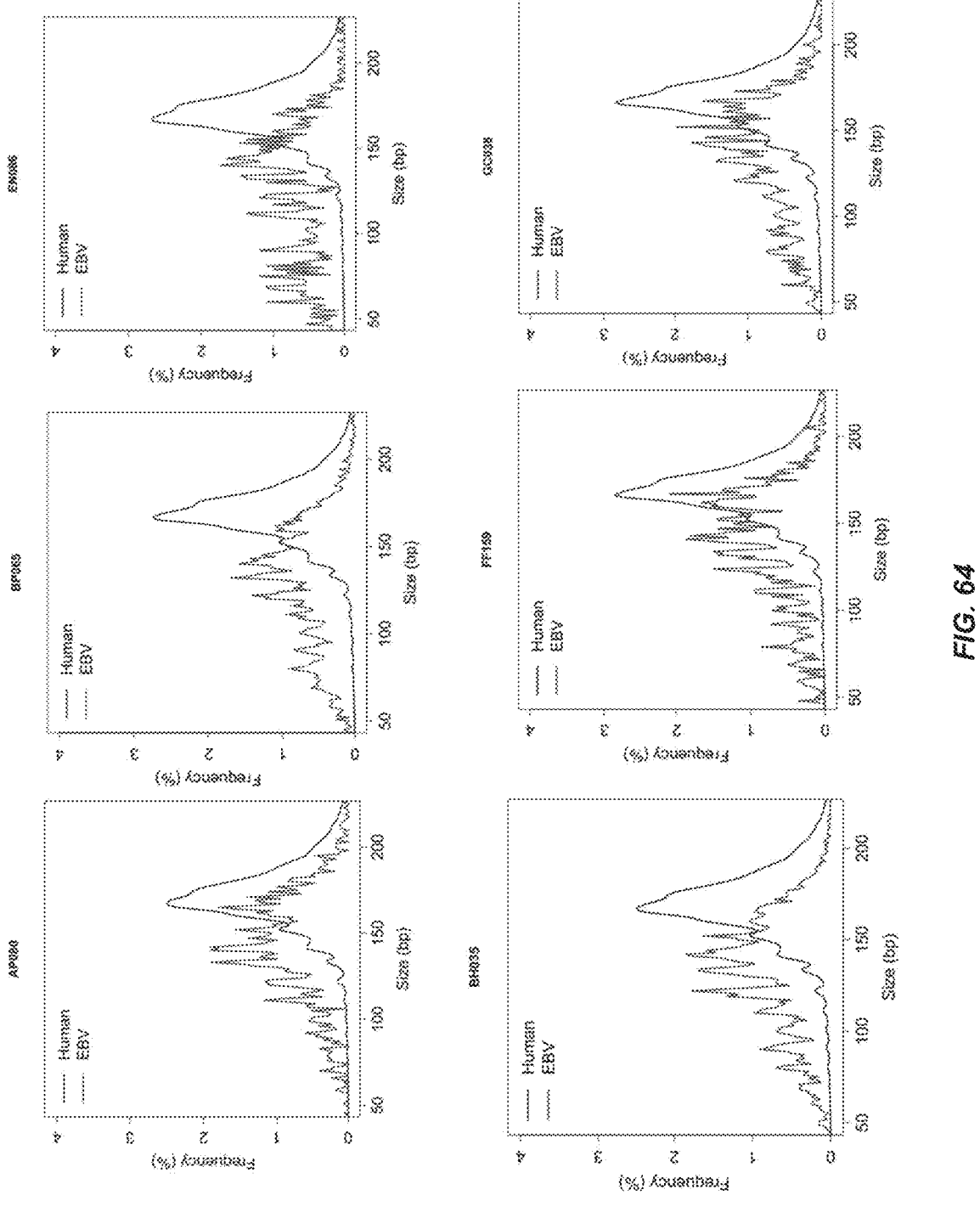
FIG. 64 shows the size distribution of sequenced plasma DNA fragments mapped to the EBV genome and human genome in 6 control subjects (AP080, BP065, EN086, BH035, FF159, and GC038).

FIG. 64 shows the size distribution of sequenced plasma DNA fragments mapped to the EBV genome and human genome in 6 control subjects (AP080, BP065, EN086, BH035, FF159, and GC038). For each of the 14 subjects with false-positive plasma EBV DNA but no observable pathology, the size distribution of the sequenced plasma EBV DNA was shorter than the fragments mapped to the human genome. This observation is surprising as it is generally believed that the EBV DNA fragments in non-cancer subjects are associated with viral particles and high molecular weight fragments are expected to be present in plasma. One possible explanation of not observing those high molecular weight EBV DNA fragments is that they might not be detected using our massively parallel sequencing protocol. In our experiments, massively parallel sequencing was performed using the Illumina platform. As this method requires the ligation of sequencing adaptors to the ends of DNA fragments to be sequenced, high molecular weight DNA of >1 kb would not be amplified and sequenced. Nonetheless, it is interesting to find the presence of short EBV DNA fragments in this group of subjects.

Figure 65:
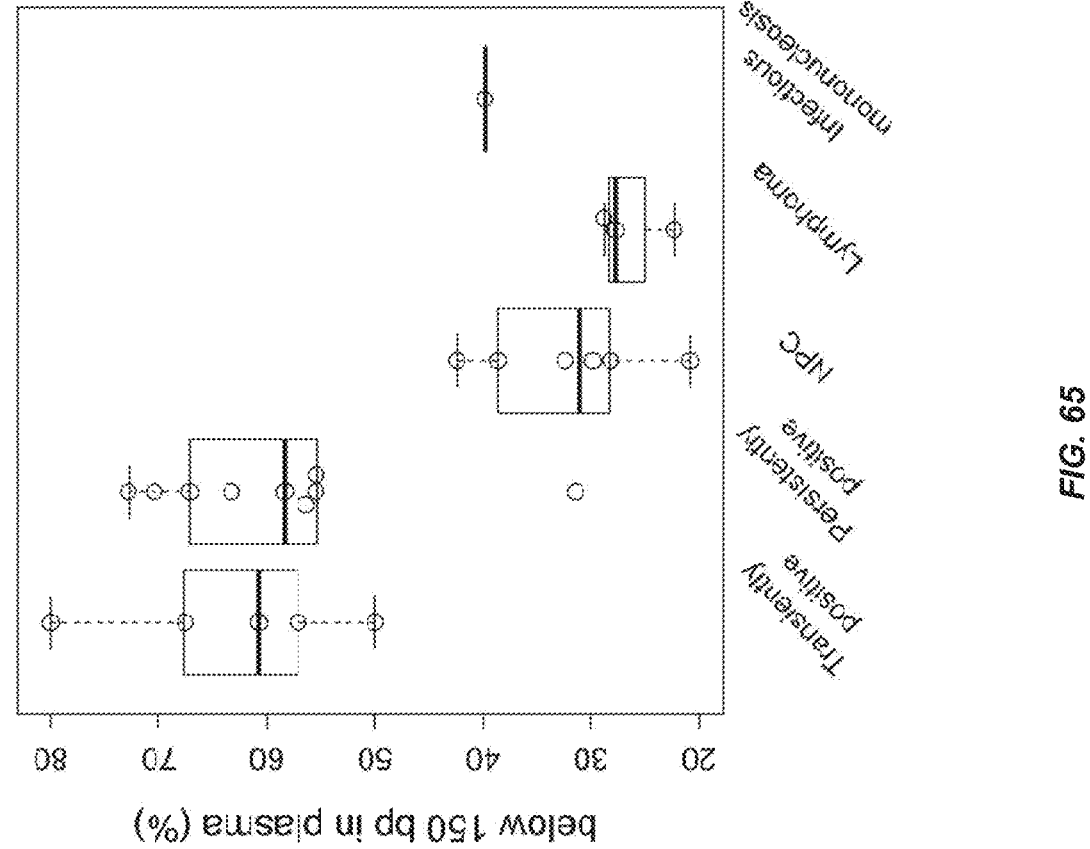
FIG. 65 shows the percentage of sequenced plasma EBV DNA fragments below 150 bp.

FIG. 65 shows the percentage of sequenced plasma EBV DNA fragments below 150 bp. The proportions of EBV DNA fragments below 150 bp were lower in subjects with NPC, lymphoma and infectious mononucleosis when compared with those with transiently positive or persistently detectable plasma EBV DNA but no observable pathology. These results suggest that the analysis of the size of sequenced plasma EBV DNA fragments can be used to differentiate subjects with cancers from those without any observable pathology.

It should be understood that the size threshold (e.g., 150 bp in FIG. 65) may be any value. The size threshold may be at least about 10 bp, 20 bp, 30 bp, 40 bp, 50 bp, 60 bp, 70 bp, 80 bp, 90 bp, 100 bp, 110 bp, 120 bp, 130 bp, 140 bp, 150 bp, 160 bp, 170 bp, 180 bp, 190 bp, 200 bp, 210 bp, 220 bp, 230 bp, 240 bp, 250 bp, or greater than 250 bp. For example, the size threshold can be 150 bp. In another example, the size threshold can be 180 bp. In some embodiments, an upper and a lower size threshold may be used (e.g., a range of values). In some embodiments, an upper and a lower size threshold may be used to select nucleic acid fragments having a length between the upper and lower cutoff values. In some embodiments, an upper and a lower cutoff may be used to select nucleic acid fragments having a length greater than the upper cutoff value and less than the lower size threshold.

1. Various Statistical Values

Various statistical values of a size distribution of nucleic acid fragments can be determined. For example, an average, mode, median, or mean of a size distribution can be used. Other statistical values can be used, e.g., a cumulative frequency for a given size or various ratios of amount of nucleic acid fragments of different sizes. A cumulative frequency can correspond to a proportion (e.g., a percentage) of DNA fragments that are of a given size or smaller, or larger than a given size. The statistical values provide information about the distribution of the sizes of nucleic acid fragments for comparison against one or more cutoffs for determining a level of pathology resulting from a pathogen. The cutoffs can be determined using cohorts of healthy subjects, subjects known to have one or more pathologies, subjects that are false positives for a pathology associated with the pathogen, and other subjects mentioned herein. One skilled in the art will know how to determine such cutoffs based on the description herein, e.g., with reference to a data depicted in FIG. 65.

To perform a size-based analysis, embodiments can calculate a first statistical value of sizes of nucleic acid molecules located in a reference genome of the pathogen (e.g., by aligning a sequence read to the reference genome or using probes). In one embodiment, the first statistical value can be determined from nucleic acid molecules located in one or more particular regions (e.g., regions associated with preferred ending positions) or just the entire reference genome. The first statistical value can be compared to a cutoff to determine a level of pathology.

In some embodiments, the first statistical value of sizes of pathogen fragments can be compared to a reference statistical value of sizes from the human genome. For example, a separation value (e.g. a difference or ratio) can be determined between the first statistical value and a reference statistical value, e.g., determined from other regions in the pathogen reference genome or determined from the human nucleic acids. The separation value can be determined from other values as well. For example, the reference value can be determined from statistical values of multiple regions. The separation value can be compared to a size threshold to obtain a size classification (e.g., whether the DNA fragments are shorter, longer, or the same as a normal region).

Some embodiments can calculate a parameter (separation value), which can be defined as a difference in the proportion of short DNA fragments between the reference pathogen genome and the reference human genome using the following equation:

$$F = P(\leq 150\,bp)_{test}\ P(\leq 150\,bp)_{ref}$$

where $P(150\,bp)_{test}$ denotes the proportion of sequenced fragments originating from the tested region with sizes≤150 bp, and $P(150\,bp)_{ref}$ denotes the proportion of sequenced fragments originating from the reference region with sizes≤150 bp. In other embodiments, other size thresholds can be used, for example but not limited to 100 bp, 110 bp, 120 bp, 130 bp, 140 bp, 160 bp and 166 bp. In other embodiments, the size thresholds can be expressed in bases, or nucleotides, or other units.

A size-based z-score can be calculated using the mean and SD values of F of control subjects.

$$\text{Size-based } z\text{-score} = \frac{F_{sample}\ \text{mean } F_{control}}{SD\ F_{control}}$$

In some embodiments, a size-based z-score of >3 indicates an increased proportion of short fragments for the pathogen, while a size-based z-score of <−3 indicates a reduced proportion of short fragments for the pathogen. Other size thresholds can be used. Further details of a size-based approach can be found in U.S. Pat. Nos. 8,620, 593 and 8,741,811, and U.S. Patent Publication 2013/0237431, all of which are incorporated by reference in its entirety.

To determine a size of a nucleic acid fragment, at least some embodiments can work with any single molecule analysis platform in which the chromosomal origin and the length of the molecule can be analyzed, e.g. electrophoresis, optical methods (e.g. optical mapping and its variants, en.wikipedia.org/wiki/Optical_mapping #cite_note-Nanocoding-3, and Jo et al. Proc Natl Acad Sci USA 2007; 104: 2673-2678), fluorescence-based method, probe-based methods, digital PCR (microfluidics-based, or emulsion-based, e.g. BEAMing (Dressman et al. Proc Natl Acad Sci USA 2003; 100: 8817-8822), RainDance (www.raindancetech-.com/technology/pcr-genomics-research.asp)), rolling circle amplification, mass spectrometry, melting analysis (or melting curve analysis), molecular sieving, etc. As an example for mass spectrometry, a longer molecule would have a larger mass (an example of a size value).

In one example, nucleic acid molecules can be randomly sequenced using a paired-end sequencing protocol. The two reads at both ends can be mapped (aligned) to a reference genome, which may be repeat-masked (e.g., when aligned to a human genome). The size of the DNA molecule can be determined from the distance between the genomic positions to which the two reads mapped.

2. Method

According to one embodiment, a method analyzes a biological sample, including a mixture of cell-free nucleic acid molecules, to determine a level of pathology in a subject from which the biological sample is obtained. The mixture includes nucleic acid molecules from the subject and potentially nucleic acid molecules from a pathogen. Parts of the method may be performed by a computer system.

At block 1, a size of a plurality of nucleic acid molecules in the biological sample are measured. The size may be measured via any suitable method, for example, methods described above.

At block 2, it is determined whether a nucleic acid molecule is from a reference genome corresponding to the pathogen. As examples, a location of the nucleic acid molecule in the reference genome can be determined by sequencing and aligning, or using probes corresponding to the reference genome.

At block 3, a statistical value of a size distribution of the plurality of nucleic acid molecules from the reference genome is determined. A cumulative frequency of fragments smaller than a size threshold is an example of a statistical value. The statistical value can provide a measure of the overall size distribution, e.g., an amount of small fragments relative to an amount of large fragments. In another embodiment, the statistical value can be a ratio of: (1) a first amount the plurality of nucleic acid molecules in the biological sample from the reference genome that are within a first size range; and (2) a second amount the plurality of nucleic acid molecules in the biological sample from the reference genome that are within a second size range that is difference than the first size range. For example, the first range can be fragments below a first size threshold and the second size range can be fragments above a second size threshold. The two ranges can overlap, e.g., when the second size range is all sizes.

At block 4, the level of pathology in the subject is determined by processing the statistical value against one or more cutoff values. For example, the percentage of fragments below a size threshold (e.g., 150) can be compared to a cutoff to determine whether the ratio is below the cutoff. In FIG. 65, a cutoff can be about 45 to discriminate between subjects that are persistently positive for EBV but no pathology (or even transiently positive) and subjects with NPC, lymphoma, or infectious mononucleosis.

C. Frequency of Ending Positions of EBV DNA Fragments

Figure 66:
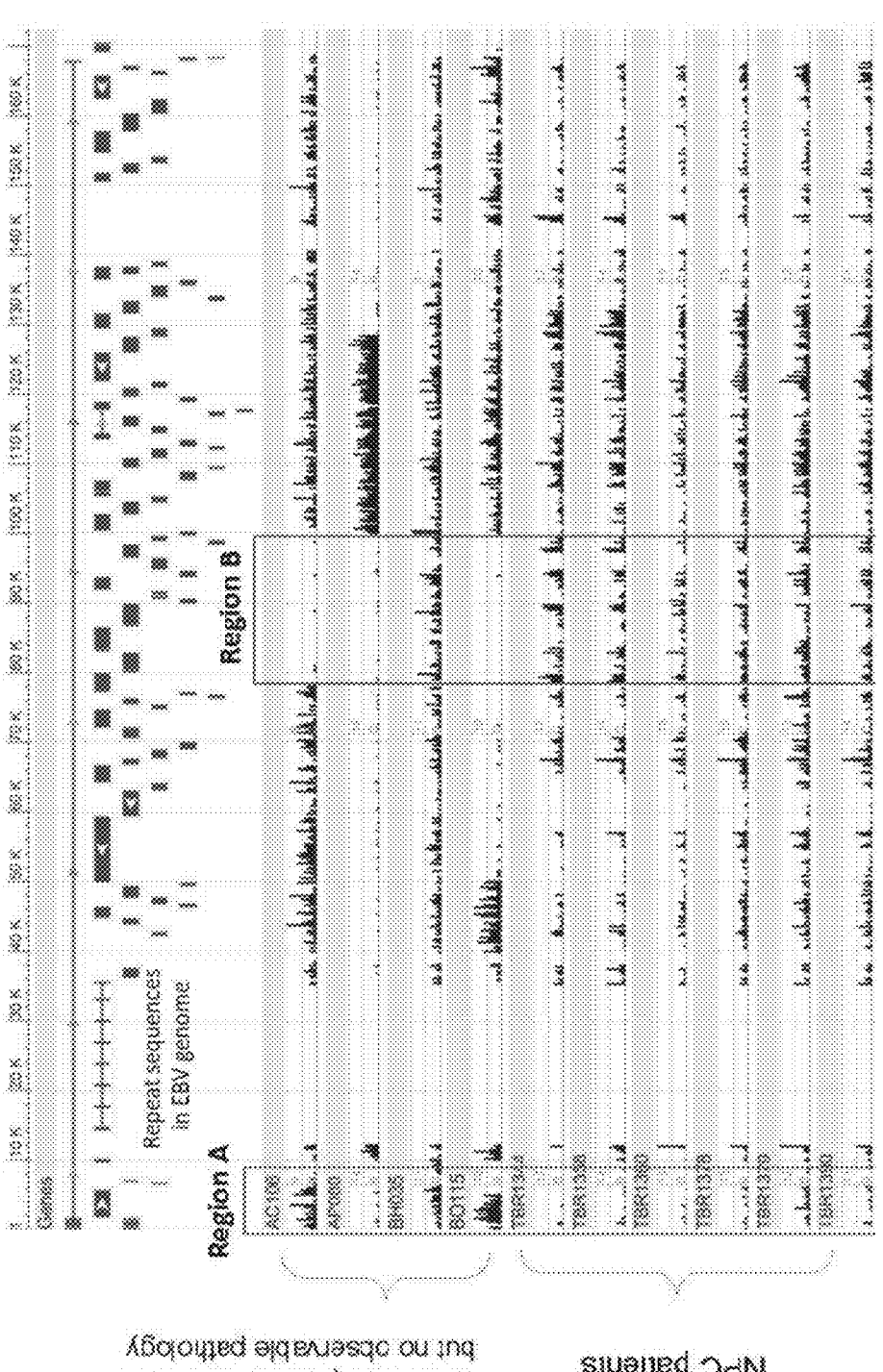
FIG. 66 shows the frequency of plasma EBV DNA fragments ending on each nucleotide in the EBV genome for 4 subjects with persistently false-positive plasma EBV DNA and no observable pathology, and 6 NPC patients.

FIG. 66 shows the frequency of a plasma EBV DNA fragments ending on each nucleotide in the EBV genome for 4 subjects with persistently false-positive plasma EBV DNA and no observable pathology, and 6 NPC subjects. As the numbers of plasma EBV DNA fragments were very small in the subjects with transiently detectable plasma EBV DNA, they are not shown as examples here. The y-axis is the number of plasma EBV DNA fragments ending on a particular nucleotide and the x-axis is the genomic coordinates in the EBV genome.

We observed that the distributions of the ending positions were different between subjects with false-positive results but no observable pathology and NPC subjects. For example, more plasma EBV DNA fragments ended on positions located within Region A in subjects without any pathology whereas more plasma EBV DNA fragments ended on positions located within Region B in NPC subjects. In the region with repeating elements in the EBV genome, the sequenced plasma EBV DNA fragments cannot be mapped to unique locations in the EBV genome. Therefore, there were no uniquely alignable sequenced reads ending within the region with repeats in the EBV genome.

These results suggest that the analysis of the ending positions of the plasma EBV DNA fragments on the EBV genome can be used for differentiating subjects with false-positive results but no pathology from the NPC subjects. The analysis of the ending positions can be performed by but not limited to non-targeted massively parallel sequencing or single molecule sequencing, massively parallel sequencing or single molecule sequencing after target enrichment, amplicon sequencing, real-time PCR, digital PCR, inverse PCR and anchor PCR. For amplicon sequencing, real-time PCR and digital PCR, one embodiment is to have primers or probes covering the specific ending positions.

The analysis can be performed with or without amplification. For amplification based approaches, oligonucleotides complementary to the specific ending positions may be used to enrich for the informative ends (e.g., a nucleic acid fragment having a particular ending-motif). Positive amplification can be interpreted as indicating the presence of such informative ends. Alternatively, the amplified products can be followed by additional steps to identify or confirm the presence of the informative ends. Methods used to detect or confirm the presence of the informative ends can include any one of the following but are not limited to hybridization methods, such as oligonucleotide probes, antibody probes, mini-sequencing, direct sequencing, massively parallel sequencing, single molecule sequencing, mass spectrometry, ligation based assays. Such detection or confirmatory methods can be applied to non-amplification based approaches. Both the amplification and non-amplification based methods for the detection of informative ends can be preceded or followed by hybridization based methods to enrich the sample with viral DNA sequences. Amplification-based methods can be used to enrich the sample with viral DNA sequences.

To demonstrate the association of ending positions with disease conditions, we randomly picked one subject with persistently detectable plasma EBV DNA but no pathology, and one NPC subject for mining the frequent ending positions. We ranked the coordinates of the EBV genome in a descending number of plasma EBV DNA fragments ending on it for the two cases. For such an analysis, the EBV genome coordinate with the largest number of fragments ending on it would be ranked number 1.

For illustration purpose, the coordinates ranking in the top 400 were selected for each of the two cases. In other embodiments, different number of top-ranked coordinates can be selected for the analysis. For examples, the coordinates ranking in the top 100, top 200, top 300, top 500, top 600, top 800 and top 1000 can be selected. In yet another embodiment, the top-ranked coordinates shared by subjects with the same disease status, for example, subjects with NPC, can be selected. In yet another embodiment, the probability of coordinates which have significantly higher probability of being an ending position for plasma EBV DNA in certain disease status can be used. Examples of the thresholds for p-values include but not limited to 0.1, 0.05, 0.01, 0.005, 0.001 and 0.0001. In one embodiment, top-ranked positions shared by a significant proportion of subjects with the same disease status can be used. In yet another embodiment, the top-ranked positions of different subjects with the same disease status can be pulled together. In yet another embodiment, the top-ranked positions shared by a larger proportion of subjects can be given a larger weight and those shared by a smaller proportion of subjects can be given a smaller weight, so that a weighted score can be calculated.

Figure 67:
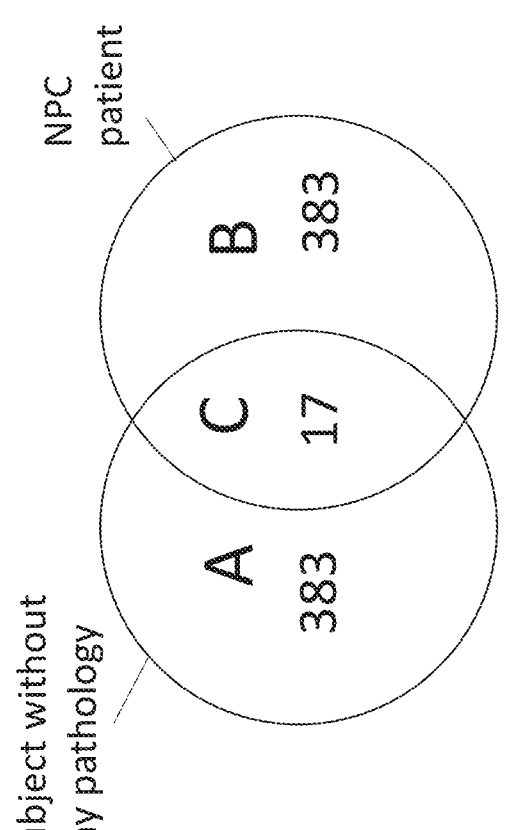
FIG. 67 shows a Venn diagram depicting (A) the number of preferred ending positions specific to subjects not having an observable pathology (383), (B) the number of preferred ending positions specific to subjects having NPC (383), and (C) the preferred ending positions shared by both groups of subjects (17).

FIG. 67 shows a Venn diagram depicting (A) the number of preferred ending positions specific to subjects not having an observable pathology (e.g., 383), (B) the number of preferred ending positions specific to subjects having NPC (e.g., 383), and (C) the preferred ending positions shared by both groups of subjects (e.g., 17). The coordinates within the top 500 rankings in the subject with false-positive EBV DNA but not top-ranked in the NPC subject are denoted as Set A positions. The coordinates within the top 500 rankings in the NPC subject but not top-ranked in the subject with false-positive plasma EBV DNA result are denoted as Set B positions. The coordinates that ranked within the top 400 in both cases are denoted as Set C positions. Only 4.25% of the common ending positions were shared by both cases.

To demonstrate if subjects with the same disease status, for example, with NPC, would share the same preferred ending positions in the EBV genome, we calculated the percentage of fragments ending on the Set A and Set B coordinates for eight subjects with persistently detectable plasma EBV DNA but no pathology and five NPC subjects. The two subjects from whom these coordinates were determined were not included in this analysis.

Figure 68:
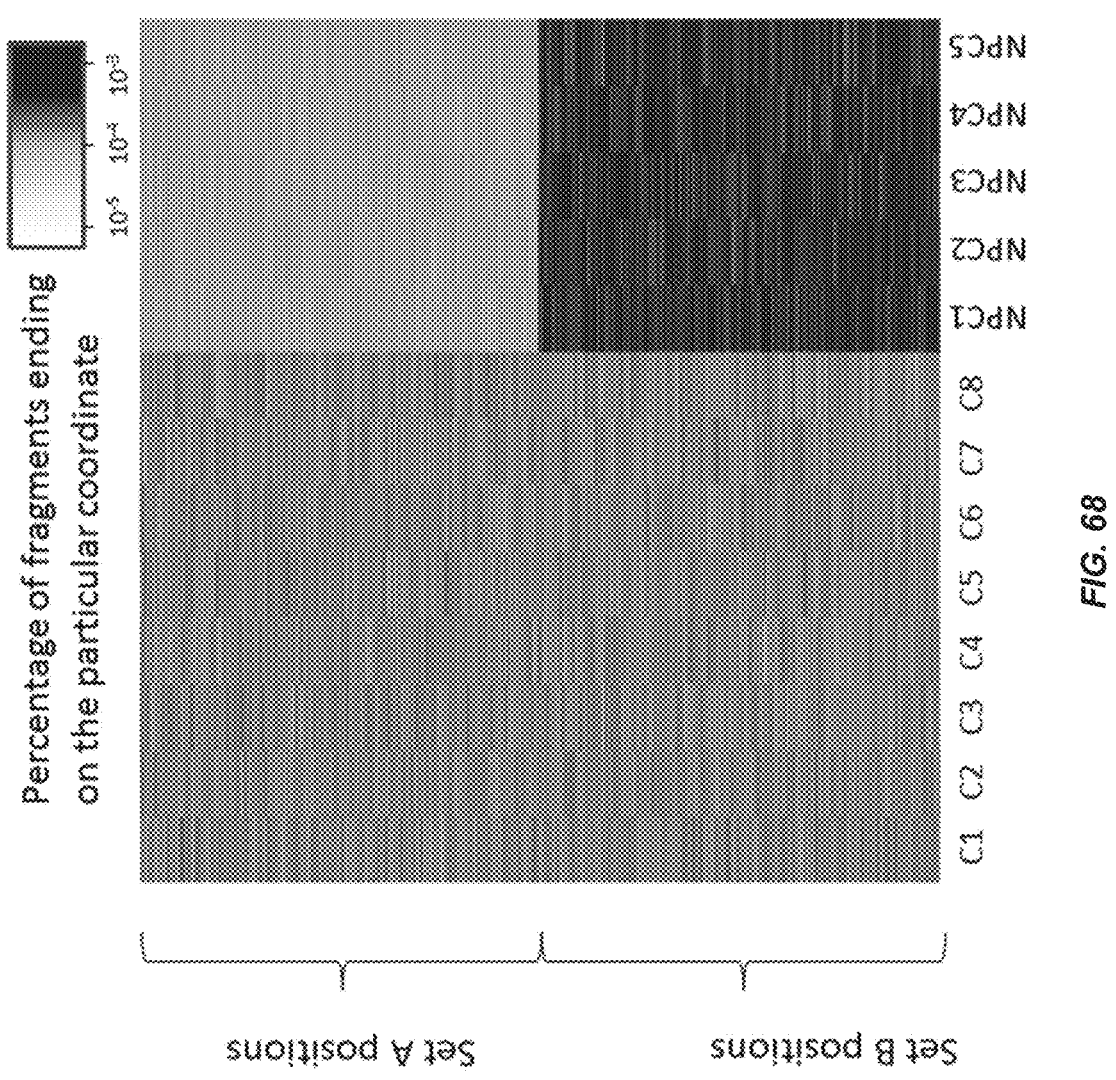
FIG. 68 shows a heat map depicting the percentage of fragments ending on either Set A positions or Set B positions for subjects not having an observable pathology and NPC subjects. A heat map is depicted for 8 subjects not having an observable pathology (left 8 columns; C1-C8) and 5 NPC subjects (right 5 columns; NPC1-NPC5). The nucleic acid fragments in NPC subjects ending on Set A ending positions are relatively less abundant than the nucleic acid fragments in NPC subjects ending on Set B ending positions.

FIG. 68 shows a heat map depicting the percentage of fragments ending on either Set A positions or Set B positions for subjects not having an observable pathology and NPC subjects. A heat map is depicted for 8 subjects not having an observable pathology (left 8 columns; C1-C8) and 5 NPC subjects (right 5 columns; NPC1-NPC5). The nucleic acid fragments in NPC subjects ending on Set A ending positions are relatively less abundant than the nucleic acid fragments in NPC subjects ending on Set B ending positions. Each row represents a particular position and each row represents one subject. Darker color (blue) indicates a higher percentage of EBV DNA fragments ending at the specific position. The five NPC subjects had higher percentages of plasma EBV DNA fragments ending on the Set B positions (the frequent ending positions from another NPC subject) compared with the subjects without pathology. In contrast, subjects without pathology had higher percentages of plasma EBV DNA fragments ending on the Set A positions (the frequent ending positions from another subject with detectable plasma EBV DNA but no observable pathology) compared with the NPC subjects. These results suggest that the top-ranked ending positions are shared by subjects with the same disease status.

As the top-ranked ending positions were shared by subjects with the same disease status, we investigated the ending positions of plasma EBV DNA in subjects with detectable plasma EBV DNA can be used to indicate the disease status, for example to differentiate NPC subjects from subjects without observable pathology.

To demonstrate the feasibility of this approach, we first determined the number of sequenced plasma EBV DNA fragments ending on Set A and Set B positions. Then we calculated the B/A ratio as:

$$\frac{B}{A} \text{ ratio} = \frac{\text{\# of fragments ending on Set } B \text{ positions}}{\text{\# of fragments ending on Set } A \text{ positions}}$$

For the five subjects with transiently positive plasma EBV DNA but no observable pathology, the number of mappable plasma DNA fragments aligned uniquely to the EBV genome were very small. These samples can be completely differentiated from the samples collected from NPC subjects, lymphoma subjects and the subject with infectious mononucleosis. For all the five subjects, the sequenced plasma EBV DNA fragments did not end on any Set A and Set B position.

Figure 69:
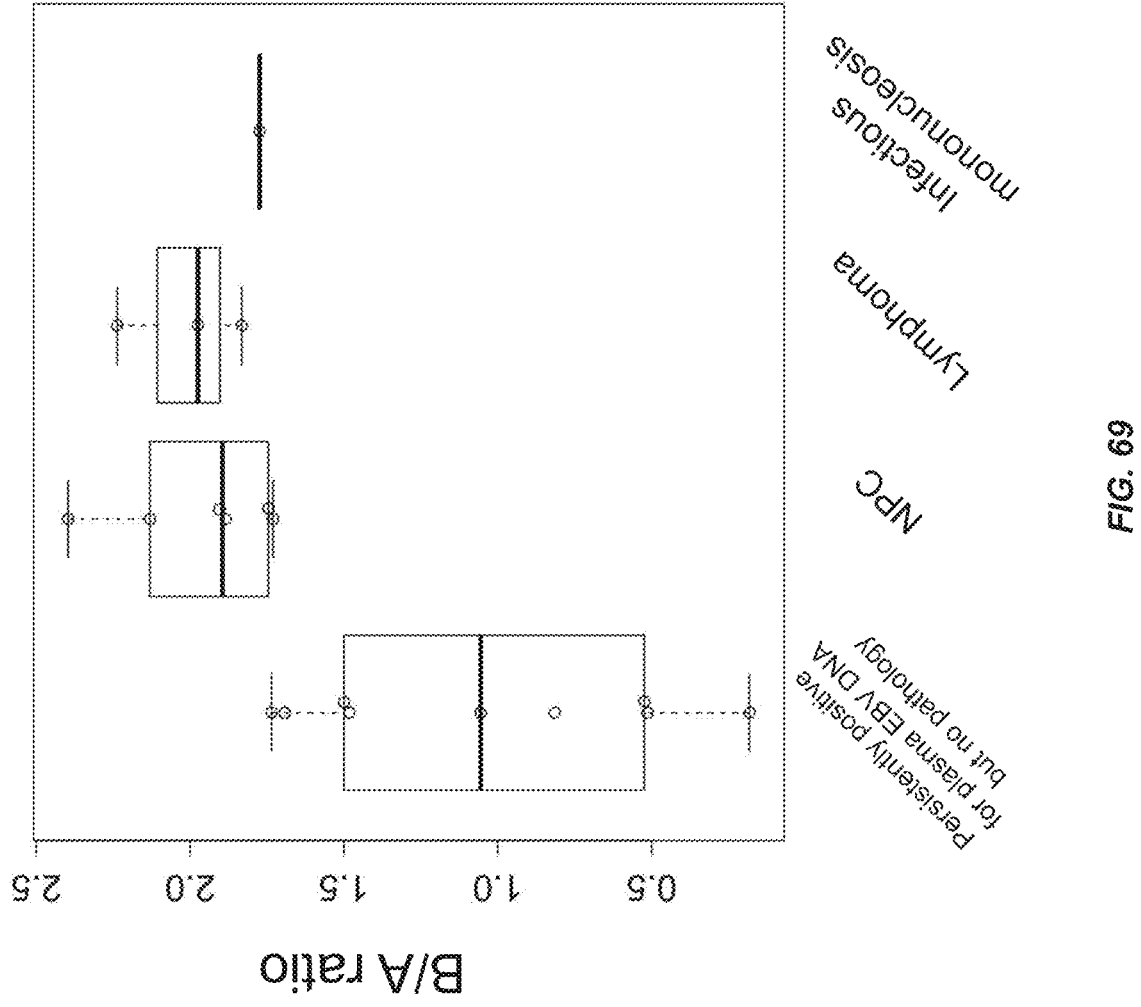
FIG. 69 shows the ratio of the number of fragments ending on Set B positions divided by the number of fragments ending on Set A positions (e.g., B/A ratios) for different groups of subjects.

FIG. 69 shows the ratio of the number of fragments ending on Set B positions divided by the number of fragments ending on Set A positions (e.g., B/A ratios) for different groups of subjects. For subjects with persistently detectable plasma EBV DNA, the B/A ratios of the subjects with no pathology were significantly lower than the NPC subjects (P<0.001, Mann-Whitney test) and the lymphoma subjects (P<0.01, Mann-Whitney test). The B/A ratio of the subject with infectious mononucleosis was higher than all the subjects with persistently detectable plasma EBV DNA but no pathology. These results suggest that the proportion of plasma EBV DNA fragments ending on positions preferentially for different disease can be useful for identifying the disease status of the subject being tested.

In some embodiments, the ending positions of a set (e.g., set A or set B) can be identified when they have a probability higher than expected for random fragmentation. In other embodiments, the most frequently seen ending positions in a pathogen genome (e.g., EBV DNA) in true pathology patients (e.g., NPC) can be identified for set B, and the most frequently seen ending positions for false-positive patients (or other subject without pathology)_can be identified as set A. The non-overlapping sets for the respective groups can be used. An amount of fragments at a set of ending positions can be quantified in various ways, with or without normalization.

1. Method

According to one embodiment, a method analyzes a biological sample, including a mixture of cell-free nucleic acid molecules, to determine a level of pathology in a subject from which the biological sample is obtained. The mixture includes nucleic acid molecules from the subject and potentially nucleic acid molecules from a pathogen. Parts of the method may be performed by a computer system.

At block 11, a first plurality of cell-free nucleic acid molecules from a biological sample of the subject are analyzed. The analyzing can comprise determining a genomic position in a reference genome corresponding to at least one end of the first plurality of cell-free nucleic acid molecules, where the reference genome corresponds to the pathogen.

At block 12, a first amount of the first plurality of cell-free nucleic acid molecules that end within one of first windows is determined. Each first window comprises at least one of a first set of genomic positions at which ends of cell-free nucleic acid molecules are present at a rate above a first threshold in subjects with a pathology associated with the pathogen.

At block 13, a relative abundance of the first plurality of cell-free nucleic acid molecules ending within one of the first windows is computed by normalizing the first amount using a second amount of the first plurality of cell-free nucleic acid molecules from the biological sample. The second amount of cell-free nucleic acid molecules can include cell-free nucleic acid molecules ending at a second set of genomic positions outside of the first windows including the first set of genomic positions.

As an example, the relative abundance can be the B/A ratio.

At block 14, the level of pathology in the subject is determined by processing the relative abundance against one or more cutoff values. For example, the B/A ratio can be compared to a cutoff to determine whether the ratio is above the cutoff. In FIG. 69, a cutoff can be about 1.7 to discriminate between subjects that are persistently positive for EBV but no pathology and subjects with NPC, lymphoma, or infectious mononucleosis.

D. Comparison of Predictive Values of Various Techniques

Figure 70:
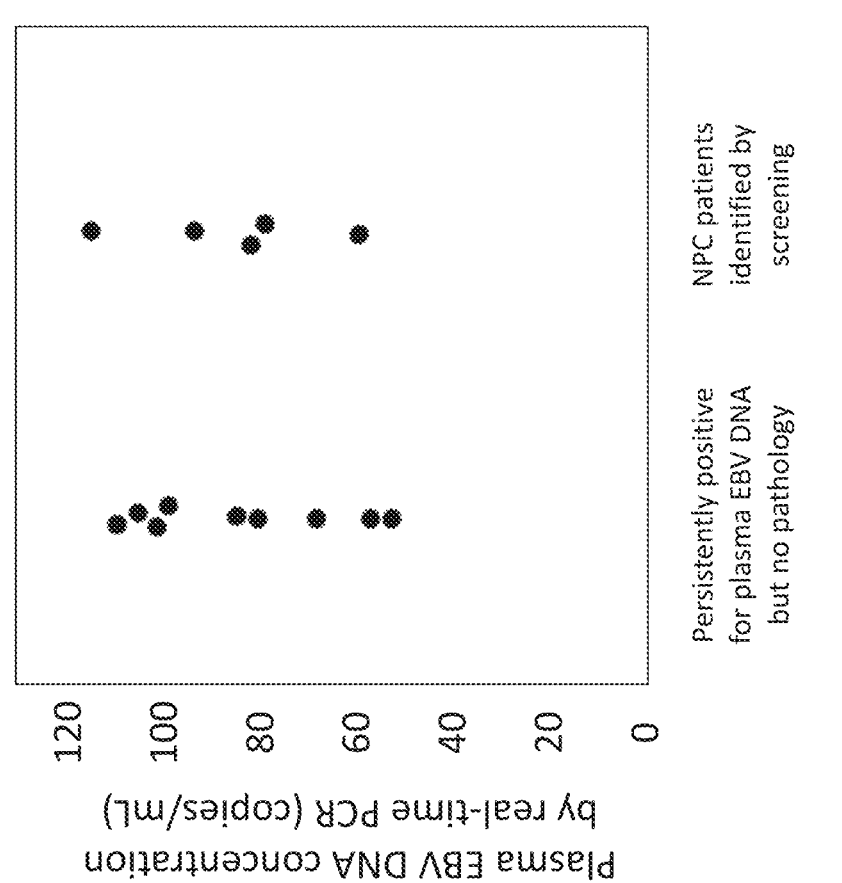
FIG. 70 shows plasma EBV DNA concentrations measured by real-time PCR for (left) subjects persistently positive for plasma EBV DNA but having no observable pathology, and (right) early-stage NPC patients identified by screening.

FIG. 70 shows plasma EBV DNA concentrations measured by real-time PCR for (left) subjects persistently positive for plasma EBV DNA but having no observable pathology, and (right) NPC subjects. After demonstrating that the size of the sequenced plasma EBV DNA fragments and the B/A ratio were useful for differentiating NPC subjects and those with false-positive plasma EBV DNA, we further validated these results with an independent cohort (Cohort 2). Five of the 34 NPC subjects who were identified through the screening of 20,174 asymptomatic subjects were included in this validation analysis. These 5 subjects were asymptomatic when they joined the study. Their plasma samples were persistently positive for EBV DNA and NPC was subsequently confirmed by endoscopy and MRI. These 5 asymptomatic NPC cases were of early stage unlike the 6 NPC subjects in cohort 1 who presented to ENT clinics with symptoms and were diagnosed with advanced stage NPC. The plasma samples were sequenced after target enrichment as described above. For the five NPC subjects in cohort 2, while their plasma samples were persistently positive for EBV DNA, the EBV DNA concentration did not show significant difference compared with the 9 subjects with false-positive plasma EBV DNA results based on real-time PCR analysis (P=0.7, Mann-Whitney test). Plasma EBV DNA concentration is known to correlate with the stage of NPC. Thus, it is no unexpected that the early stage NPC subjects had lower levels of plasma EBV DNA.

Figure 71:
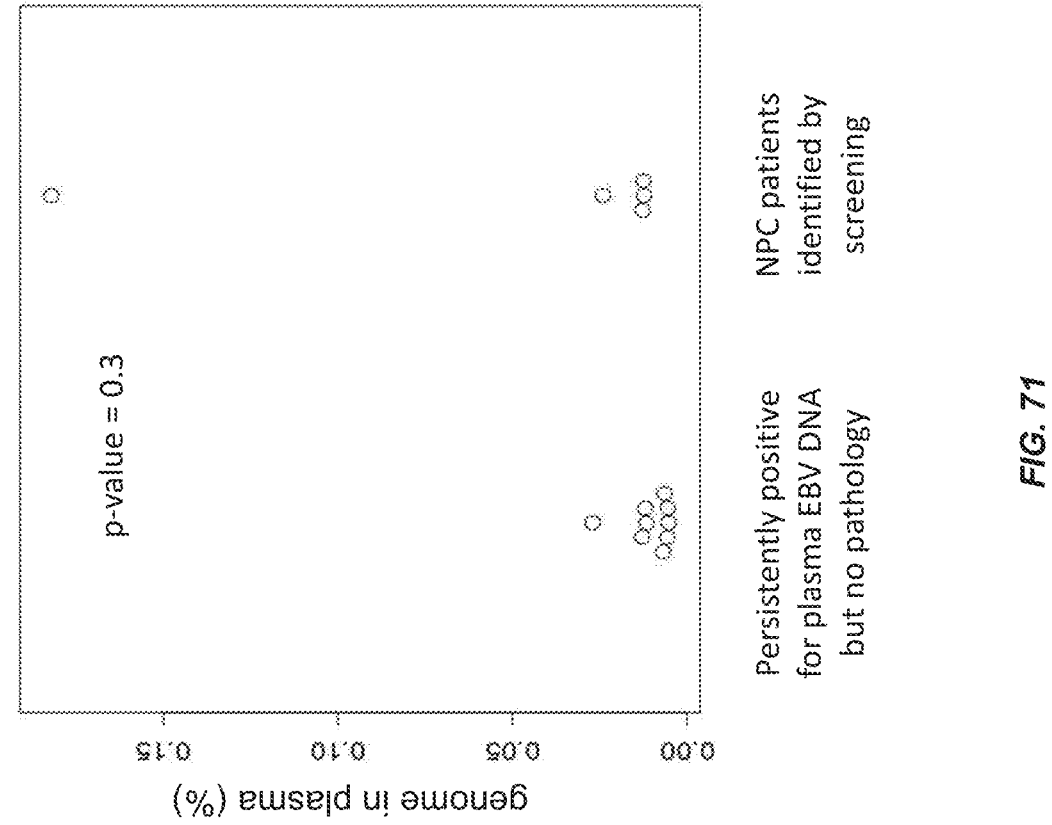
FIG. 71 shows the proportion of reads mapped to the EBV genome in plasma for (left) subjects persistently positive for plasma EBV DNA but having no observable pathology, and (right) early-stage NPC patients identified by screening.

FIG. 71 shows the proportion of reads mapped to the EBV genome in plasma for (left) subjects persistently positive for plasma EBV DNA but having no observable pathology, and (right) NPC subjects. The proportion of sequenced plasma DNA reads mapped to the EBV genome were not significantly different between the false-positive cases and the cohort 2 NPC cases. These data show that the approaches shown in FIGS. 70 and 71 do not work well in differentiating false-positives from the early stage NPCs.

Figure 72:
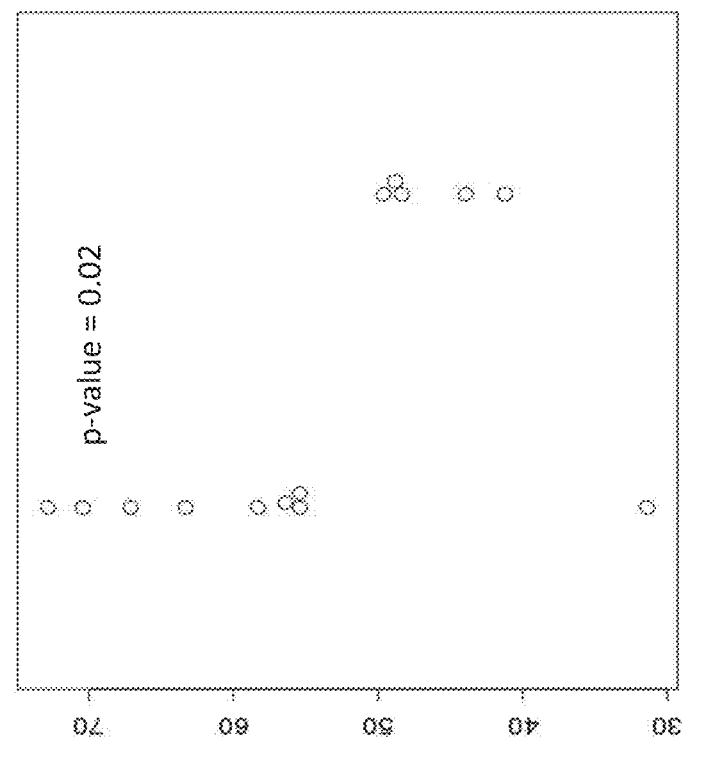
FIG. 72 shows the percentage of EBV DNA fragments below 150 base pairs (bp) in plasma for (left) subjects persistently positive for plasma EBV DNA but having no observable pathology, and (right) early-stage NPC patients identified by screening.

FIG. 72 shows the percentage of EBV DNA fragments below 150 base pairs (bp) in plasma for (left) subjects persistently positive for plasma EBV DNA but having no observable pathology, and (right) NPC subjects. While the proportion of sequenced plasma DNA reads mapped to the EBV genome were not significantly different between the false-positive cases and the cohort 2 NPC cases, the cohort 2 NPC subjects showed significantly lower proportion of short plasma EBV DNA fragments than the subjects with false-positive results (P=0.02, Mann-Whitney test). These results support that the analysis of the size of sequenceable plasma EBV DNA can be used to differentiate NPC subjects from subjects with false-positive plasma EBV DNA results even when the concentrations of plasma EBV DNA for the two groups are similar.

Figure 73:
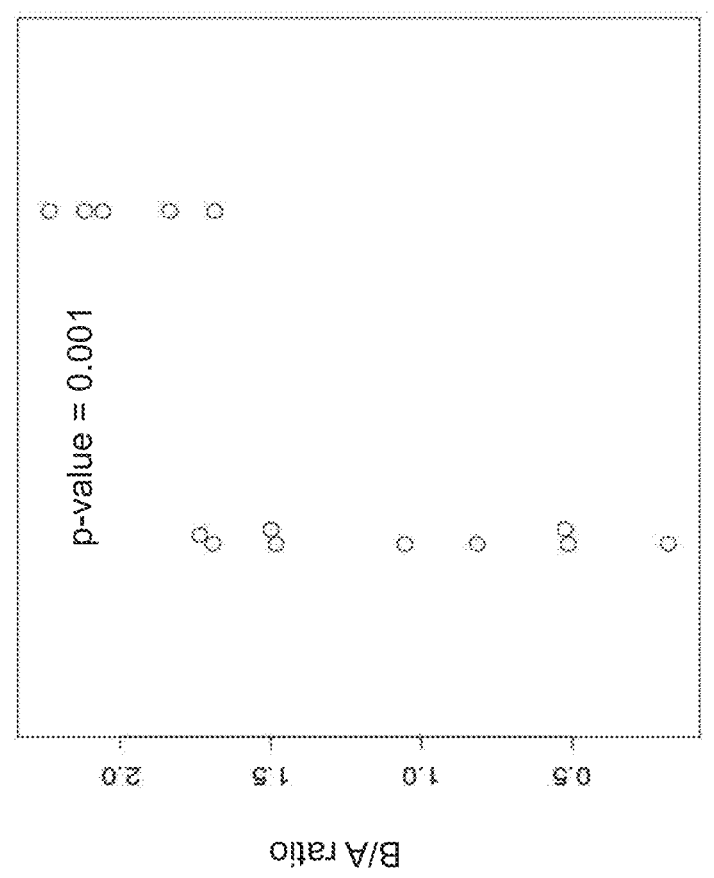
FIG. 73 shows the B/A ratio for (left) subjects persistently positive for plasma EBV DNA but having no observable pathology, and (right) early-stage NPC patients identified by screening.

FIG. 73 shows the B/A ratio for (left) subjects persistently positive for plasma EBV DNA but having no observable pathology, and (right) NPC subjects. The B/A ratio of the two groups were also significantly different (P=0.001, Mann-Whitney test). As the preferred ending positions in the Set B were determined using an independent group of NPC subjects, these results suggest that the preferred ending position are shared between different NPC subjects regardless of the plasma EBV DNA concentration.

Figure 74:
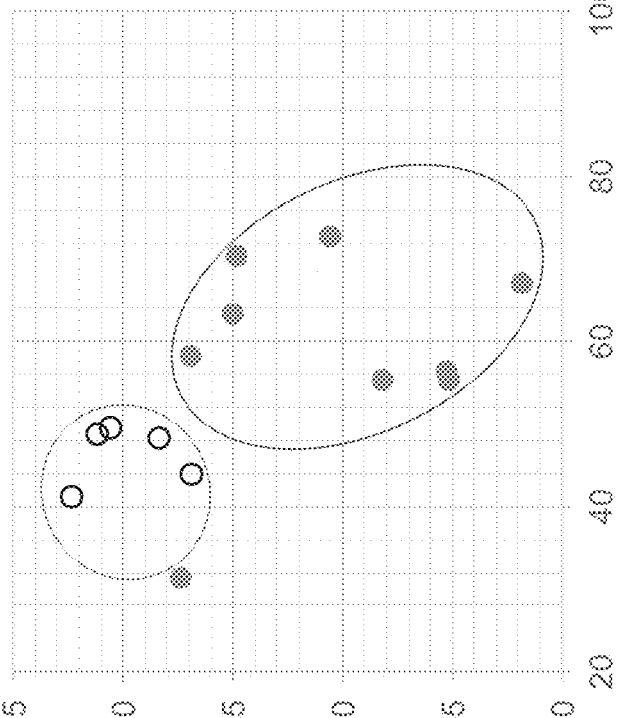
FIG. 74 shows a scatter plot of the B/A ratio vs the percentage of EBV DNA fragments below 150 bp in plasma for (closed circle) subjects persistently positive for plasma EBV DNA but having no observable pathology, and (open circle) early-stage NPC patients identified by screening.

FIG. 74 shows a scatter plot of the B/A ratio vs the percentage of EBV DNA fragments below 150 bp in plasma for (closed circle) subjects persistently positive for plasma EBV DNA but having no observable pathology, and (open circle) NPC subjects. Based on the percentage of sequenced plasma EBV DNA fragments of <150 bp and the B/A ratio, NPC subjects can be differentiated from those with false-positive plasma EBV DNA results. Only one subject with a false-positive result was clustered with the NPC subjects using these two parameters.

Figure 75:
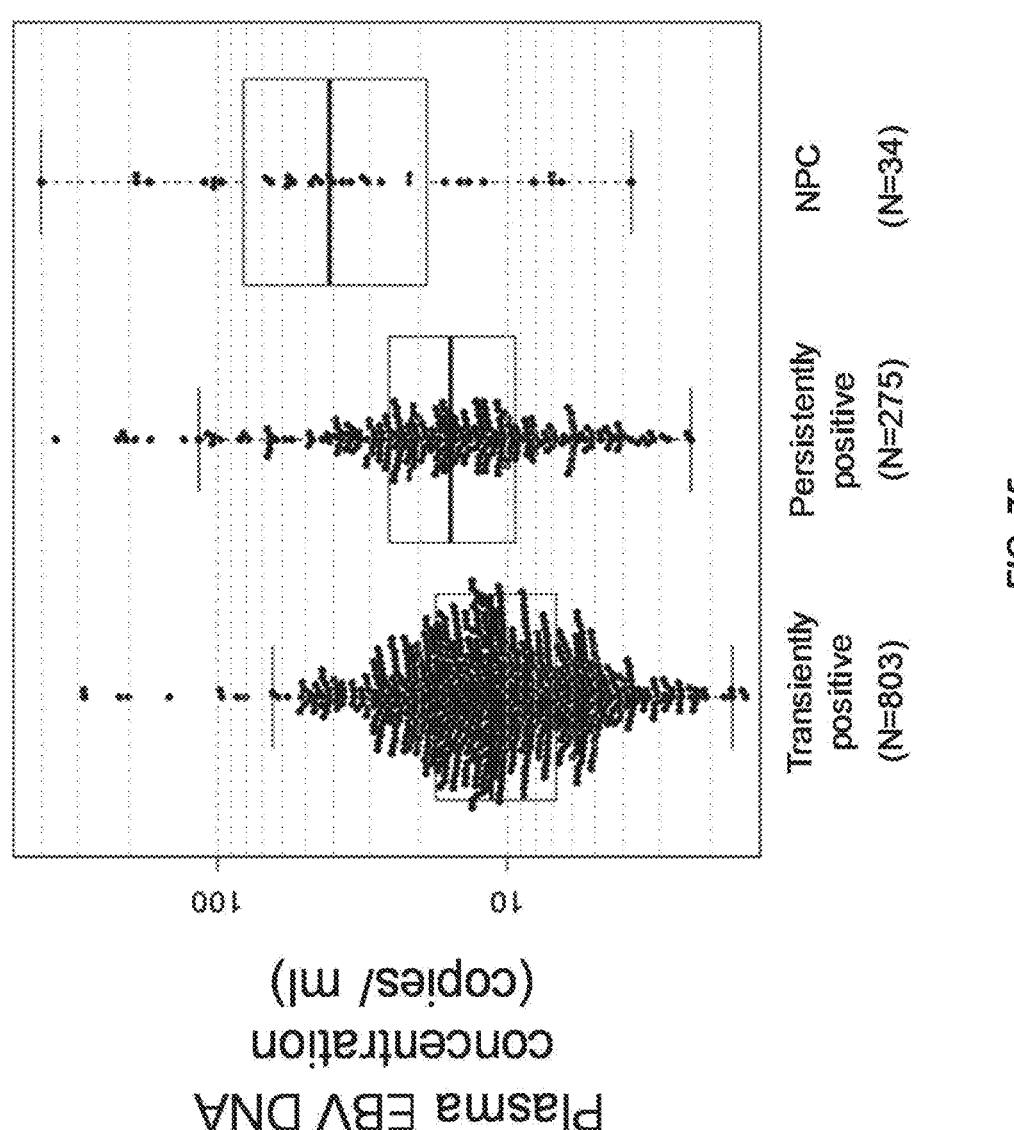
FIG. 75 shows plasma EBV DNA concentrations (copies/milliliter) measured by real-time PCR in subjects that are transiently positive or persistently positive for plasma EBV DNA (left or middle, respectively) but have no observable pathology, and subjects identified as having NPC.

FIG. 75 shows a box and whiskers plot of the concentration of EBV DNA fragments (copies per milliliter) from the plasma of subjects that are transiently positive (n=803) or persistently positive (n=275) for plasma EBV DNA (left or middle, respectively) but have no observable pathology, and subjects identified as having NPC (n=34). The concentration of EBV DNA fragments (copies per milliliter) was measured by real-time PCR analysis.

Figure 76A:
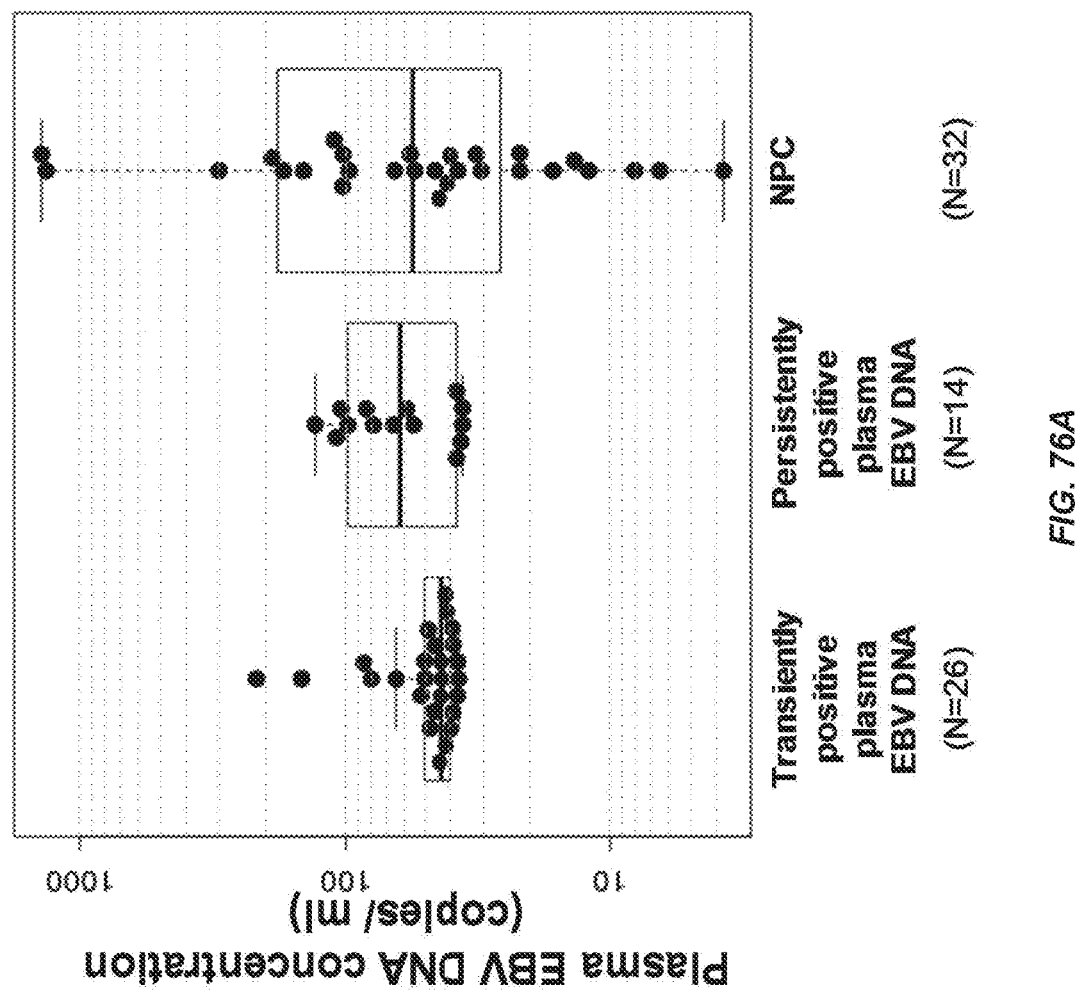
FIG. 76A shows plasma EBV DNA concentrations (copies/milliliter) measured by real-time PCR in subjects that are transiently positive or persistently positive for plasma EBV DNA (left or middle, respectively) but have no observable pathology, and subjects identified as having NPC.
Figure 76B:
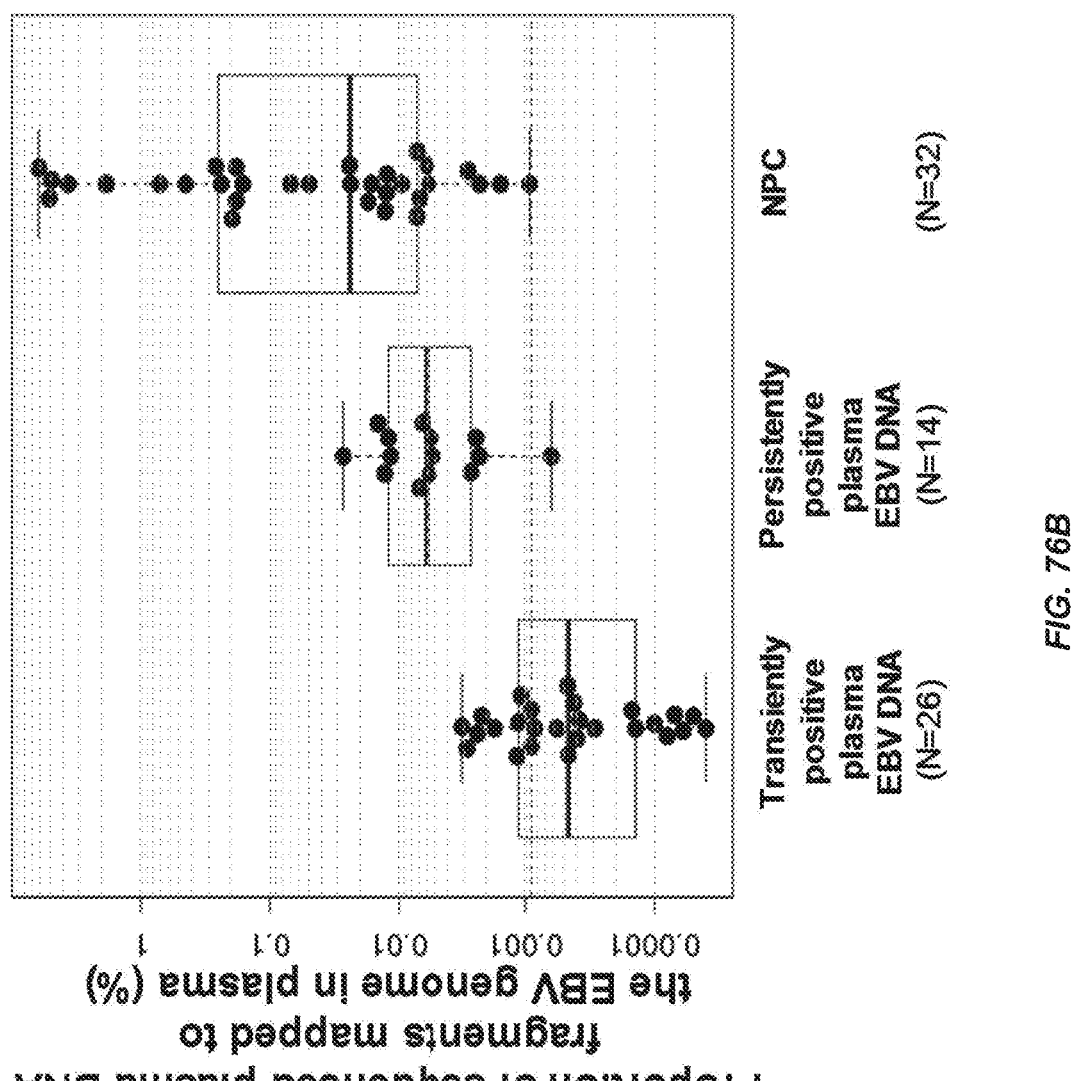
FIG. 76B shows the proportion of plasma DNA fragments mapped to the EBV genome in subjects that are transiently positive or persistently positive for plasma EBV DNA (left or middle, respectively) but have no observable pathology, and subjects identified as having NPC.

FIG. 76A shows plasma EBV DNA concentrations (copies/milliliter) measured by real-time PCR in subjects that are transiently positive or persistently positive for plasma EBV DNA (left or middle, respectively) but have no observable pathology, and subjects identified as having NPC. In this cohort of 72 subjects, there was no statistically significant difference in the plasma EBV DNA concentrations measured by real-time PCR among different groups of subjects (p-value=0.19; Kruskal-Wallis test). In some cases, an assay to screen for a condition (e.g., tumor, e.g., NPC) after an initial assay (e.g., qPCR assay)_can comprise using massively parallel sequencing to assess proportion of sequence reads from a sample that map to an EBV reference genome. FIG. 76B shows the proportion of plasma DNA fragments mapped to the EBV genome in subjects that are transiently positive or persistently positive for plasma EBV DNA (left or middle, respectively) but have no observable pathology, and subjects identified as having NPC. Using massively parallel sequencing following targeted capture and sequencing of DNA fragments, there was a statistically significant difference in the EBV quantity as deduced from the proportion of reads uniquely mapped to the EBV genome among all sequenced reads (p-value=0.01; Kruskal-Wallis test). In one embodiment, the cutoff value for the proportion of plasma DNA fragments mapped to the EBV genome can be determined as any value below lowest proportion of the NPC patients being analyzed. In FIG. 76B, a cutoff value of 0.0009% can be set to capture all the NPC patients. In other embodiments, the cutoff values can be determined by, for example, but not limited to, the mean proportion of the NPC patients minus one standard deviation (SD), mean minus 2 SD, and mean minus 3 SD. In yet other embodiments, the cutoff can be determined after the logarithmic transformation of the proportion of plasma DNA fragments mapped to the EBV genome, for example but not limited to mean minus SD, mean minus 2SD, mean minus 3 SD after the logarithmic transformation of the values of the NPC patients. In yet other embodiments, the cutoff can be determined using Receiver Operator Characteristics (ROC) curves or by nonparametric methods, for example but not limited to including about 100%, about 95%, about 90%, about 85%, or about 80% of the NPC patients being analyzed. By applying a cutoff value of 0.0009% for the proportion of plasma EBV DNA fragments among all the sequenced reads, subjects with NPC and persistently positive plasma EBV DNA from the majority of subjects with transiently positive plasma EBV DNA results were able to be differentiated. The proportion of EBV reads in plasma was highest in the group of subjects having NPC. The proportion of plasma EBV DNA fragments measured at enrollment was higher in the subjects with persistently positive results compared with those who would become negative in the follow-up test (i.e. with transiently detectable plasma EBV DNA). In some embodiments, the cutoff value for proportion of plasma EBV DNA reads among all sequenced reads can be greater than 0.00001%, greater than 0.00005%, greater than 0.0001%, greater than 0.0002%, greater than 0.0003%, greater than 0.0004%, greater than 0.0005%, greater than 0.0006%, greater than 0.0007%, greater than 0.0008%, greater than 0.0009%, greater than 0.001%, greater than 0.002%, greater than 0.003%, greater than 0.004%, greater than 0.005%, greater than 0.01%, greater than 0.1%, or greater than 1%.

Figure 77:
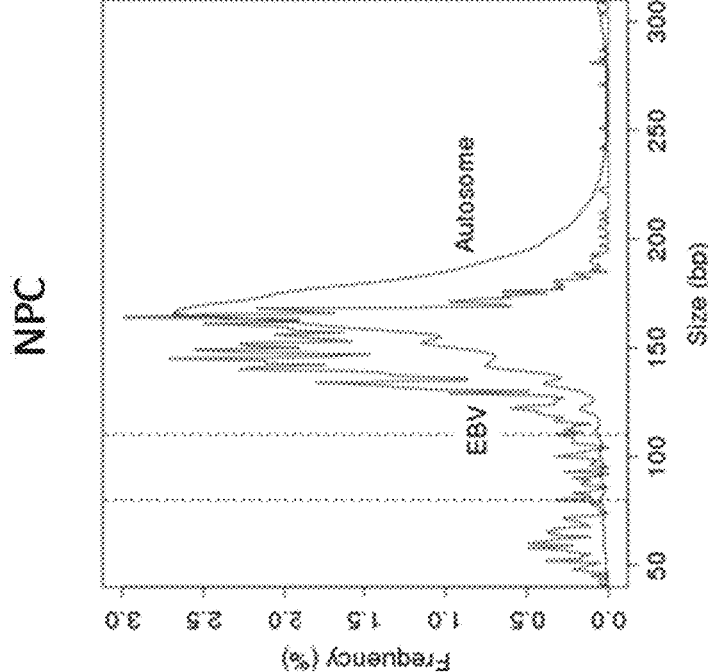
FIG. 77 shows the size profiles of sequenced plasma DNA fragments in subjects having NPC (left) and subjects that are persistently positive for plasma EBV DNA (right) mapped to the EBV genome and human genome.

In some cases, an assay to screen for a condition (e.g., tumor, e.g., NPC) after an initial assay (e.g., qPCR assay) _can comprise using massively parallel sequencing to assess size of cell-free EBV nucleic acids in a sample. FIG. 77 shows the size profiles of sequenced plasma DNA fragments in subjects having NPC (left) and subjects that are persistently positive for plasma EBV DNA (right) mapped to the EBV genome and human genome. A difference in the size profile pattern of plasma EBV DNA fragments aligned to the EBV genome and those aligned to the autosomal genome (e.g., reference) were observed; those differences were used to differentiate subjects with NPC from subjects with false-positive plasma EBV DNA results. Massively parallel sequencing of the fragments results in variations in target capture and PCR efficiencies. These variations lead to inter-individual variations in the size profile patterns of sequenced plasma DNA. To compare the proportion of plasma EBV DNA reads within a certain size range (e.g., between 80 and 110 base pairs) among individuals, the amount of plasma EBV DNA fragments was normalized to the amount of autosomal DNA fragments within the same size range. This metric is denoted as a size ratio. A size ratio can be defined by the proportion of plasma EBV DNA fragments within a certain size range divided by the proportion of autosomes (e.g., autosomal DNA fragments) within the corresponding size range. For example, a size ratio of fragments between 80 and 110 base pairs would be:

$$\text{Size}_{80-110\,bp} \text{ ratio} =$$
$$\frac{\text{Proportion of } EBV\ DNA \text{ fragments within } 80-110\,bp}{\text{Proportion of autosomal } DNA \text{ fragments within } 80-110\,bp}$$

Figure 78:
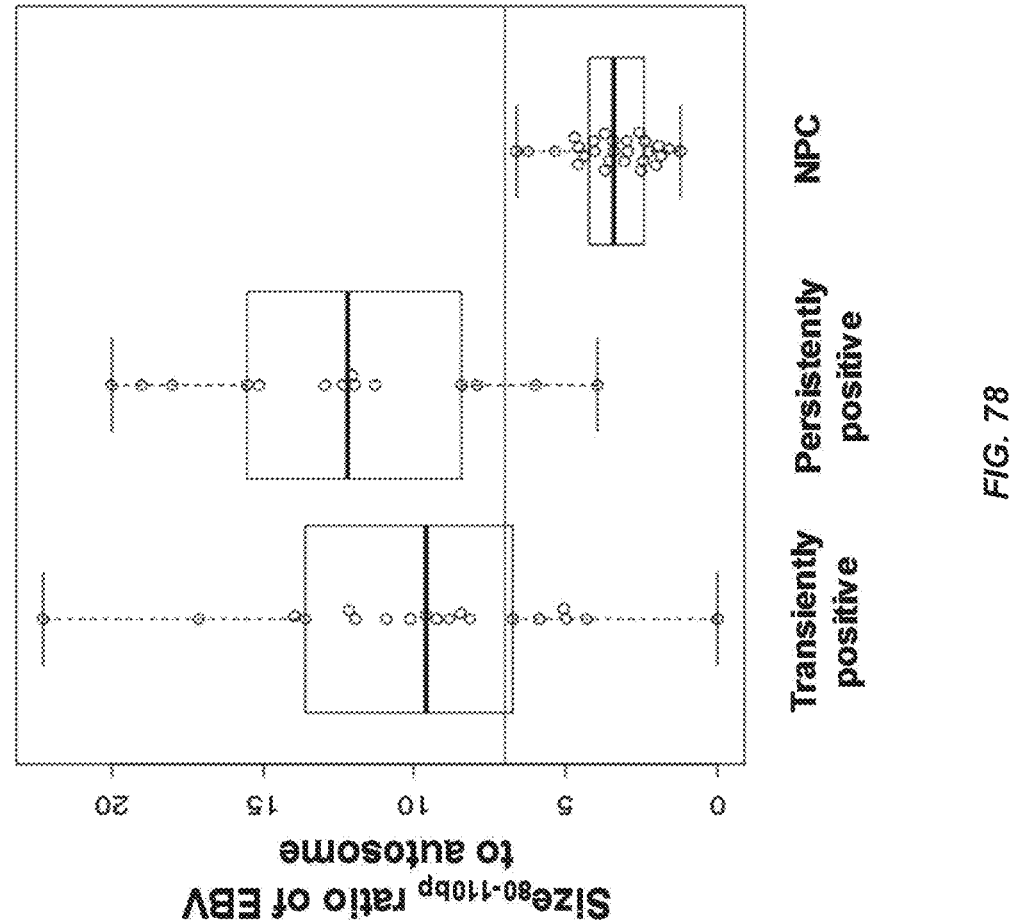
FIG. 78 shows the size ratio of plasma EBV DNA fragments between 80 and 110 base pairs in length to autosomal DNA fragments between 80 and 110 base pairs in length in subjects that are transiently positive or persistently positive for plasma EBV DNA (left or middle, respectively) but have no observable pathology, and subjects identified as having NPC.

FIG. 78 shows the size ratio of plasma EBV DNA fragments between 80 and 110 base pairs in length to autosomal DNA fragments between 80 and 110 base pairs in length in subjects that are transiently positive or persistently positive for plasma EBV DNA (left or middle, respectively) but have no observable pathology, and subjects identified as having NPC. By determining the size ratio (e.g. the proportion of plasma EBV DNA fragments within a certain size range divided by the proportion of autosomal DNA fragments within the corresponding size range) of fragments between 80 and 110 base pairs, we could observe a statistically significant difference between subjects with NPC and subjects with false-positive plasma EBV DNA results (p-value<0.0001; Mann-Whitney U test). Subjects with NPC have a lower size ratio within the size range of 80 to 110 bp than subjects with false-positive plasma EBV DNA results. Accordingly, patients with NPC had a lower proportion of plasma EBV reads within the size range of 80-110 bp among all sequenced EBV reads compared to subjects with transiently positive or persistently positive plasma EBV results. Any nucleic acid fragment size or size range may be used to determine the size ratio. In one example, the size ratio can be a ratio of the proportion of EBV DNA fragments having a size within 50-75 base pairs in length to the proportion of autosomal DNA fragments having a size within 50-75 base pairs in length. In another example, the size ratio can be a ratio of the proportion of EBV DNA fragments having a size within 60-90 base pairs in length to the proportion of autosomal DNA fragments having a size within 60-90 base pairs in length. In another example, the size ratio can be a ratio of the proportion of EBV DNA fragments having a size within 70-100 base pairs in length to the proportion of autosomal DNA fragments having a size within 70-100 base pairs in length. In yet another example, the size ratio can be a ratio of the proportion of EBV DNA fragments having a size within 90-120 base pairs in length to the proportion of autosomal DNA fragments having a size within 90-120 base pairs in length. In yet another example, the size ratio can be a ratio of the proportion of EBV DNA fragments having a size within 120-150 base pairs in length to the proportion of autosomal DNA fragments having a size within 120-150 base pairs in length. In yet another example, the size ratio can be a ratio of the proportion of EBV DNA fragments having a size within 150-180 base pairs in length to the proportion of autosomal DNA fragments having a size within 150-180 base pairs in length. In yet another example, the size ratio can be a ratio of the proportion of EBV DNA fragments having a size within 180-210 base pairs in length to the proportion of autosomal DNA fragments having a size within 180-210 base pairs in length. In yet another example, the size ratio can be a ratio of the proportion of EBV DNA fragments having a size of about 95 base pairs in length to the proportion of autosomal DNA fragments having a size of about 95 base pairs in length. In some embodiments, the size range for EBV DNA fragments and the size range for autosomal DNA fragments used to determine the size ratio may be different. For example, the size ratio can be a ratio of the proportion of EBV DNA fragments having a size of about 80-110 base pairs in length to the proportion of autosomal DNA fragments having a size of about 120-150 base pairs in length. In another example, the size ratio can be a ratio of the proportion of EBV DNA fragments having a size within 80-110 base pairs in length to the proportion of autosomal DNA fragments having a size of about 105 base pairs in length. In some embodiments, a cutoff for the size of a DNA fragment used to determine a size ratio can be base pairs, 10 base pairs, 15 base pairs, 20 base pairs, 25 base pairs, 30 base pairs, 35 base pairs, 40 base pairs, 45 base pairs, 50 base pairs, 55 base pairs, 60 base pairs, 65 base pairs, 70 base pairs, 75 base pairs, 80 base pairs, 85 base pairs, 90 base pairs, 95 base pairs, 100 base pairs, 105 base pairs, 110 base pairs, 115 base pairs, 120 base pairs, 125 base pairs, 130 base pairs, 135 base pairs, 140 base pairs, 145 base pairs, 150 base pairs, 155 base pairs, 160 base pairs, 165 base pairs, 170 base pairs, 175 base pairs, 180 base pairs, 185 base pairs, 190 base pairs, 195 base pairs, 200 base pairs, 210 base pairs, 220 base pairs, 230 base pairs, 240 base pairs, 250 base pairs, or a range of sizes within any two sizes thereof. In some embodiments, a cutoff value for the size ratio may be used to determine if a subject has a condition (e.g., NPC), is falsely positive for a condition, or does not have a condition. For example, subjects with NPC have a lower size ratio within the size range of 80 to 110 bp than subjects with false-positive plasma EBV DNA results. In some embodiments, a cutoff value for a size ratio can be about 0.1, about 0.5, about 1, about 2, about 3, about 4, about 5, about 6, about 7, about 8, about 9, about 10, about 11, about 12, about 13, about 14, about 15, about 16, about 17, about 18, about 19, about 20, about 25, about 50, about 100, or greater than about 100. In some embodiments, a size ratio at and/or below a cutoff value can be indicative of having a condition (e.g., NPC). In some embodiments, a size ratio at and/or above a cutoff value can be indicative of having a condition (e.g., NPC).

Figure 79:
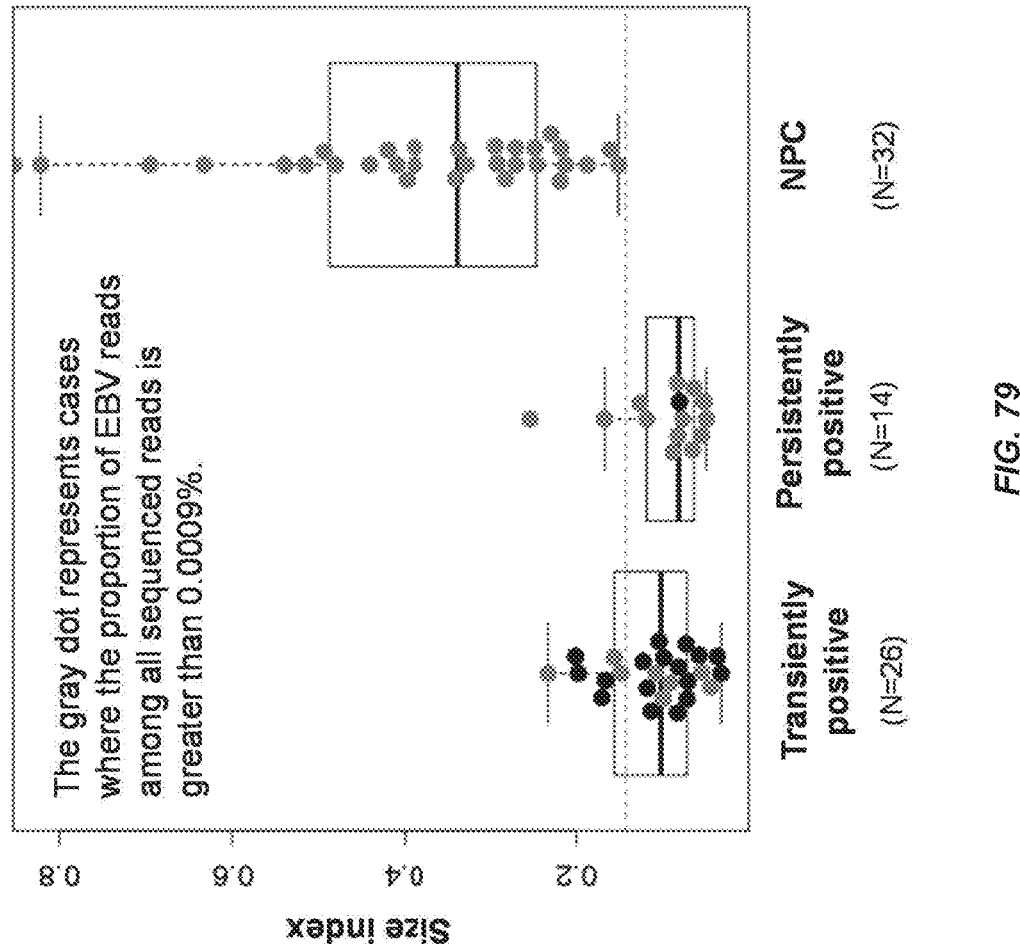
FIG. 79 shows a size index (e.g., an inverse of the size ratio) in subjects that are transiently positive or persistently positive for plasma EBV DNA (left or middle, respectively) but have no observable pathology, and subjects identified as having NPC.

FIG. 79 shows a size index (e.g., an inverse of the size ratio) in subjects that are transiently positive or persistently positive for plasma EBV DNA (left or middle, respectively) but have no observable pathology, and subjects identified as having NPC. A size index can be defined as the inverse of the size ratio, and the size ratio is defined as the proportion of plasma EBV DNA fragments within a certain size range divided by the proportion of autosomal DNA fragments within the corresponding size range. Subjects with NPC were differentiated from subjects with persistently positive plasma EBV DNA based on the difference in the size profile of plasma EBV DNA reads. Using a cutoff value for the size ratio of 7 (e.g., size index greater than 0.14), subjects having NPC were differentiated from the majority of subjects with persistently positive plasma EBV DNA. Gray dots represent cases where the proportion of plasma EBV DNA reads among all sequenced reads were greater than 0.0009% (see, e.g., FIG. 76B). Three out of the eight subjects with transiently positive plasma EBV DNA had the size index greater than 0.14. Two out of the thirteen subjects with persistently positive plasma EBV DNA had the size index greater than 0.14. All patients with NPC had the size index greater than 0.14. In some embodiments, a cutoff value for the size index may be used to determine if a subject has a condition (e.g., NPC), is falsely positive for a condition, or does not have a condition. In some embodiments, a cutoff value for a size index can be about or least 10, about or least 2, about or least 1, about or least 0.5, about or least 0.333, about or least 0.25, about or least 0.2, about or least 0.167, about or least 0.143, about or least 0.125, about or least 0.111, about or least 0.1, about or least 0.091, about or least 0.083, about or least 0.077, about or least 0.071, about or least 0.067, about or least 0.063, about or least 0.059, about or least 0.056, about or least 0.053, about or least 0.05, about or least 0.04, about or least 0.02, about or least 0.001, or less than about 0.001. In some embodiments, a size index at and/or below a cutoff value can be indicative of having a condition (e.g., NPC). In some embodiments, a size index at and/or above a cutoff value can be indicative of having a condition (e.g., NPC).

Figure 80:
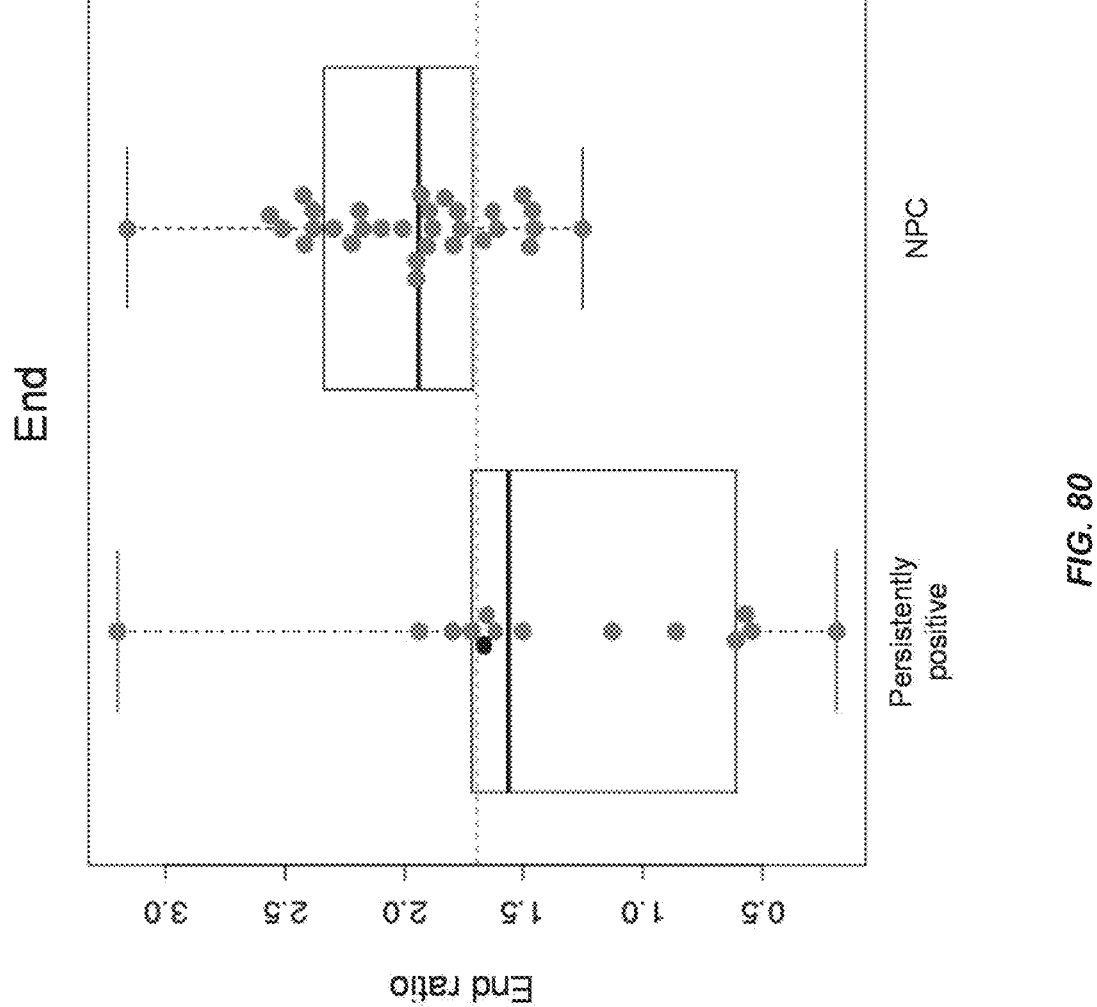
FIG. 80 shows an end ratio (e.g., a ratio of a number of sequenced plasma EBV DNA fragments ending on Set B positions and a number of sequenced plasma EBV DNA fragments ending on Set A positions) in subjects that are persistently positive for plasma EBV DNA (left) but have no observable pathology, and subjects identified as having NPC.

FIG. 80 shows an end ratio (e.g., a ratio of a number of sequenced plasma EBV DNA fragments ending on Set B positions and a number of sequenced plasma EBV DNA fragments ending on Set A positions) in subjects that are persistently positive for plasma EBV DNA (left) but have no observable pathology, and subjects identified as having NPC. For subjects with persistently detectable plasma EBV DNA, the ends ratios of the subjects with no pathology were significantly lower than the end ratios in subjects having NPC (p=0.001; Mann-Whitney test). It is contemplated that the end ratio could serve as a parameter to differentiate subjects with NPC from subjects with persistently positive plasma EBV DNA but without observable pathology.

Figure 81:
FIG. 81 shows the number of subjects identified as being transiently positive or persistently positive for plasma EBV DNA but have no observable pathology, and subjects identified as having NPC following a first analysis using a proportion of sequenced plasma DNA fragments mapped to the EBV genome (e.g., greater than or equal to 0.0009%) and a subsequent second analysis using a size ratio (e.g., less than or equal to 7%).

FIG. 81 shows the number of subjects identified as being transiently positive or persistently positive for plasma EBV DNA but have no observable pathology, and subjects identified as having NPC following a first analysis using a proportion of sequenced plasma DNA fragments mapped to the EBV genome (e.g., greater than or equal to 0.0009%) and a subsequent second analysis using a size ratio (e.g., less than or equal to 7%). Using a combination of the plasma EBV quantity analysis (e.g., a proportion of EBV DNA reads among all sequenced reads) and the size ratio, the NPC detection rate, false positive rate and positive predictive value in the cohort of 72 subjects may be calculated. The NPC detection rate was 100%. The false positive rate is 13.5% and the positive predictive value is 86.5%. In contrast, using only real-time PCR analysis to screen for subjects having NPC, the false positive rate was 30.4% and the positive predictive value was 69.6%. Therefore, we can observe an almost three-fold reduction in the false positive rate using a combined analysis of EBV DNA quantity and size analysis from targeted capture sequencing.

Figure 82A:
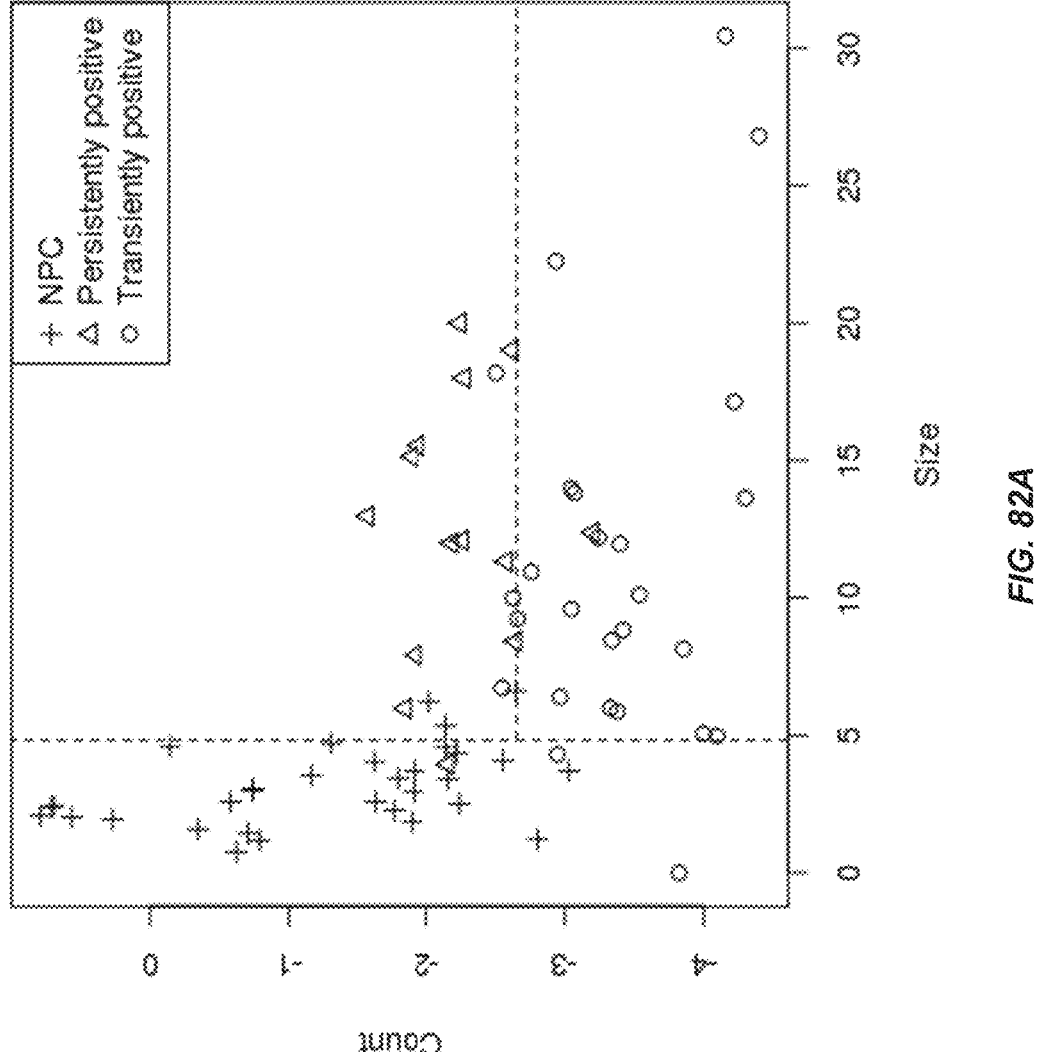
FIGS. 82A and 82B show the results of a classification and regression tree (CART) analysis to determine optimal cutoff values in various parameters for distinguishing between subjects that are transiently positive or persistently positive for plasma EBV DNA but have no observable pathology, or subjects identified as having NPC.
Figure 82B:
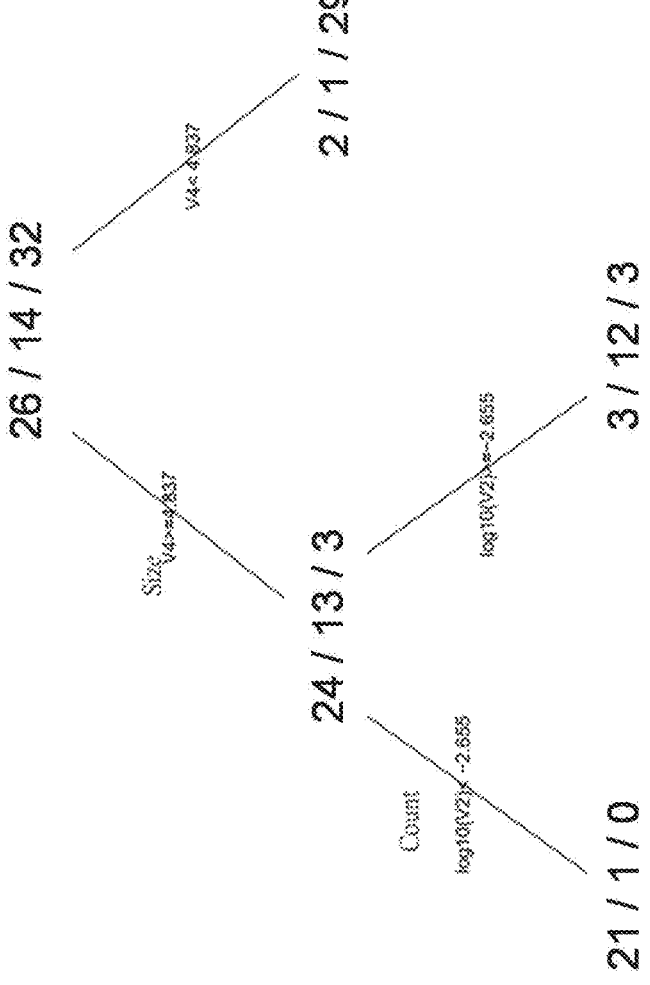

FIGS. 82A and 82B show the results of a classification and regression tree (CART) analysis to determine optimal cutoff values in various parameters for distinguishing between subjects that are transiently positive or persistently positive for plasma EBV DNA but have no observable pathology, or subjects identified as having NPC. A person having ordinary skill in the art will appreciate that a variety of methods may be used to determine the cutoff values used to distinguish between different groups within the cohort or population. A non-limiting example of such a method is CART analysis. In the CART analysis, the goal is to find an optimal cutoff value in the parameters to achieve the largest separation among the different groups (or the highest detection rate of each group). CART analysis yielded that the size ratio cut-off value=4.837, and the log (EBV count) cut-off value=−2.655. Using these cutoff values, the NPC detection rate was 90.6% and the positive predictive value is 90.6%.

In other embodiments, the analysis of ending positions can be determined by the number of fragments ending at the preferred positions for the particular condition. For example, the number of fragments ending at the Set B positions can be used to determine the likelihood of a tested subject of having NPC. In another embodiment, the number of fragments ending at such positions can be normalized based on the total number of sequenced fragments or the number of sequenced fragments mapped to the EBV genome or number of sequenced fragments mapped to one or multiple regions of the EBV genome. When a subject is screened for NPC using plasma EBV DNA analysis and shows a positive result. Based on the arrangement used in the study we have performed, we would collect another blood sample in around four weeks and determine if the plasma EBV DNA is persistently positive. Based on the results shown, one alternative arrangement is to analyze the size and the percentage of plasma EBV DNA fragments ending at the NPC-preferred ending positions using B/A ratio. For those cases with high percentage of fragments<150 bp and low B/A ratio, they can be regarded as low risk for NPC whereas those with low percentage of fragments<150 bp and high B/A ratio can be referred for further investigations. This arrangement can improve the logistics of the tests and obviate the need for asking the subjects to come back for further blood collection.

Apart from NPC, the analysis of the size of viral DNA fragments and their ending positions in plasma can also be used for the detection of other cancers associated with viral infection. In this regard, we analyzed three HCC subjects and three subjects with chronic hepatitis B infection but without HCC. In China and Southeast Asia, a large proportion of HCC are associated with HBV infection. The plasma DNA samples of these subjects were sequenced after target enrichment using the protocol described above.

E. Analysis of EBV DNA in HCC Subject

Figure 83:
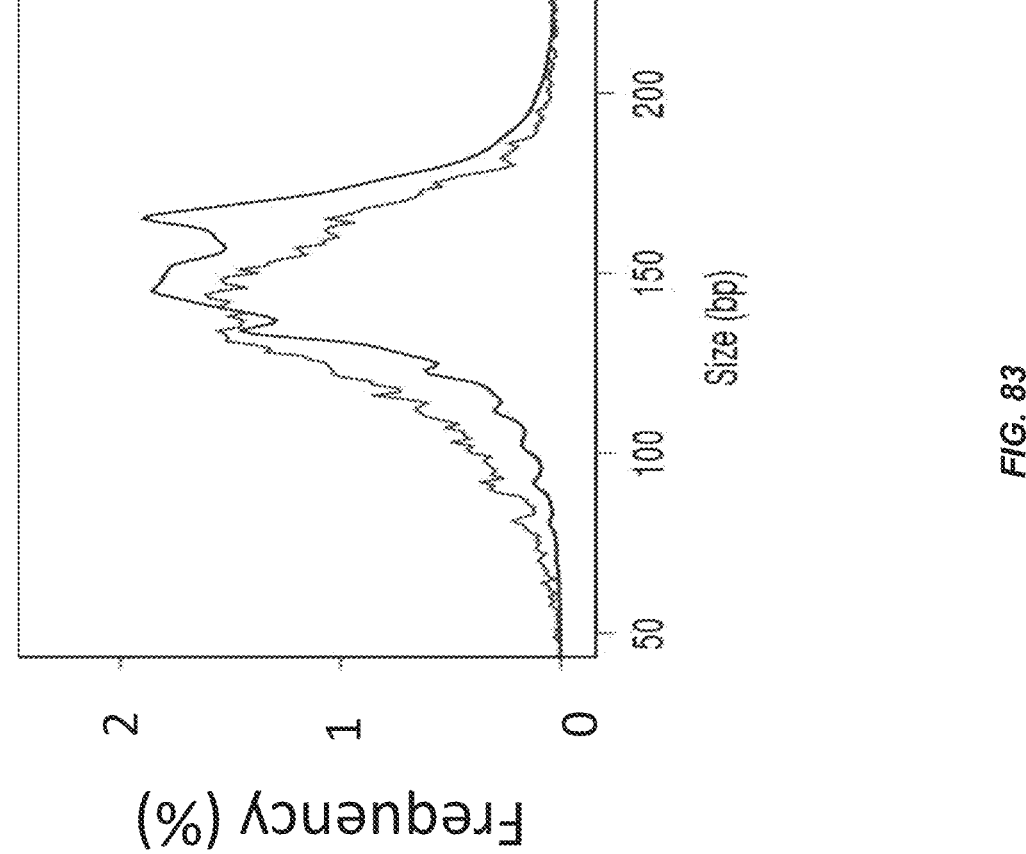
FIG. 83 shows the size distribution of sequenced plasma DNA fragments mapped to the EBV genome and human genome in an HCC subject.

FIG. 83 shows the size distribution of sequenced plasma DNA fragments mapped to the EBV genome and human genome in a HCC subject. Similar to the pattern of the NPC subjects, the size distribution of plasma DNA fragments aligned to the HBV genome was shorter than that of the fragments aligned to the human genome.

Figure 84:
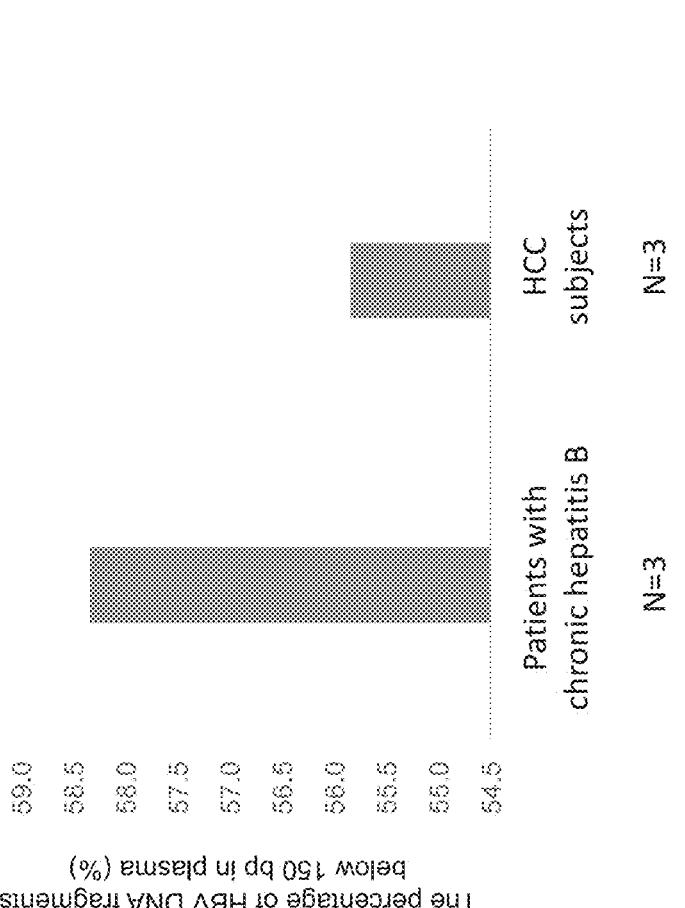
FIG. 84 shows a bar plot of the percentage of HBV DNA fragments below 150 bp in plasma in (left) subjects having chronic hepatitis B and (right) HCC subjects.

FIG. 84 shows a bar plot of the percentage of HBV DNA fragments below 150 bp in plasma in (left) subjects having chronic hepatitis B and (right) HCC subjects. The mean percentage of sequenced plasma HBV DNA of <150 bp was higher in the chronic HBV carriers compared with the HCC subjects. This observation is consistent with the size difference between NPC subjects and those with false-positive plasma EBV DNA results.

One HCC subject was randomly selected for the analysis of preferred ending positions. The coordinates of the HBV genome were ranked in descending order of the number of plasma DNA fragments ending on these positions in this particular HCC subject. For illustration purpose, the top 800 positions were identified. These positions are denoted as the HCC-preferred positions. In other embodiments, other numbers of positions can be used, for example, but not limited to 100, 200, 400, 600, 1000, or 1500. For illustration purpose, another 2000 positions were randomly selected for normalizing the number of plasma DNA fragments aligning to the HBV genome. Other numbers can be used for this normalization process, for example, but not limited to 200, 400, 600, 800, 1000, 1500 and 2500. In other embodiments, the normalization with the total DNA in the plasma sample or the total number of sequenced reads or total number of reads aligned to the HBV genome can be used.

Figure 85:
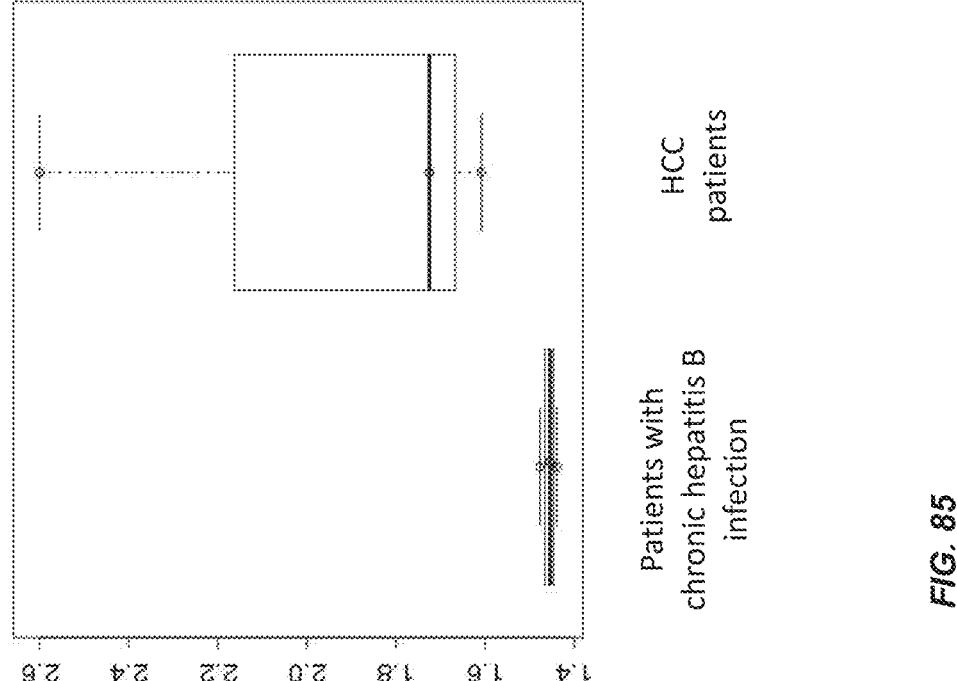
FIG. 85 shows a box and whiskers plot of the number of plasma HBV DNA fragments ending at HCC preferred ending positions normalized to fragments ending at other positions in (left) subjects having chronic hepatitis B and (right) HCC subjects.

FIG. 85 shows a box and whiskers plot of the number of plasma HBV DNA fragments ending at HCC preferred ending positions normalized to fragments ending at other positions in (left) subjects having chronic hepatitis B and (right) HCC subjects. The number of plasma HBV DNA fragments ending at the HCC-preferred positions were higher in the HCC subjects compared with the subjects with chronic HBV infection but without HCC. These results suggest that the number of fragments ending at the HCC-preferred positions can be used to distinguish HCC subjects from chronic HBV carriers without HCC.

It should be understood that, when normalizing the number of plasma DNA fragments ending at preferred ending positions to fragments ending at 'other positions', the 'other positions' may be one or more of any other position of a gene or genome. While the 'other positions' can correspond to preferred ending positions (e.g., the preferred ending positions of nucleic acid fragments aligned to a reference genome), it is not necessary that the 'other positions' be preferred ending positions. In one embodiment, the 'other positions' may correspond to the least preferred ending positions for a plurality of nucleic acids. In another embodiment, the 'other positions' may correspond to a random set of positions.

For the HBV and HPV (below) work, some embodiments identified the most frequently seen (e.g. top 1,000) ends in the HCC or cervical cancer cases, respectively, and identified the least frequent ends (e.g. bottom 1,000) in the same case, where the latter is used for normalization. The data shown in FIG. 85 shows a quantification of the most frequent HCC ends expressed as a ratio of other ends (e.g., the least frequent or any random ends).

F. HPV Example

The analysis of the fragmentation pattern of viral DNA in plasma can be generalized to other cancers associated with viral infection. As an illustrative example, we analyzed the plasma of a subject with a head and neck squamous cell carcinoma. This cancer has a close association with HPV infection. The plasma DNA was sequenced after target enrichment as described above. The plasma DNA fragments uniquely aligned to the HPV were analyzed.

FIG. 86 shows the number of plasma HPV DNA fragments ending at different positions of the HPV genome. Similar to the patterns observed in the NPC subjects and the HCC subjects, there were positions in the HPV genome that were more likely to be the ending positions of the plasma DNA of the head and neck squamous cell carcinoma subject. These positions can be applied for detecting this type of cancer. Our data also suggest that a similar approach can be used for detecting cervical cancer associated with HPV infection. In one embodiment, the preferred ending positions for cervical cancers can be determined. Then, any subjects with a positive plasma HPV DNA result can be tested if those plasma HPV DNA would end on the cervical cancer-preferred ending positions. Those subjects with plasma HPV DNA ending on such positions are more likely to have cervical cancers whereas those with plasma HPV DNA ending on other positions are more likely to have false-positive results.

G. Uses of EBV DNA Fragments

In the NPC subjects, plasma EBV DNA fragments with a terminal nucleotide ending exactly at one or more of the NPC-specific ending positions would be more likely to be derived from the tumor. Based on this assumption, the number of sequenced plasma EBV DNA fragments that ended on the NPC-specific ending positions can be used to indicate the presence or absence of NPC or other cancers having a similar plasma DNA fragmentation pattern. In another embodiment, this parameter can also be used for reflecting the level of cancer, for example but not limited to the size of the tumor, the stage of the cancer, tumor load and the presence of metastasis. Interestingly, in the control subjects, EBV DNA fragments have terminal nucleotides ending at a set of ending positions (e.g., control-specific ending positions) that are unique to control subjects, or at least different from NPC-specific ending positions. As healthy subjects do not have a tumor, the plasma EBV DNA fragments are not derived from a tumor. It is contemplated that the difference in the fragmentation pattern of EBV DNA in control subjects and NPC subjects is related to the specific mechanisms by which DNA fragments. It is contemplated that the NPC-specific fragmentation pattern may be a result of tumor cell apoptosis-induced DNA fragmentation. Additionally, it is contemplated that the control-specific fragmentation pattern may be a result of EBV DNA replication-induced DNA fragmentation.

Both NPC subjects and reference subjects (e.g., healthy subjects, or subjects that are false positive for a disease, such as a tumor) can both have EBV DNA in their blood. However, each population can have a unique EBV DNA fragmentation pattern. By normalizing a first amount of nucleic acids (e.g., than can correspond to a number of EBV DNA fragments from a biological sample from the subject that end at NPC-specific preferred ending locations) with a second amount (e.g., that can correspond to a number of EBV DNA fragments from a reference sample from a healthy subject that end at healthy- or false-positive-specific preferred ending locations), a method of the present disclosure can better distinguish between subjects that are true positive for a condition, and subjects that are false-positive or otherwise healthy.

The identification and application of unique DNA fragmentation patterns for control subjects (e.g., subjects having no observable pathology) and tumor subjects can have tremendous practical value. For example, the abundance of nucleic acid fragments ending on tumor-specific ending positions may not be significantly different in a control subject and a tumor subject. In another example, in tumor subjects having low tumor burden, the EBV DNA abundance may be lower and more difficult to detect, as compared to control subjects, in whom the EBV DNA abundance can be higher, and more easy to detect. In some embodiments, the preferred ending positions for a given subject (e.g., a healthy subject or a tumor subject) can be highly specific (e.g., few of the preferred ending positions for a control subject are also preferred ending positions for a tumor subject).

In some embodiments, an end ratio (e.g., a ratio of a first amount of nucleic acid molecules ending on a first set of genomic positions to a second amount of nucleic acid molecules ending on a second set of genomic positions) can be used to determine a classification of a proportional contribution of a tissue type. In one example, the number of EBV DNA fragments ending on NPC-specific ending positions can be normalized using the number of EBV DNA fragments ending on the control-specific ending positions. In some embodiments, a combination of metrics (e.g., at least two of an end ratio, copy number, and nucleic acid fragment size) may be used to detect a condition (e.g., a tumor) in a subject. For example, as discussed above, NPC subjects can exhibit a higher number of EBV DNA fragments, a higher B/A ratio, and a lower proportion of reads less than 150 base pairs in length, as compared to control subjects.

X. Determining Genotype

Given that preferred ending positions can be determined for a particular tissue type, cell-free DNA molecules ending at such preferred ending positions have high likelihood of being from that tissue. In some situations, a particular tissue type in a cell-free DNA mixture can have a different genotype at a particular genomic position relative to other tissue types. For example, fetal tissue or tumor tissue can have a different genotype. As the cell-free DNA molecules have a high likelihood of being from the tissue type of interest, the cell-free DNA molecule ending at such a position can be analyzed to determine a genotype of the tissue type at that position. In this manner, the preferred ending position can be used as a filter to identify DNA from the tissue type.

A. Fetal Genotype

The information regarding the ending positions of the sequenced plasma DNA fragments can be used for determining which maternal allele has been inherited by the fetus from the pregnant woman. Here, we use a hypothetical example to illustrate the principle of this method. We assume that the genotypes of the mother, the father and the fetus are AT, TT and TT, respectively. To determine the fetal genotype, we need to determine if the fetus has inherited the A or the T allele from the mother. We have previously described a method called relative mutation dosage (RMD) analysis (Lun et al. Proc Natl Acad Sci USA 2008; 105: 19920-5). In this method, the dosage of the two maternal alleles in the maternal plasma would be compared. If the fetus has inherited the maternal T allele, the fetus would be homozygous for the T allele. In this scenario, the T allele would be overrepresented in the maternal plasma compared with the A allele. On the other hand, if the fetus has inherited the A allele from the mother, the genotype of the fetus would be AT. In this scenario, the A and T alleles would be present in approximately the same dosage in the maternal plasma because both the mother and the fetus would be heterozygous for AT. Thus, in RMD analysis, the relative dosage of the two maternal alleles in the maternal plasma would be compared. The ending positions of the sequenced reads can be analyzed for improving the accuracy of the RMD approach.

Figure 87:
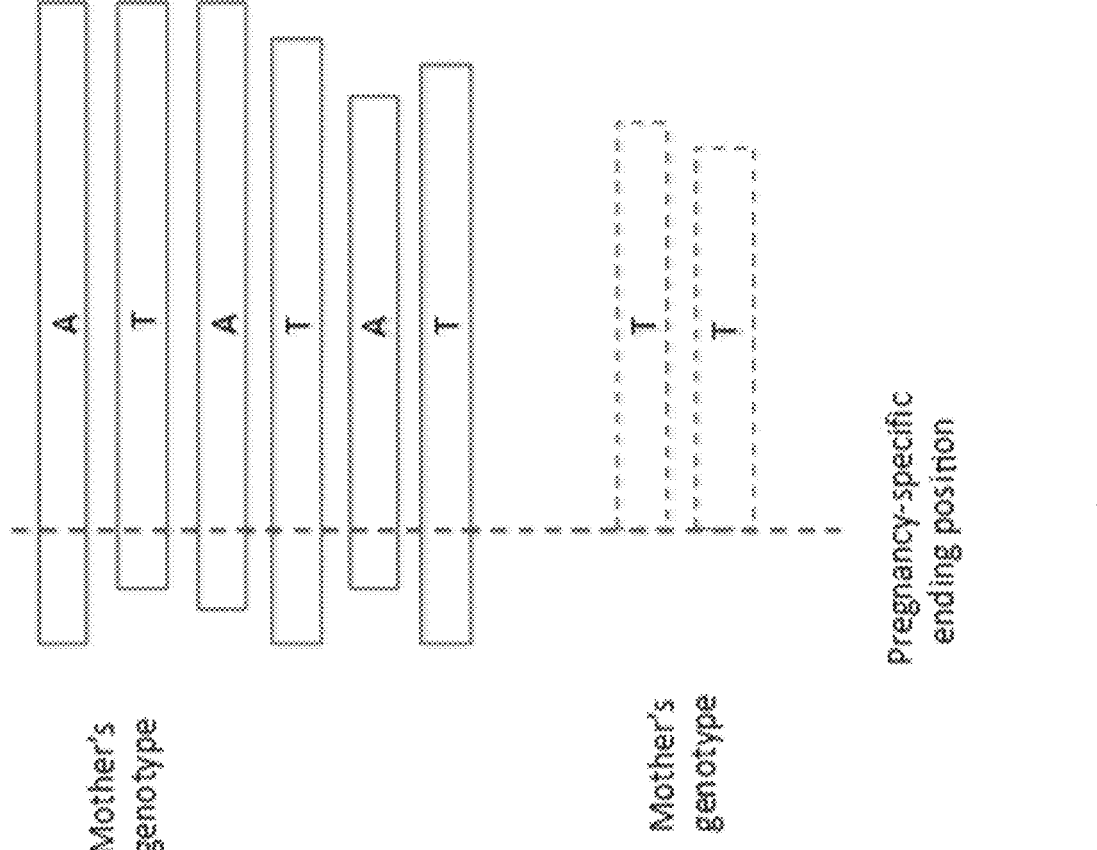
FIG. 87 shows maternal plasma DNA molecules carrying different alleles as they are aligned to a reference genome near a fetal-preferred ending position.

FIG. 87 shows maternal plasma DNA molecules carrying different alleles as they are aligned to a reference genome near a fetal-specific ending position. Molecules in solid lines are derived from the mother and the molecules in dotted lines are derived from the fetus. The fetal DNA molecules are more likely to end on the pregnancy-specific ending positions. In one embodiment, the molecules ending on the pregnancy-specific ending positions can be given more weight in the RMD analysis. In another embodiment, only plasma DNA fragments ending on pregnancy-specific positions are used for downstream analysis. This selection can potentially enrich the fetal derived plasma DNA fragments for downstream analysis.

FIG. 87 shows plasma DNA molecules in a pregnant woman whose genotype is AT. The DNA fragments derived from maternal tissues are in solid line and the DNA fragments derived from the fetus are in dotted line. The fetal DNA molecules are more likely to end on the pregnancy-specific ending position.

In this illustrative example, both of the two molecules ending on the pregnancy-specific ending position carry the T allele. In one embodiment, only the two molecules ending on the pregnancy-specific ending position were used for downstream analysis and the fetal genotype would be deduced as TT. In another embodiment, the two fetal derived molecules carrying the T allele would be given a higher weigh in the RMD analysis because these two molecules ended on a pregnancy-specific ending position. Different weight can be given to the molecules ending on the pregnancy-specific ending positions, for example but not limited to 1.1, 1.2, 1.3, 1.4, 1.5, 2, 2.5, 3 and 3.5.

As an example, the criteria for determining whether a locus is heterozygous can be a threshold of two alleles each appearing in at least a predetermined percentage (e.g., 30% or 40%) of reads aligned to the locus. If one nucleotide appears at a sufficient percentage (e.g., 70% or greater) then the locus can be determined to be homozygous in the CG.

B. Cancer Genotype

A similar technique can be performed for cancer-specific ending positions. For example, a cancer-preferred ending position can be identified as described above. The cell-free DNA molecules ending on the cancer-preferred ending position can be identified and analyzed. The base corresponding (e.g., aligned) to this position can be determined for each cell-free DNA molecule of this set, and the percentages of the total bases can be computed for each base. For example, a percentage of Cs seen on the cell-free DNA molecules ending at the position can be determined. If C is not seen in the healthy tissue of the subject, then C can be identified as a mutation if a sufficient number of Cs are identified, e.g., above a threshold number, which can depend on the measured tumor DNA fraction in the sample.

C. Filtering Techniques

Other criteria besides using an ending position can be used to filter for cell-free DNA molecules that are from the tumor tissue. The other criteria can also be used for the fetal scenario.

The specificity in identifying a cancer genotype (e.g., including a cancer-specific mutation) and any tests using such genotypes (e.g., use of mutational load to determine a level of cancer) can be improved by applying filtering criteria to loci where one or more sequence reads having a mutation have been aligned. As an example for cancer, high specificity can be achieved by scoring a genetic or genomic signature as positive only when there is high confidence that it is cancer associated. This can be achieved by minimizing the number of sequencing and alignment errors that may be misidentified as a mutation, e.g., by comparing to the genomic profile of a group of healthy controls, and/or may be achieved by comparing with the person's own constitutional DNA and/or may be achieved by comparing with the person's genomic profile at an earlier time.

Various criteria can be applied as filtering criteria to assess the likelihood of a cell-free DNA fragment being derived from the tumor and hence qualify to be an informative cancer DNA fragment. Each filtering criterion can be used individually, independently, collectively with equal weighting or different weightings, or serially in a specified order, or conditionally depending on the results of the prior filtering operations. For conditional usage, a Bayesian-based approach can be used, as well as a classification or decision tree based approach. An individual use of a criterion can mean using just one criterion. An independent use may involve more than one filtering criterion, but each filtering criterion does not depend on the application of another filtering criterion (e.g., parallel application can be performed), in contrast to a serial application in specific orders. As an example of collective usage using weightings, machine learning techniques can be used. For example, supervised learning can use measured mutational loads of samples with known classifications to train any models. Sequencing data from a large number of individuals (e.g. hundreds, thousands, or millions) can be used to train the models. In a simpler form, such known samples can be used to determine threshold values for one or more scores determined from the filtering criteria to determine whether a mutation is valid or not.

A DNA fragment can be given a higher weighting of informativeness or cancer-specificity if it shows more than one cancer-specific change. For example, many cancers are globally hypomethylated, especially at the non-promoter regions. Cancer DNA has been shown to be shorter than the non-cancer DNA in plasma. Tumor-derived plasma DNA fragments tend to fragment at some specific locations. Therefore, a plasma DNA fragment that is short in size (for example<150 bp) (Jiang et al. Proc Natl Acad Sci USA 2015; 112: E1317-1325), with one or both ends that fall on cancer-associated end locations, shows a single nucleotide mutation, and localizes to a non-promoter region, and has a hypomethylated CpG site would be deemed as more likely to be cancer-associated. The detection of hypomethylated DNA can be achieved with the use of bisulfite DNA conversion or direct single molecule sequencing that can distinguish methyl-cytosine from non-methyl-cytosine. In this application, we describe processes, protocols and operations to increase the specificity in the identification of informative cancer DNA fragments. For example, one or more filtering criteria can be used to increase the specificity. For example, one or more filtering criteria can be used to increase the specificity, such as to about at least a specificity of 80%, 90%, 95% or 99%.

1. Use of Plasma DNA End Location

As described above, filtering of potential cancer-specific or cancer-associated or fetal mutations based on the coordinate of the terminal nucleotide (ending position) can be performed. As described above, we have identified terminal locations of DNA fragments that are not random and that vary based on a tissue of origin. Thus, the terminal location can be used to determine a likelihood that a sequence read with a putative mutation is actually from fetal tissue or tumor tissue.

Recently, it has been shown that the fragmentation pattern of plasma DNA is non-random (Snyder et al. Cell 2016; 164: 57-68 and PCT WO 2016/015058 A2). The plasma DNA fragmentation pattern is influenced by nucleosomal positioning, transcription factor binding sites, DNase cutting or hypersensitive sites, expression profiles (Snyder et al. Cell 2016; 164: 57-68 and PCT WO 2016/015058; Ivanov et al. BMC Genomics 2015; 16 Suppl 13:S1) and DNA methylation profiles (Lun et al. Clin Chem 2013; 59: 1583-1594) in the genome of the cells that have contributed the plasma DNA molecules. Thus, the fragmentation patterns are different for cells of different tissue origins. While there are genomic regions that show more frequent fragments, the actual plasma DNA cutting sites within the region can still be random.

We hypothesized that different tissues are associated with the release of plasma DNA fragments that have different cutting sites, or end locations. In other words, even the specific cutting sites are non-random. Indeed, we show that a subset of plasma DNA molecules in cancer patients show different end locations than patients without cancer. Some embodiments can use plasma DNA molecules with such cancer-associated end locations as informative cancer DNA fragments, or use such end location information as a filtering criterion, e.g., along with one or more other filtering criteria. Thus, with the identification of such cancer-associated plasma DNA end locations, one can score the plasma DNA fragment as an informative cancer DNA fragment or attribute a differential weighting based on the nature of the end location of such a fragment. Such criteria can be used to assess the likelihood of the fragments originating from cancer, certain organs, or cancer of certain organs. Such weighting can be used to modify the contribution of a particular base of a particular DNA fragment to the total percentage of a particular base seen at the position.

Accordingly, the chance that a plasma DNA fragment is an informative cancer DNA fragment would be much higher if it shows a putative mutation and/or cancer-associated methylation change, as well as end locations that are cancer-associated. Various embodiments can also take into consideration the status of such a fragment and its length, or any combination of such and other parameters. For a plasma DNA fragment having two ends (or potentially up to four ends, as described in a following section), one can further modify the weighting for identifying it as a cancer-derived fragment by considering if one or both of its ends are associated with cancer or from a tissue type associated with cancer. In one embodiment, a similar approach based on end locations can also be used for detection mutations associated with other pathologies or biological processes (e.g. mutations due to the ageing process or mutations due to environmental mutagenic factors).

A similar approach can also be used for identifying de novo mutation of a fetus by sequencing the DNA in the plasma of a pregnant woman carrying the fetus. Hence, following the identification of end locations that are specific or relatively specific for the placenta, one can attribute a higher weighting to a putative fetal de novo mutation being a true one if such a DNA fragment in maternal plasma also carries a placental-specific or placental-enriched end location. As a plasma DNA fragment has two ends, one can further modify the weighting for identifying it as a fetal-derived fragment by considering if one or both of its ends are associated with the placenta.

As shown in FIG. 38, Plasma DNA fragments with terminal nucleotides ending exactly at the 536,772 HCC-specific ending positions would be more likely to be derived from the tumor. In contrast, plasma DNA fragments with terminal nucleotide ending exactly at the pregnancy-specific ending positions or the positions shared by the two cases would be less likely to be derived from the tumor, with pregnancy-specific ending positions potentially being less likely and given a lower weighting in any embodiment using weights.

Therefore, the list of top ending positions that are specific for the HCC case can be used to select the cancer-associated mutations, and the list of top ending positions that are specific for the pregnant case or shared by both cases can be used to filter out false-positive mutations. A similar procedure can be used for identifying fetal mutations and filtering out false-positive mutations for noninvasive prenatal testing.

In general, to identify such biologically-relevant plasma DNA end locations, plasma DNA samples from groups of individuals with different diseases or epidemiological backgrounds or physiological profiles can be compared with samples from another group of individuals without such diseases or backgrounds or profiles. In one embodiment, each of these samples can be sequenced deeply so that the common end positions of plasma DNA fragments can be identified within each sample. In another embodiment, the sequence data from the group of persons with complimentary profile can be pooled together for the identification of common end locations representative of the disease or physiological profile.

Each plasma DNA fragment in a sample can be interrogated individually and a likelihood score be assigned based on the end location. The likelihood score for a certain end location can be dependent on the separation in an amount of sequence reads (e.g., a percentage of sequence reads or other value normalized by sequencing depth across the samples) ending at the end location for the target individuals (e.g., cancer) relative to the amount of sequence reads ending for the control group. A larger separation would lead to a higher specificity, and thus a higher likelihood score can be applied. Therefore, classification of plasma DNA fragments with specific end locations into likely disease-associated or not, fetal or maternal, etc., can be performed.

Alternatively, plasma DNA fragments originating from the same region can be interpreted collectively, namely the rate of ending at a particular nucleotide can be calculated by normalizing to the sequencing depth. In this manner, certain nucleotides can be identified as being common end locations relative to other locations in the genome, e.g., just based on the analysis of one sample of a particular type, although more samples can be used. Therefore, classification of plasma DNA fragments with specific end locations into likely disease-associated or not, fetal, or maternal, etc., can be performed. For positions that show high frequencies of plasma DNA fragments with such biologically-relevant plasma DNA end locations, a determination can be made that such loci are enriched with the biologically-relevant DNA and thus be included as a group of plasma DNA fragments being of high likelihood as cancer-associated or fetus-specific or associated with other diseases or biological processes. The level of likelihood can be based on how high the rate is for a given nucleotide relative to other nucleotides, in a similar manner as comparisons across different groups, as described above.

2. Results

To illustrate the efficacy of this approach, potential cancer-associated mutations were identified directly from the plasma DNA sequencing data of the HCC patient. Single nucleotide changes that were present in the sequence reads of at least two plasma DNA fragments were considered as potential cancer-associated mutations. The tumor tissue was also sequenced and the mutations that were present in the tumor tissue were considered as true cancer-associated mutations.

On chromosome 8, a total of 20,065 potential mutations were identified from the plasma DNA sequencing data of the HCC patient without using the dynamic cutoff analysis. A sequence variant would be regarded as a potential mutation if the sequence variant was present in at least two sequenced DNA fragments. 884 true somatic mutations were identified from the sequencing result of the tumor tissue. The 20,065 putative mutations included 802 (91%) of the real mutations. Thus, only 4% of the putative mutations were true somatic mutations in the tumor tissue giving a PPV of 4%.

To enhance the accuracy of detecting the somatic mutations, thereby leading to a cancer genotype, we used the following filtering algorithms based on the terminal nucleotide positions of the sequence reads carrying the putative mutations. (1). For any putative mutation, if there is at least one sequence read carrying the mutation and ending on HCC-specific ending positions, the mutation would be qualified for downstream mutational analysis. (2). A sequence read that carried a putative mutation but ended on any pregnancy-specific ending positions or the positions shared by both cases would be removed. A mutation would be qualified for downstream mutational analysis only if there were two or more sequence reads showing the same mutation after the removal of the reads based on this algorithm.

Applying both 1 and 2 filtering algorithms stated above, the results in table 4 were obtained. The effects of applying different filtering algorithms based on the position of the terminal nucleotides, or end locations, of the DNA fragments carrying the putative mutations.

TABLE 4

|  | No filter | Inclusion of mutations with HCC-specific ends (filter 1) | Removal of reads with shared or pregnancy-specific ends (filter 2) | Applying both filtering algorithms |
| --- | --- | --- | --- | --- |
| No. of putative mutations identified | 20,065 | 1,526 | 2,823 | 484 |
| Percentage of true mutations detected | 91% | 29% | 88% | 40% |
| PPV | 4% | 17% | 28% | 71% |

There was a substantial improvement in the PPV by adopting any one of the three algorithms requiring the end locations being HCC-specific or the algorithm filtering out the pregnancy-specific or the shared positions. By applying both algorithms, the PPV increased to 71%.

Other number of HCC- and pregnancy-associated end locations can be identified for each chromosome, or indeed for another genomic region, or indeed for the entire genome, for example, but not limited to, 0.5 million, 2 million, 3 million, 4 million, 5 million, 6 million, 7 million, 8 million, 9 million or 10 million. In various embodiments, the most frequently seen end locations in plasma DNA molecules can be determined in one or more cohorts of cancer patients, each cohort being of one cancer type. In addition, the most frequently end locations in plasma DNA molecules can be determined for subjects without cancer. In one embodiment, such patients with cancer and subjects without cancer can be further subdivided into groups with different clinical parameters, e.g. sex, smoking status, previous health (e.g. hepatitis status, diabetes, weight), etc.

As part of using such filtering criteria, statistical analysis can be used to identify the positions that have higher probability of being terminal nucleotides or end locations for circulating DNA for different physiological and pathological conditions. Examples of the statistical analyses include but not limited to the Student t-test, Chi-square test, and tests based on binomial distribution or Poisson distribution. For these statistical analyses, different p-value cutoffs can be used, for example but not limited to 0.05, 0.01, 0.005, 0.001, and 0.0001. The p-value cutoffs can also be adjusted for multiple comparisons.

D. Method for Determining Genotype

FIG. 88 is a flowchart of a method 5800 of analyzing a biological sample to determine a genotype of the first tissue type according to embodiments of the present invention. The biological sample includes a mixture of cell-free DNA molecules from a plurality of tissues types that includes the first tissue type. The first tissue type potentially has a different genotype than other tissue types of the plurality of tissue types. Genotypes at multiple genomic positions can be determined.

At block 5810, a first genomic position at which ends of cell-free DNA molecules of the first tissue type occur at a rate above a threshold is identified. Block 5810 can be performed in a similar manner as block 3610. Section X.B provides additional examples for performing block 5810.

At block 5820, a first plurality of cell-free DNA molecules from the biological sample of a subject is analyzed. Analyzing a cell-free DNA molecule includes determining a genomic position in a reference genome corresponding to at least one end of the cell-free DNA molecule. Block 3620 can be performed in a similar manner as other blocks for analyzing cell-free DNA molecules.

At block 5830, a set of cell-free DNA molecules that end at the first genomic position is identified based on the analyzing of the first plurality of cell-free DNA molecules. As examples, the set can be identified using alignment of sequence reads of detected probes having known ending positions. Other examples are provided herein.

In some embodiments, further filtering can be performed, e.g., as described above. For example, a size of a cell-free DNA molecule can be required to be less than a specified amount, e.g., as fetal tissue and tumor tissue are generally shorter than DNA fragments from healthy cells. In one implementation, the set of cell-free DNA molecules can be filtered to exclude or modify a weighting of at least one of the cell-free DNA molecules that end at the first genomic position. The genotype can be determined using a filtered set of cell-free DNA molecules.

In various embodiments, the filtering can use at last one of: a size of a cell-free DNA molecule, a methylation status of the cell-free DNA molecule at one or more positions (e.g., whether a CpG site is methylated or not methylated), and whether the cell-free DNA molecule covers one or more other genomic position at which ends of cell-free DNA molecules of the first tissue type occur at a rate above a threshold. The methylation status can provide a signature of the first tissue type, as described above.

At block 5840, for each cell-free DNA molecule of the set of cell-free DNA molecules, a corresponding base (nucleotide) occurring at the first genomic position is determined. The total number of molecules with each base can be determined and a percentage can be calculated for each base.

At block 5850, the genotype of the first tissue type at the first genomic position is determined using the corresponding bases occurring at the first genomic position in the set of cell-free DNA molecules. In various implementations, a high percentage of just one base (e.g., above 80%, 85%, or 90%) can indicate the genotype is homozygous for the base, while two bases having similar percentages (e.g., between 30-70%) can lead to a determination of the genotype being heterozygous. Accordingly, the percentages for each base can be compared to cutoff values to the genotype. In some embodiments, a cutoff value can be determined based on a proportional contribution of the first tissue type to the sample.

Thus, in some embodiments, determining the genotype of the first tissue type at the first genomic position can include determining a percentage contribution for each of a plurality of bases and comparing each of the percentage contributions to one or more cutoff values. In one example, a first cutoff value can correspond to a homozygous genotype of a first base when the percentage contribution of the first base is above the first cutoff value. IN another examples, a first cutoff value and a second cutoff value can correspond to a heterozygous genotype for a first base and a second base when the percentage contributions of the first base and the second base are above the first cutoff value and below the second cutoff value.

In some embodiments, a weighting can be performed for each cell-free DNA molecule in the set identified in block 5830. For example, if a likelihood that the cell-free DNA molecule is from the first tissue type is 80%, then 0.8 can be the weighting. The total contribution of all weightings for a particular base can summed to determine respective amounts for each base. The respective amounts can be used to determine a percentage contribution for each base, where the percentages can be used to determine the genotype.

Accordingly, the filtering can assign a weight to the cell-free DNA molecule corresponding to a likelihood that the cell-free DNA molecule is from the first tissue type. A weighted sum can be determined for each of a plurality of bases (e.g., just those detected, which may be 2, 3, or 4). If only one base is detected, then a homozygous genotype for that one base can be determined. A percentage contribution for each of the plurality of bases can be determined using the weighted sums, where the genotype is determined using the percentage contributions.

XI. Further Details

Various embodiments described above identify preferred ending positions for particular tissues, where some of the preferred ending positions can be contiguous, thereby forming a preferred ending window. Different metrics can be used to identify rates of occurrence of cell-free DNA molecules at genomic windows (e.g., a genomic position for the smallest window). Further details about such operations are provided below, as well as details about determining an ending position of a cell-free DNA molecule in a reference genome. Such specific techniques can be used with embodiments described above.

A. Determination of Ending Position

When sequencing cell-free DNA molecules, there are various possibilities of the ending patterns of DNA fragments. There are generally four configurations of ends for plasma DNA: (A) A double stranded DNA molecule with two flushed ends; (B) A double strand DNA molecule with one flushed end, and one non-flushed end (showing each of the two scenarios, as either one of the two strands can protrude out); (C) A double strand DNA molecule with two non-flushed end, with different combinations of protruding ends; and (D) A single stranded DNA molecule.

For the configurations with non-flushed ends, there are different patterns depending on whether the 5' or the 3' end of the DNA molecule is protruded. For (B), the double-stranded DNA molecules has one flushed end and one non-flushed end. In an example B1, the 5' end is protruded and in an example B2, the 3' end is protruded. For (C), there are three possible patterns when both ends are non-flushed. In (C1), 5' end protrudes on both sides. In (C2), 3' end protrudes on both sides. In (C3), 5' end protrudes on one side and 3' end protrudes on the other side.

For sequencing, paired-end sequencing protocols commonly sequence one end of each of the stands. They are therefore considered double-stranded DNA sequencing protocols. When the two ends are not flushed, protocols can either cut nucleotides off or add nucleotides to the end to make them flushed. The Klenow fragment is an enzyme that can carry out such operations. Other protocols in the field use single-stranded DNA sequencing protocols.

Regardless of the specific technique used (including use of probes), as long as the ending positions are repeatable and show correlation, as is shown here, whether a true end of a DNA fragment is obtained in sequencing does not affect the results, as any offset is repeatable, and thus cancel out. Further, certain techniques can be used for identifying an ending position, as is described in the Terms section.

B. Identification of Tissue-Specific Ending Positions

As described above, in a particular tissue type, certain genomic regions have a greater variation for the likelihood that a cell-free DNA molecule will end on a particular position than for other regions. For example, liver tissue can have a region that is a DNase hypersensitivity site, but other tissues do not have that region as a DNase hypersensitivity site. Accordingly, certain positions within such a region will have a high number of cell-free DNA molecules ending on those positions relative to other positions. As examples, such positions can be identified as maximum in a rate of cell-free DNA molecules for a region known to have a high amount of cleavage for a particular tissue (thus, a high amplitude in the likelihood function), e.g., as described in section III. In other examples, the genomic positions can be identified where a left peak and right peak are sufficiently separate, e.g., as described in section IV.

In yet other examples, a difference in sets of high rate ending positions (e.g., rate above a threshold) for samples having and not having a condition (e.g., pregnancy or cancer, possibly of a particular type) can be used to identify preferred ending sites for a particular tissue type associated with the condition, e.g., as described with the use of Venn diagrams in sections V, VI, and VII. As yet other examples, a significantly higher rate in one sample with a condition than with another sample not having the condition can provide preferred ending sites of a particular tissue type. In various embodiments, some or all of such example techniques can be used together. The rate can be measured by any metric of relative abundance.

In some embodiments of above methods, a first set of genomic positions at which ends of cell-free DNA molecules of the first tissue type occur at a rate above a threshold can be identified in the following manner. A calibration sample can be analyzed in a similar manner as the test sample, where the two samples of a same type (e.g., plasma, serum, urine, etc.) and the calibration sample is known to include the first tissue type (e.g., fetal tissue from a sample of a pregnant female or tumor tissue of the liver for an HCC patient). A number of cell-free DNA molecules ending in a genomic window (e.g., of width one or more) can be compared to a reference value to determine whether a rate of ending positions is above a threshold for that position. In some embodiments, if the rate exceeds the reference value, each of the genomic positions within the first genomic window can be identified as having the rate be above the threshold when the corresponding number exceeds the reference value. Such a process can identify preferred ending windows, which include preferred ending positions.

The reference value can be such that only the top N genomic windows have a rate above the threshold. For example, the first set of genomic positions can have the highest N values for the corresponding numbers. As examples, N can be at least 10, at least 100, at least 1,000, at least 2,500, at least 5,000, at least 10,000, at least 50,000, at least 100,000, at least 500,000, at least 1,000,000, or at least 5,000,000.

As another example, the reference value can be an expected number of cell-free DNA molecules ending within the genomic window according to a probability distribution and an average length of cell-free DNA molecules in a sample, e.g., as described in section VI.A.1. A p-value can be determined using the corresponding number and the expected number, wherein the threshold corresponds to a cutoff p-value (e.g., 0.01). The p-value being less than the cutoff p-value indicates that the rate is above the threshold. As yet another example, the reference value can include a measured number of cell-free DNA molecules ending within the genomic window from a sample identified as having a reduced amount of the first tissue type, e.g., as described for FIGS. 51A and 51B.

The genomic positions that satisfy the rate threshold are not necessarily added to the first set of genomic positions. Further filter criteria can be added. Examples of such filtering criteria are specified in section VI.A.3 and IX.C. For a filtering criteria of size, a size (e.g., length or mass) of cell-free DNA molecules can be measured, e.g., as described in U.S. Patent publications 2011/0276277, 2013/0040824, and 2013/0237431, each of which is entirely incorporated herein by reference. A first statistical value can be determined of a size distribution of cell-free DNA molecules ending within a first genomic window (e.g., on a genomic position when the window has a width of one) determined to have the rate above the threshold. The genomic positions of the first genomic window can be excluded from the first set of genomic positions when the first statistical value does not exceed a size threshold, e.g., the average size is not small enough or there are not a sufficient number of small DNA fragments (e.g., below a specified size) compared to all cell-free DNA molecules or those in a larger range.

The first statistical value can be compared to a second statistical value of a size distribution for cell-free DNA molecules determined to not have a rate above the threshold. If the two values are similar (e.g., which would not be expected for fetal or tumor tissue), then the first genomic window can be excluded from a set of preferred ending positions. Comparing the corresponding number to the reference value can include computing a first ratio (e.g., PETR) of the corresponding number and a number of cell-free DNA molecules covering any part of the genomic window for one sample, and optionally not ending in the genomic window, as described in section VII.A.2. The reference value can include a reference ratio of the measured number of reads ending within the genomic window and a number of cell-free DNA molecules covering the genomic window and not ending within the genomic window for the other sample. The first ratio can be required to be greater than a multiplicative factor (e.g., 4) times the reference ratio.

Another filter criteria can be that each genomic position of the first set of genomic positions can be required to have at least a specified number of cell-free DNA molecules ending on the genomic position. Using any of these techniques, the first set of genomic positions may comprise between 600 and 10,000 genomic positions.

In embodiments taking a difference among sets (e.g., use of Venn diagrams), the genomic positions whose rate (e.g., as determined from a genomic window) is above the threshold comprises a first superset, e.g., as shown in FIG. 50A as Set P and Set S. A third plurality of cell-free DNA molecules can be analyzed from at least one second additional sample having a reduced amount of the first tissue type (e.g., less or no fetal tissue or HCC tissue, as depicted in FIG. 50A) to identify a second superset, e.g., Set Q and Set S. The first set of genomic positions can include the genomic positions that are in the first superset and that are not in the second superset, e.g., Set P or Set S, depending on which tissue type is being analyzed.

As described in section VI, the first tissue type can have first tissue-specific alleles. A count can be made of the cell-free DNA molecule ending on the genomic position and including at least one of the plurality of first tissue-specific alleles. This count (number) of cell-free DNA molecules can be compared to the reference value.

C. Relative Abundance

Various examples of relative abundance values are provided herein, e.g., intact probability ($P_I$), p-value described in section VI.A.1, and the PETR value determined using a genomic window or a genomic position when the window is of width one. For PETR for a genomic position (window of width one), a corresponding number of the first plurality of cell-free DNA molecules ending on the genomic position can be computed for each genomic position of the first set of genomic positions. This can be done as part of determining that the first number (e.g., numerator) of the first plurality of cell-free DNA molecules end on any one of the first set of genomic positions. A third number (e.g., denominator) of cell-free DNA molecules covering the genomic position and not ending on the genomic position can be computed as part of determining the second number of cell-free DNA molecules. A first ratio of the corresponding number and the third number can be determined, and a mean of the first ratios used as the relative abundance.

For w-PETR, a corresponding number of cell-free DNA molecules ending within a first window (e.g., window A in FIG. 55A) including the genomic position can be computed for each genomic position of the first set of genomic positions. A third number of cell-free DNA molecules ending within a second window (e.g., of window B in FIG. 55A) including the genomic position can be computed. In some cases, first ratios of the corresponding numbers and the third numbers can be used as the relative abundance.

Another examples of a relative abundance value is a proportion of cell-free DNA molecules ending on a genomic window, e.g., measured as a proportion of sequenced DNA fragments ending on a preferred ending position. Thus, the second set of genomic positions can include all genomic positions corresponding to an end of at least one of the first plurality of cell-free DNA molecules.

D. Calibration Values

In various embodiments, the calibration value(s) can correspond to the calibration value(s) of the calibration data point(s) determined from the calibration sample(s) or any calibration values determined therefrom, e.g., of a calibration function that approximates the calibration data points. The one or more calibration samples may or may not include any additional sample used to determine the preferred ending sites.

For each of the one or more calibration samples, a corresponding proportional contribution of the first tissue type can be measured, e.g., using a tissue-specific allele. A corresponding relative abundance can be determined using the corresponding numbers of cell-free DNA molecules ending within the plurality of windows corresponding to the first set of genomic positions. The measured proportional contribution and relative abundance can provide a calibration data point. The one or more calibration data points can be a plurality of calibration data points that form a calibration function that approximates the plurality of calibration data points. Further details of use of calibration values can be found in U.S. Patent Publication 2013/0237431, which is entirely incorporated herein by reference.

E. Classification of Proportional Contribution

In some embodiments, the preferred ending positions for a particular tissue can also be used to measure the absolute contribution of a particular tissue type in a sample, e.g. in number of genomes per unit volume (e.g. per milliliter). For example, a concentration of the tissue of interest can be measured in relation to the volume or weight of the cell-free DNA samples. In one implementation, quantitative PCR can be used to measure the number of cell-free DNA molecules ending at one or more preferred ends in a unit volume or unit weight of the extracted cell-free DNA sample. Similar measurements can be made for calibration samples, and thus the proportional contribution can be determined as a proportional contribution, as the contribution is a concentration per unit volume or unit weight.

In various embodiments when the first tissue type corresponds to tumor tissue, the classification can be selected from a group consisting of: an amount of tumor tissue in the subject, a size of the tumor in the subject, a stage of the tumor in the subject, a tumor load in the subject, and presence of tumor metastasis in the subject.

In yet another embodiment, a first assay or a second assay can comprise performing sequencing to determine a size distribution of cell-free nucleic acid molecules in a sample, and comparing the size distribution to a reference to determine if the size distribution of cell-free nucleic acid molecules in the sample are indicative of cancer.

Figure 20:
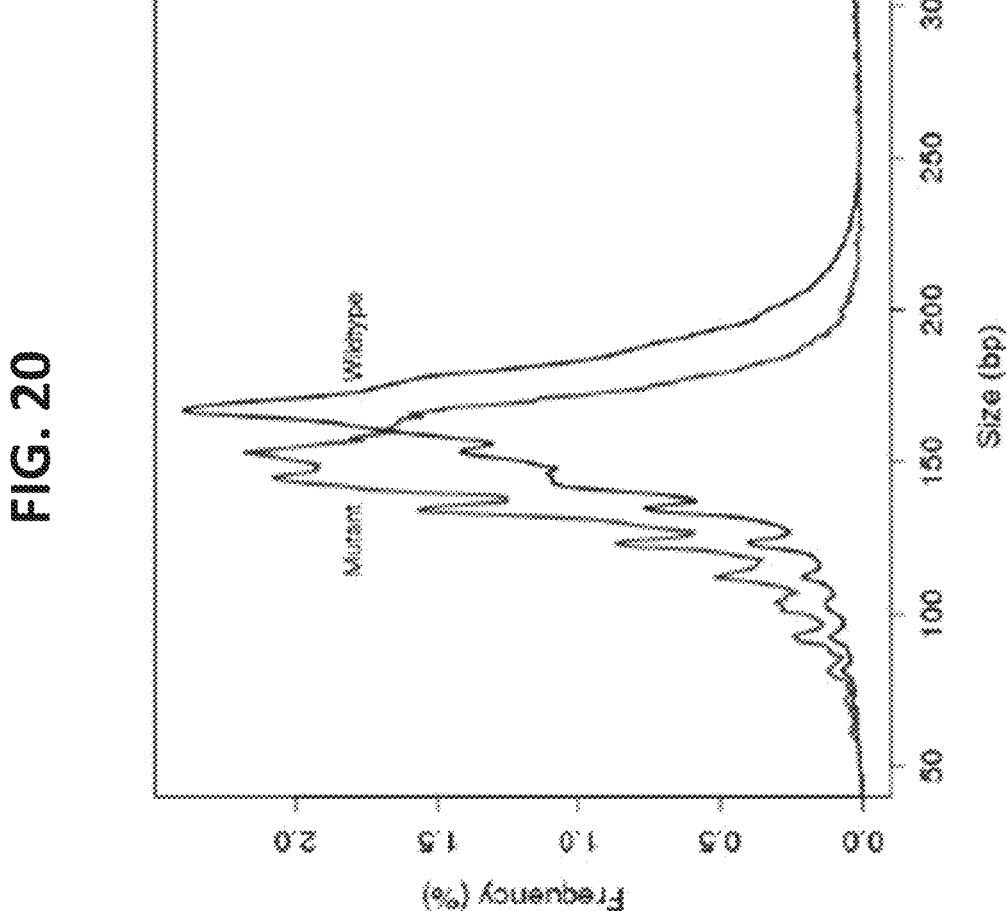
FIG. 20 depicts the size of distribution of wildtype DNA fragments and fragments having one or more mutations associated with a condition (e.g., a tumor).
Figure 21:
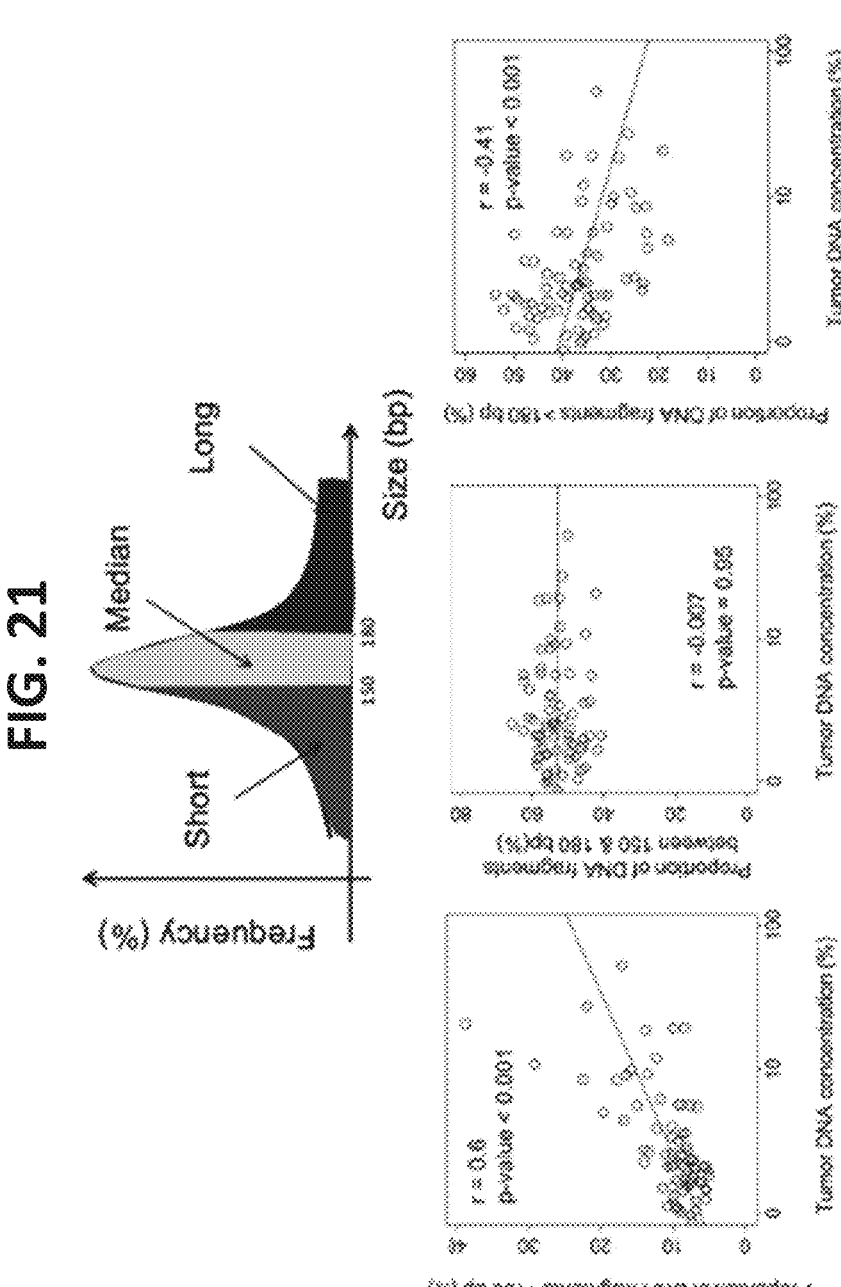
FIG. 21 depicts a scatter plot of the proportion of cancer-derived DNA fragments less than 150 base pairs (bottom left), between 150 and 180 base pairs (bottom center), and greater than 180 base pairs (bottom right) against the cancer DNA concentration in the sample.

While examples and embodiments have been provided herein, additional techniques and embodiments related to, e.g., fragment size distributions, can be found, e.g., in PCT IB/2013/00312, filed Mar. 8, 2013, which is entirely incorporated herein by reference. As shown in FIG. 20, tumor-derived DNA can be shorter than the non-cancer-derived DNA in a cancer patient's plasma (see, e.g., Diehl F et al. Proc Natl Acad Sci USA 2005; 102:16368-16373). As shown in FIG. 21, the size of DNA fragments can be correlated to a fractional concentration (also referred to as a percentage); accordingly embodiments can use this correlation to determine a fractional concentration of a particular type of DNA (e.g., DNA from a tumor) in a sample. Accordingly, a method of the present disclosure can comprise an assay capable of estimating a fractional concentration of clinically-relevant DNA in a biological sample based on a measured size of the DNA fragments.

In an example, a biological sample, comprising tumor-derived DNA and in some cases other DNA (e.g., DNA from healthy tissue) can be obtained from a patient suspected of having a tumor. In one implementation, the biological sample can be received at a machine, e.g., a sequencing machine, which outputs measurement data (e.g., sequence reads) that can be used to determine sizes of the DNA fragments.

Amounts of DNA fragments corresponding to various sizes are measured. For each size of a plurality of sizes, an amount of a plurality of DNA fragments from the biological sample corresponding to the size can be measured. For instance, the number of DNA fragments having a length of less than 180 bases can be measured. In a particular example, in subjects with NPC, a cutoff off for DNA fragment length about 180 base pairs can be used to separate tumor-derived fragments (e.g., non-virion derived EBV DNA fragments) from non-tumor derived fragments (e.g., virion-derived EBV DNA fragments or DNA from healthy tissues). The amounts can be saved as a histogram. In one embodiment, a size of each of the plurality of nucleic acids from the biological sample is measured, which can be done on an individual basis (e.g., by single molecule sequencing) or on a group basis (e.g., via electrophoresis). The sizes can correspond to a range. Thus, an amount can be for DNA fragments that have a size within a particular range.

The plurality of DNA fragments can be chosen at random or preferentially selected from one or more predetermined regions of a genome. For example, targeted enrichment can be performed, as described above. In another embodiment, DNA fragments can be randomly sequenced (e.g., using random sequencing), and the resulting sequence reads can be aligned to a genome corresponding to the subject (e.g., a reference human genome). Then, only DNA fragments whose sequence reads align to the one or more predetermined regions can be used to determine the size.

In various embodiments, the size can be mass, length, or other suitable size measures. The measurement can be performed in various ways, as described herein. For example, paired-end sequencing and alignment of DNA fragments can be performed, or electrophoresis can be used. A statistically significant number of DNA fragments can be measured to provide an accurate size profile of the biological sample. Examples of a statistically significant number of DNA fragments include greater than 100,000; 1,000,000; 2,000,000, or other suitable values, which can depend on the precision required.

In one embodiment, the data obtained from a physical measurement, such as paired-end sequencing or electrophoresis, can be received at a computer and analyzed to accomplish the measurement of the sizes of the DNA fragments. For instance, the sequence reads from the paired-end sequencing can be analyzed (e.g., by alignment) to determine the sizes. As another example, the electropherogram resulting from electrophoresis can be analyzed to determine the sizes. In one implementation, the analyzing of the DNA fragments does include the actual process of sequencing or subjecting DNA fragments to electrophoresis, while other implementations can just perform an analysis of the resulting data.

A first value of a first parameter can be calculated based on the amounts of DNA fragments at multiple sizes. In one aspect, the first parameter provides a statistical measure of a size profile (e.g., a histogram) of DNA fragments in the biological sample. The parameter can be referred to as a size parameter since it can be determined from the sizes of the plurality of DNA fragments.

The first parameter can be of various forms. Such a parameter can be a number of DNA fragments at a particular size divided by the total number of fragments, which can be obtained from a histogram (any data structure providing absolute or relative counts of fragments at particular sizes). As another example, a parameter can be a number of fragments at a particular size or within a particular range divided by a number of fragments of another size or range. The division can act as a normalization to account for a different number of DNA fragments being analyzed for different samples. Normalization can be performed by analyzing a same number of DNA fragments for each sample, which effectively provides a same result as dividing by a total number fragments analyzed. Other examples of parameters are described herein.

One or more first calibration data points can be obtained. Each first calibration data point can specify a fractional concentration of clinically-relevant DNA corresponding to a particular value (a calibration value) of the first parameter. The fractional concentration can be specified as a particular concentration or a range of concentrations. A calibration value can correspond to a value of the first parameter (i.e., a particular size parameter) as determined from a plurality of calibration samples. The calibration data points can be determined from calibration samples with known fractional concentrations, which can be measured via various techniques described herein. At least some of the calibration samples can have a different fractional concentration, but some calibration samples can have the same fractional concentration.

In various embodiments, one or more calibration points can be defined as one discrete point, a set of discrete points, as a function, as one discrete point and a function, or any other combination of discrete or continuous sets of values. As an example, a calibration data point can be determined from one calibration value of a size parameter (e.g., number of fragments in a particular size or size range) for a sample with a particular fractional concentration. A plurality of histograms can be used, with a different histogram for each calibration sample, where some of the calibration samples can have the same fractional concentration.

In one embodiment, measured values of a same size parameter from multiple samples at the same fractional concentration can be combined to determine a calibration data point for a particular fractional concentration. For example, an average of the values of the size parameter can be obtained from the size data of samples at the same fractional concentration to determine a particular calibration data point (or provide a range that corresponds to the calibration data point). In another embodiment, multiple data points with the same calibration value can be used to determine an average fractional concentration.

In one implementation, the sizes of DNA fragments are measured for many calibration samples. A calibration value of the same size parameter can be determined for each calibration sample, where the size parameter can be plotted against the known fractional concentration of the sample. A function can then be fit to the data points of the plot, where the functional fit defines the calibration data points to be used in determining the fractional concentration for a new sample.

The first value can then be compared to a calibration value of at least one calibration data point. The comparison can be performed in a variety of ways. For example, the comparison can be whether the first value is higher or lower than the calibration value. The comparison can involve comparing to a calibration curve (composed of the calibration data points), and thus the comparison can identify the point on the curve having the first value of the first parameter. For example, a calculated value X of the first parameter (as determined from the measured sizes of DNA in the new sample) can be used as input into a function $F(X)$, where F is the calibration function (curve). The output of $F(X)$ is the fractional concentration. An error range can be provided, which can be different for each X value, thereby providing a range of values as an output of $F(X)$.

The fractional concentration of the clinically-relevant DNA in the biological sample is then estimated based on the comparison. In one embodiment, one can determine if the first value of the first parameter is above or below a threshold calibration value, and thereby determine if the estimated fractional concentration of the instant sample is above or below the fractional concentration corresponding to the threshold calibration value. For example, if the calculated first value $X_i$ for the biological is above a calibration value $X_c$ then the fractional concentration $FC_1$ of the biological sample can be determined as being above the fractional concentration $FC_c$ corresponding to $X_c$. This relationship of above and below can depend on how the parameter is defined. In such an embodiment, only one calibration data point can be needed.

In another embodiment, the comparison is accomplished by inputting the first value into a calibration function. The calibration function can effectively compare the first value to calibration values by identifying the point on a curve corresponding to the first value. The estimated fractional concentration is then provided as the output value of the calibration function.

In one embodiment, the value of more than one parameter can be determined for the biological sample. For example, a second value can be determined for a second parameter, which corresponds to a different statistical measure of the size profile of DNA fragments in the biological sample. The second value can be determined using the same size measurements of the DNA fragments, or different size measurements. Each parameter can correspond to a different calibration curve. In one implementation, the different values can be compared independently to different calibration curves to obtain a plurality of estimated fractional concentrations, which can then be averaged or used to provide a range as an output.

In another implementation, a multidimensional calibration curve can be used, where the different values of the parameters can effectively be input to a single calibration function that outputs the fractional concentration. The single calibration function can result from a functional fit of all of the data points obtained from the calibration samples. Thus, in one embodiment, the first calibration data points and the second calibration data points can be points on a multidimensional curve, where the comparison includes identifying the multidimensional point having coordinates corresponding to the first value and the one or more second values.

The size distribution of plasma DNA can be determined, for example, but not limited to, using real-time PCR, electrophoresis and mass spectrometry analysis. In various embodiments, the measured size is a length, a molecular mass, or a measured parameter that is proportional to the length or mass, such as the mobility in a electrophoretogram and the time required to travel a fixed distance in electrophoresis or mass spectrometer. A parameter can be defined using the sizes of all of the DNA fragments analyzed, or just a portion. In one embodiment, a parameter provides a relative abundance of short and long DNA fragments, where the short and long DNA can correspond to specific sizes or ranges of sizes.

Other examples of parameters are the frequency counters of a histogram. In one embodiment, multiple parameters can be used. For example, the value of each parameter can give a difference percentage and then an average percentage can be determined. In another embodiment, each parameter corresponds to a different dimension of a multidimensional calibration function, where the values of the parameters for a new sample corresponds to a coordinate on the corresponding multidimensional surface.

In yet another embodiment, a first assay or a second assay can comprise performing sequencing to determine a fragmentation pattern of cell-free nucleic acid molecules in a sample, and comparing the fragmentation pattern to a reference to determine if the fragmentation pattern of cell-free nucleic acid molecules in the sample are indicative of cancer. While examples and embodiments have been provided herein, additional techniques and embodiments related to, e.g., determining fragmentation patterns, can be found, e.g., in U.S. application Ser. No. 15/218,497, filed Jul. 25, 2016, which is entirely incorporated herein by reference. There can exist a non-random fragmentation process of cell-free DNA. The non-random fragmentation process can take place to some extent in various types of biological samples that contain cell-free DNA, e.g., plasma, serum, urine, saliva, cerebrospinal fluid, pleural fluid, amniotic fluid, peritoneal fluid, and ascitic fluid. Cell-free DNA can occur naturally in the form of short fragments. Cell-free DNA fragmentation can refer to the process whereby high molecular weight DNA (such as DNA in the nucleus of a cell) are cleaved, broken, or digested to short fragments when cell-free DNA molecules are generated or released.

The specific locations of where cell-free DNA molecules are cut can be non-random. High molecular weight genomic tissue DNA that are sheared or sonicated in vitro can show DNA molecules with ending positions randomly scattered across the genome. However, there can be certain ending positions of cell-free DNA molecules that are highly represented within a sample, such as plasma. The number of occurrence or representation of such ending positions can be statistically significantly higher than expected by chance alone. The process of cell-free DNA fragmentation can be orchestrated even down to the specific nucleotide position of cutting or cleavage.

To reflect the fragmentation patterns, intact probability (PI) can be determined for each nucleotide for the genome based on the sequencing results of the maternal plasma DNA.

$$P_I = \frac{N_z}{N_T}$$

where Nz is the number of full length sequenced reads covering at least z nucleotides (nt) on both sides (5' and 3') of the target nucleotide; and NT is the total number of sequenced reads covering the target nucleotide.

The value of PI can reflect the probability of having an intact DNA molecule centered at a particular position with a length of twice the value of z plus 1 (2z+1). The higher the value of intact probability (PI), the less likely is the plasma DNA being fragmented at the particular nucleotide position.

In one embodiment, $P_I$ can be calculated using 25 as the value of z. Thus, the intact plasma DNA fragments can be defined as fragments covering at least 25 nt upstream of the target position to 25 nt downstream of the target position. In other embodiments, other values of z can be used, for example, but not limited to, 10, 15, 20, 30, 35, 40, 45, 50, 55, 60, 65, 70, 75 and 80.

$P_I$ is an example of a relative abundance of cell-free DNA molecules ending within a window of genomic positions. Other metrics can be used, e.g., the reciprocal of $P_I$, which can have an opposite relationship with the probability of having an intact DNA molecule. A higher value of the reciprocal of $P_I$ can indicate a higher probability of being an ending position or an ending window. Other examples are a p-value for a measured number of ending DNA fragments vs. an expected number of ending DNA fragments, a proportion of DNA fragments ending out of all aligned DNA fragments, or a proportion of preferred end termination ratio (PETR), all of which are described in more detail below. All such metrics of a relative abundance can measure a rate at which cell-free DNA fragments end within a window, e.g., with a width of 2z+1, where z can be zero, thereby causing the window to be equivalent to a genomic position.

Certain regions of the genome can be prone to a higher rate (frequency) of breakage of a chromosomal region in a particular tissue, and thus have a higher rate of cell-free DNA fragments ending within a window in the region. A plot of the relative abundance can show a fragmentation pattern, which can have a periodic structure. The periodic structure can show positions of maximum ending positions (high cleavage) and positions of minimum ending positions (low cleavage). When using $P_I$, a maximum value corresponds to a window of low cleavage, as $P_I$ can measure an intact probability as opposed to a cleavage probability (ending position probability), which can have an inverse relationship to each other.

In some cases, the fragmentation of plasma DNA is not random close to the transcriptional start site (TSS) (see e.g., Fan et al. PNAS 2008; 105:16266-71). The probability of any plasma DNA ending on a specific nucleotide can vary with the distance to a TSS with a periodicity of approximately the size of nucleosomes. This fragmentation pattern can be a consequence of apoptotic degradation of the DNA. The size of plasma DNA can resemble the size of DNA associated with a histone complex.

The size of plasma DNA can resemble the size of DNA associated with a nucleosome (see e.g., Lo et al. Sci Transl Med 2010; 2(61):61ra91). Plasma DNA can be generated through an apoptotic degradation of cellular DNA (nuclear DNA and mitochondrial DNA). In some cases, there is a lack of this nucleosomal pattern in circulating mitochondrial DNA as in some cases, mitochondrial DNA is not associated with histones in cells. In some cases, the nucleotide position that a plasma DNA fragment ends is not random close to transcriptional start sites (see e.g., Fan et al. PNAS 2008; 105:16266-71).

The size of plasma DNA can be different in regions with different sequence contexts (see e.g., Chandrananda et al. BMC Med Genomics 2015; 8:29). Cell-free DNA fragments can be more likely to start and end on nucleosome linker regions, rather than at nucleosomal cores. There can be nucleotide-to-nucleotide variation in intact probability. The amplitude of the variation in the intact probability can vary across different genomic regions.

The amplitude of variation in $P_I$ can vary across different genomic regions. The amplitude of variation of $P_I$ can be related to the accessibility of the chromatin to degradation during apoptosis. The fragmentation pattern of plasma DNA can be affected by its relative position to the TSS. Other sites where the amplitude corresponds to the tissue being tested can be used. One example of such a type of site is one that is identified using the Assay for Transposase-Accessible Chromatin with high throughput sequencing (ATAC-Seq) (see e.g., Buenrostro et al. Nat Methods 2013; 10: 1213-1218). Another example of such a type of site is one that is identified using micrococcal nuclease (MNase).

The amplitude of $P_I$ variation in two types of genomic regions can be compared:
  i. Regions that are TSS but not DNase hypersensitivity sites; and
  ii. Regions that are DNase hypersensitivity sites but not TSS.

The coordinates of the TSS and the DNase hypersensitivity sites can be retrieved from the ENCODE database (genome.ucsc.edu/ENCODE/downloads.html).

The $P_I$ patterns around TSS and DNase I sites can be profiled using the following approach.
  1. The upstream and downstream 2 kb regions around targeted reference sites can be retrieved.
  2. Then the absolute genomic coordinates can be re-scaled according to the distance to a reference site. For example, if a particular window with 60 bp in size is 50 bp from a reference site in an upstream direction, it can be marked as −50. Otherwise if a particular window with 60 bp in size is 50 bp from reference site in a downstream direction, it can be marked as +50.
  3. The $P_I$ value in a particular window with the same rescaled new coordinates can be recalculated using the count of intact fragments and all fragments which are overlapped with the said window.

The relative position to the DNase hypersensitivity sites can be an important factor governing the fragmentation pattern of plasma DNA. Profiles of DNase hypersensitivity sites can be different in different types of tissues. The profiles can correspond to genomic locations of the sites; locations of DNase hypersensitivity sites can be different for different tissues. Thus, we reason that the plasma DNA released from different types of tissues can exhibit tissue-specific fragmentation patterns. In a similar manner, other regions where the amplitude for a region varies from tissue to tissue can be used.

Plasma DNA derived from tissue A can have a lower probability of fragmenting at nucleotide positions with high $P_I$ (peaks, denoted by P). Therefore, the ends of plasma DNA derived from tissue A can have a lower probability of being located at these nucleotide positions. In contrast, the ends of plasma DNA derived from tissue A can have a higher probability of being located at nucleotide positions with low $P_I$ (troughs, denoted by T). On the other hand, as this site is not a DNase hypersensitivity site for tissue B, the amplitude of $P_I$ variation can be low for plasma DNA derived from tissue B. Therefore, the probability of plasma DNA from tissue B ending on the positions P and positions T can be similar, at least relative to the amount of variation seen for tissue A.

The fragment end ratio at regions that are DNase hypersensitivity sites of tissue A ($FR_A$) can be defined as follows:

$$FR_A = \frac{N_T}{N_P}$$

where $N_T$ is the number of plasma DNA fragments ending on nucleotide positions of the troughs of $P_I$ and $N_P$ is the number of plasma DNA fragments ending on nucleotide positions of the peaks of $P_I$. $FR_A$ is an example of a separation value, and more specifically an example of relative abundance of DNA fragments ending on the trough relative to ending on the peak. In other embodiments, separate ratios of neighboring troughs (local minimum) and peaks (local maximum) can be determined, and an average of the separate ratios can be determined.

For tissue A, $FR_A$ can be larger than 1 because $N_T$ can be larger than $N_P$. For tissue B, $FR_A$ can be approximately 1 because $N_T$ and $N_P$ can be similar. Therefore, in a mixture containing the plasma DNA derived from both tissues A and B, the value of $FR_A$ can have a positive correlation with the proportional contribution of tissue A. In practice, $FR_A$ for tissue B does not need to be 1. As long as $FR_A$ for tissue B is different from the $FR_A$ for tissue A, the proportional contribution of the two types of tissues can be determined from $FR_A$.

In such regions, the high variation in likelihood for DNA fragments to end at the troughs can result in a higher number of DNA fragments ending at such positions than ending at the peaks (Note that for different defined relative abundance values, a higher likelihood can occur for the peaks). When more DNA fragments are from tissue type A, the larger the difference will be in the number of DNA fragments ending at the troughs and the peaks. Thus, as the proportional contribution of tissue A increases, the larger can be the separation between the number of DNA fragments ending on a trough and the number of DNA fragments ending on a peak. This separation value corresponds to the high amplitude in the likelihood function.

A mixture containing more than two types of tissues can be analyzed similarly for the proportional contribution of tissues A as long as the $FR_A$ of other tissues is relatively constant. Such methods can be practically useful for the analysis of different clinical scenarios, for example but not limited to cancer detection, transplantation monitoring, trauma monitoring, infection and prenatal diagnosis.

In one embodiment, the fractional concentration of the affected tissue in the plasma of a cancer patient can be determined. For example, in a patient with liver cancer, the fractional contribution of the liver DNA can be determined via the analysis of the liver-specific open chromatin regions, e.g., DNase hypersensitivity sites. In one embodiment, this can be done using DNase-Seq (see e.g., Boyle et al. Cell 2008; 132: 311-322; Madrigal et al. Front Genet 2012; 16: 123-131). In another embodiment, this can be performed by Formaldehyde-Assisted Isolation of Regulatory Elements (FAIRE)-Seq (see e.g., Giresi et al. Genome Res 2007; 17: 877-885). In yet another embodiment, this can be performed by ATAC-Seq (see e.g., Buenrostro et al. Nat Methods 2013; 10: 1213-1218). The $FR_{liver}$ can be determined at these sites and compared with normal healthy subjects. At the liver-specific DNase hypersensitivity sites, the variation in $P_I$ between peak and trough regions can be mainly contributed from the liver. Through the comparison with a calibration curve, the contribution of the liver can be determined. The value of $FR_{liver}$ of the tested case can be compared with a range of the contribution of the liver in the healthy subjects. Other regions that have a high variation in amplitude in the likelihood function of DNA fragments ending at a genomic position among various tissues of a mixture can be used. Examples of such other regions are described in more detail in later sections.

Similarly, the contribution of the transplanted organ in a patient who has received organ transplantation can be determined by this method. Patients with rejection can lead to an increased release of DNA from the transplanted organ resulting in an elevated concentration of the DNA from the transplanted organ in plasma. The analysis of FR of the transplanted organ can be a useful way for the detection and monitoring of organ rejection. The regions used for such analysis can vary depending on which organ is transplanted.

Some embodiments of the present disclosure can comprise analyzing a biological sample to determine a classification of a proportional contribution of the first tissue type as described herein. The biological sample can include a mixture of cell-free DNA molecules from a plurality of tissues types that includes the first tissue type. The first tissue type (e.g., liver tissue) can be selected based on the specific subject. For example, if the subject previously had liver cancer, then screening can be performed to check whether the liver cancer has returned, which can result in an increase in the proportional contribution from liver tissue. Such a selection criteria can apply to other methods described herein.

In some embodiments, at least one genomic region having a fragmentation pattern specific to the first tissue type can be identified. As an example, the at least one genomic region can include one or more DNase hypersensitivity sites. Each of the at least one genomic region having a fragmentation pattern specific to the first tissue type can include one or more first tissue-specific alleles in at least one additional sample. As another example, the at least one genomic region can include one or more ATAC-seq or micrococcal nuclease sites. The first tissue type can correspond to a particular organ or even to a particular cancer of the organ.

In some embodiments, a plurality of cell-free DNA molecules from the biological sample can be analyzed. The analyzing of a cell-free DNA molecule can include determining a genomic position (ending position) in a reference genome corresponding to at least one end of the cell-free DNA molecule. Thus, two ending positions can be determined, or just one ending position of the cell-free DNA molecule.

In some embodiments, the ending positions can be determined in various ways, as described herein. For example, the cell-free DNA molecules can be sequenced to obtain sequence reads, and the sequence reads can be mapped (aligned) to the reference genome. If the organism is a human, then the reference genome can be a reference human genome, in some cases from a particular subpopulation. As another example, the cell-free DNA molecules can be analyzed with different probes (e.g., following PCR or other amplification), where each probe corresponds to a genomic location, which can cover the at least one genomic region.

In some embodiments, a statistically significant number of cell-free DNA molecules can be analyzed so as to provide an accurate determination the proportional contribution from the first tissue type. In some embodiments, at least 1,000 cell-free DNA molecules are analyzed. In other embodiments, at least 10,000 or 50,000 or 100,000 or 500,000 or 1,000,000 or 5,000,000 cell-free DNA molecules, or more, can be analyzed.

In some embodiments, a first set of first genomic positions can be identified. Each first genomic position has a local minimum of ends of cell-free DNA molecules corresponds to the first genomic position. Multiple neighboring genomic positions can be defined as a local extremum (maximum or minimum), and thus a local maximum is not limited to just one position.

In some embodiments, a ratio can be determined for each of a plurality of genomic positions. A first amount of cell-free DNA molecules that end at the genomic position and extend at least a specified number of nucleotides to both sides of the genomic position can be determined. A second amount of cell-free DNA molecules that are located at the genomic position can be used with the first amount to determine the ratio. A plurality of local minima and a plurality of local maxima can be identified in the ratios, e.g., by stepping through the ratio values to identify one or more contiguous genomic positions occurring at each of the extremum (maximum or minimum).

In some embodiments, a second set of second genomic positions can be identified. Each second genomic position having a local maximum of ends of cell-free DNA molecules corresponds to the second genomic position. The second set can be identified in a similar manner as the first set.

In some embodiments, a first number of cell-free DNA molecules ending on any one of the first genomic positions in any one of the at least one genomic region can be determined. The first number can be determined in various ways, e.g., as a sum across all first genomic positions. As another example, separate amount can be determined at each genomic position. Thus, determining the first number of cell-free DNA molecules can include determining a first amount of cell-free DNA molecules ending on each first genomic position, thereby determining a plurality of first amounts.

In some embodiments, a second number of cell-free DNA molecules ending on any one of the second genomic positions in any one of the at least one genomic region can determined. The second number can be determined in a similar manner as the first number. Thus, determining the second number of cell-free DNA molecules can include determining a second amount of cell-free DNA molecules ending on each second genomic position, thereby determining a plurality of second amounts.

In some embodiments, a separation value using the first number and the second number is computed. The separation value can be computed in various ways, e.g., by a ratio of the first number and the second number. In another implementation using multiple maxima and minima, an amount at each such genomic position can be determined. Computing the separation value can include determining a plurality of separate ratios, each separate ratio of one of the plurality of first amounts and one of the plurality of second amounts. The separation value can be determined using the plurality of separate ratios, e.g., a mean or median of the separate ratios.

In some embodiments, the classification of the proportional contribution of the first tissue type can be determined by comparing the separation value to one or more calibration values determined from one or more calibration samples whose proportional contributions of the first tissue type are known.

Any of the embodiments of the present disclosure can comprise an assay, wherein analyzing cell-free DNA fragments of a biological sample is amplification-free. When using PCR, the sequencing depth (i.e., the number of sequence reads covering a particular nucleotide or ending on the particular nucleotide in a reference genome) can not directly reflect how many plasma DNA molecules covering that particular nucleotide are analyzed. This can be because one plasma DNA molecule can generate multiple replicates during the PCR process, and multiple sequence reads can originate from a single plasma DNA molecule. This duplication problem can become more prevalent with i) a higher number of PCR cycles for amplifying the sequencing library; ii) an increased sequencing depth, and iii) a smaller number of DNA molecules in the original plasma sample (e.g., a smaller volume of plasma).

In addition, the PCR step can introduce further errors (e.g., Kinde et al. Proc Natl Acad Sci USA 2011; 108: 9530-9535) because in some cases the fidelity of a DNA polymerase is not 100%, and occasionally, an erroneous nucleotide can be incorporated into the PCR daughter strand. If this PCR error occurs during the early PCR cycles, clones of daughter molecules showing the same error can be generated. The fractional concentration of the erroneous base can reach such a high proportion among other DNA molecules from the same locus that the error can be misinterpreted, e.g., as a tumor-derived mutation. Examples of PCR-free protocols include: Berry Genomics (see e.g., investor.illumina.com/ mobile.view?c=121127&v=203&d=1&id=1949110); Illumina (see e.g., www.illumina.com/products/truseq-dna-pcr-free-sample-prep-kits.html), and various single molecule sequencing techniques. Further details of an amplification-free analysis can be found in PCT Application No. PCT/CN2016/073753, which is incorporated by reference in its entirety.

Accordingly, some embodiments can include obtaining template DNA molecules from the biological sample to be analyzed; preparing a sequencing library of analyzable DNA molecules using the template DNA molecules, the preparation of the sequencing library of analyzable DNA molecules not including a step of DNA amplification of the template DNA molecules; sequencing the sequencing library of analyzable DNA molecules to obtain a plurality of sequence reads corresponding to the first plurality of cell-free DNA molecules. Analyzing the first plurality of cell-free DNA molecules can include receiving, at the computer system, the plurality of sequence reads and aligning, by the computer system, the plurality of sequence reads to the reference genome to determine genomic positions for the plurality of sequence reads.

In some embodiments, the regions having a tissue-specific fragmentation pattern can be identified using tissue-specific alleles. The plasma (220× coverage), buffy coat (48×) and tumor tissue (45×) of a patient suffering from hepatocellular carcinoma (HCC) can be sequenced. The mutational profile of the patient can be obtained by comparing the genotypes of the tumor tissue and the buffy coat. To determine the preferred ending positions for cancer-derived plasma DNA fragments, we analyzed the plasma DNA fragments carrying the cancer mutations.

Figure 14:
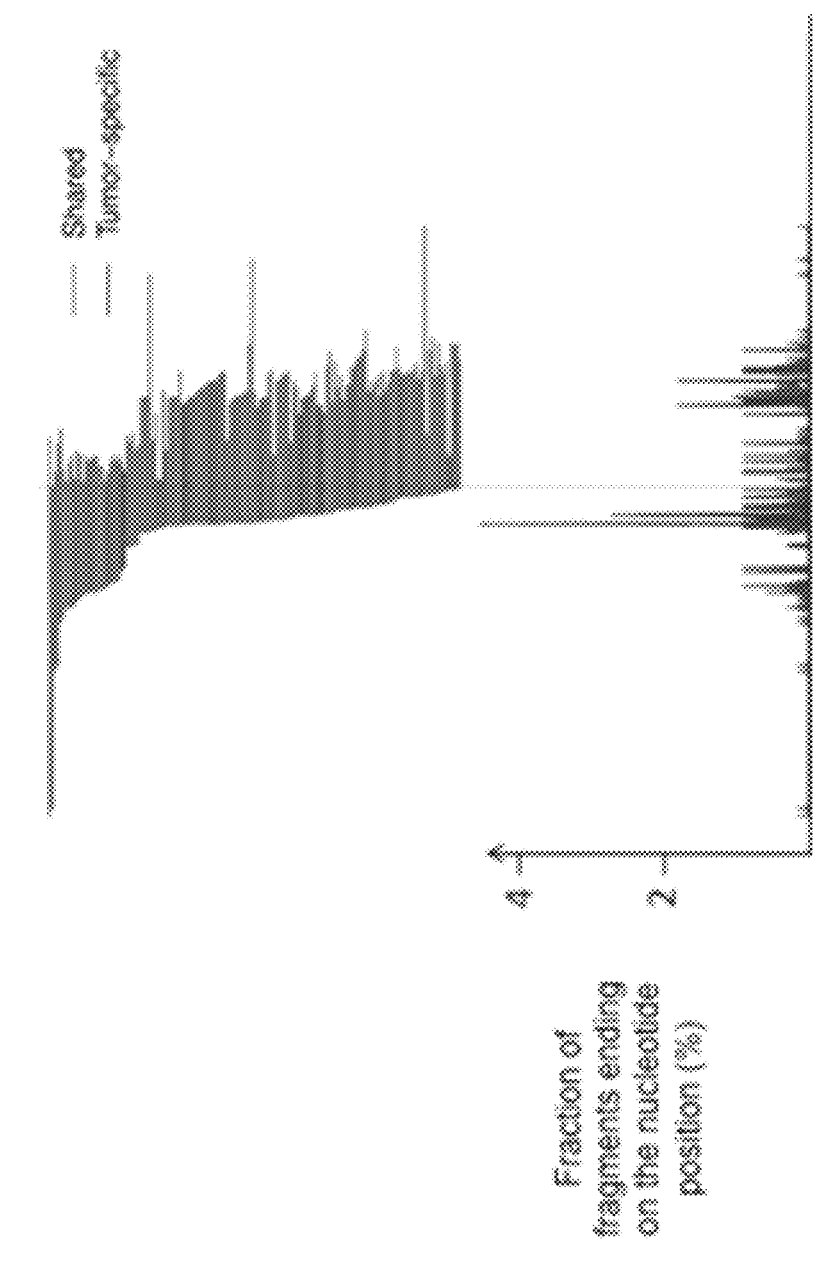
FIG. 14 depicts the non-random fragmentation patterns of plasma DNA of an HCC patient.

FIG. 14 shows an illustrative example of the non-random fragmentation patterns of plasma DNA of the HCC patient. On the upper part of the figure, each horizontal line represents one sequenced DNA fragment. The light gray and dark gray lines represent DNA fragments carrying the wildtype and mutant alleles, respectively. The ends of the DNA fragments represent the ending position of the sequenced read. The fragments are sorted according to the coordinate of the left outermost nucleotide (smallest genomic coordinate). On the lower part of figure, the percentage of fragments ending on a particular position is shown. The X-axis represents the genomic coordinates and the mutation is located at the center indicated by the dotted line.

Genomic positions that have increased probability of being an end of plasma DNA fragments carrying mutant alleles and wildtype alleles can be identified using Poisson probability distribution function. A p-value of 0.01 can be used as the threshold. The reverse is also true, as described in PCT Application No. PCT/CN2016/073753, namely when a plasma DNA molecule with a specific end is identified, the SNP allele or mutation on the molecule can be more likely to be cancer-derived or disease-associated, depending which set of ends was used in the plasma DNA data interpretation.

Figure 15:
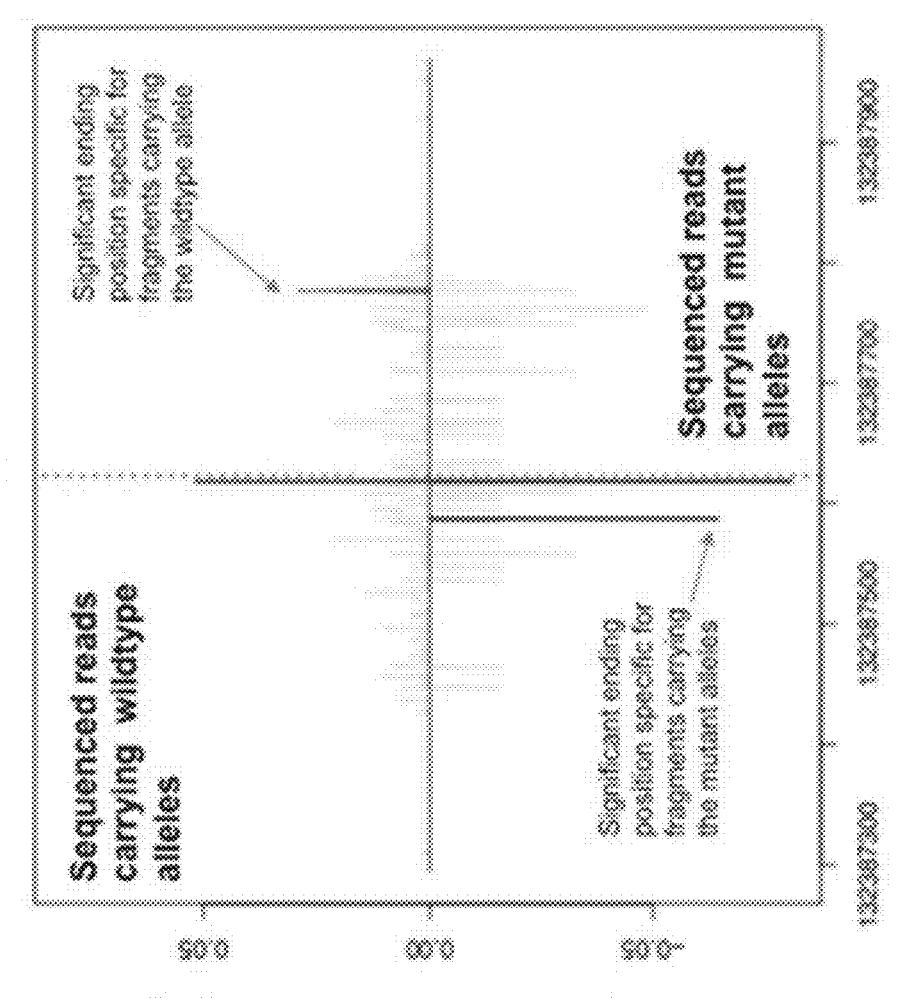
FIG. 15 depicts a plot of probability that a genomic coordinate is an ending position of plasma DNA fragments across a genomic region with a mutation site.

FIG. 15 is a plot of probability a genomic coordinate being an ending position of plasma DNA fragments across a region with a mutation site. Results for nucleotide positions with a significantly increased probability of being an end of plasma DNA fragments carrying a wildtype allele and a mutant allele are shown in light gray and dark gray, respectively. The X-axis represents the genomic coordinates and the mutation is located at the center indicated by the dotted line. As shown, there are coordinates that have a high rate of occurrence of ending positions for just the mutant-specific allele, for just the wildtype allele, and some are common to both.

Figure 16:
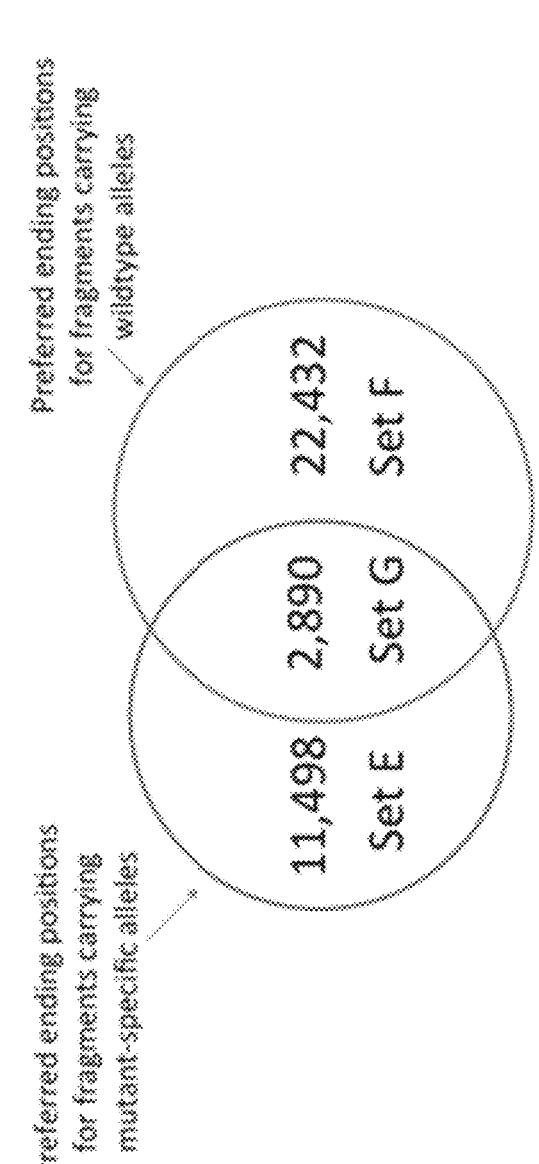
FIG. 16 depicts a Venn diagram classifying ending positions for plasma DNA fragments across genomic positions where mutations were present in a tumor tissue.

FIG. 16 shows an analysis of ending positions for plasma DNA fragments across genomic positions where mutations are present in the tumor tissue. Set E includes preferred ending positions for fragments carrying mutant alleles. Set F includes preferred ending positions for fragments carrying wildtype alleles. Set G includes preferred ending positions for both types of plasma DNA fragments.

As Set E positions are preferred ending sites for cancer-derived DNA and Set F positions are preferred ending sites for background DNA predominantly derived from non-tumor tissues, the ratio between the fragments ending on these two set of positions can correlate with the DNA derived from the tumor. The plasma of 71 HCC patients whose plasma contains at least 1% of tumor-derived DNA can be analyzed. These patients can be previously analyzed for copy number aberrations in plasma DNA and the tumor DNA fractions can be estimated by the magnitude of the copy number aberrations. (see e.g., Jiang et al. *Proc Natl Acad Sci USA.* 2015; 112:E1317-25). The ratio between the fragments ending on these two sets of positions ($\text{Ratio}_{M/WT}$) can be defined as:

$$\text{Ratio}_{M/WT} = \frac{No. \text{ of plasma } DNA \text{ fragments ending on Set } E \text{ positions}}{No. \text{ of plasma } DNA \text{ fragments ending on Set } F \text{ positions}}$$

A positive correlation between $\text{Ratio}_{M/WT}$ and the tumor DNA fraction in plasma was observed (r=0.53, p<0.001, Pearson correlation). These results suggest that the number of fragments ending on these cancer-preferred ending positions may be useful for predicting the amount of tumor-derived DNA in the plasma of cancer patients.

Some embodiments can increase the number of accessible informative cancer DNA fragments by the combined detection of a variety of cancer-specific or cancer-associated changes, for example, single nucleotide mutations, in combination with cancer-specific or cancer-associated DNA methylation signatures (e.g., location of 5-methycytosine and hydroxymethylation), cancer-specific or cancer-associated short plasma DNA molecules, cancer-specific or cancer-associated histone modification marks, and cancer-specific or cancer-associated plasma DNA end locations. Certain cancer-specific or cancer-associated changes may be used as filtering criteria in identifying mutations.

In other embodiments, the preferred ending positions can be obtained by (A) comparing the ending positions of plasma DNA fragments from different individuals or (B) comparing the ending positions of plasma DNA fragments of samples from one individual taken at different time points.

In another embodiment, the preferred ending sites can be identified by determining the ratio between the number of fragments ending on such a position and the number of fragments covering the position but not ending on it.

$$PETR = \frac{No. \text{ of } DNA \text{ fragments end on the nucleotide}}{No. \text{ of } DNA \text{ fragments covering the nucleotide but not ned on it}}$$

Figure 17:
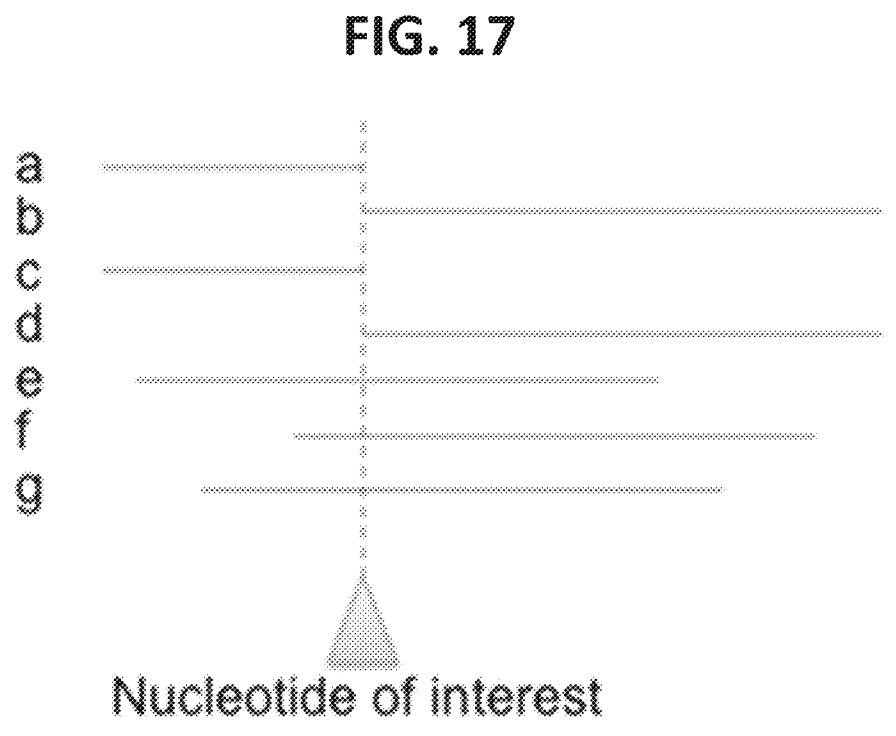

FIG. 17 shows an illustration of the concept of PETR. Each line represents one plasma DNA fragment. These fragments are labeled as a to g. Fragments a, b, c and d terminated on the nucleotide of interest. Fragments e, f and g cover the nucleotide of interest but do not end on such position. In this illustrative example, PETR equals to 4/3, i.e., 1.33. In other embodiments, the denominator can be the number of DNA fragments covering the nucleotide, regardless of whether the DNA fragment ends on the position.

The calculation of PETR can be used to identify nucleotide positions that are preferred ends in individuals suffering from different disease conditions. The following example demonstrates the utility of PETR. The plasma samples of the previously mentioned HCC patient and a subject with chronic hepatitis B virus (HBV) infection but without a cancer (HBV carrier) were compared. The plasma DNA samples of the HBV carrier was sequenced to 215× haploid genome coverage. PETR was calculated for each genomic position for each subject. 7,350,067 genomic positions (Set H) were identified as having PETR at least 4 folds higher in the HCC patient compared with the HBV carrier. These positions had at least 4-fold increased chance of being an end of plasma DNA fragments in the HCC patient compared with the HBV carrier. Other fold differences can be used, e.g., 1.5 fold, 2 fold, and 3 fold.

Plasma samples from 11 independent HCC patients were further sequenced to a much lower sequencing depth. A mean of 28 million sequenced reads were obtained from these 11 plasma samples. The mean PETR at the 7,350,067 Set H positions were calculated for each of these 11 HCC patients and correlated with the tumor DNA fraction in plasma. The tumor DNA fraction in plasma was calculated based on the magnitude of the copy number aberrations in plasma as previously described (Chan et al. Proc Natl Acad Sci USA. 2015; 112:E1317-25).

Figure 18:
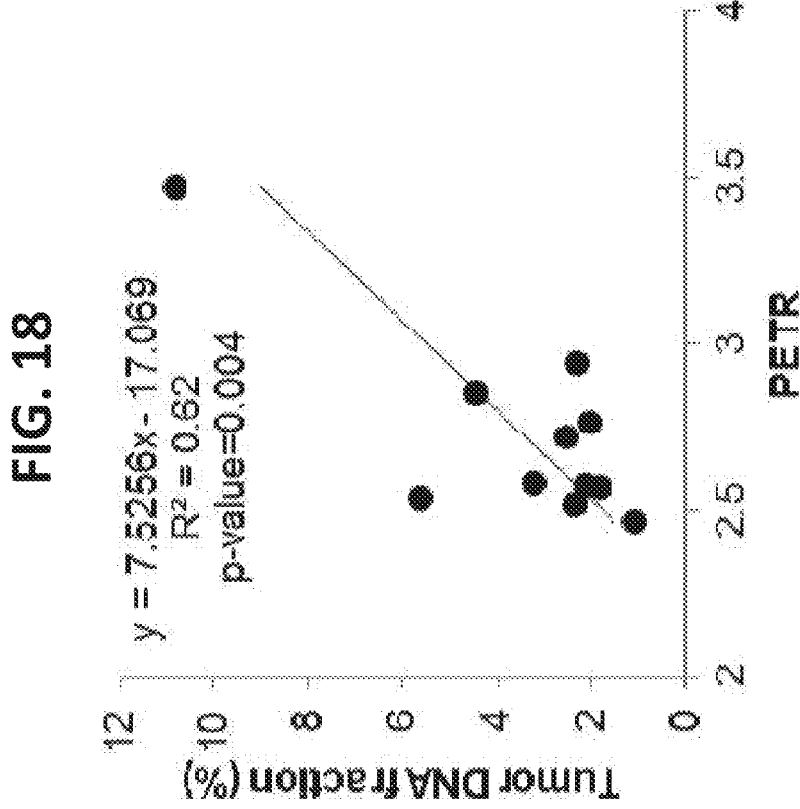
FIG. 18 depicts the correlation between tumor DNA fraction in plasma with various PETR ratios at a set of genomic positions.

FIG. 18 shows a correlation between tumor DNA fraction in plasma with PETR at the Set H positions in 11 HCC patients. A positive correlation between the two parameters may be observed suggesting that the average PETR at the HCC-preferred (Set H) positions may be useful to indicate the amount of tumor DNA in the plasma.

To show that the preferred ending positions present in the HCC plasma DNA sample or in the HBV plasma DNA sample were liver-related, we searched for their presence in plasma samples collected from patients before and after surgical removal of HCC. The data are shown in Table 5. The pre- and post-surgical samples were sequenced to 17× and 20× haploid genomic coverages, respectively.

TABLE 5

|  | HCC-preferred ending sites | HBV-preferred ending sites |
|---|---|---|
| Pre-surgery preferred ending sites in HCC 1 | 92 | 16 |
| Post-surgery preferred ending sites in HCC 1 | 5 | 4 |

Table 5 shows HCC-preferred ending positions and HBV-preferred ending positions in plasma sample collected before and after surgery to remove the liver tumor in the patient with HCC.

As shown in Table 5, there are reductions in the number of both HCC- and HBV-preferred ending positions. The HBV data suggest that the majority of the preferred ending positions are liver-derived and their reduction is due to the reduction in the liver cell mass after surgery. There is therefore reduced release of liver-derived cell-free DNA molecules into plasma. It is interesting to note that there are more than 5-fold more HCC-preferred ending positions in the pre-surgical sample that disappeared post-surgically. Some of the preferred ends that showed post-surgical disappearance are liver-derived. Given the observation that many more HCC-preferred ends than the HBV-preferred ends were detected in the same pre-surgical sample suggests that the majority of those ends are HCC-specific and are not just generically liver-associated.

There are a number of applications that may be derived from these data. The data indicate that the detection of cell-free DNA or plasma DNA preferred ends may be used for cancer treatment monitoring. For example, the post-surgical reduction in the preferred ends indicates the success of the surgical removal of the HCC. If the tumor was not removed completely or successfully, the amount or quantity of plasma DNA preferred ends may not show a substantial reduction after the surgery. This is because the remaining tumor or metastatic foci may be a source for continued release of cell-free DNA or plasma DNA with the HCC-preferred ending positions. The data show that treatment monitoring based on the analysis of cell-free DNA preferred ends may be achieved at relatively shallow sequencing depth.

The data also show that tissue-associated or cancer associated plasma DNA preferred ending positions may be used to identify the tissue of pathology, including the tissue that is harboring the cancer. For example, one may use multiple sets of cell-free DNA preferred ends that are derived from different organs. One may then be able to determine the relative amounts of cell-free DNA originating from various tissues. Thus, this may serve as an approach for cell-free DNA tissue deconvolution. The tissue shown by this approach to have the most deviation (significantly increased or significantly reduced) from reference values established from control samples may be the organ or tissue with the pathology (e.g., inflammation or viral infection just like in the chronic hepatitis B virus carrier) or cancer.

Another piece of evidence to support that the plasma DNA HCC-preferred ends are cancer- or HCC-specific, we studied the size profile of plasma DNA molecules showing the HCC- or HBV-preferred ends. A proportion of short DNA (<150 bp) were detected among plasma DNA molecules ending with HCC-preferred ends, HBV-preferred ends or the shared ends. Plasma DNA molecules exhibiting the HCC-preferred ends are generally much shorter (high proportion of short DNA) than those showing HBV-preferred ends. Jiang et al (Jiang et al. Proc Natl Acad Sci USA. 2015; 112:E1317-25) previously used another approach to show that tumor-derived plasma DNA molecules are shorter than the background non-tumor DNA. Because the plasma DNA molecules with the HCC-preferred ends are much shorter, they are highly likely to be tumor-derived. Thus, one may improve the chance of detecting the plasma DNA molecules with the HCC-preferred ends at even lower sequencing depth, one may enrich the sample with short DNA.

In another embodiment, the HCC-preferred positions can be extended to include the neighboring nucleotides. The window-based PETR (w-PETR) ratio between the numbers of fragments ending within Window A and those ending within Window B can be determined. The size of Window A and Window B can be adjusted to achieve the desired performance. The performance of difference window sizes can be obtained experimentally. The size of Window A can be set, for example but not limited to at least about 5 base pairs (bp), 6 bp, 7 bp, 8 bp, 9 bp, 10 bp, 15 bp, 20 bp, 25 bp, 30 bp, 40 bp, 50 bp or 100 bp. The size of Window B can be larger than that of Window A and can be set, for example but not limited to at least about 20 bp, 25 bp, 30 bp, 40 bp, 50 bp, 60 bp, 70 bp, 80 bp, 100 bp, 120 bp, 140 bp, 160 bp, 180 bp or 200 bp. In the follow illustrative example, the sizes of Window A and Window B were set as 20 bp and 150 bp, respectively.

The preferred ending positions of a particular condition can also be obtained by comparing the fragment ends of samples collected at different time points. For example, in a cancer patient, one plasma sample can be collected at the time of diagnosis and the other sample can be collected after treatment (e.g., after surgical resection of the tumor). The difference in the ending positions can reflect the absence of the contribution of the cancer-derived DNA in the latter or the bodily response to the cancer.

Given that preferred ending positions can be determined for a particular tissue type, cell-free DNA molecules ending at such preferred ending positions can have high likelihood of being from that tissue. In some situations, a particular tissue type in a cell-free DNA mixture can have a different genotype at a particular genomic position relative to other tissue types. For example, tumor tissue can have a different genotype. As the cell-free DNA molecules can have a high likelihood of being from the tissue type of interest, the cell-free DNA molecule ending at such a position can be analyzed to determine a genotype of the tissue type at that position. In this manner, the preferred ending position can be used as a filter to identify DNA from the tissue type. For example, a cancer-preferred ending position can be identified as described above. The cell-free DNA molecules ending on the cancer-preferred ending position can be identified and analyzed. The base corresponding (e.g., aligned) to this position can be determined for each cell-free DNA molecule of this set, and the percentages of the total bases can be computed for each base. For example, a percentage of Cs seen on the cell-free DNA molecules ending at the position can be determined. If C is not seen in the healthy tissue of the subject, then C can be identified as a mutation if a sufficient number of Cs are identified, e.g., above a threshold number, which can depend on the measured tumor DNA fraction in the sample.

Other criteria, e.g., besides using an ending position, can be used to filter for cell-free DNA molecules that are from the tumor tissue.

The specificity in identifying a cancer genotype (e.g., including a cancer-specific mutation) and any tests using such genotypes (e.g., use of mutational load to determine a level of cancer) can be improved by applying filtering criteria to loci where one or more sequence reads having a mutation have been aligned. As an example for cancer, high specificity can be achieved by scoring a genetic or genomic signature as positive only when there is high confidence that it is cancer associated. This can be achieved by minimizing the number of sequencing and alignment errors that can be misidentified as a mutation, e.g., by comparing to the genomic profile of a group of healthy controls, and/or can be achieved by comparing with the person's own constitutional DNA and/or can be achieved by comparing with the person's genomic profile at an earlier time.

Various criteria can be applied as filtering criteria to assess the likelihood of a cell-free DNA fragment being derived from the tumor and hence qualify to be an informative cancer DNA fragment. Each filtering criterion can be used individually, independently, collectively with equal weighting or different weightings, or serially in a specified order, or conditionally depending on the results of the prior filtering steps. For conditional usage, a Bayesian-based approach can be used, as well as a classification or decision tree based approach. An individual use of a criterion can mean using just one criterion. An independent use can involve more than one filtering criterion, but each filtering criterion does not depend on the application of another filtering criterion (e.g., parallel application can be performed), in contrast to a serial application in specific orders. As an example of collective usage using weightings, machine learning techniques can be used. For example, supervised learning can use measured mutational loads of samples with known classifications to train any models. Sequencing data from a large number of individuals (e.g., hundreds, thousands, or millions) can be used to train the models. In a simpler form, such known samples can be used to determine threshold values for one or more scores determined from the filtering criteria to determine whether a mutation is valid or not.

A DNA fragment can be given a higher weighting of informativeness or cancer-specificity if it shows more than one cancer-specific change. For example, many cancers can comprise nucleic acids that are globally hypomethylated, especially at the non-promoter regions. Cancer DNA can be shorter than the non-cancer DNA in plasma. Tumor-derived plasma DNA fragments can tend to fragment at some specific locations. Therefore, a plasma DNA fragment that is short in size (for example<150 bp) (see e.g., Jiang et al. Proc Natl Acad Sci USA 2015; 112: E1317-1325), with one or both ends that fall on cancer-associated end locations, can show a single nucleotide mutation, and can localize to a non-promoter region, and can have a hypomethylated CpG site that can be deemed as more likely to be cancer-associated. The detection of hypomethylated DNA can be achieved with the use of bisulfite DNA conversion or direct single molecule sequencing that can distinguish methyl-cytosine from non-methyl-cytosine. Processes, protocols and steps to increase the specificity in the identification of informative cancer DNA fragments are described herein. For example, one or more filtering criteria can be used to increase the specificity. For example, one or more filtering criteria can be used to increase the specificity, such as to at least a specificity of 80%, 90%, 95% or 99%.

As described above, filtering of potential cancer-specific or cancer-associated mutations based on the coordinate of the terminal nucleotide (ending position) can be performed. As described above, terminal locations of DNA fragments that are not random and that vary based on a tissue of origin can be identified. Thus, the terminal location can be used to determine a likelihood that a sequence read with a putative mutation is actually from tumor tissue.

The fragmentation pattern of plasma DNA can be non-random (see e.g., Snyder et al. *Cell* 2016; 164: 57-68 and PCT WO 2016/015058 A2). The plasma DNA fragmentation pattern can be influenced by nucleosomal positioning, transcription factor binding sites, DNase cutting or hypersensitive sites, expression profiles (see e.g., Snyder et al. Cell 2016; 164: 57-68 and PCT WO 2016/015058; Ivanov et al. BMC Genomics 2015; 16 Suppl 13:S1) and DNA methylation profiles (see e.g., Lun et al. Clin Chem 2013; 59: 1583-1594) in the genome of the cells that have contributed the plasma DNA molecules. Thus, the fragmentation patterns can be different for cells of different tissue origins. While there are genomic regions that show more frequent fragments, the actual plasma DNA cutting sites within the region can still be random.

Different tissues can be associated with the release of plasma DNA fragments that have different cutting sites, or end locations. In other words, even the specific cutting sites are non-random. A subset of plasma DNA molecules in cancer patients can show different end locations than patients without cancer. Some embodiments can use plasma DNA molecules with such cancer-associated end locations as informative cancer DNA fragments, or use such end location information as a filtering criterion, e.g., along with one or more other filtering criteria. Thus, with the identification of such cancer-associated plasma DNA end locations, one can score the plasma DNA fragment as an informative cancer DNA fragment or attribute a differential weighting based on the nature of the end location of such a fragment. Such criteria can be used to assess the likelihood of the fragments originating from cancer, certain organs, or cancer of certain organs. Such weighting can be used to modify the contribution of a particular base of a particular DNA fragment to the total percentage of a particular base seen at the position.

Accordingly, the chance that a plasma DNA fragment is an informative cancer DNA fragment can be much higher if it shows a putative mutation and/or cancer-associated methylation change, as well as end locations that are cancer-associated. Various embodiments can also take into consideration the status of such a fragment and its length, or any combination of such and other parameters. For a plasma DNA fragment having two ends (or up to four ends, as described in a following section), one can further modify the weighting for identifying it as a cancer-derived fragment by considering if one or both of its ends are associated with cancer or from a tissue type associated with cancer. In one embodiment, a similar approach based on end locations can also be used for detection mutations associated with other pathologies or biological processes (e.g., mutations due to the ageing process or mutations due to environmental mutagenic factors).

In general, to identify biologically-relevant plasma DNA end locations, plasma DNA samples from groups of individuals with different diseases or epidemiological backgrounds or physiological profiles can be compared with samples from another group of individuals without such diseases or backgrounds or profiles. In one embodiment, each of these samples can be sequenced deeply so that the common end positions of plasma DNA fragments can be identified within each sample. In another embodiment, the sequence data from the group of persons with complimentary profile can be pooled together for the identification of common end locations representative of the disease or physiological profile.

Each plasma DNA fragment in a sample can be interrogated individually and a likelihood score be assigned based on the end location. The likelihood score for a certain end location can be dependent on the separation in an amount of sequence reads (e.g., a percentage of sequence reads or other value normalized by sequencing depth across the samples) ending at the end location for the target individuals (e.g., cancer) relative to the amount of sequence reads ending for the control group. A larger separation can lead to a higher specificity, and thus a higher likelihood score can be applied. Therefore, classification of plasma DNA fragments with specific end locations into likely disease-associated or not can be performed.

Alternatively, plasma DNA fragments originating from the same region can be interpreted collectively, namely the rate of ending at a particular nucleotide can be calculated by normalizing to the sequencing depth. In this manner, certain nucleotides can be identified as being common end locations relative to other locations in the genome, e.g., just based on the analysis of one sample of a particular type, although more samples can be used. Therefore, classification of plasma DNA fragments with specific end locations into likely disease-associated or not can be performed. For positions that show high frequencies of plasma DNA fragments with such biologically-relevant plasma DNA end locations, a determination can be made that such loci are enriched with the biologically-relevant DNA and thus be included as a group of plasma DNA fragments being of high likelihood as cancer-associated or associated with other diseases or biological processes. The level of likelihood can be based on how high the rate is for a given nucleotide relative to other nucleotides, in a similar manner as comparisons across different groups, as described above.

5. Mutational Status Assays

Some embodiments of the present disclosure can comprise an assay for detecting a mutational status of a biological sample in a patient. A mutational status can generally refer to a cancer-specific change or mutation, or a mutational load in a sample. While examples and embodiments have been provided herein, additional techniques and embodiments (e.g., filtering techniques, sequencing methods, cutoff values, determining a level of cancer, mutational analysis) can be found, e.g., in PCT/IB2013/054898 filed Jun. 14, 2013, and PCT/CN2016/073753 filed Feb. 14, 2016, each of which is entirely incorporated herein by reference. To identify cancer mutations and determine a mutational load of an individual, embodiments can analyze a sample with circulating cell-free DNA. Tumors, cancers, and malignancies are known to release its DNA content into the circulation (see e.g., Bettegowda et al. Sci Transl Med 2014; 6: 224ra24). Thus, the mutations associated with tumors, cancers, and malignancies can be detected in plasma and serum. Such mutations can also be detected in other body fluids, such as, but not limited to urine, other urogenital fluids, cervical lavage fluid, nipple discharge, saliva, pleural fluid, ascitic fluid and cerebrospinal fluid (see e.g., Togneri et al. Eur J Hum Genet 2016; doi: 10.1038/ejhg.2015.281; De Mattos-Arruda et al. Nat Commun 2015; doi: 10.1038/ncomms9839; Liu et al. J Clin Pathol 2013; 66:1065-1069).

The mutations can be detected in these body fluids because of the direct shedding of cells or cell-free DNA into the fluid from those organs that are in direct contact with the fluid, e.g., from the urinary (e.g., from the kidney or bladder) or genital (e.g., from the prostate) tract to the urine, transrenally from the plasma into the urine, from the brain to the cerebrospinal fluid, from the pancreas into pancreatic juice, from the gallbladder into bile, from the oropharynx to the saliva, from mammary cells to the nipple discharge fluid, from the abdominal organs to the ascitic fluid, or from the lungs to the pleural fluid. In addition, the mutations can be detected in the body fluids because they are partly derived from the filtration of plasma. Hence, contents in plasma, including the tumor-derived mutations from other organs more distant from the site of the fluid, can be detected in the body fluids.

The detection of mutations among cell-free nucleic acids in plasma, serum, and the other body fluids can be attractive for the development of cancer screening tests because they can provide access to the tumor-associated genetic and genomic changes relatively noninvasively and in lieu of the direct assessment of a tumor biopsy. In addition, nearly all forms of genetic and genomic changes associated with tumor, cancers, or malignancies can be detected among the cell-free nucleic acid population. Examples of cancer-associated changes or cancer-specific changes are provided herein. Cancer-specific can refer to a change that can come from a cancer cell, and cancer-associated can refer to a change that can come from a cancer cell, or a premalignant lesion, or other tissues due to anatomical proximity, physiological association, developmental association or a reaction to the presence of the cancer. Due to the noninvasive access to the tumor-associated genetic and genomic profile (especially determined from plasma and serum cell-free nucleic acids), if used as a screening test, the tumor-associated profile can be measured repeatedly, either within shorter interval (e.g., days or weeks) to "rule in" or "rule out" disease or over longer intervals, such as biennially, annually, or biannually.

Plasma DNA molecules can naturally exist in the form of short DNA fragments (see e.g., Yu et al. Proc Natl Acad Sci USA 2014; 111: 8583-8588). They can be <200 bp long, and can fragment at certain cancer-associated locations, as is discussed in more detail herein. The majority of the DNA molecules in human plasma can originate from hematopoietic cells. When a person develops a non-hematopoietic malignancy, especially during the early stages, the tumor-derived DNA can represent a minor fraction in plasma mixed with a background of non-tumor-derived hematopoietic DNA. The amount of tumor-derived DNA in a plasma sample can be expressed as a fraction of the total DNA or the number of genomic-equivalents or cell-equivalent of cancer cells. In the case of a hematopoietic malignancy, the fraction of malignancy-associated DNA in plasma can be expected to be higher than that in a non-hematopoietic malignancy and can be detected using the same embodiments described in this application.

In this disclosure, protocols are described that can be generically applied to the detection of any cancer as long as the tumor contributes DNA to the body fluid (see e.g., Bettegowda et al. Sci Transl Med 2014; 6: 224ra24). In some cases, embodiments described herein are not dependent on the detection of biomarkers that are typical of just a certain cancer type. The classification scheme used to differentiate individuals with and without cancer can be based on mutational load assessment that can also be generically applied for the purpose of the detection of any cancer. To develop a test for the screening of other cancers with high clinical sensitivity and specificity, the ability to detect a wide range and large number of mutations can be needed. There are several reasons to justify this test requirement. Unlike the association of EBV with NPC, some other cancers are not associated with a non-human genetic marker that can be distinguished from the non-cancer human DNA with relative ease. Therefore, to develop a screening test for the non-EBV related cancers, the test can need to detect the other varieties of cancer-associated changes.

Breadth

Cancers can be highly heterogeneous. The mutation profile varies greatly between cancers of different organs, varies greatly between different subjects with cancers of the same organ or even between different tumor foci in the same organ of the same subject (Gerlinger et al N Engl J Med 2012; 366: 883-892). Therefore, any one tumor-associated mutation can be only positive in a small subset of any cancer subject. For example, the Catalogue of Somatic Mutations in Cancer (COSMIC) database documents the range of genetic mutations that can be detected in tumor tissues (see e.g., cancer-.sanger.ac.uk/cosmic). In some cases, only a proportion of each tumor type can exhibit any one of the most commonly identified mutations among cancers. In some cases, a large proportion of tumors do not feature any one of the top mutations listed in the COSMIC database. In other words, if one designs a cancer screening test based on the exclusive detection of the top mutations, in some cases many tumors can not be detected due to the absence of such mutations. These data can suggest that the need to detect a large number of somatic mutations, as demonstrated by embodiments in this application, can be important to realize a screening test that can be generic to different tumors and yet can yield positive findings in a large proportion of the cancer population.

To develop a plasma DNA test for cancer detection or primary screening, one can scout through a much wider search space within the genome in order to collect enough mutations (e.g., copy number aberrations and sequence variants relative to a reference genome, such as a constitutional genome or parental genomes) or other cancer-specific or cancer-associated changes (e.g., methylation changes) to make up the sum of 500 cancer-specific plasma DNA fragments per cancer cell. Assuming the chance of any one well-documented cancer-associated mutation occurring in any one tumor is 1%, the test can need to target the detection of 50,000 putative mutation sites in order to have at least 500 mutations detected per tumor (based on Poisson probability distribution). 500,000 putative mutations or cancer-associated changes can need to be tested in order to have at least 5,000 mutations or cancer-associated changes represented for any one tumor. On the other hand, if the chance of any one well-documented cancer-associated mutations or changes occurring in any one tumor is 0.1%, then 50,000 mutations or changes can need to be tested in order to have at least 50 mutations or changes represented for any one tumor.

Therefore, to maximize the cancer detection rate, or clinical sensitivity, of the cancer screening test, the test m can need to achieve a broad survey of plasma DNA fragments in a sample in order to identify enough fragments bearing any one type of cancer-associated change or mutation. The breadth of the survey can be achieved either with the use of genome-wide approaches or targeted approaches that cover a large fraction of the genome, for example enough to cover at least 50,000 targets.

Depth

The depth of the survey can also matter. Depending on the number of mutations detected per tumor, multiple plasma DNA fragments that bore that mutation can need to be detected to reach a specified threshold, e.g., 500 informative cancer DNA fragments for each genome-equivalent of cancer cell. For example, if only one mutation is identified in a particular tumor, then 500 plasma DNA fragments covering that mutation can be needed. On the other hand, if 50 different mutations are present in the tumor, on average, one can need to detect at least 10 informative cancer DNA fragments covering each one of those 50 mutations.

Tumor DNA can represent a minor DNA population in plasma. Furthermore, some cancer-associated changes can be heterozygous in nature (i.e., with one change per diploid genome). Thus, to detect 10 copies of informative cancer DNA fragment (i.e., plasma DNA fragments that carry at least one cancer-associated change) per locus, one can need to analyze at least 100 molecules from the locus in a plasma sample with 20% tumor DNA fraction. Hence, the ability to detect multiple plasma DNA fragments covering any single mutation site can be dependent on how deep the plasma sample is surveyed. Yet, there can be only a finite number of cancer cell genomes in the plasma sample, which can affect both the required depth and breadth of the plasma DNA analysis.

For illustration of the detection of early cancers, assume one aims to develop a test or protocol that can detect a tumor fraction of 1% in a sample. Given that there can be 1,000 genome-equivalents of DNA in every milliliter of plasma, there can be 10 cancer cell-equivalent of DNA in a milliliter sample with 1% tumor DNA fraction. Even if one can detect every single cancer-specific DNA fragment in the sample, there can only be a maximum of 10 genome-equivalents of any one cancer-associated change that can be available for detection. Accordingly, even if one has prior knowledge that a particular mutation is present in a tumor, its targeted detection can only provide a signal of 10 genome-equivalents in the best-case scenario, which can lack the analytical sensitivity for robust detection of a cancer at 1% fractional concentration. If the mutation to be detected is heterozygous, there can only be 5 plasma DNA fragments showing this mutation.

In the best-case scenario with 1% tumor DNA fraction, the depth of the analysis at this mutation site can need to be covered at least 1,000 times to be able to detect the 10 genome-equivalents of plasma DNA with the mutation. In this situation, the breadth of the analysis can need to make up for the relatively low number of copies detected per mutation site. The selective detection of a handful or even just hundreds of mutation sites can be unlikely to be able to achieve the sensitivity required for a screening test to detect early cancer.

In order to achieve a high PPV or high NPV, the cancer screening test can need to show a high specificity profile. High specificity can be achieved at a number of levels. The specificity of the mutations and any cancer-associated changes to be detected can need to be as specific for cancer as possible. This can be achieved by, but not limited to, scoring a genetic or genomic signature as positive only when there is high confidence that it is cancer associated. This can be achieved by including signatures that have been previously reported in other cancers. For example, one can focus particularly on signatures that can be prevalent in the cancer type that the individual is predisposed to, e.g., based on his or her demographic profile. Or, one can pay particular attention to mutational signatures that can be associated with the mutagenic exposure that a subject has been exposed to (see e.g., Alexandrov et al. Nature 2013; 500: 415-421). This can also be achieved by minimizing the number of sequencing and alignment errors that can be misidentified as a mutation. This can be achieved by comparing to the genomic profile of a group of healthy controls, and/or can be achieved by comparing with the person's own constitutional DNA.

These criteria can be applied as filtering criteria to assess the likelihood of a plasma DNA fragment being derived from the tumor and hence qualifies to be an informative cancer DNA fragment. Each filtering criterion can be used individually, independently, collectively with equal weighting or different weightings, or serially in a specified order, or conditionally depending on the results of the prior filtering steps. For conditional usage, a Bayesian-based approach can be used, as well as a classification or decision tree based approach. An independent use can involve more than one filtering criterion, but in some cases each filtering criterion does not depend on the application of another filtering criterion (e.g., parallel application can be performed), in contrast to a serial application in specific orders. As an example of collective usage using weightings, machine learning techniques can be used. For example, supervised learning can use measured mutational loads of samples with known classifications to train any models.

Sequencing data from a large number of individuals (e.g., hundreds, thousands, or millions) can be used to train the models. In a simpler form, such known samples can be used to determine threshold values for one or more scores determined from the filtering criteria to determine whether a mutation is valid or not.

In one embodiment, if a plasma DNA fragment fulfills some or all of the criteria, one can deem it to be an informative cancer DNA fragment, while the others that do not fulfill some or all can be deemed a non-informative plasma DNA fragment. In another embodiment, each plasma DNA fragment can be given a weighting of informativeness of being an informative cancer DNA fragment depending on how strongly it fulfills the list of criteria. In some cases, the higher the confidence that the fragment is tumor-derived, the higher the weighting. In one embodiment, the weighting can be adjusted based on the clinical profile of the test subject (e.g., sex, ethnicity, risk factor for cancer, such as smoking or hepatitis status, etc).

On another level, the specificity of the cancer screening test can be achieved by assessing if the amount (e.g., number) of cancer-associated changes detectable in plasma of patients with cancer reflects a mutational load commensurate with that expected for cancer. In one embodiment, one can compare the mutational load in plasma with the mutational load measured in the constitutional DNA, e.g., when the mutational load is determined with respect to a reference genome. In other embodiments, one can compare the mutational load in plasma with that observed in plasma of the subject at a different time, or of a cancer patient with known prognosis (good or bad) or stage of cancer, or of a healthy cancer-free population. The reference population can be age- or sex- or ethnicity-matched, as the mutational load in the body or in tissues can increase with age even in persons not shown to have cancer (see e.g., Slebos et al. Br J Cancer 2008; 98: 619-626). Broad and deep plasma DNA analysis can be performed to capture an adequate mutational load to enhance the differentiation between cancer subjects from the healthy population. In some cases, not all of the DNA fragments in the plasma sample need to be detected to achieve cancer detection, e.g., if a sample has sufficient mutational information.

Whether an observed mutational load is suggestive of cancer can, in one embodiment, be based on cancer-specific reference ranges. Cancers of different organs can harbor an expected range of mutation load. The number can range from 1,000 to several 10,000 s (see e.g., Lawrence et al. Nature 2013; 499: 214-218). Thus, if the plasma DNA cancer screening test shows evidence that a person's mutational load is approaching numbers in the range of any cancer group, a classification for high risk of cancer can be made. In another embodiment, a classification for cancer can be made if the mutational load in the plasma of a person is significantly higher than a reference range established from a healthy population without cancer.

Evidence for significantly higher mutational load can be based on statistical distributions, e.g., more than three standard deviations from the mean of the control reference data, or a number of multiples of the median of the control reference data, or greater than a particular percentile (for example the 99th centile) of the control reference data, or at least 1 or 2 or 3 orders of magnitude greater than the mean, median, or 99th centile of the control reference data. Various statistical approaches can be used to identify statistically significantly increased mutational load. In another embodiment, the classification can take into account variables that have been shown to affect the sensitivity and specificity profiles of the cancer screening test, such as the measured or presumed or inferred tumor DNA fraction of the sample, sequencing depth, sequencing breadth, and sequencing error rates.

The mutational load can be determined in various ways. The mutational load can be expressed as the number of mutations detected. The number of mutations can be normalized to the amount of sequencing data obtained, e.g., expressed as a percentage of the sequenced nucleotides or a density of mutations detected for the amount of sequencing performed. The number of mutations can also be normalized to the size of the human genome, e.g., expressed as a proportion of the genome or a density per region within the genome. The number of mutations can be reported for each occasion when mutation load assessment is performed or can be integrated over time, e.g., the absolute change, percentage change or fold change compared to a previous assessment. The mutational load can be normalized to the amount of the sample (e.g., volume of plasma) analyzed, to the amount of DNA obtained from the sample, or the amount of analyzable or sequenceable DNA. In one embodiment, the mutational load can be normalized to a biometric parameter of the tested subject, e.g., weight, height, or body mass index.

Ultra-deep and broad sequencing can be used to achieve performance profiles for the cancer screening test. A number of embodiments for achieving ultra-deep and broad sequencing are described herein. Such embodiments include, but not limited to, exhaustive sequencing, total template sequencing, PCR-free sequencing, single molecule sequencing (a type of PCR-free sequencing), and targeted sequencing. A combination of approaches can be used to achieve the needed depth and broadness. Such a combination can be used for a screening program as a whole, or for screening a particular individual or groups of individuals.

For the purpose of cancer screening, to detect the cancer-associated mutations from plasma DNA sequencing, the sequencing depth can affect the ability to differentiate true cancer mutations and false-positives due to sequencing errors. A higher sequencing depth can be required when the tumor DNA fraction in the plasma is lower. Using a dynamic cutoff analysis, when the tumor DNA fraction is 2%, a sequencing depth of 200 folds can be able to detect 5.3% of the cancer associated mutations. The number of mutations detected can be higher than the expected number of false-positives, assuming that random sequencing errors occur with a frequency of 0.3%. The portion of the genome to be searched can be dependent on the expected number of mutations in the tumor tissue.

The portion of the genome to be searched can need to be large enough to obtain sufficient number of mutations to be detected. This breadth parameter can be dependent on the desired lower limit of detection of tumor DNA fraction and the type of cancer to be screened for. For example, in melanoma, the median frequency of mutation can be around 10 per 1 Mb. In other words, there can be approximately 30,000 mutations in a genome. Assuming that the tumor DNA fraction is 2% and $\frac{1}{10}$ of the genome is searched, it can be expected that approximately mutations can be detected by plasma DNA sequencing at 200×. On the other hand, if rhabdoid tumor is the target to be screened, the median frequency of mutations can be only 0.2 per 1 Mb. Thus, the search of $\frac{1}{10}$ of the genome can yield approximately 3 cancer mutations when the tumor DNA fraction is 2%. In some cases, this number is not sufficient to be differentiated from sequencing errors.

In some cases, for the purpose of cancer screening, it is not necessary to identify 100% of the cancer-associated mutations. In one embodiment, one only has to show that a particular individual has a higher number of mutations detected in plasma (or other biological sample) than that in a reference control population without cancer. However, for this strategy to be highly accurate, in some cases the proportion of true mutations detected by a mutational load assessment protocol can need to be as high as possible (or the proportion of false positives can need to be as low as possible), so that the high number of variants detected by the assessment is reflective of the presence of cancer. If this can not be achieved, the high number of putative mutations detected in a sample can simply be reflective of a high number of false-positive variants and hence in some cases can not allow the discrimination of a subject with cancer and those without cancer. Embodiments in this application describe how to reduce the detection of false positives and how to increase the detection of true mutations to achieve effective mutational load assessment.

Ultra-deep and broad sequencing can be achieved by exhaustive sequencing or other techniques, e.g., light (non-exhaustive) sequencing of multiple targeted sequencing panels. Light sequencing can be used to minimize PCR duplicates so one can obtain the required depth. Multiple targeted sequencing panels can be used to provide broad coverage across the genome.

Various filtering criteria can be used to determine the mutational status of a biological sample (e.g., identify cancer-associated somatic mutations). Non-limiting examples of filtering criteria include realignment to a reference genome, size based analysis, histone modification analysis, mutant fraction, methylation analysis, plasma DNA end location, and single-stranded sequencing.

Realignment

Each of a first set of candidate loci identified as having a somatic mutation can be analyzed. Each of the sequence reads aligning to the candidate locus using a first alignment procedure and having the sequence variant can be further analyzed in a realignment procedure. It can be determined whether the sequence read aligns to the candidate locus using a second alignment procedure that uses a different matching algorithm than used for the first alignment procedure. When the sequence read realigns to the candidate locus using the second alignment procedure, a mapping quality of the realignment for the second alignment procedure can be determined.

Once the mapping quality for the second alignment is determined, the mapping quality can be compared to a quality threshold, so as to determine whether the sequence read is low quality. It can then be determined whether to discard the sequence read based on the comparing of the mapping quality to the quality threshold. The determination can be that reads below the threshold can be discarded. In other embodiments, a score (e.g., a weight) can be determined based on the comparison, where comparisons to multiple quality thresholds can be performed to determine the score, e.g., each threshold corresponding to a different realignment score. The score can then be used in a collective manner with scores from one or more other filtering criteria to determine whether to discard the read. Regardless of the specific manner (and inclusive of the examples provided above), the mapping quality being less than the quality threshold provides a higher likelihood of discarding the sequence read than the mapping quality being greater than the quality threshold.

As part of this filtering process, a number of remaining sequence reads can be obtained. The number of remaining sequence reads can be compared to a candidate threshold, which can be the same threshold value originally used to identify candidate loci. In a similar likelihood analysis as for the sequence read, it can be determined whether to discard the candidate locus based on the comparing of the number of remaining sequence reads to the candidate threshold. The analysis can be strict based on the comparison to the threshold, or use a scoring (weighting) system as mentioned above. Regardless, the number of remaining sequence reads being less than the candidate threshold can provide a higher likelihood of discarding the candidate locus than the number of remaining sequence reads being greater than the candidate threshold. The filtered set of loci can be identified as having somatic mutations using the remaining candidate loci.

Size

Each of a set of candidate loci can be analyzed. A size difference can be determined between a first group of DNA fragments having the sequence variant and a second group of DNA fragments having a wildtype allele. Such size analyses have been described herein. The size difference can be between any statistical value of size distributions for the two groups. For example, a difference in a median size of the first group of DNA fragments and the second group of DNA fragments can be used. Another example can be a maximum in a cumulative frequency by size between the first group and the second group. Any size value can be as described, e.g., in U.S. Patent publications 2011/0276277 and 2013/0237431.

The size difference can be compared to a size threshold, which can be determined from samples known to have cancer or other status that is being classified. It can then be determined whether to discard the candidate locus as a mutation based on the comparison. As for other filtering criteria, the comparison can be used strictly or as a score. Regardless, the size difference being less than the size threshold can provide a higher likelihood of discarding the candidate locus than the size difference being greater than the size threshold. The filtered set of loci can be identified as having somatic mutations in the human subject using the remaining candidate loci.

Histone Modification

A group of regions known to be associated with histone modifications that are associated with cancer can be identified. Each of a set of candidate loci can be analyzed by determining whether to discard the candidate locus based on whether the candidate locus is in one of the group of regions. As for other filtering criteria, the comparison can be used strictly or as a score. Regardless, the candidate locus not being in one of the group of regions can provide a higher likelihood of discarding the candidate locus than when the candidate locus is in one of the group of regions. The filtered set of loci can be identified as having somatic mutations in the human subject using the remaining candidate loci.

Mutant Fraction

Each of a set of candidate loci can be analyzed. A fraction of sequence reads having the sequence variant can be determined, and then compared to the fraction threshold. It can then be determined whether to discard the candidate locus as a mutation based on the comparison, e.g., using scores or strict cutoffs. Either way, the fraction being less than the fraction threshold provides a higher likelihood of discarding the candidate locus than the fraction being greater than the fraction threshold (e.g., 5%, 10%, 20%, or 30%). The filtered set of loci can be identified as having somatic mutations in the human subject using the remaining candidate loci.

In some embodiments, the fraction threshold can be determined based on a measured fractional concentration of tumor DNA in the biological sample. The fractional concentration of tumor DNA in the biological sample can be measured for each of a plurality of regions (e.g., using similar techniques but with data specific to one or more loci in the regions). The fraction threshold used for a candidate locus can be the fractional concentration measured for the region that the candidate locus resides.

In another embodiment, aberrant regions can be used to determine a fraction threshold. One or more aberrant regions that have a copy number aberration can be identified. The fraction threshold used for a candidate locus in an aberrant region can be dependent on whether the aberrant region exhibits a copy number gain or a copy number loss. A higher threshold can be used for a gain, and a lower threshold for a loss.

One or more aberrant regions that have a copy number aberration can also be used as part of determining whether to discard sequence reads for determining the number of the sequence reads having a sequence variant relative to the constitutional genome for each of the filtered set of loci. A first sequence read from a first aberrant region exhibiting a copy number gain can be more likely to have a somatic mutation than a second sequence read from a second aberrant region exhibiting a copy number loss.

One or more aberrant regions can be identified by analyzing a set of candidate loci. An apparent mutant fraction of a sequence variant relative to the constitutional genome can be calculated. A variance in the apparent mutant fractions of the candidate loci in the aberrant region can be determined for each of a plurality of regions. The variance can be compared to a variance threshold, where an aberrant region exhibiting a copy number gain has a variance greater than the threshold.

Methylation Status

The sequencing cam be methylation-aware sequencing. Methylation-aware sequencing can refer to any sequencing method in which the methylation status at various genomic locations is determined (e.g., bisulfite sequencing). Each of a set of candidate loci can be analyzed, with each of the sequence reads aligning to the candidate locus and having the sequence variant being analyzed. For a sequence read, a methylation status of the corresponding analyzable DNA molecule at one or more sites (e.g., CpG sites) can be determined. It can be determined whether to discard the sequence read based on the methylation status. As for other filtering criteria, the comparison can be used strictly or as a score. Regardless, the methylation status not being methylated can provide a higher likelihood of discarding the sequence read than the methylation status being methylated.

The number of remaining sequence reads can be compared to a candidate threshold, which can be the same as used to identify the candidate loci (as is also true for other uses of a candidate threshold for other filtering criteria). In a similar likelihood analysis as for the sequence read, it can be determined whether to discard the candidate locus based on the comparing of the number of remaining sequence reads to the candidate threshold. The analysis can be strict based on the comparison to the threshold, or use a scoring (weighting) system as mentioned above. Regardless, the number of remaining sequence reads being less than the candidate threshold provides a higher likelihood of discarding the candidate locus than the number of remaining sequence reads being greater than the candidate threshold. The filtered set of loci can be identified as having somatic mutations using the remaining candidate loci.

Plasma DNA End Locations

For the plasma DNA end locations, each of a set of candidate loci can be analyzed, with each of the sequence reads aligning to the candidate locus and having the sequence variant being analyzed. For a sequence read, an end location corresponding to where an end of the sequence read aligns can be determined. The end location can be compared to a plurality of cancer-specific or cancer-associated terminal locations. Whether to discard the sequence read can be determined based on the comparison. The end location not being a cancer-specific or cancer-associated terminal location can provide a higher likelihood of discarding the sequence read than the end location being a cancer-specific or cancer-associated terminal location. The remaining number of sequence reads can be used to determine whether to discard the candidate locus.

Single Stranded Sequencing

The sequencing can be performed using a single-stranded sequencing library preparation process that can provide a subsequent sequencing step to yield two strand reads for each template DNA molecule. One example of a single-stranded sequencing library preparation process is described in Snyder et al. Cell 2016; 164: 57-68. Each of a set of candidate loci can be analyzed, with each pair of strand reads aligning to the candidate locus being analyzed. Whether both strands have the sequence variant can be determined. It can then be determined whether to discard the sequence read based on whether both strands have the sequence variant. Both strands not having the sequence variant provides a higher likelihood of discarding the strand reads than the only one strand read having the sequence variant. The remaining number of sequence reads can be used to determine whether to discard the candidate locus.

Sequencing

In some embodiments, a method of the present disclosure can comprise sequencing a nucleic acid (e.g., a DNA fragment). Sequencing the nucleic acid can be performed using any method known in the art. In some embodiments, sequencing can include next generation sequencing. In some embodiments, sequencing the nucleic acid can be performed using chain termination sequencing, hybridization sequencing, Illumina sequencing, ion torrent semiconductor sequencing, mass spectrophotometry sequencing, massively parallel signature sequencing (MPSS), Maxam-Gilbert sequencing, nanopore sequencing, polony sequencing, pyro-sequencing, shotgun sequencing, single molecule real time (SMRT) sequencing, SOLiD sequencing, universal sequencing, or any combination thereof. In some embodiments, the sequencing can comprise digital PCR. While examples and embodiments have been provided herein, additional techniques and embodiments related to, e.g., digital PCR and random sequencing, can be found in U.S. Pat. No. 8,722,334, filed Oct. 28, 2010, US Provisional Application 60/951,438, filed Jul. 23, 2007, and U.S. Pat. No. 9,121,069, filed Jul. 8, 2013, each of which is entirely incorporated herein by reference.

The number or the average number of times that a particular nucleotide within the nucleic acid is read during the sequencing process (e.g., the sequencing depth) can be multiple times larger than the length of the nucleic acid being sequenced. In some instances, when the sequencing depth is sufficiently larger (e.g., by at least a factor of 5) than the length of the nucleic acid, the sequencing can be referred to as "deep sequencing." In any of the embodiments disclosed herein, sequencing a DNA fragment can comprise deep sequencing. For example, a DNA fragment can be sequenced such that the sequencing depth is about 20 times greater than the length of the nucleic acid. In some instances, when the sequencing depth is at least about 100 times greater than the length of the nucleic acid, the sequencing can be referred to as "ultra-deep sequencing." In any of the embodiments disclosed herein, analyzing the nucleic acid can comprise ultra-deep sequencing. In some embodiments, the sequencing depth can be on average at least about 5 times greater, at least about 10 times greater, at least about 20 times greater, at least about 30 times greater, at least about 40 times greater, at least about 50 times greater, at least about 60 times greater, at least about 70 times greater, at least about 80 times greater, at least about 90 times greater, at least about 100 times greater than the length of the nucleic acid being sequenced.

In some embodiments, the sample can be enriched for a particular analyte (e.g., a nucleic acid fragment, or a cancer-specific nucleic acid fragment). Sequencing after such an enrichment results in a higher proportion of the resulting sequence data being relevant to determining the sequence of the region of interest, since a higher percentage of the sequence reads are generated from the region of interest, e.g., by single-molecule sequencing. At least a 10-fold, 25-fold, 100-fold, 200-fold, 300-fold, 500-fold, 700-fold, 1000-fold, 10,000-fold, or greater molar enrichment of the target region of interest can be achieved relative to the concentration of the target region in the original sample. In some embodiments, nucleic acids can be enriched using a pull down assay. Pull-down assays can be used to selectively extract a nucleic acid from a sample. In some embodiments, a pull-down assay can comprise a DNA probe labeled with a high affinity tag (e.g., biotin), which allows the probe to be recovered or immobilized. In some embodiment, the DNA probe can bind to a nucleic acid fragment of interest (e.g., a cancer-specific DNA fragment). Following recovery of the probe, the nucleic acid, DNA probe and/or high affinity probe can be dissociated and separated to purify the nucleic acid of interest.

Computer System

Any of the computer systems mentioned herein can utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems can be interconnected via a system bus. Additional subsystems include a printer, keyboard, storage device(s), and monitor, which is coupled to display adapter. Peripherals and input/output (I/O) devices, which couple to I/O controller, can be connected to the computer system by any number of connections known in the art such as an input/output (I/O) port (e.g., USB, FireWire®). For example, an I/O port or external interface (e.g., Ethernet, Wi-Fi, etc.) can be used to connect computer system to a wide area network such as the Internet, a mouse input device, or a scanner. The interconnection via system bus allows the central processor to communicate with each subsystem and to control the execution of a plurality of instructions from system memory or the storage device(s) (e.g., a fixed disk, such as a hard drive, or optical disk), as well as the exchange of information between subsystems. The system memory and/or the storage device(s) can embody a computer readable medium. Another subsystem is a data collection device, such as a camera, microphone, accelerometer, and the like. Any of the data mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g., an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application can be implemented as software code to be executed by a processor using any suitable computer language such as, for example, Java, C, C++, C#, Objective-C, Swift, or scripting language such as Perl or Python using, for example, conventional or object-oriented techniques. The software code can be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium can be any combination of such storage or transmission devices.

Such programs can also be encoded and transmitted using carrier signals adapted for transmission via wired, optical, and/or wireless networks conforming to a variety of protocols, including the Internet. As such, a computer readable medium can be created using a data signal encoded with such programs. Computer readable media encoded with the program code can be packaged with a compatible device or provided separately from other devices (e.g., via Internet download). Any such computer readable medium can reside on or within a single computer product (e.g., a hard drive, a CD, or an entire computer system), and can be present on or within different computer products within a system or network. A computer system can include a monitor, printer, or other suitable display for providing any of the results mentioned herein to a user.

Any of the methods described herein can be totally or partially performed with a computer system including one or more processors, which can be configured to perform the steps. Thus, embodiments can be directed to computer systems configured to perform the steps of any of the methods described herein, with different components performing a respective steps or a respective group of steps. Although presented as numbered steps, steps of methods herein can be performed at a same time or in a different order. Additionally, portions of these steps can be used with portions of other steps from other methods. Also, all or portions of a step can be optional. Additionally, any of the steps of any of the methods can be performed with modules, units, circuits, or other approaches for performing these steps.

Other Embodiments

In some aspects, the present disclosure describes a method for determining a classification of a proportional contribution of a tissue type or pathogen in a biological sample of a subject. In some embodiments, the method comprises analyzing, by a computer system, a first plurality of cell-free nucleic acid molecules from a biological sample of a subject, wherein the analyzing comprises determining a genomic position in a reference genome corresponding to at least one end of the first plurality of cell-free nucleic acid molecules. In some embodiments, the method comprises determining a first amount of the first plurality of cell-free nucleic acid molecules that end within one of a plurality of windows, each window comprising at least one of a first set of genomic positions at which ends of cell-free nucleic acid molecules of a tissue type or pathogen are present at a rate above a first threshold. Techniques related to tissue type can also be used for contribution of a pathogen.

In some embodiments, the method comprises computing a relative abundance of the first plurality of cell-free nucleic acid molecules ending within one of the plurality of windows by normalizing the first amount of the first plurality of cell-free nucleic acid molecules using a second amount of a second plurality of cell-free nucleic acid molecules from the biological sample, wherein the second amount of cell-free nucleic acid molecules comprises the second plurality of cell-free nucleic acid molecules ending at a second set of genomic positions, wherein the second set of genomic positions are such that ends of cell-free nucleic acid molecules from a reference sample are present at a rate above a second threshold, and wherein a sequence of the cell-free nucleic acid molecules from the reference sample correspond to a sequence of cell-free nucleic acid molecules of the first plurality. In some embodiments, the method comprises determining the classification of the proportional contribution of the tissue type by processing the relative abundance against one or more calibration values determined from one or more calibration samples whose proportional contributions of the tissue type are known.

In some embodiments, the first plurality of cell-free nucleic acid molecules from the biological sample comprises Epstein-Barr virus (EBV) DNA, human papillomavirus (HPV) DNA or fragments thereof. A first set of genomic positions at which ends of cell-free DNA molecules of a first tissue type occur at a rate above a first threshold can be identified. In some embodiments, identifying the first set of genomic positions comprises analyzing, by a computer system, a third plurality of cell-free nucleic acid molecules from at least one first additional sample to identify ending positions of the third plurality of cell-free nucleic acid molecules, wherein the at least one first additional sample is known to include the tissue type and is of a same sample type as the biological sample.

In some embodiments, identifying the first set of genomic positions comprises, for each genomic window of a plurality of genomic windows, computing a corresponding number of the third plurality of cell-free nucleic acid molecules ending on the genomic window. In some embodiments, identifying the first set of genomic positions comprises, for each genomic window of a plurality of genomic windows, comparing the corresponding number to a reference value to determine whether the rate of cell-free nucleic acid molecules ending on one or more genomic positions within the genomic window is above the first threshold. In some embodiments, a first genomic window of the plurality of genomic windows has a width of at least one genomic position, and wherein each of the genomic positions within the first genomic window are identified as having the rate of cell-free nucleic acid molecules ending on the genomic position be above the first threshold when the corresponding number exceeds the reference value. In some embodiments, the first set of genomic positions have the highest N values for the corresponding numbers, wherein N is at least 10,000.

In some embodiments, the method further comprises determining a size of each of the third plurality of cell-free nucleic acid molecules, wherein identifying the first set of genomic positions further comprises determining a first statistical value of a size distribution of cell-free nucleic acid molecules of the third plurality of cell-free nucleic acid molecules ending within a first genomic window determined to have the rate above the first threshold. In some embodiments, the method further comprises determining a size of each of the third plurality of cell-free nucleic acid molecules, wherein identifying the first set of genomic positions further comprises comparing the first statistical value to a size threshold. In some embodiments, the method further comprises determining a size of each of the third plurality of cell-free nucleic acid molecules, wherein identifying the first set of genomic positions further comprises excluding the first genomic window from the first set of genomic positions when the first statistical value does not exceed the size threshold.

In some embodiments, the one or more calibration samples include the at least one first additional sample. In some embodiments, the method further comprises, for each of the one or more calibration samples, measuring a corresponding proportional contribution of the tissue type. In some embodiments, the method further comprises, for each of the one or more calibration samples, determining a corresponding relative abundance using the corresponding numbers of the third plurality of cell-free nucleic acid molecules ending within the plurality of windows corresponding to the first set of genomic positions, thereby obtaining a calibration data point, wherein each calibration data point specifies the measured proportional contribution of the tissue type for the additional biological sample and the corresponding relative abundance. In some embodiments, the one or more calibration data points are a plurality of calibration data points that form a calibration function that approximates the plurality of calibration data points.

In some embodiments, each genomic position of the first set of genomic positions has at least a specified number of cell-free nucleic acid molecules of the third plurality of cell-free nucleic acid molecules ending on the genomic position. In some embodiments, the reference value is an expected number of cell-free nucleic acid molecules ending within the genomic window according to a probability distribution and an average length of cell-free nucleic acid molecules in the at least one first additional sample. In some embodiments, the probability distribution is a Poisson distribution, and wherein determining whether the rate of cell-free nucleic acid molecules ending on one or more genomic positions within the genomic window is above the first threshold comprises determining a corresponding p-value using the corresponding number and the expected number, wherein the first threshold corresponds to a cutoff p-value, the corresponding p-value being less than the cutoff p-value indicating that the rate of cell-free nucleic acid molecules ending within the genomic window is above the first threshold.

In some embodiments, the genomic positions whose rate of the third plurality of cell-free nucleic acid molecules ending on the genomic position is above the first threshold comprises a first superset, and wherein identifying the first set of genomic positions further comprises analyzing, by the computer system, a third plurality of cell-free nucleic acid molecules from at least one second additional sample identified as having a reduced amount of the tissue type to identify a second superset of the third plurality of cell-free nucleic acid molecules ending on the genomic position is above the first threshold. In some embodiments, the genomic positions whose rate of the third plurality of cell-free nucleic acid molecules ending on the genomic position is above the first threshold comprises a first superset, and wherein identifying the first set of genomic positions further comprises identifying the first set of genomic positions as comprising the genomic positions that are in the first superset and that are not in the second superset. In some embodiments, the reference value comprises a measured number of cell-free nucleic acid molecules ending within the genomic window, the measured number determined from a third plurality of cell-free nucleic acid molecules of at least one second additional sample identified as not having the tissue type.

In some embodiments, the method further comprises determining a size of each of the third plurality of cell-free nucleic acid molecules, wherein identifying the first set of genomic positions further comprises determining a first statistical value of a first size distribution of cell-free nucleic acid molecules of the third plurality of cell-free nucleic acid molecules ending on a first genomic position determined to have the rate above the first threshold. In some embodiments, the method further comprises determining a size of each of the third plurality of cell-free nucleic acid molecules, wherein identifying the first set of genomic positions further comprises determining a second statistical value of a second size distribution of cell-free nucleic acid molecules of the third plurality of cell-free nucleic acid molecules ending on one or more second genomic positions determined to have the rate above the first threshold. In some embodiments, the method further comprises determining a size of each of the third plurality of cell-free nucleic acid molecules, wherein identifying the first set of genomic positions further comprises comparing the first statistical value to second statistical value. In some embodiments, the method further comprises determining a size of each of the third plurality of cell-free nucleic acid molecules, wherein identifying the first set of genomic positions further comprises excluding the first genomic position from the first set of genomic positions when the first statistical value does not exceed the second statistical value by at least a specified amount to indicate that the first size distribution is smaller than the second size distribution.

In some embodiments, comparing the corresponding number to the reference value comprises computing a first ratio of the corresponding number and a third number of the third plurality of cell-free nucleic acid molecules covering the genomic window. In some embodiments, comparing the corresponding number to the reference value comprises comparing the first ratio to the reference value, the reference value comprising a reference ratio of the measured number of reads ending within the genomic window and a fourth number of the third plurality of cell-free nucleic acid molecules covering the genomic window and not ending within the genomic window. In some embodiments, the third number of the third plurality of cell-free nucleic acid molecules do not end within the genomic window. In some embodiments, determining whether the rate of cell-free nucleic acid molecules ending within the genomic window is above the first threshold comprises determining whether the first ratio is greater than a multiplicative factor times the reference ratio. In some embodiments, the sample type of the biological sample and the at least one first additional sample is selected from a group consisting of plasma, serum, cerebrospinal fluid, and urine.

In some embodiments, the genomic window is a genomic position, and wherein the tissue type has a plurality of tissue-specific alleles, and wherein computing the corresponding number of the third plurality of cell-free nucleic acid molecules ending on the genomic position comprises identifying whether the cell-free nucleic acid molecule ending on the genomic position comprises at least one of the plurality of tissue-specific alleles. In some embodiments, the genomic window is a genomic position, and wherein the tissue type has a plurality of tissue-specific alleles, and wherein computing the corresponding number of the third plurality of cell-free nucleic acid molecules ending on the genomic position comprises comprising the cell-free nucleic acid molecule in the corresponding number when the cell-free nucleic acid molecule comprises a tissue-specific allele. In some embodiments, the genomic window is a genomic position, and wherein the tissue type has a plurality of tissue-specific alleles, and wherein computing the corresponding number of the third plurality of cell-free nucleic acid molecules ending on the genomic position comprises not comprising the cell-free nucleic acid molecule in the corresponding number when the cell-free nucleic acid molecule does not include a tissue-specific allele.

In some embodiments, the tissue type has a plurality of tissue-specific alleles in at least one additional sample, and wherein the first set of genomic positions are determined using cell-free nucleic acid molecules of at least one additional sample that include at least one of the plurality of tissue-specific alleles. In some embodiments, the method further comprises identifying a second set of genomic positions, wherein the identifying comprises analyzing, by a computer system, the cell-free nucleic acid molecules of a reference sample from a reference subject, wherein analyzing each of the plurality of cell-free nucleic acid molecules comprises determining a genomic position in the reference genome corresponding to at least one end of the cell-free nucleic acid molecule. In some embodiments, the reference subject is healthy. In some embodiments, the cell-free nucleic acid molecules of the reference sample comprise EBV DNA, HPV DNA, or fragments thereof. In some embodiments, the relative abundance comprises a ratio of the first amount and the second amount.

In some embodiments, the plurality of windows have a width of one genomic position (e.g., one base), and wherein the relative abundance is computed by, for each genomic position of the first set of genomic positions computing a corresponding number of the first plurality of cell-free nucleic acid molecules ending on the genomic position as part of determining that the first amount of the first plurality of cell-free nucleic acid molecules end on any one of the first set of genomic positions. In some embodiments, the plurality of windows have a width of one genomic position, and wherein the relative abundance is computed by, for each genomic position of the first set of genomic positions computing a third number of the first plurality of cell-free nucleic acid molecules covering the genomic position and not ending on the genomic position as part of determining the second amount of cell-free nucleic acid molecules. In some embodiments, the plurality of windows have a width of one genomic position, and wherein the relative abundance is computed by, for each genomic position of the first set of genomic positions computing a first ratio of the corresponding number and the third number. In some embodiments, the plurality of windows have a width of one genomic position, and wherein the relative abundance is computed by, for each genomic position of the first set of genomic positions computing a mean of the first ratios as the relative abundance.

In some embodiments, the relative abundance is computed by, for each genomic position of the first set of genomic positions, computing a corresponding number of the first plurality of cell-free nucleic acid molecules ending within a first window comprising the genomic position as part of determining that the first amount of the first plurality of cell-free nucleic acid molecules end within one of the plurality of windows. In some embodiments, the relative abundance is computed by, for each genomic position of the first set of genomic positions, computing a third number of the first plurality of cell-free nucleic acid molecules ending within a second window comprising the genomic position, the second window larger than the first window. In some embodiments, the relative abundance is computed by, for each genomic position of the first set of genomic positions, computing a first ratio of the corresponding number and the third number. In some embodiments, the relative abundance is computed by, for each genomic position of the first set of genomic positions, computing a mean of the first ratios as the relative abundance. In some embodiments, the second set of genomic positions and the first set of genomic positions do not overlap. In some embodiments, the second set of genomic positions comprises all genomic positions corresponding to an end of at least one of the first plurality of cell-free nucleic acid molecules.

In some embodiments, analyzing one or more of the cell-free nucleic acid molecules comprises determining both genomic positions corresponding to both ends of the cell-free nucleic acid molecule. In some embodiments, the classification of the proportional contribution corresponds to a range above a specified percentage. In some embodiments, the tissue type is a tumor, and the tumor is selected from the group consisting of bladder cancer, bone cancer, a brain tumor, breast cancer, cervical cancer, esophageal cancer, gastrointestinal cancer (e.g. colorectal cancer), hematopoietic malignancy, leukemia, lung cancer, lymphoma, myeloma, nasal cancer, nasopharyngeal carcinoma (NPC), oral cancer, oropharyngeal cancer, ovarian cancer, prostate cancer, sarcoma, stomach cancer, or thyroid cancer. In some embodiments, the classification is selected from a group consisting of: an amount of tumor tissue in the subject, a size of the tumor in the subject, a stage of the tumor in the subject, a tumor load in the subject, and presence of tumor metastasis in the subject. In some embodiments, the one or more additional biological samples are from the subject and are obtained at a different time than the biological sample. In some embodiments, the method further comprises obtaining template DNA molecules from the biological sample to be analyzed.

In some embodiments, the method further comprises preparing a sequencing library of analyzable DNA molecules using the template DNA molecules, the preparing of the sequencing library of analyzable DNA molecules may or may not comprise an operation of DNA amplification of the template DNA molecules. In some embodiments, the method further comprises sequencing the sequencing library of analyzable DNA molecules to obtain a plurality of sequence reads corresponding to the first plurality of cell-free nucleic acid molecules, wherein analyzing the first plurality of cell-free nucleic acid molecules comprises receiving, at the computer system, the plurality of sequence reads. In some embodiments, the method further comprises sequencing the sequencing library of analyzable DNA molecules to obtain a plurality of sequence reads corresponding to the first plurality of cell-free nucleic acid molecules, wherein analyzing the first plurality of cell-free nucleic acid molecules comprises aligning, by the computer system, the plurality of sequence reads to the reference genome to determine genomic positions for the plurality of sequence reads. In some embodiments, the method further comprises providing a therapeutic intervention based on the classification or performing imaging of the subject based on the classification. In some embodiments, the first set of genomic positions or the second set of genomic positions comprises between 600 and 10,000 genomic positions. In some embodiments, the cell-free nucleic acid molecules are deoxyribonucleic acid (DNA) molecules.

Example Systems

Figure 89:
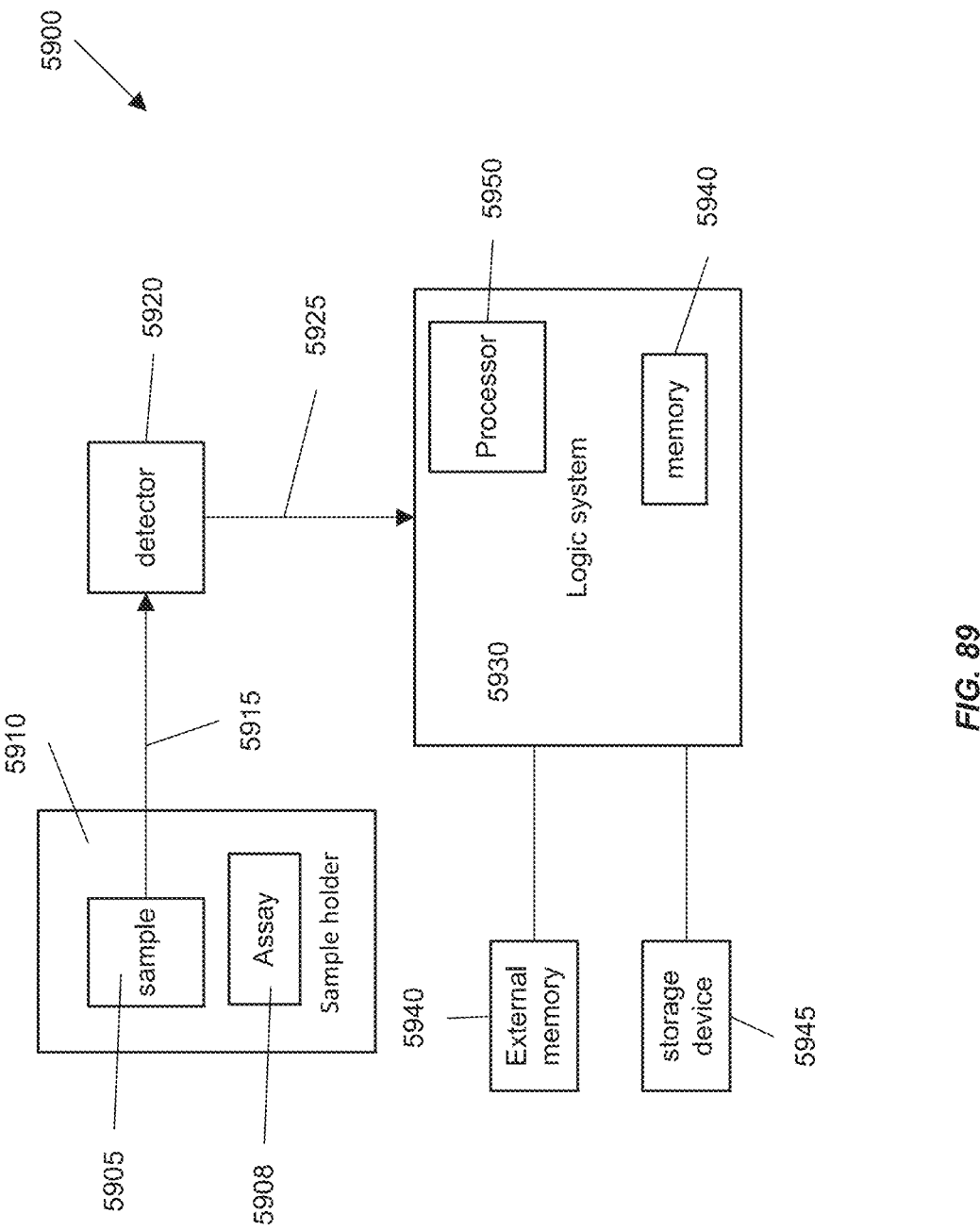
FIG. 89 illustrates a system 5900 according to an embodiment of the present invention.

FIG. 89 illustrates a system 5900 according to an embodiment of the present invention. The system as shown includes a sample 5905, such as cell-free DNA molecules within a sample holder 5910, where sample 5905 can be contacted with an assay 5908 to provide a signal of a physical characteristic 5915. An example of a sample holder can be a flow cell that includes probes and/or primers of an assay or a tube through which a droplet moves (with the droplet including the assay). Physical characteristic 5915, such as a fluorescence intensity value, from the sample can be detected by detector 5920. Detector can take a measurement at intervals (e.g., periodic intervals) to obtain data points that make up a data signal. In one embodiment, an analog to digital converter converts an analog signal from the detector into digital form at a plurality of times. A data signal 5925 can be sent from detector 5920 to logic system 5930. Data signal 5925 can be stored in a local memory 5935, an external memory 5940, or a storage device 5945.

Logic system 5930 can be, or can include, a computer system, ASIC, microprocessor, etc. It can also include or be coupled with a display (e.g., monitor, LED display, etc.) and a user input device (e.g., mouse, keyboard, buttons, etc.). Logic system 5930 and the other components can be part of a stand-alone or network connected computer system, or they can be directly attached to or incorporated in a thermal cycler device. Logic system 5930 can also include optimization software that executes in a processor 5950.

Figure 90:
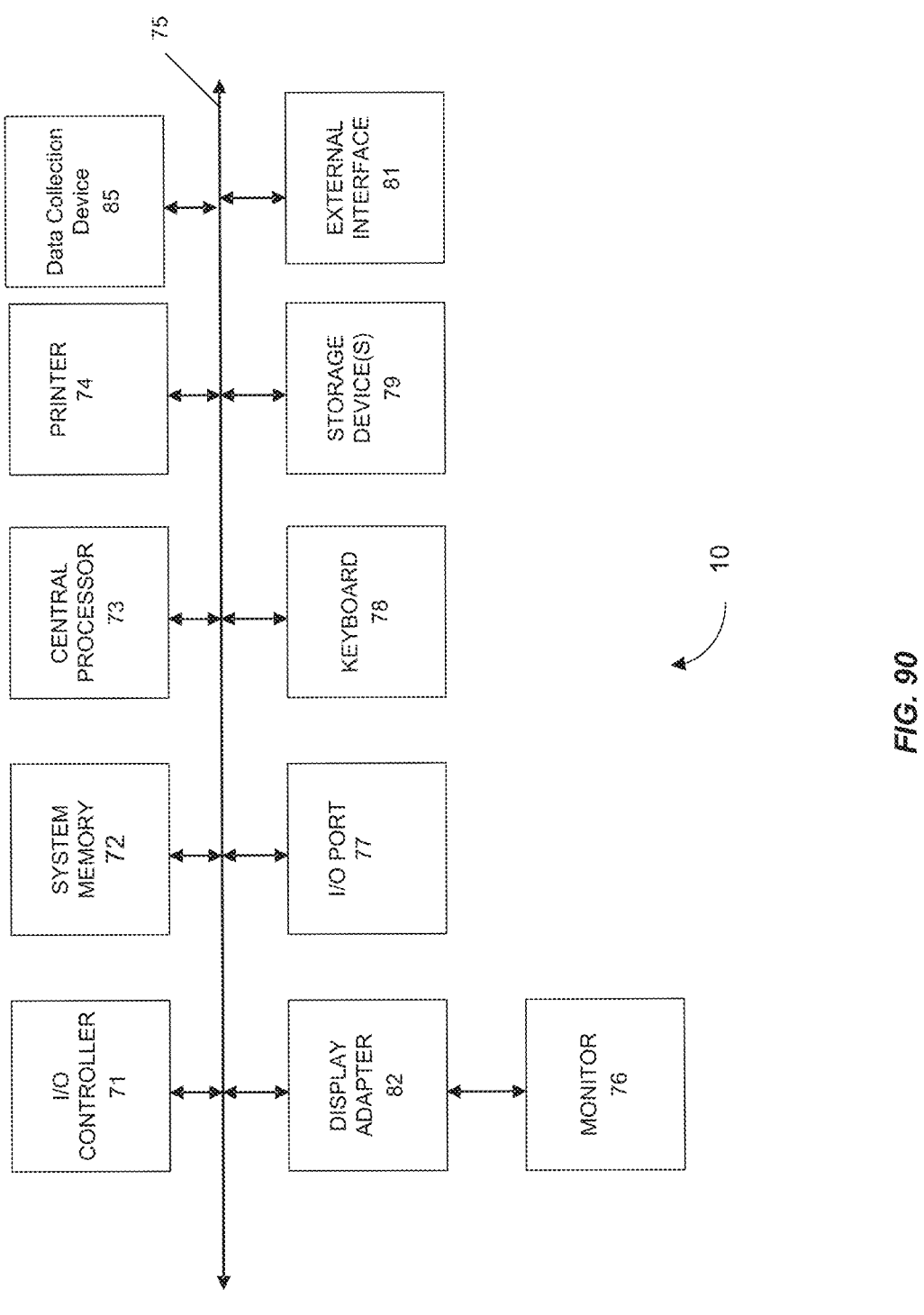
FIG. 90 shows a block diagram of an example computer system 10 usable with system and methods according to embodiments of the present invention.

Any of the computer systems mentioned herein can utilize any suitable number of subsystems. Examples of such subsystems are shown in FIG. 90 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 90 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of connections known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 can embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application can be implemented as software code to be executed by a processor using any suitable computer language such as, for example, Java, C, C++, C#, Objective-C, Swift, or scripting language such as Perl or Python using, for example, conventional or object-oriented techniques. The software code can be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium can be any combination of such storage or transmission devices.

Such programs can also be encoded and transmitted using carrier signals adapted for transmission via wired, optical, and/or wireless networks conforming to a variety of protocols, including the Internet. As such, a computer readable medium can be created using a data signal encoded with such programs. Computer readable media encoded with the program code can be packaged with a compatible device or provided separately from other devices (e.g., via Internet download). Any such computer readable medium can reside on or within a single computer product (e.g. a hard drive, a CD, or an entire computer system), and can be present on or within different computer products within a system or network. A computer system can include a monitor, printer, or other suitable display for providing any of the results mentioned herein to a user.

Any of the methods described herein can be totally or partially performed with a computer system including one or more processors, which can be configured to perform the operations. Thus, embodiments can be directed to computer systems configured to perform the operations of any of the methods described herein, potentially with different components performing a respective operations or a respective group of operations. Although presented as numbered operations, operations of methods herein can be performed at a same time or in a different order. Additionally, portions of these operations can be used with portions of other operations from other methods. Also, all or portions of an operation can be optional. Additionally, any of the operations of any of the methods can be performed with modules, units, circuits, or other approaches for performing these operations.

Examples

Example 1. Screening for Nasopharyngeal Cancer Using qPCR and Next-Generation Sequencing As shown in FIG. 22, two blood samples are obtained 2201 using separate blood collection tubes. Cells are removed from plasma containing cell-free DNA (cfDNA) by performing centrifugation 2 times in series 2202. Centrifugation is performed for 10 minutes at 2,000×g to deplete platelets and cells from the plasma sample. Approximately 0.8 milliliters of plasma from one of the two blood samples collected is used for qPCR analysis to detect a copy number of tumor-derived DNA in the sample 2203. cfDNA extraction is performed 2204 on the plasma sample to enrich the plasma sample for cfDNA, and prepare the sample for qPCR analysis. The denaturing, annealing, and extension temperatures for the qPCR analysis are determined 2205 (e.g., based on the length/GC contents of the primers used, and/or the concentration of total cfDNA in the sample), and qPCR analysis is performed 2206 to detect an amount of tumor-derived cfDNA in the sample. To detect EBV DNA, primers flanking the BamHI sequence of the genome are used. If the amount of EBV DNA detected is below threshold 2207, a negative result is provided and a second assay is not performed. If the amount of cfDNA detected is at or above threshold 2208, a second assay is performed using the plasma from the second blood sample collected. Approximately 4 milliliters of plasma are used for next generation sequencing 2209 to determine a size profile of the cfDNA in the sample. cfDNA extraction is performed 2210 on the second plasma sample to enrich the plasma sample for cfDNA, and prepare the sample for next-generation sequencing analysis. Library preparation is performed 2211 to ligate adapter oligonucleotides to the cfDNA fragments in the sample to be sequenced. cf DNA is fragmented to an optimal length for the downstream platform (e.g., Because DNA fragmentation does not result in homogeneous, blunt-ended fragments, end repair is needed to ensure that each molecule is free of overhangs, and contains 5' phosphate and 3' hydroxyl groups. Incorporation of a non-templated deoxy-adenosine 5'-monophosphate (dAMP) onto the 3' end of blunted DNA fragments, a process known as dA-tailing, can be performed if necessary. Targeted enrichment of EBV DNA is performed 2212; targeted enrichment of EBV DNA enables sequencing of specific regions of interest instead of the entire genome, thereby achieving more sensitive copy number detection. Next generation sequencing is performed on the enriched sample 2213. Sequence reads corresponding to the sequenced cfDNA in the enriched plasma sample are obtained, and optionally aligned to a reference genome. An analysis is performed, e.g., EBV quantity is assessed and a size profile of EBV DNA fragments in generated 2214A report is outputted indicating if the subject from which the sample was obtained has nasopharyngeal cancer 2215.

Example 2. Improving False Positive Rate and Positive Predictive Value of NPC Detection by Performing a Next-Generation Sequencing Assay on an Initial Blood Sample To investigate if plasma EBV DNA is useful for the screening of early NPC in asymptomatic individuals, 20,174 subjects without symptoms of NPC were screened using plasma EBV DNA analysis. Subjects with detectable plasma EBV DNA were retested in approximately 4 weeks later with a follow-up plasma EBV DNA analysis. Subjects with persistently positive results on the two serial analyses were further investigated with nasal endoscopic examination and magnetic resonance imaging (MRI) of the nasopharynx. Out of the 20,174 subjects recruited, 1,112 were positive for plasma EBV DNA at enrollment. Among them, 309 were persistently positive on the follow-up test. Within the cohort of subjects who were persistently positive for EBV DNA in plasma, 34 were subsequently confirmed of having NPC after being investigated with nasal endoscopic examination and MRI. These results showed that the retesting of the subjects with initial positive plasma EBV DNA results can differentiate NPC subjects from those with transiently positive results and substantially reduce the proportion of subjects requiring the more invasive and costly investigations, namely endoscopy and MRI. However, the sequential testing of plasma EBV DNA can require the collection of an additional blood sample from subjects with initial positive results, which can present logistical challenges.

A method for differentiating NPC subjects from non-NPC subjects with detectable plasma EBV DNA based on the analysis of plasma EBV DNA fragmentation patterns was performed. A next-generation sequencing assay is performed on the initial (first) blood samples. The next-generation sequencing based assay analyzes a fragmentation pattern and/or size profile of EBV DNA in the initial (first) blood samples.

A study was designed to analyze the initial (first) blood samples in a biobank; 4 ml of the blood samples were used. A training cohort and a validation cohort were established. The training set included 15 transiently positive samples; 20 persistently positive samples, and 10 samples from subjects confirmed to have NPC; all samples of the training cohort are from the cohort of 20,174 subjects. A validation set included 56 transiently positive samples; 44 persistently positive samples, and 29 samples from subject confirmed to have NPC; all the transiently positive samples and persistently positive samples, and 22 of the samples from subjects confirmed to have NPC, came from the cohort of 20,174 subjects, and 7 samples from confirmed NPC subjects were from an independent cohort. Next generation sequencing was performed to assess EBV quantity and size profile of EBV DNA fragments.

Figure 91A:
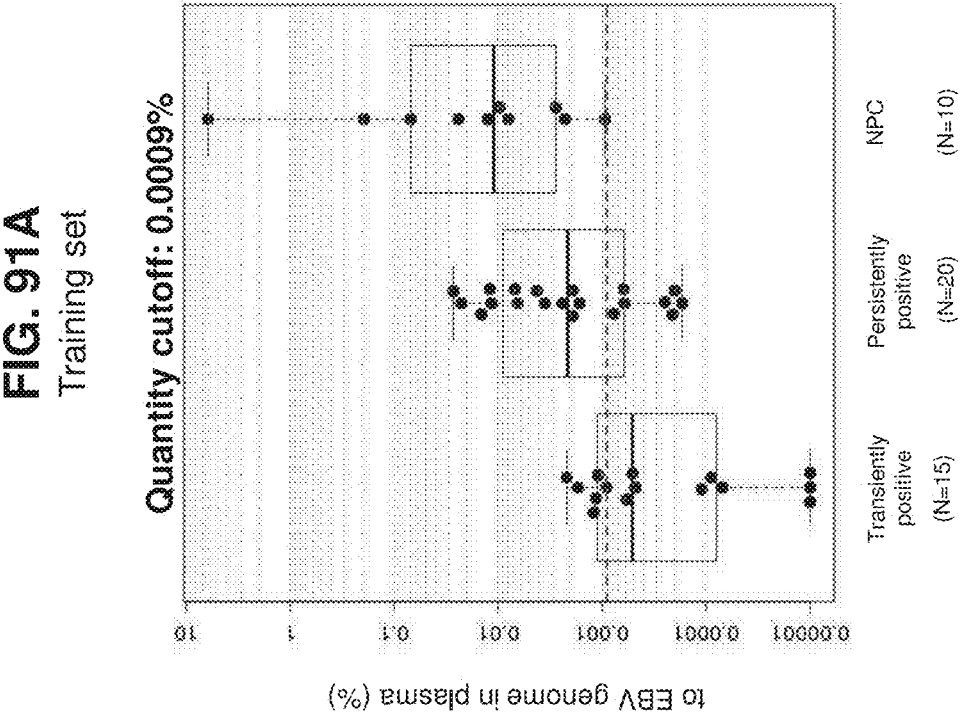
FIG. 91A shows a proportion of reads mapped to EBV genome in plasma (%) for a training set of 15 transiently positive samples, 20 persistently positive samples, and 10 samples from confirmed NPC subjects.

For the training set, FIG. 91A shows the proportion of plasma DNA fragments mapped to the EBV genome in subjects that are transiently positive or persistently positive for plasma EBV DNA (left or middle, respectively) but have no observable pathology, and subjects identified as having NPC (right). Using massively parallel sequencing following targeted capture and sequencing of DNA fragments, there was a statistically significant difference in the EBV quantity as deduced from the proportion of reads uniquely mapped to the EBV genome among all sequenced reads (p-value<0.0001; Kruskal-Wallis test). In one embodiment, the cutoff value for the proportion of plasma DNA fragments mapped to the EBV genome can be determined as any value below lowest proportion of the NPC patients being analyzed. In the current example, a cutoff value of 0.0009% can be set to capture all the NPC patients. In other embodiments, the cutoff values can be determined for example but not limited to the mean proportion of the NPC patients minus one standard deviation (SD), mean minus 2 SD, and mean minus 3 SD. In yet other embodiments, the cutoff can be determined after the logarithmic transformation of the proportion of plasma DNA fragments mapped to the EBV genome, for example but not limited to mean minus SD, mean minus 2SD, mean minus 3 SD after the logarithmic transformation of the values of the NPC patients. In yet other embodiments, the cutoff can be determined using Receiver Operator Characteristics (ROC) curves or by nonparametric methods, for example but not limited to including about 100%, about 95%, about 90%, about 85%, or about 80% of the NPC patients being analyzed. By applying a cutoff value of 0.0009% for the proportion of plasma EBV DNA fragments among all the sequenced reads, subjects with NPC and persistently positive plasma EBV DNA from the majority of subjects with transiently positive plasma EBV DNA results were able to be differentiated. The proportion of EBV reads in plasma was highest in the group of subjects having NPC. The proportion of plasma EBV DNA fragments was higher in the subjects with persistently positive results compared with those with transiently detectable plasma EBV DNA. Those samples with values above the 0.0009% cutoff value (5 transiently positive samples; 13 persistently positive samples, and 10 NPC samples) were evaluated for size index.

In some embodiments, targeted capture can be performed using capture probes designed to bind to any portion of the 176 EBV genome. In some embodiments, capture probes can be biotinylated, and magnetic beads (e.g., streptavidin coated beads) are used to pull down or enrich the capture probes hybridized to a nucleic acid target (e.g., an EBV genome fragment) after library preparation. In some embodiments, the panel of capture probes used can also target a portion of the human genome. For example, capture probes may be designed to hybridize to at least a portion of one or more chromosomes (e.g., either copy of chromosomes 1, 8, and/or 13). In some embodiments, at least about 1 mb, at least 5 mb, at least 10 mb, at least 20 mb, at least 30 mb, at least 40 mb, at least 50 mb, at least 60 mb, at least 70 mb, at least 80 mb, at least 90 mb, or at least 100 mb of the human genome is targeted using capture probes in the panel. In some embodiments, the capture probe panel can pull down about 285 sequence reads corresponding to the EBV. In some embodiments, the capture probe panel can pull down about 40 million sequence reads corresponding to the human genome.

Figure 91B:
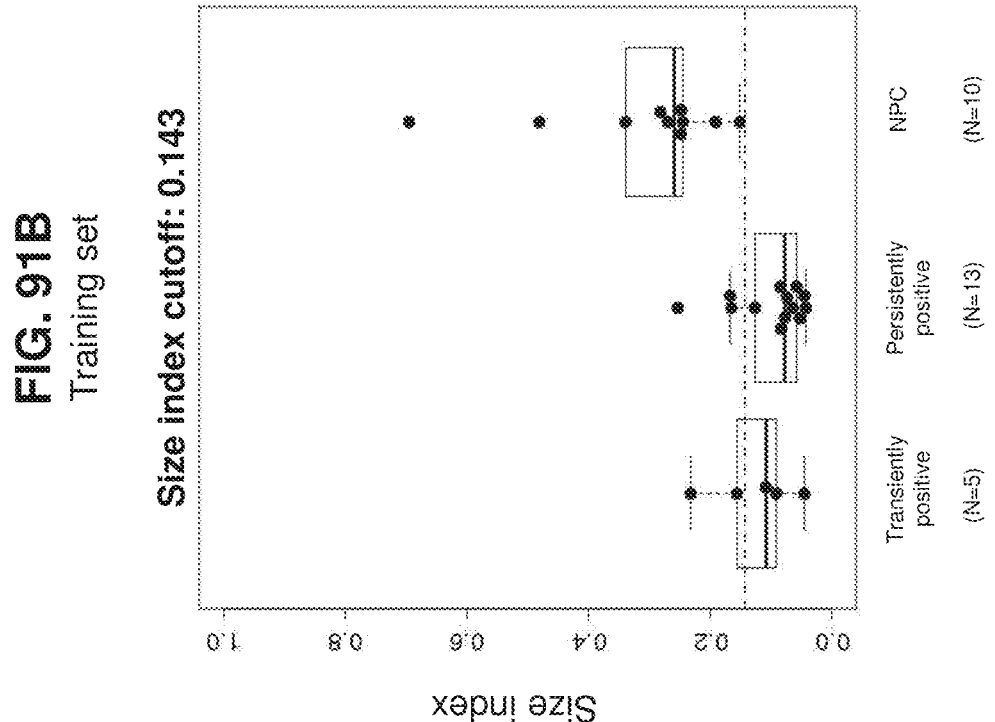
FIG. 91B shows a size index (e.g., an inverse of the size ratio) in subjects that are transiently positive or persistently positive for plasma EBV DNA (left or middle, respectively) but have no observable pathology, and subjects identified as having NPC (right) for a training set.

For the training set, FIG. 91B shows a size index (e.g., an inverse of the size ratio) in subjects that are transiently positive or persistently positive for plasma EBV DNA (left or middle, respectively) but have no observable pathology, and subjects identified as having NPC (right). A size index can be defined as the inverse of the size ratio, and the size ratio can be defined as the proportion of plasma EBV DNA fragments within a certain size range divided by the proportion of autosomal DNA fragments within the corresponding size range. Subjects with NPC were differentiated from subjects with persistently positive plasma EBV DNA based on the difference in the size profile of plasma EBV DNA reads. In one embodiment, the cutoff value for the size index can be determined as any value below lowest proportion of the NPC patients being analyzed. In the current example, a cutoff value of greater than 0.143% (i.e. size ratio of less than 7) can be set to capture all the NPC patients. In other embodiments, the cutoff values can be determined for example but not limited to the mean size index of the NPC patients minus one standard deviation (SD), mean minus two SD, and mean minus three SD. In yet other embodiments, the cutoff can be determined after the logarithmic transformation of the proportion of plasma DNA fragments mapped to the EBV genome, for example but not limited to mean minus one SD, mean minus two SD, mean minus three SD after the logarithmic transformation of the values of the NPC patients. In yet other embodiments, the cutoff can be determined using Receiver Operator Characteristics (ROC) curves or by nonparametric methods, for example but not limited to including 100%, 95%, 90%, 85%, 80% of the NPC patients being analyzed. Using a cutoff value for the size index greater than 0.143, subjects having NPC were differentiated from the majority of subjects with persistently positive plasma EBV DNA. All patients with NPC had the size index greater than 0.143.

Figure 92A:
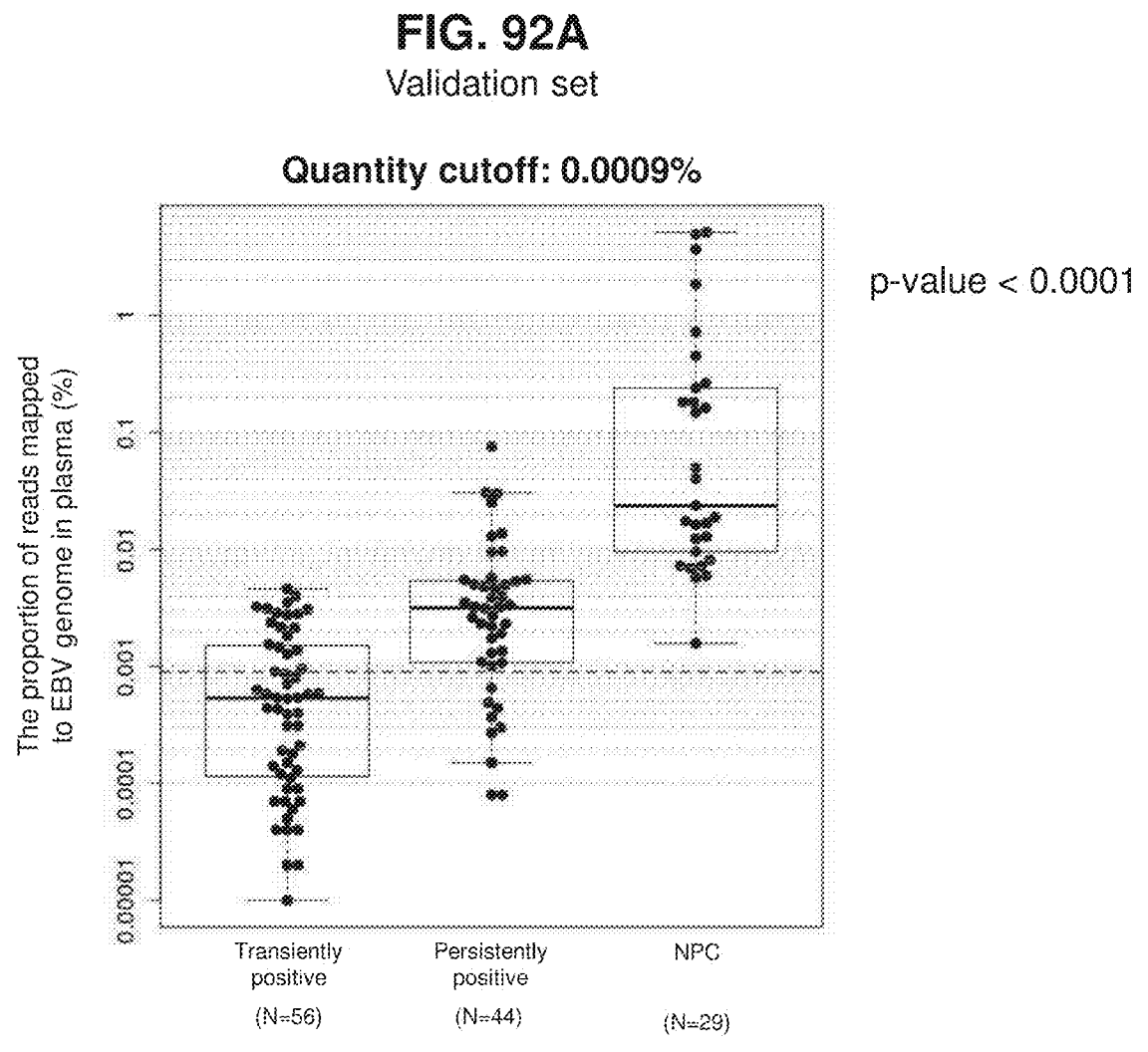

For the validation set, FIG. 92A shows the proportion of plasma DNA fragments mapped to the EBV genome in subjects that are transiently positive or persistently positive for plasma EBV DNA (left or middle, respectively) but have no observable pathology, and subjects identified as having NPC (right). Using massively parallel sequencing following targeted capture and sequencing of DNA fragments, there was a statistically significant difference in the EBV quantity as deduced from the proportion of reads uniquely mapped to the EBV genome among all sequenced reads (p-value<0.0001; Kruskal-Wallis test). By applying a cutoff value of 0.0009% for the proportion of plasma EBV DNA fragments among all the sequenced reads, subjects with NPC and persistently positive plasma EBV DNA from the majority of subjects with transiently positive plasma EBV DNA results were able to be differentiated. The proportion of EBV reads in plasma was highest in the group of subjects having NPC. The proportion of plasma EBV DNA fragments was higher in the subjects with persistently positive results compared with those with transiently detectable plasma EBV DNA. A size index was evaluated for the samples above the cutoff value (18 transiently positive samples; 35 persistently positive samples, and 29 NPC samples).

Figure 92B:
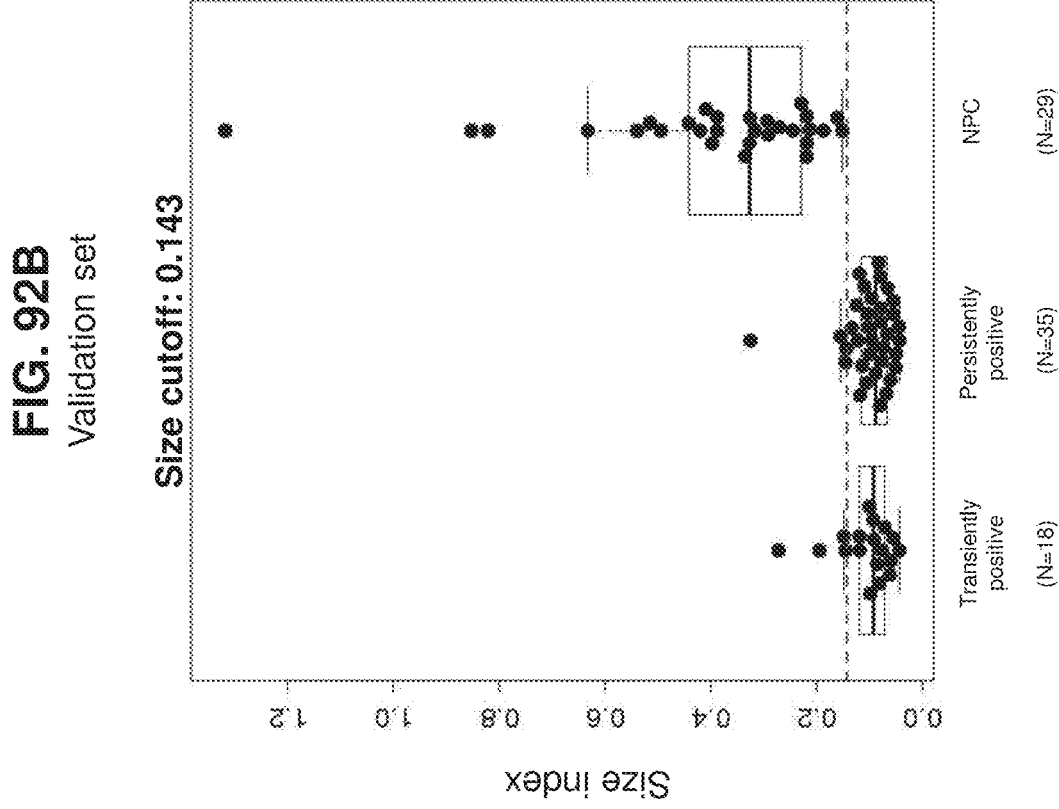
FIG. 92B shows a size index (e.g., an inverse of the size ratio) in subjects that are transiently positive or persistently positive for plasma EBV DNA (left or middle, respectively) but have no observable pathology, and subjects identified as having NPC (right) for a validation set.

For the validation set, FIG. 92B shows a size index (e.g., an inverse of the size ratio) in subjects that are transiently positive or persistently positive for plasma EBV DNA (left or middle, respectively) but have no observable pathology, and subjects identified as having NPC (right). A size index can be defined as the inverse of the size ratio, and the size ratio is defined as the proportion of plasma EBV DNA fragments within a certain size range divided by the proportion of autosomal DNA fragments within the corresponding size range. Subjects with NPC were differentiated from subjects with persistently positive plasma EBV DNA based on the difference in the size profile of plasma EBV DNA reads. Using a cutoff value for the size index of greater than 0.143, subjects having NPC were differentiated from the majority of subjects with persistently positive plasma EBV DNA. All patients with NPC had the size index greater than 0.143.

Figure 93:
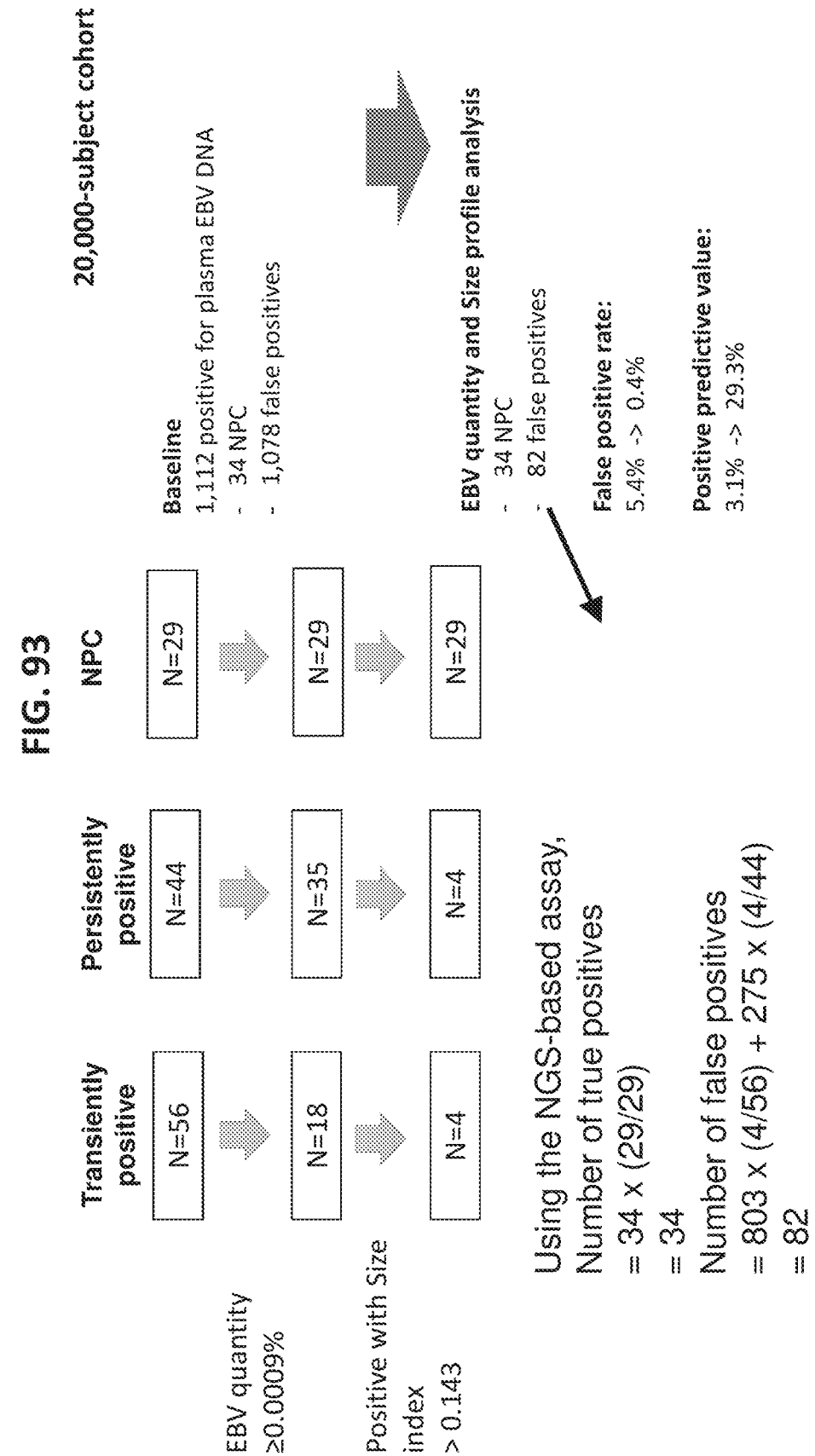
FIG. 93 illustrates that a next-generation sequencing assay performed on an initial samples positive for plasma EBV DNA can reduce a false positive rate and increase a positive predictive value.

FIG. 93 shows an overview of the analysis of the validation set. The analysis started with a validation set that included 56 transiently positive samples; 44 persistently positive samples, and 29 confirmed NPC samples. Setting a cutoff value for the proportion of plasma DNA fragments mapped to the EBV genome in subjects at 0.0009%, 18 of the transitively positive samples were above the threshold; 35 of the persistently positive samples were above the threshold; and 29 of the NPC samples were above the threshold. Using a size index cutoff of greater than 0.143, 4 of the transiently positive were above the cutoff, 4 of the persistently positive were above the cutoff, and 29 of the NPC were above the cutoff.

Starting with an over 20,000-subject cohort, 1,112 subjects were positive for plasma EBV DNA. 34 of those subjects had NPC; 1078 were false positives. Using the next generation sequencing based assay for EBV quantity and size profile analysis, the number of false positives was estimated to be reduced to 82 (803 transitively positive samples×(4/56)+275 persistently positive×(4/44) gives an estimate of 82 false positives). The false positive rate of the initial assay was 5.4% (1078/(20174−34)*100%). Using the next generation sequencing assays for EBV quantity and size profile analysis can reduce the false positive rate to 0.4% (82 false positives/(20,174−34) total*100%). The positive predictive value of the initial assay was 3.1% (34/1112*100%). Using the next generation sequencing assays for EBV quantity and size profile analysis can increase the positive predictive value to 29.3%. (34 true positives/(34 true positives +82 false positives) *100%=29.3%). An improved false positive and positive predictive value is provided, without comprising sensitivity, all based on an initial blood sample.

Example 3. Detecting Nasopharyngeal Cancer in a Subject Using Nucleic Acid Copy Number and Size Analyses A 42 year old asymptomatic man presents for a routine bi-annual evaluation for nasopharyngeal cancer. Peripheral blood is drawn in order to evaluate for the presence of extracellular (e.g., cell-free) tumor-derived Epstein-Barr (EBV) DNA in the subject's plasma. Cells are removed from plasma containing EBV DNA by centrifugation for 5 minutes at 2,000×g using a refrigerated centrifuge. Centrifugation for 15 minutes at 2,000×g depletes platelets in the plasma sample. Following centrifugation, the plasma sample is immediately transferred into a clean polypropylene tube using a Pasteur pipette. The sample is maintained at 2-8° C. while handling.

A first assay including quantitative PCR(qPCR) is performed while the subject waits at the clinic for the results. The qPCR assay is performed using a primer set that is sensitive for (e.g., binds to sequences that flank) the BamHI recognition sequence (5'-GGATCC-3') within the EBV DNA. After determining a value for the number of copies of EBV DNA per milliliter of subject's blood (copies/mL), the value is compared to a cutoff threshold of 100 copies/mL.

If the subject's blood level of EBV DNA exceeds the threshold value, a second assay including a size analysis of cell-free DNA fragments in the plasma sample is performed. Paired-end sequencing is first performed to obtain sequence reads corresponding to each end of the cell-free DNA fragments in the sample. The sequence reads are aligned to a reference genome to determine a location of each pair of sequence reads in the reference genome, and the size of the cell-free DNA fragment is determined as the distance between the outer ends of each sequence read. Sequencing and alignment are performed for each cell-free DNA fragment in the sample to obtain a distribution corresponding to the sizes of the cell-free DNA fragments. If the proportion of cell-free DNA fragments below 150 base pairs in length in the subject's sample is determined to be greater than a cutoff value of 10%, then nasopharyngeal cancer is considered to be detected in the subject.

Example 4. Performing Targeted Enrichment to Improve Specificity of Detecting Nasopharyngeal Cancer in a Subject The specificity of detecting tumor-derived nucleic acids can be proportional with the concentration of tumor-derived nucleic acids in the sample. Accordingly, target-specific enrichment can be used to increase the concentration of tumor-derived nucleic acids in the sample.

A blood sample obtained from a human patient is centrifuged to separate plasma from remaining blood components (e.g., red blood cells, white blood cells, and platelets). Cells are removed from plasma by centrifugation for 10 minutes at 1,000×g using a refrigerated centrifuge. Centrifugation for 15 minutes at 2,000×g depletes platelets in the plasma sample. Following centrifugation, the plasma sample is immediately transferred into a clean polypropylene tube using a Pasteur pipette. The sample is maintained at 2-8° C. while handling. A DNA probe having a sequence complementary to, and capable of binding, BamHI sequence (5'-GGATCC-3') in EBV DNA is used to perform targeted enrichment of the EBV DNA fragments in the sample. The DNA probe is also labeled with a high affinity tag (e.g., biotin), which allows the target-bound probe to be recovered. Following recovery of the target-bound probe, the EBV DNA is dissociated and separated from the probe. Subsequently, the enriched sample is analyzed according the methods (e.g., first assay and second assay) described in Example 1.

Example 5. Detecting Oropharyngeal Cancer in a Subject Using Nucleic Acid Copy Number and Sequence Analyses A 54 year old female smoker presents with blood discharge from the mouth, ear pain, and trouble swallowing. Peripheral blood is drawn in order to evaluate for the presence of extracellular (e.g., cell-free) tumor-derived human papillomavirus (HPV) DNA in the subject's plasma. Cells are removed from plasma containing HPV DNA by centrifugation for 8 minutes at 1,500×g using a refrigerated centrifuge. Centrifugation for 15 minutes at 2,000×g depletes platelets in the plasma sample. Following centrifugation, the plasma sample is immediately transferred into a clean polypropylene tube using a Pasteur pipette. The sample is maintained at 2-8° C. while handling. A first assay including quantitative PCR is performed while the subject waits at the clinic for the results. After determining the value of the number of copies of HPV DNA per milliliter of subject's blood (copies/mL), the value is compared to a cutoff threshold of copies/mL.

If the subject's blood level of HPV DNA exceeds the threshold value, a second assay including a size analysis of cell-free DNA fragments in the plasma sample is performed. Massively parallel sequencing is performed to obtain sequence reads corresponding to each of the cell-free DNA fragments in the sample. The sequence reads are aligned to a reference genome to determine a location of the sequence read in the reference genome, and the number of cell-free DNA fragments having at least one sequence mutation is determined. If the proportion of cell-free DNA fragments having a sequence mutation is determined to be greater than a cutoff value of 3%, then oropharyngeal cancer is detected in the subject.

Example 6. Using Size Analysis to Detect the Presence of Cancer, and Methylation Analysis to Detect the Tissue of Origin A 21 year old asymptomatic female presents for a routine annual evaluation for cancer. Peripheral blood is drawn in order to evaluate for the presence of short (e.g., less than 150 base pairs in length) extracellular (e.g., cell-free) DNA fragments in the subject's plasma. Cells are removed from plasma containing cell-free DNA by centrifugation for 5 minutes at 2,000×g using a refrigerated centrifuge. Centrifugation for 15 minutes at 2,000×g depletes platelets in the plasma sample. Following centrifugation, the plasma sample is immediately transferred into a clean polypropylene tube using a Pasteur pipette. The sample is maintained at 2-8° C. while handling. A first assay including a size analysis of cell-free DNA fragments in the plasma sample is performed. Paired-end sequencing is performed to obtain sequence reads corresponding to each end of the cell-free DNA fragments in the sample. The sequence reads are aligned to a reference genome to determine a location of each pair of sequence reads in the reference genome, and the size of the cell-free DNA fragment is determined as the distance between the outer ends of each sequence read. Sequencing and alignment are performed for each cell-free DNA fragment in the sample to obtain a distribution corresponding to the sizes of the cell-free DNA fragments. The proportion of cell-free DNA fragments below 150 base pairs in length in the subject's sample is determined, and the proportion is compared to a threshold value of 15%, If the subject's blood level of short cell-free DNA fragments exceeds the threshold value, a second assay including a methylation analysis of cell-free DNA fragments in the plasma sample is performed. Methylation-sensitive sequencing is first performed to obtain sequence reads corresponding to each end of the cell-free DNA fragments in the sample. The sequence reads are aligned to a reference genome to determine a location of each sequence read, as well as the methylation status at various genomic locations. Sequencing and alignment are performed for each cell-free DNA fragment in the sample to obtain a methylation pattern (e.g., an amount of methylation and/or a methylation status at multiple genomic locations) corresponding to the methylation of the cell-free DNA fragments. The methylation pattern is compared to a reference obtained from the MethHC database to determine a tissue of origin from which the cancer-derived cell-free DNA fragments are derived.

The section headings used herein are for organizational purposes only and are not to be construed as limiting the subject matter described.

It is to be understood that the methods described herein are not limited to the particular methodology, protocols, subjects, and sequencing techniques described herein and as such can vary. It is also to be understood that the terminology used herein is for the purpose of describing particular embodiments only, and is not intended to limit the scope of the methods and compositions described herein, which will be limited only by the appended claims. While some embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

While some embodiments have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

All patents, patent applications, publications, and descriptions mentioned herein are incorporated by reference in their entirety for all purposes. None is admitted to be prior art.

What is claimed is:

1. A method of non-invasively detecting a tumor in a subject, comprising:

obtaining, through a non-invasive procedure, a first biological sample from the subject, wherein the first biological sample comprises substantially cell-free DNA (cfDNA) derived from normal cells and comprises or is suspected of comprising tumor-derived cfDNA;

performing a first assay using the first biological sample, wherein the first assay has a sensitivity for a first set of markers indicative of the tumor, and wherein the first assay comprises:

measuring a methylation status of the tumor-derived cfDNA in the first biological sample; and determining if the first biological sample includes the first set of markers indicative of the tumor based on a comparison of the methylation status of the tumor-derived cfDNA in the first biological sample to at least one first calibration value;

responsive to determining that the first biological sample includes the first set of markers indicative of the tumor, obtaining, through a non-invasive procedure, a second biological sample from the subject, wherein the second biological sample comprises cfDNA derived from normal cells and comprises or is suspected of comprising tumor-derived cfDNA;

only when the first biological sample includes the first set of markers indicative of the tumor, performing a second assay using the second biological sample, wherein the second assay has a specificity for a second set of markers indicative of the tumor, and wherein the second assay comprises:

measuring a methylation status of the tumor-derived cfDNA in the second biological sample;

identifying the tumor in the subject based on the comparison of the methylation status of the tumor-derived cfDNA in the second biological sample to at least one second calibration value; and outputting a report indicative of the tumor in the subject.

2. The method of claim 1, wherein the second biological sample is obtained between 1 day and 12 weeks after obtaining the first biological sample.

3. The method of claim 1, wherein a positive predictive value of the method of non-invasively detecting a tumor in a subject is greater than a positive predictive value of the first assay or second assay alone.

4. The method of claim 3, wherein the positive predictive value of the method of non-invasively detecting a tumor in a subject is at least 1.5-fold, at least 2-fold, at least 4-fold, at least 10-fold, or at least 20-fold greater than the positive predictive value of the first assay or second assay alone.

5. The method of claim 1, wherein the sensitivity of the method of non-invasively detecting a tumor in a subject is same or greater than the sensitivity of the first assay alone, and wherein the specificity of the method is same or greater than a specificity of the first assay alone.

6. The method of claim 1, wherein the first set of markers and the second set of markers are the same set of markers.

7. The method of claim 1, wherein the sensitivity of the first assay for the first set of markers is at least about 35%.

8. The method of claim 1, wherein the specificity of the second assay for the second set of markers is at least about 95%.

9. The method of claim 1, wherein the tumor is selected from a group consisting of liver cancer, nasopharyngeal cancer, oropharyngeal cancer, oral cancer, bladder cancer, bone cancer, a brain tumor, breast cancer, esophageal cancer, gastrointestinal cancer, hematopoietic malignancy, leukemia, lung cancer, lymphoma, myeloma, ovarian cancer, prostate cancer, sarcoma, stomach cancer, and thyroid cancer.

10. The method of claim 1, wherein at least one of the first biological sample and the second biological sample are independently selected from a group consisting of whole blood, blood plasma, blood serum, urine, buffy coat, and a combination thereof.

11. The method of claim 1, wherein the first assay and the second assay further comprise using methylation-aware sequencing to detect the methylation status of tumor-derived cfDNA in the first biological sample and second biological sample, respectively.

12. The method of claim 11, wherein the methylation-aware sequencing comprises using bisulfite DNA conversion with the tumor-derived cfDNA prior to sequencing.

13. The method of claim 1, further comprising performing an imaging examination on the subject, wherein the imaging examination is responsive to the first assay and/or the second assay.

14. The method of claim 1, wherein the first assay and the second assay further comprise enriching the sample for targeted cfDNA fragments corresponding to one or more predetermined regions of a genome.

15. The method of claim 1, wherein the first biological sample or second biological sample further comprises virus-derived DNA fragments, the method further comprising detecting the virus-derived DNA, wherein detection of the virus-derived DNA is a negative control for tumor-derived DNA.

16. A method of non-invasively detecting a tumor in a subject, comprising:

obtaining, through a non-invasive procedure, a first biological sample from the subject, wherein the first biological sample comprises substantially cell-free DNA (cfDNA) derived from normal cells and comprises or is suspected of comprising tumor-derived cfDNA;

performing a first assay using the first biological sample, wherein the first assay has a specificity for a first set of markers indicative of the tumor, and wherein the first assay comprises:

measuring a methylation status of the tumor-derived cfDNA in the first biological sample; and determining if the first biological sample includes the first set of markers indicative of the tumor based on a comparison of the methylation status of the tumor-derived cfDNA in the first biological sample to at least one first calibration value;

responsive to determining that the first biological sample includes the first set of markers indicative of the tumor, obtaining, through a non-invasive procedure, a second biological sample from the subject, wherein the second biological sample comprises cfDNA derived from normal cells and comprises or is suspected of comprising tumor-derived cfDNA;

only when the first biological sample includes the first set of markers indicative of the tumor, performing a second assay using the second biological sample, wherein the second assay has a sensitivity for a second set of markers indicative of the tumor, and wherein the second assay comprises:

measuring a methylation status of the tumor-derived cfDNA in the second biological sample;

identifying the tumor in the subject based on the comparison of the methylation status of the tumor-derived cfDNA in the second biological sample to at least one second calibration value; and outputting a report indicative of the tumor in the subject.

17. The method of claim 16, wherein the second biological sample is obtained between 1 day and 12 weeks after obtaining the first biological sample.

18. The method of claim 16, wherein a positive predictive value of the method of non-invasively detecting a tumor in a subject is greater than a positive predictive value of the first assay or second assay alone.

19. The method of claim 18, wherein the positive predictive value of the method of non-invasively detecting a tumor in a subject is at least 1.5-fold, at least 2-fold, at least 4-fold, at least 10-fold, or at least 20-fold greater than the positive predictive value of the first assay or second assay alone.

20. The method of claim 16, wherein the sensitivity of the method of non-invasively detecting a tumor in a subject is same or greater than the sensitivity of the second assay alone, and wherein the specificity of the method is same or greater than the specificity of the first assay alone.

21. The method of claim 16, wherein the first set of markers and the second set of markers are the same set of markers.

22. The method of claim 16, wherein the specificity of the first assay for the first set of markers is at least about 95%.

23. The method of claim 16, wherein the sensitivity of the second assay for the second set of markers is at least about 35%.

24. The method of claim 16, wherein the tumor is selected from a group consisting of liver cancer, nasopharyngeal cancer, oropharyngeal cancer, oral cancer, bladder cancer, bone cancer, a brain tumor, breast cancer, esophageal cancer, gastrointestinal cancer, hematopoietic malignancy, leukemia, lung cancer, lymphoma, myeloma, ovarian cancer, prostate cancer, sarcoma, stomach cancer, and thyroid cancer.

25. The method of claim 16, wherein at least one of the first biological sample and the second biological sample are independently selected from a group consisting of whole blood, blood plasma, blood serum, urine, buffy coat, and a combination thereof.

26. The method of claim 16, wherein the first assay and the second assay further comprise using methylation-aware sequencing to detect the methylation status of tumor-derived cfDNA in the first biological sample and second biological sample, respectively.

27. The method of claim 26, wherein the methylation-aware sequencing comprises using bisulfite DNA conversion with the tumor-derived cfDNA prior to sequencing.

28. The method of claim 16, further comprising performing an imaging examination on the subject, wherein the imaging examination is responsive to the first assay and/or the second assay.

29. The method of claim 16, wherein the first assay and the second assay further comprise enriching the sample for targeted cfDNA fragments corresponding to one or more predetermined regions of a genome.

30. The method of claim 16, wherein the first biological sample or second biological sample further comprises virus-derived DNA fragments, the method further comprising detecting the virus-derived DNA, wherein detection of the virus-derived DNA is a negative control for tumor-derived DNA.

* * * * *